(12) United States Patent
Georges et al.

(10) Patent No.: US 10,501,521 B2
(45) Date of Patent: Dec. 10, 2019

(54) DISULFIDE-LINKED MULTIVALENT MHC CLASS I COMPRISING MULTI-FUNCTION PROTEINS

(71) Applicant: Hoffmann-La Roche Inc., Little Falls, NJ (US)

(72) Inventors: Guy Georges, Habach (DE); Sabine Imhof-Jung, Planegg (DE); Hendrik Knoetgen, Penzberg (DE); Martina Schmittnaegel, Tutzing (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/745,170

(22) PCT Filed: Dec. 18, 2013

(86) PCT No.: PCT/EP2013/077109
§ 371 (c)(1),
(2) Date: Jun. 19, 2015

(87) PCT Pub. No.: WO2014/096015
PCT Pub. Date: Jun. 26, 2014

(65) Prior Publication Data
US 2015/0344586 A1    Dec. 3, 2015

(30) Foreign Application Priority Data

Dec. 21, 2012  (EP) .................................... 12198904
Jul. 8, 2013    (EP) .................................... 13175469

(51) Int. Cl.
| | | |
|---|---|---|
| *C07K 14/70* | (2006.01) | |
| *C07K 14/74* | (2006.01) | |
| *C12N 7/00* | (2006.01) | |
| *C07K 16/28* | (2006.01) | |
| *C07K 16/30* | (2006.01) | |

(52) U.S. Cl.
CPC .... *C07K 14/70539* (2013.01); *C07K 16/2863* (2013.01); *C07K 16/3053* (2013.01); *C12N 7/00* (2013.01); *C07K 2317/35* (2013.01); *C07K 2317/52* (2013.01); *C07K 2317/622* (2013.01); *C07K 2317/64* (2013.01); *C07K 2317/71* (2013.01); *C07K 2319/30* (2013.01); *C07K 2319/33* (2013.01); *C12N 2710/16133* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,500,362 A | 3/1996 | Robinson et al. |
| 5,624,821 A | 4/1997 | Winter et al. |
| 5,648,237 A | 7/1997 | Carter |
| 5,648,260 A | 7/1997 | Winter et al. |
| 5,789,199 A | 8/1998 | Joly et al. |
| 5,821,337 A | 10/1998 | Carter et al. |
| 5,840,523 A | 11/1998 | Simmons et al. |
| 5,959,177 A | 9/1999 | Hein et al. |
| 6,040,498 A | 3/2000 | Stomp et al. |
| 6,171,586 B1 | 1/2001 | Lam et al. |
| 6,194,551 B1 | 2/2001 | Idusogie et al. |
| 6,267,958 B1 | 7/2001 | Andya et al. |
| 6,268,411 B1 | 7/2001 | Schneck et al. |
| 6,361,964 B1 * | 3/2002 | Kaiser .................. C07K 1/1133 435/233 |
| 6,417,429 B1 | 7/2002 | Hein et al. |
| 6,420,548 B1 | 7/2002 | Vezina et al. |
| 6,548,067 B1 | 4/2003 | Seeman et al. |
| 6,602,684 B1 | 8/2003 | Umana et al. |
| 6,734,013 B2 | 5/2004 | Schneck et al. |
| 6,737,056 B1 | 5/2004 | Presta |
| 7,125,978 B1 | 10/2006 | Vezina et al. |

(Continued)

FOREIGN PATENT DOCUMENTS

| | | |
|---|---|---|
| EP | 0 061 888 A2 | 10/1982 |
| EP | 0 307 434 B1 | 9/1993 |

(Continued)

OTHER PUBLICATIONS

Truscott et al. (Journal of Immunology, 178: 6280-6289, 2007, in IDS from Apr. 23, 2018).*
Greten et al., "Peptide-β2-microglobulin-MHC fusion molecules bind antigen-specific T cells and can be used for multivalent MHC-Ig complexes" Journal of Immunological Methods 271:125-135 ( 2002).
Oelke et al., "Ex vivo induction and expansion of antigen-specific cytotoxic T cells by HLA-Ig-coated artificial antigen-presenting cells" Nature Medicine 9(5):619-624 (May 2013).
Robert et al., "Antibody-conjugated MHC class I tetramers can target tumor cells for specific lysis by T lymphocytes" Eur. J. Immunol. 30:3165-3170 ( 2000).

(Continued)

*Primary Examiner* — Nelson B Moseley, II
(74) *Attorney, Agent, or Firm* — Julie A. Heider

(57) ABSTRACT

Herein is reported a disulfide-linked multivalent multi-function protein, characterized in that it comprises two or more antigen presenting domains, exactly one antibody Fc-region, and at least one antigen binding site, wherein the antigen presenting domain comprises in N- to C-terminal direction either (i) a β2-microglobulin, and (ii) the extracellular domains α1, α2, and α3 of a class I MHC molecule with a relative frequency of less than 1%, or (i) a T-cell response eliciting peptide, (ii) a β2-microglobulin, and (iii) the extracellular domains α1, α2, and α3 of a class I MHC molecule with a relative frequency of 1% or more, wherein the antigen binding site binds to a cancer cell surface antigen or a virus-infected cell surface antigen and wherein the antigen presenting domain has at least two non-naturally occurring cysteine residues which form an intrachain/inter-domain disulfide bond.

9 Claims, 28 Drawing Sheets

Figure 1:
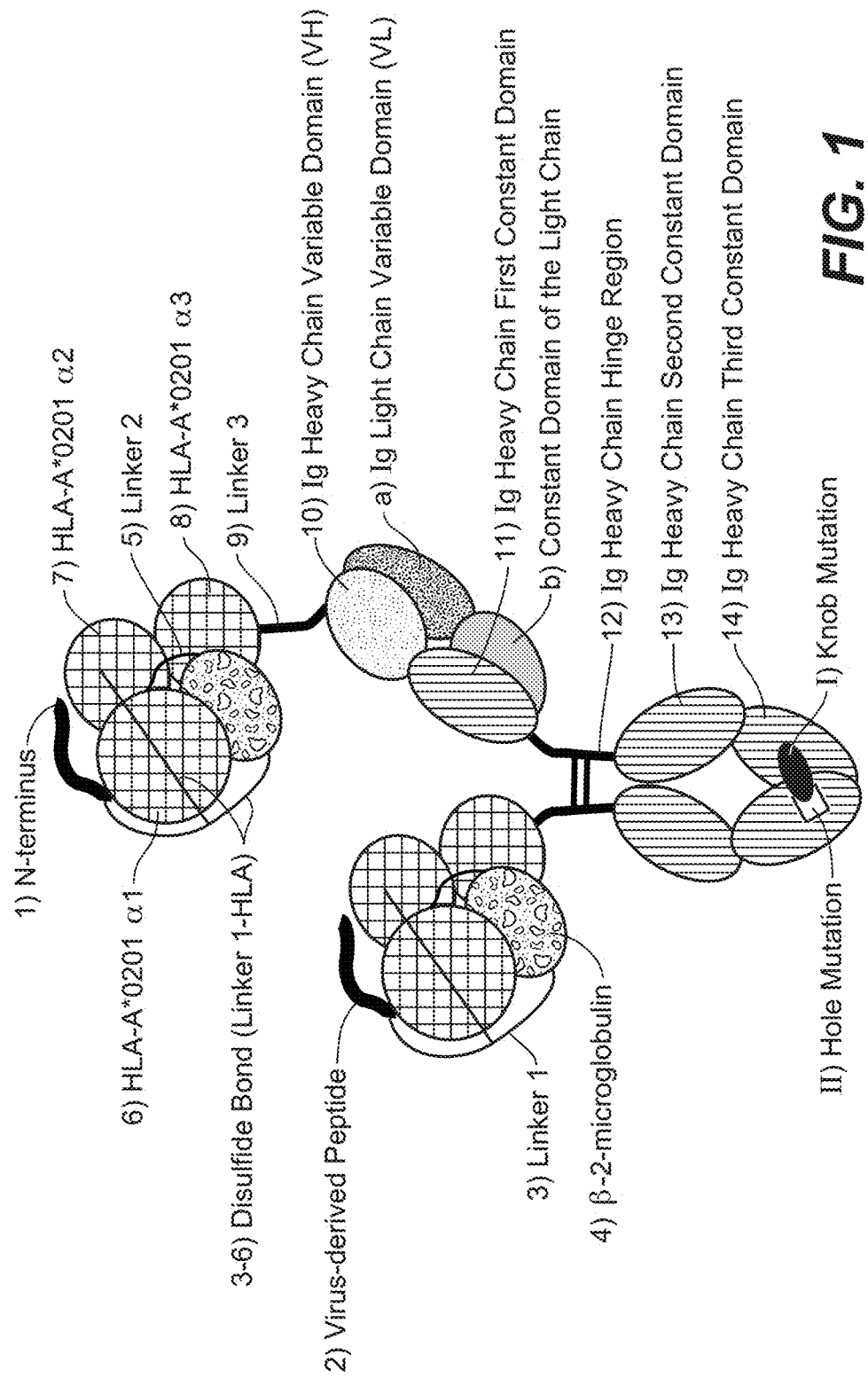

Specification includes a Sequence Listing.

(56) References Cited

U.S. PATENT DOCUMENTS

| | | | |
|---|---|---|---|
| 7,332,581 | B2 | 2/2008 | Presta |
| 7,371,826 | B2 | 5/2008 | Presta |
| 7,521,197 | B2 | 4/2009 | Savage |
| 2002/0006903 | A1 | 1/2002 | Schneck et al. |
| 2002/0164328 | A1 | 11/2002 | Shinkawa et al. |
| 2003/0115614 | A1 | 6/2003 | Kanda et al. |
| 2003/0157108 | A1 | 8/2003 | Presta |
| 2003/0166277 | A1 | 9/2003 | Zauderer et al. |
| 2003/0199024 | A1 | 10/2003 | Hansen |
| 2004/0091488 | A1 | 5/2004 | Seeman et al. |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0110707 | A1 | 6/2004 | Maden et al. |
| 2004/0132140 | A1 | 7/2004 | Satoh et al. |
| 2004/0204565 | A1 | 10/2004 | Schneck et al. |
| 2004/0259150 | A1 | 12/2004 | Nakamura et al. |
| 2005/0014934 | A1 | 1/2005 | Hinton et al. |
| 2005/0031613 | A1 | 2/2005 | Nakamura et al. |
| 2005/0042218 | A1* | 2/2005 | Zauderer .......... C07K 14/70539 424/144.1 |
| 2005/0123546 | A1 | 6/2005 | Umana et al. |
| 2005/0260186 | A1 | 11/2005 | Bookbinder et al. |
| 2005/0276805 | A1 | 12/2005 | Hanai et al. |
| 2006/0104968 | A1 | 5/2006 | Bookbinder et al. |
| 2007/0134759 | A1 | 6/2007 | Nishiya et al. |
| 2008/0138354 | A1* | 6/2008 | Zaia .................. C07K 14/005 424/184.1 |
| 2008/0219947 | A1 | 9/2008 | Linette et al. |
| 2008/0241884 | A1 | 10/2008 | Shitara et al. |
| 2009/0117153 | A1 | 5/2009 | Hansen et al. |
| 2009/0203078 | A1 | 8/2009 | Ogawa et al. |
| 2011/0236411 | A1* | 9/2011 | Scholler ............. A61K 39/0011 424/193.1 |
| 2015/0152161 | A1 | 6/2015 | Reiter et al. |
| 2015/0344586 | A1 | 12/2015 | Georges et al. |
| 2017/0095544 | A1 | 4/2017 | Santamaria et al. |

FOREIGN PATENT DOCUMENTS

| | | |
|---|---|---|
| EP | 0 580 979 A2 | 2/1994 |
| EP | 1 012 320 B1 | 10/2007 |
| JP | 3-240498 | 10/1991 |
| RU | 2379055 | 1/2010 |
| WO | 1990/005301 A1 | 5/1990 |
| WO | 1990/011511 A1 | 10/1990 |
| WO | 1992/014138 A1 | 8/1992 |
| WO | 1994/029351 A2 | 12/1994 |
| WO | 1997/030087 A1 | 8/1997 |
| WO | 1998/058964 A1 | 12/1998 |
| WO | 99/13095 | 3/1999 |
| WO | 1999/022764 A1 | 5/1999 |
| WO | 1999/051642 A1 | 10/1999 |
| WO | 1999/064597 A1 | 12/1999 |
| WO | 02/031140 A1 | 4/2002 |
| WO | 2002/102299 A2 | 12/2002 |
| WO | 2003/011878 A2 | 2/2003 |
| WO | 2003/085107 A1 | 10/2003 |
| WO | 2004/056312 A2 | 7/2004 |
| WO | 2004/084798 A2 | 10/2004 |
| WO | 2004/087756 A2 | 10/2004 |
| WO | 2005/053742 A1 | 6/2005 |
| WO | 2005/099361 A2 | 10/2005 |
| WO | 2005/100402 A1 | 10/2005 |
| WO | 2006/029879 A2 | 3/2006 |
| WO | 2006/044908 A2 | 4/2006 |
| WO | 2007/025554 A1 | 3/2007 |
| WO | 2007/025705 A2 | 3/2007 |
| WO | 2007/115814 A2 | 10/2007 |
| WO | 2008/077546 A1 | 7/2008 |
| WO | 2012/107417 A1 | 8/2012 |
| WO | 2012/175508 A1 | 12/2012 |

OTHER PUBLICATIONS

Hammer et al., "Construction and Destruction of MHC Class I in the Peptide-Loading Complex" Nature Immunology 8(8):793-794 (Aug. 2007).

Anonymous, The Biology Project, University of Arizona, Jun. 12, 2000 (biology.arizona.edu/immunology/tutorials/antibody/structure.html, accessed Sep. 4, 2015).

Bluemel et al., "Epitope distance to the target cell membrane and antigen size determine the potency of T cell-mediated lysis by BiTE antibodies specific for a large melanoma surface antigen" Cancer Immunol Immunother 59:1197-1209 (2010).

Brock "Capítulo 20 Conceptos de inmunología" (English translation), Brock-Octava edition, Prentice Hall:813-862.

Bruggemann et al., "Comparison of the effector functions of human immunoglobulins using a matched set of chimeric antibodies" J. Exp. Med. 166:1351-1361 (Nov. 1, 1987).

Cesson et al., "Active Antiviral T-Lymphocyte Response Can Be Redirected against Tumor Cells by Antitumor Antibody MHC/Viral Peptide Conjugates" Clin Cancer Res 12(24):7422-7430 (Dec. 15, 2006).

Charlton, Antibody Engineering; Methods and Protocols "14 Expression and Isolation of Recombinant Antibody Fragments in *E. coli*" ed. Lo, Benny, Totowa, NJ: Humana Press, vol. 248:245-54 (2004).

Chen et al., "Selection and analysis of an optimized anti-VEGF antibody: crystal structure of an affinity-matured Fab in complex with antigen" J Mol Biol 293(4):865-881 (1999).

Clackson et al., "Making antibody fragments using phage display libraries" Nature 352:624-628 (Aug. 15, 1991).

Clynes et al., "Fc receptors are required in passive and active immunity to melanoma" P Natl Acad Sci Usa 95:652-656 (Jan. 1998).

Cragg et al., "Antibody specificity controls in vivo effector mechanisms of anti-CD20 reagents" Blood 103(7):2738-2743 (Apr. 1, 2004).

Cragg et al., "Complement-mediated lysis by anti-CD20 mAb correlates with segregation into lipid rafts" Blood 101(3):1045-1052 (Feb. 1, 2003).

Dal Porto et al., "A soluble divalent class I major histocompatibility complex molecule inhibits alloreactive T cells at nanomolar concentrations" Proc. Natl. Acad. Sci. USA 90:6671-6675 (Jul. 1993).

Davison et al., "The human cytomegalovirus genome revisited: comparison with the chimpanzee cytomegalovirus genome" Journal of General Virology 84:17-28 (2003).

Duncan et al., "The binding site for Clq on IgG" Nature 322:738-740 (Apr. 21, 1988).

Gazzano-Santoro et al., "A non-radioactive complement-dependent cytotoxicity assay for anti-CD20 monoclonal antibody" J Immunol Methods 202:163-171 (1997).

Gerngross, "Advances in the production of human therapeutic proteins in yeasts and filamentous fungi" Nature Biotechnology 22(11):1409-1414 (Nov. 2004).

Godeau et al., "Purification and Ligand Binding of a Soluble Class I Major Histocompatibility Complex Molecule Consisting of the First Three Domains of H-2K$^d$ Fused to $\beta_2$-Microglobulin Expressed in the Baculovirus-Insect Cell System" Journal of Biological Chemistry 267(34):24223-24229 (Dec. 5, 1992).

Graham et al., "Characteristics of a human cell line transformed by DNA from human adenovirus type 5" J Gen Virol 36(1):59-72 (Jul. 1977).

Guyer et al., "Immunoglobulin binding by mouse intestinal epithelial cell receptors" J Immunol 117(2):587-593 (Aug. 1976).

Hansen et al., "Translational and basic applications of peptide-MHCI single chain trimers" Trends Immunol 31(10):363-369 ( 2010).

Hellstrom et al., "Antitumor effects of L6, an IgG2a antibody that reacts with most human carcinomas" P Natl Acad Sci Usa 83:7059-7063 (Sep. 1986).

Hellstrom et al., "Strong antitumor activities of IgG3 antibodies to a human melanoma-associated ganglioside" P Natl Acad Sci Usa 82:1499-1502 (Mar. 1985).

(56) References Cited

OTHER PUBLICATIONS

Idusogie et al., "Mapping of the C1q binding site on Rituxan, a chimeric antibody with a human IgG1 Fc" J Immunol 164:4178-4184 (2000).
Kabat et al. Sequences of Proteins of Immunological Interest. Fifth edition, NIH Publication:91-3242 (1991).
Kam et al., "Carbon nanotubes as multifunctional biological transporters and near-infrared agents for selective cancer cell destruction" P Natl Acad Sci Usa 102(33):11600-11605 (Aug. 16, 2005).
Kanda et al., "Comparison of cell lines for stable production of fucose-negative antibodies with enhanced ADCC" Biotechnol Bioeng 94(4):680-688 (Jul. 5, 2006).
Khan et al., "Cytomegalovirus Seropositivity Drives the CD8 T Cell Repertoire Toward Greater Clonality in Healthy Elderly Individuals" Journal of Immunology 169:1984-1992 (2002).
Kim et al., "Localization of the site of the murine IgG1 molecule that is involved in binding to the murine intestinal Fc receptor" Eur J Immunol 24:2429-2434 (1994).
Kindt et al. Kuby Immunology "Antigens and Antibodies Chapter 4" $6^{th}$ edition, N.Y.:W.H. Freeman and Co:p. 91 (2007).
Lev et al., "Recruitment of CTL Activity by Tumor-Specific Antibody-Mediated Targeting of Single-Chain Class I MHC-Peptide Complexes" Journal of Immunology 169:2988-2996 (2002).
Lev et al., "Tumor-specific Ab-mediated targeting of MHC-peptide complexes induces regression of human tumor xenografts in vivo" PNAS 101(24):9051-9056 (Jun. 15, 2004).
Li et al., "Optimization of humanized IgGs in glycoengineered Pichia pastoris" Nature Biotechnology 24(2):210-215 (Feb. 2006).
Looney et al., "Role of Cytomegalovirus in the T Cell Changes Seen in Elderly Individuals" Clinical Immunology 90(2):213-219 (Feb. 1999).
Lund et al., "Oligosaccharide-protein interactions in IgG can modulate recognition by Fc gamma receptors" FASEB J. 9(1):115-119 (1995).
Mage et al., "A recombinant, soluble, single-chain class I major histocompatibility complex molecule with biological activity" Proc. Natl. Acad. Sci. USA 89:10658-10662 (Nov. 1992).
Mather et al., "Culture of testicular cells in hormone-supplemented serum-free medium" Ann NY Acad SCI 383:44-68 (1982).
Mather, "Establishment and characterization of two distinct mouse testicular epithelial cell lines" Biol Reprod 23:243-252 (1980).
McLaughlin-Taylor et al., "Identification of the major late human cytomegalovirus matrix protein pp65 as a target antigen for CD8+ virus-specific cytotoxic T lymphocytes" J Med. Virol. 43(1):103-110 (1994).
Michaelis et al., "The Story of Human Cytomegalovirus and Cancer: Increasing Evidence and Open Questions" Neoplasia 11(1):1-9 (Jan. 2009).
Morgan et al., "The N-terminal End of the $C_{H}2$ Domain of Chimeric Human IgG1 anti-HLA-DR is Necessary for C1q, FcγRI and FcγRIII Binding" Immunology 86:319-324 (1995).
Moss et al., "CD8+ T-Cell Immunity to Cytomegalovirus" Human Immunology 65:456-464 (2004).
Mottez et al., "A single-chain murine class I major transplantation antigen" Eur. J. Immunol. 21:467-471 (1991).
Mottez et al., "Cells Expressing a Major Histocompatibility Complex Class I Molecule with a Single Covalently Bound Peptide Are Highly Immunogenic" J. Exp. Med. 181:493-502 (Feb. 1995).
Mous et al., "Redirection of CMV-specific CTL towards B-CLL via CD20-targeted HLA/CMV complexes" Leukemia 20:1096-1102 (2006).
Novak et al., "Selective antibody-mediated targeting of class I MHC to EGFR-expressing tumor cells induces potent antitumor CTL activity in vitro and in vivo" Int. J. Cancer 120:326-336 (2006).
Okazaki et al., "Fucose depletion from human IgG1 oligosaccharide enhances binding enthalpy and association rate between IgG1 and FcγRIIIa" J Molec Biol 336:1239-1249 (2004).
Oved et al., "Antibody-mediated targeting of human single-chain class 1 MHC with covalently linked peptides induces efficient killing of tumor cells by tumor or viral-specific cytotoxic T lymphocytes" Cancer Immunol Immunother 54:867-879 (2005).
Pace et al., "How to measure and predict the molar absorption coefficient of a protein" Protein Science 4(11):2411-2423 (Nov. 1995).
Petkova et al., "Enhanced half-life of genetically engineered human IgG1 antibodies in a humanized FcRn mouse model: potential application in humorally mediated autoimmune disease" International Immunology 18(12):1759-69 (Dec. 2006).
Player et al., "Differences in Frequency Distribution of HLA-A2 Subtypes Between North American and Italian White Melanoma Patients: Relevance for Epitope Specific Vaccination Protocols" Journal of Immunotherapy 19(5):357-363 (1996).
Portolano et al., "Lack of promiscuity in autoantigen-specific H and L chain combinations as revealed by human H and L chain 'Roulette'" J Immunol 150(3):880-887 (Feb. 1, 1993).
Ravetch et al., "Fc receptors" Annu Rev Immunol 9:457-492 (1991).
Ripka et al., "Two chinese hamster ovary glycosylation mutants affected in the conversion of GDP-mannose to GDP-fucose" Archives of Biochemistry and Biophysics 249(2):533-545 (Sep. 1986).
Robert et al., "Redirecting anti-viral CTL against cancer cells by surface targeting of monomeric MHC class I-viral peptide conjugated to antibody fragments" Cancer Immunity 1:2 (Mar. 30, 2001).
Rojas et al. Immunología De Rojas (English translation), 14th edition (2007).
Sela-Culang et al., "A Systematic Comparison of Free and Bound Antibodies Reveals Binding-Related Conformational Changes" Journal of Immunology:189 (2012).
Shields et al., "High resolution mapping of the binding site on human IgG1 for Fc gamma RI, Fc gamma RII, Fc gamma RIII, and FcRn and design of IgG1 variants with improved binding to the FC gamma R" J Biol Chem 276(9):6591-6604 (Mar. 2, 2001).
Thakur et al., "Cancer therapy with bispecific antibodies: Clinical experience" Curr Opin Mol Ther 12(3):340-349 (Jun. 2010).
Torisu-Itakura et al., "Redirected Lysis of Human Melanoma Cells by a MCSP/CD3-bispecific BiTE Antibody That Engages Patient-derived T Cells" Journal of Immunotherapy 34(8):597-605 (Oct. 1, 2011).
Urlaub et al., "Isolation of chinese hamster cell mutants deficient in dihydrofolate reductase activity" P Natl Acad Sci Usa 77(7):4216-4220 (Jul. 1980).
Wills et al., "The Human Cytotoxic T-Lymphocyte (CTL) Response to Cytomegalovirus Is Dominated by Structural Protein pp65: Frequency, Specificity, and T-Cell Receptor Usage of pp65-Specific CTL" Journal of Virology:7569-7579 (Nov. 1996).
Wright et al., "Effect of glycosylation on antibody function: implications for genetic engineering" Trends Biotechnol. 15(1):26-32 (1997).
Yamane-Ohnuki et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).
Yazaki et al., "Expression of recombinant antibodies in mammalian cell lines" Methods Molec Biol 248:255-268 (2004).
Mitaksov et al., "Structural Engineering of pMHC Reagents for T Cell Vaccines and Diagnostics" Chemistry & Biology 14:909-922 (Aug. 2007).
Barzaga-Gilbert et al., "Species Specificity and Augmentation of Responses to Class II Major Histocompatibility Complex Molecules in Human CD4 Transgenic Mice" J EXP MED 175(6):1707-15 (Jun. 1, 1992).
Casares et al., "Antigen-specific downregulation of T cells by doxorubicin delivered through a recombinant MHC II-peptide chimera" Nature Biotechnology 19(2):142-7 (Feb. 2001).
Donda et al., "In vivo targeting of an anti-tumor antibody coupled to antigenic MHC class I complexes induces specific growth inhibition and regression of established syngeneic tumor grafts" Cancer Immunity 3(11):1-17 (Aug. 14, 2003).
Geiser et al., "Identification of the Human Melanoma-associated Chondroitin Sulfate Proteoglycan Antigen Epitope Recognized by the Antitumor Monoclonal Antibody 763.74 from a Peptide Phage Library" Cancer Research 59:905-910 (Feb. 15, 1999).

(56) References Cited

OTHER PUBLICATIONS

Girolamo et al., "Diversified Expression of NG2/CSPG4 Isoforms in Glioblastoma and Human Foetal Brain Identifies Pericyte Subsets" PLOS One 8(12 SUPPL e84883):1-19 (Dec. 2013).
Novak et al., "Selective antibody-meidated targeting of class I MHC to EGFR-expressing tumor cells induces potent antitumor CTL activity in vitro and in vivo" Int. J. Cancer 120(2):329-36 (2006).
Ogg et al., "Sensitization of tumour cells to lysis by virus-specific CTL using antibody-targeted MHC class I/peptide complexes" British Journal of Cancer 82(5):1058-62 (Mar. 2000).
Petrovskaya et al., "Alternative Scaffold Proteins" 37(5):517-526 (2011).
Savage et al., "Anti-Viral Cytotoxic T Cells Inhibit the Growth of Cancer Cells with Antibody Targeted HLA Class I/Peptide Complexes in SCID Mice" Int. J. Cancer 98:561-566 (Apr. 1, 2002).
Truscott et al., "Disulfide Bond Engineering to Trap Peptides in the MHC Class I Binding Groove" The Journal of Immunology 178(10):6280-9 (May 15, 2007).
Zafir-Lavie et al., "Novel antibodies as anticancer agents" Oncogene 26(25):3714-33 (May 28, 2007).

\* cited by examiner

| Signal Peptide | Virus-derived-peptide | β2-microglobulin | MHCI α1-α2-α3 | Antibody Light Chain / Antibody Heavy Chain Hinge Region Comprising Polypeptide |

| Signal Peptide | | β2-microglobulin | MHCI α1-α2-α3 | Antibody Light Chain / Antibody Heavy Chain Hinge Region Comprising Polypeptide |

| Signal Peptide | Virus-derived-peptide | MHCI α1-α2-α3 | β2-microglobulin | Antibody Light Chain / Antibody Heavy Chain Hinge Region Comprising Polypeptide |

| Signal Peptide | | MHCI α1-α2-α3 | β2-microglobulin | Antibody Light Chain / Antibody Heavy Chain Hinge Region Comprising Polypeptide |

*FIG. 2*

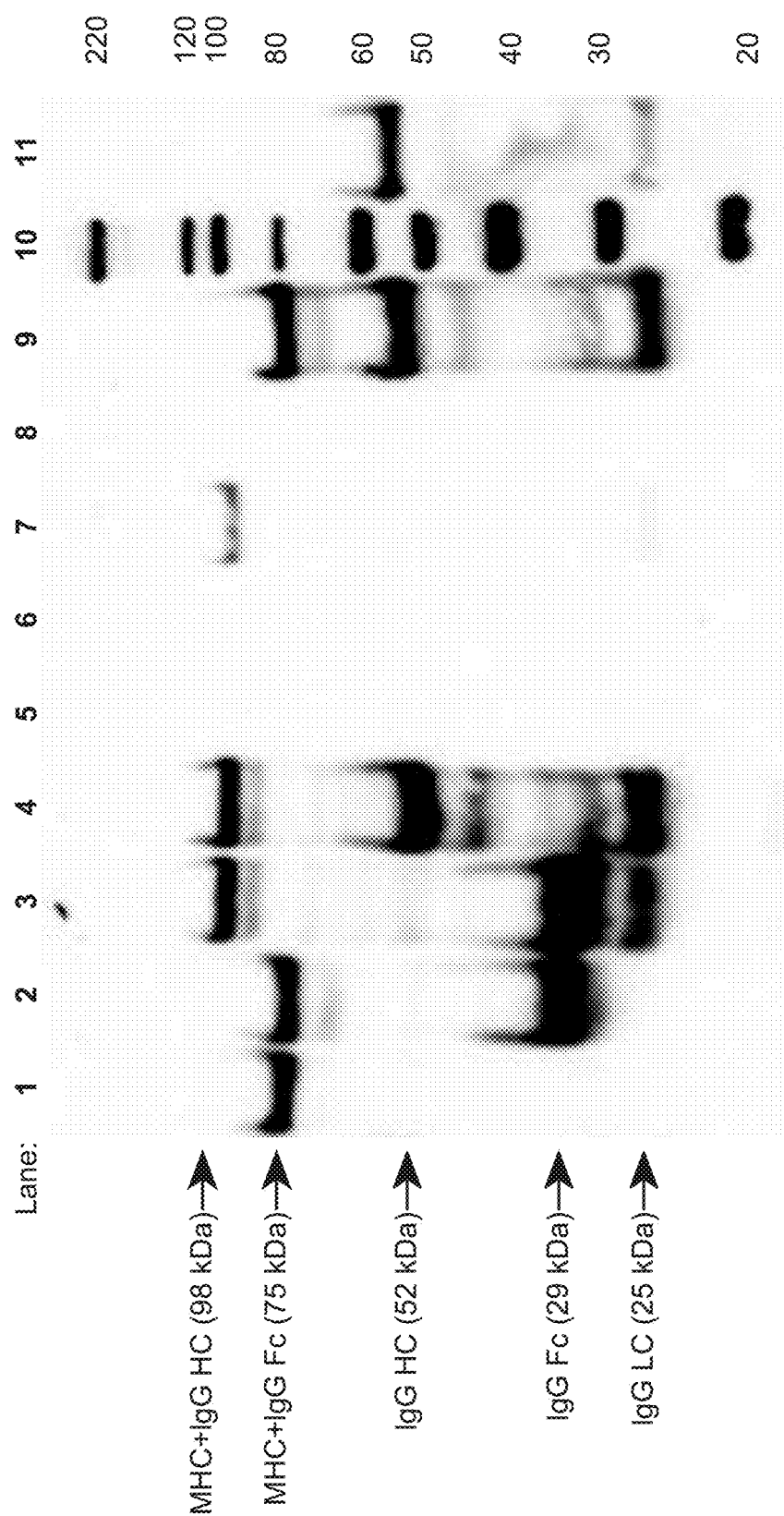

DISULFIDE-LINKED MULTIVALENT MHC CLASS I COMPRISING MULTI-FUNCTION PROTEINS

CROSS-REFERENCE TO RELATED APPLICATIONS

This application is a 371 of PCT International Application No. PCT/EP2013/077109, filed on Dec. 18, 2013, currently pending, the contents of which are incorporated by reference in its entirety, and which claims priority to European Application No. EP12198904.0, filed Dec. 21, 2012, now expired, and European Application No. 13175469.9, filed Jul. 8, 2013, now expired.

SEQUENCE LISTING

The sequence listing includes the sequences identified as Seq ID Nos: 1-142. This file is named P31397-US_Sequence_Listing.txt, is 164,338 bytes in size, was created on May 1, 2015, and is IBM PC/XT/AT: MS-windows compatible.

FIELD OF THE INVENTION

Herein is reported a disulfide-linked multivalent multi-function protein comprising an antibody fragment and one, two or more disulfide-linked MHC class I components and its use for removal of cancer cells or virus infected cells by targeted attraction of circulating virus-specific cytotoxic T-cells.

BACKGROUND OF THE INVENTION

The MHC Class I protein consists of an α-chain (α-1 to 3 and a transmembrane domain) and β2-microglobulin. It is polygenic (3 gene loci for MHC-class I protein in the haploid genome) giving rise to six different MHC class I protein α-chains (in humans two HLA-A, two HLA-B, two HLA-C). The MHC is further polymorphic. The human HLA-A allele A*0201 is prevalent in about 30% to 50% of the caucasian population (see e.g. Player, et al., J. Immunother. Emphasis Tumor Immunol. 19 (1996) 357-363).

Human cytomegalovirus huCMV (=human herpesvirus 5, HHV-5) is one of the largest human viruses. Its genome comprises around 230,000 bp linear double stranded DNA and encodes more than 160 proteins (see e.g. Davison, A J., et al., J. Gen. Virol. 84 (2003) 17-28).

The CMV has evolved to become a sublime parasite of the human genome and it is a potent immunogen and triggers strong immune responses from all arms of the immune system. This virus appears to be among the most immunodominant antigens known to the human immune system and stimulates $CD8^+$-T-cell responses of unprecedented magnitude.

The CMV "latency" depends on chronic immune suppression of CMV viruses rather than a change in the pattern of viral transcription (see e.g. Moss & Khan, Human Immunology 65 (2004) 456-464).

$CD8^+$-T-cell immune responses are not directed evenly against all CMV proteins but are focused. The CMV proteins pp65 and IE-1 are the predominant targets (see e.g. McLaughlin-Taylor, E., et al., J. Med. Virol. 43 (1994) 103-110; Moss & Khan, Human Immunology 65 (2004) 456-464).

The frequency of CMV-specific T-cells is very high with frequencies for individual peptides in the order of up to 1 to 2% of the total $CD8^+$-T-cell repertoire (see e.g. Moss & Khan, Human Immunology supra; Wills, M. R., et al., J. Virol. 70 (1996) 7569-7579).

The CMV-specific $CD8^+$-T-cell response increases markedly with age and individual HLA-peptide tetramers frequently stain in excess of 10% of the total $CD8^+$-T-cell pool (see e.g. Khan, N., et al., J. Immunol. 169 (2002) 1984-1992).

The total $CD8^+$-T-cell response in healthy elderly donors could constitute approximately 50% of the $CD8^+$-T-cell repertoire.

The enormous $CD8^+$-T-cell expansions are often very clonally restricted, and it is estimated that CMV is the cause of at least 30% of the clonal $CD8^+$-T-cell expansions that are seen in peripheral blood with aging. The total $CD8^+$-T-cell count is twice as high in CMV-seropositive donors older than age 60 years in comparison to a CMV-seronegative cohort (see e.g. Looney, R. J., et al., Clin. Immunol. 90 (1999) 213-219).

A fusion of soluble HLA and β-2-microglobulin is reported by Mottez et al. (Eur. J. Immunol. 21 (1991) 467-471); Godeau et al. (J. Biol. Chem. 267 (1992) 24223-24229) and Mage et al. (Proc. Natl. Acad. Sci. 89 (1992) 10658-10662). A fusion of viral-derived peptide with soluble HLA and β-2-microglobulin is reported by Mottez et al. (J. Exp. Med. 181 (1995) 493-502). A fusion of an immunoglobulin heavy chain with soluble HLA and co-expressed β-2-microglobulin is reported by Dal Porto et al. (Proc. Natl. Acad. Sci. USA 90 (1993) 6671-6675). A tetrameric multi-function protein of biotinylated peptide-soluble HLA and β-2-microglobulin with streptavidin chemically coupled to a Fab is described by Robert et al. (Eur. J. Immun. 30 (2000) 3165-3170). A chemically coupled Fab with a fusion of viral-derived peptide with soluble HLA and β-2-microglobulin is reported by Robert et al. (Cancer Immunity 1 (2001) 2). A fusion of a viral-derived peptide with soluble HLA and β-2-microglobulin to a murine monoclonal antibody heavy chain is reported by Greten et al. (J. Immunol. Methods 271 (2002) 125-135). An E. coli expression of scFv fusions without peptide, in vitro refolding and peptide loading is reported by Lev et al. (J. Immunol. 169 (2002) 2988-2996; Proc. Natl. Acad. Sci. 101 (2004) 9051-9056), and Novak et al. (Int. J. Cancer 120 (2006) 329-336). The use of biotinylated soluble MHC loaded with peptides and coupled to streptavidin fused Fab or scFv antibodies is reported by Mous et al. (Leukemia 20 (2006) 1096-1102).

In WO 2005/099361 are reported MHC class I—peptide-antibody conjugates with modified beta-2-microglobulin. Exemplary conjugates as reported in WO 2005/099361 are obtained by in vitro conjugation of the alpha chain of the MHC-multi-function protein (HLA) or by the co-expression from separate genes in the same cell.

In US 2004/0091488 antigenic constructs of major histocompatibility multi-function protein class I antigens with specific carrier molecules are reported. These reported fusion polypeptides lack the hinge region.

In WO 99/13095 the use of multivalent chimeric peptide-loaded MHC/IG molecules to detect, activate or suppress antigen-specific T cell-dependent immune responses. Methods and pharmaceutical compositions for immune depletion, particularly useful in the treatment of cancer are reported in WO 02/102299. Oelke, M., et al. (Nat. Med. 9 (2003) 619-624) report the ex vivo induction and expansion of antigen-specific cytotoxic T cells by HLA-Ig coated artificial antigen presenting cells. The removal of target cells by circulating virus-specific cytotoxic T-cells using MHC class I comprising complexes is reported in WO 2012/175508. Robert, B., et al. (Eur. J. Immunol. 30 (2000) 3165-3170) report that antibody-conjugated MHC class I tetramers can target tumor cells for specific lysis by T lymphocytes.

SUMMARY OF THE INVENTION

Herein is reported a disulfide-linked multivalent multi-function protein comprising one, two or more, in one embodiment one, in another embodiment two or four, antigen presenting domains as first part, one antibody Fc-region as second part, and at least one antigen binding site that is derived from an antibody and that specifically binds to a target antigen as third part.

With the disulfide-linked multivalent multi-function protein as reported herein existing virus-specific circulating cytotoxic T-cells (T-memory-cells and/or T-effector-cells) of an individual can be directed to cells expressing the target antigen, to which the antibody derived part of the disulfide-linked multivalent multi-function protein specifically binds to. Thereafter by dressing these cells with a MHC class I complex an acute viral infection by the virus-derived peptide linked to the MHC class I protein multi-function protein is mimicked and cytotoxic cells are attracted resulting in the removal of the targeted cell.

One aspect as reported herein is a disulfide-linked multivalent multi-function protein, characterized in that it comprises
  one, two or more than two antigen presenting domains,
  exactly one antibody Fc-region, and
  one or more antigen binding sites,
  wherein the antigen presenting domains comprise independently of each other in N- to C-terminal direction either
    (i) a β2-microglobulin, and
    (ii) the extracellular domains α1, α2, and α3 of a class I MHC molecule with a relative frequency of less than 1%,
  or
    (i) a T-cell response eliciting peptide,
    (ii) a β2-microglobulin, and
    (iii) the extracellular domains α1, α2, and α3 of a class I MHC molecule with a relative frequency of 1% or more,
  or
    (i) the extracellular domains α1, α2, and α3 of a class I MHC molecule with a relative frequency of less than 1%, and
    (ii) a β2-microglobulin,
  or
    (i) a T-cell response eliciting peptide,
    (ii) the extracellular domains α1, α2, and α3 of a class I MHC molecule with a relative frequency of 1% or more, and
    (iii) a β2-microglobulin,
  wherein the antigen binding site or sites bind to a cancer cell surface antigen or a virus-infected cell surface antigen, and
  wherein the antigen presenting domain has at least two non-naturally occurring cysteine residues that form an intrachain/interdomain disulfide bond.

In one embodiment one non-naturally occurring cysteine residue in the antigen presenting domain is in the linker between T-cell response eliciting peptide and one non-naturally occurring cysteine residue is in one of the extracellular domains α1, α2, and α3 of the class I MHC molecule. In one embodiment the antigen presenting domain has cysteine residues at least at position 11 and at position 227 and the cysteine residues at position 11 and position 227 form a disulfide bond (position 11 corresponds to position 2 of the linker, position 227 corresponds to position 84 of SEQ ID NO: 72 or SEQ ID NO: 140).

In one embodiment one non-naturally occurring cysteine residue in the antigen presenting domain is in the linker between T-cell response eliciting peptide and one non-naturally occurring cysteine residue is in one of the extracellular domains α1, α2, and α3 of the class I MHC molecule. In one embodiment the antigen presenting domain has cysteine residues at least at position 11 and at position 108 and the cysteine residues at position 11 and position 108 form a disulfide bond (position 11 corresponds to position 2 of the linker, position 108 corresponds to position 84 of SEQ ID NO: 71).

In one embodiment one non-naturally occurring cysteine residue in the antigen presenting domain is in the linker between T-cell response eliciting peptide and one non-naturally occurring cysteine residue is in the β2-microglobulin.

In one embodiment one non-naturally occurring cysteine residue in the antigen presenting domain is in the linker between T-cell response eliciting peptide and one non-naturally occurring cysteine residue is in the linker between the β2-microglobulin and the extracellular domain α1 of a class I MHC molecule.

In one embodiment the antibody Fc-region comprises a first and second disulfide-linked Fc-region polypeptide, whereby the antigen binding site or one of the antigen binding sites comprises the first Fc-region polypeptide and the second antigen binding site, if present, comprises the second Fc-region polypeptide.

In one embodiment the antigen binding site comprises i) a (cognate) pair of an antibody heavy chain and an antibody light chain, whereby the individual chains can be wild-type chains or modified chains (substituted, mutated or domain exchanged), or ii) a scFv fusion polypeptide comprising in N- to C-terminal direction a scFv antibody fragment and an antibody Fc-region polypeptide, or iii) a scFab fusion polypeptide comprising in N- to C-terminal direction a scFab and an antibody Fc-region polypeptide.

In one embodiment the antigen binding sites comprise independently of each other i) a (cognate) pair of an antibody heavy chain and an antibody light chain, whereby the individual chains can be wild-type chains or modified chains (substituted, mutated or domain exchanged), or ii) a scFv fusion polypeptide comprising in N- to C-terminal direction a scFv antibody fragment and an antibody Fc-region polypeptide, or iii) a scFab fusion polypeptide comprising in N- to C-terminal direction a scFab and an antibody Fc-region polypeptide.

In one embodiment i) an antigen presenting domain is linked to the N-terminus of the heavy chain or to the N-terminus of the light chain of an antigen binding site (if one antigen presenting domain is present), or ii) one antigen presenting domain is linked to each N-terminus of the heavy chain or to each N-terminus of the light chain of each antigen binding site (if two antigen presenting domains are present), or iii) an antigen presenting domain is linked to the C-terminus of the heavy chain or to the C-terminus of the light chain of the antigen binding site (if one antigen presenting domain is present), or vi) one antigen presenting domain is linked to each C-terminus of the heavy chain or to each C-terminus of the light chain of each antigen binding site (if two antigen presenting domains are present), or v) an antigen presenting domain is linked to the N- or C-terminus of an scFv fusion polypeptide (if one antigen presenting domain is present), or vi) one antigen presenting domain is linked to each N- or C-terminus of each scFv fusion polypeptide (if two antigen presenting domains are present), or vii) an antigen presenting domain is linked to the N- or C-terminus of a scFab fusion polypeptide (if one antigen presenting domain is present), or viii) one antigen presenting domain is linked to each N- or C-terminus of each scFab fusion polypeptide (if two antigen presenting domains are present), or ix) an antigen presenting domain is linked to the N- or C-terminus of the second Fc-region polypeptide (if one antigen presenting domain is present), or x) one antigen presenting domain is linked to the N- or C-terminus of the first Fc-region polypeptide and one antigen presenting domain is linked to the N- or C-terminus of the second Fc-region polypeptide (if two antigen presenting domains are present).

In one embodiment the cell surface antigen is a cancer cell surface antigen. In one embodiment the cancer cell surface antigen is melanoma-associated chondroitin sulfate proteoglycan (MCSP).

In one embodiment the disulfide-linked multivalent multi-function protein is a covalent disulfide-linked multivalent multi-function protein.

In one embodiment the T-cell response eliciting peptide is a virus-derived peptide. In one embodiment the T-cell response eliciting peptide is a CD8$^+$-T-cell response eliciting peptide.

In one embodiment the virus is selected from human cytomegalovirus, adenovirus, human herpesvirus 1, human herpesvirus 2, human herpesvirus 4 (Epstein-Barr virus), hepatitis-B-virus, hepatitis-C-virus, human immunodeficiency virus, human papillomavirus type 16, human papillomavirus type 18, human papillomavirus type 31, human papillomavirus type 33, human papillomavirus type 35, human papillomavirus type 39, human papillomavirus type 45, human papillomavirus type 51, human papillomavirus type 52, human papillomavirus type 56, human papillomavirus type 58, human papillomavirus type 59, human papillomavirus type 68, human papillomavirus type 73, human papillomavirus type 82, human T-cell lymphotropic virus type I, human influenza A virus, human influenza B virus, vaccinia virus, dengue virus.

In one embodiment the virus-derived peptide is selected from the peptides NLVPMVATV (SEQ ID NO: 01), VTEHDTLLY (SEQ ID NO: 02), NTDFRVLEL (SEQ ID NO: 03), CVETMCNEY (SEQ ID NO: 04), VLEETSVML (SEQ ID NO: 05), NLVPMVATV (SEQ ID NO: 06), RIFAELEGV (SEQ ID NO: 07), IIYTRNHEV (SEQ ID NO: 08), VLAELVKQI (SEQ ID NO: 09), AVGGAVASV (SEQ ID NO: 10), TVRSHCVSK (SEQ ID NO: 11), IMREFNSYK (SEQ ID NO: 12), GPISHGHVLK (SEQ ID NO: 13), ATVQGQNLK (SEQ ID NO: 14), VYALPLKML (SEQ ID NO: 15), AYAQKIFKIL (SEQ ID NO: 16), QYDPVAALF (SEQ ID NO: 17), YVKVYLESF (SEQ ID NO: 18), DIYRIFAEL (SEQ ID NO: 19), VFETSGGLVV (SEQ ID NO: 20), KARDHLAVL (SEQ ID NO: 21), QARLTVSGL (SEQ ID NO: 22), KARAKKDEL (SEQ ID NO: 23), QIKVRVDMV (SEQ ID NO: 24), RRRHRQDAL (SEQ ID NO: 25), ARVYEIKCR (SEQ ID NO: 26), KMQVIGDQY (SEQ ID NO: 27), NVRRSWEEL (SEQ ID NO: 28), CPSQEPMSIYVY (SEQ ID NO: 29), KPGKISHIMLDVA (SEQ ID NO: 30), ELRRKMMYM (SEQ ID NO: 31), IPSINVHHY (SEQ ID NO: 32), YAYIYTTYL (SEQ ID NO: 33), FEQPTETPP (SEQ ID NO: 34), QEFFWDANDIY (SEQ ID NO: 35), YEQHKITSY (SEQ ID NO: 36), QEPMSIYVY (SEQ ID NO: 37), SEHPTFTSQY (SEQ ID NO: 38), QAIRETVEL (SEQ ID NO: 39), TRATKMQVI (SEQ ID NO: 40), DALPGPCI (SEQ ID NO: 41), CEDVPSGKL (SEQ ID NO: 42), HERNGFTVL (SEQ ID NO: 43), PTFTSQYRIQGKL (SEQ ID NO: 44), QMWQARLTV (SEQ ID NO: 45), HELLVLVKKAQL (SEQ ID NO: 46), DDYSNTHSTRYV (SEQ ID NO: 47), SLYNTVATL (SEQ ID NO: 48), GLCTLVAML (SEQ ID NO: 49), GILGFVFTL (SEQ ID NO: 50), STNRQSGRQ (SEQ ID NO: 51), LLFGYPVYV (SEQ ID NO: 52), FAEGFVRAL (SEQ ID NO: 53), LIVIGILIL (SEQ ID NO: 54), or ILHTPGCV (SEQ ID NO: 55), WYAQIQPHW (SEQ ID NO: 56), AFSGVSWTM (SEQ ID NO: 57), ILIGVVITW (SEQ ID NO: 58), MMIPTVVAF (SEQ ID NO: 59), PFPQSNAPI (SEQ ID NO: 60), LLLTLLATV (SEQ ID NO: 61), IVLEHGSCV (SEQ ID NO: 62), LLFKTENGV (SEQ ID NO: 63), PLNEAIMAV (SEQ ID NO: 64), NLVRLQSGV (SEQ ID NO: 65), LVISGLFPV (SEQ ID NO: 66), LLLVAHYAI (SEQ ID NO: 67), LALLAAFKV (SEQ ID NO: 68), VILAGPMPV (SEQ ID NO: 69), HVLGRLITV (SEQ ID NO: 70), or a variant thereof comprising of from 1 to 3 amino acid exchanges, additions, and/or deletions.

In one embodiment the virus-derived peptide is a human cytomegalovirus-derived peptide. In one embodiment the virus-derived peptide has an amino acid sequence selected from the group of SEQ ID NO: 01 to SEQ ID NO: 70. In one embodiment the virus-derived peptide has an amino acid sequence selected from the group of SEQ ID NO: 01 to SEQ ID NO: 47.

In one embodiment the virus-derived peptide has the amino acid sequence of SEQ ID NO: 01.

In one embodiment the class I MHC molecule with a relative frequency of I % or more has a relative frequency of 10% or more.

In one embodiment the class I MHC molecule with a relative frequency of 1% or more is HLA-A*0201, or HLA-A*1101, or HLA-A*2402, or HLA-A*340101, or HLA-C*0304, or HLA-C*0401, or HLA-C*0702.

In one embodiment the class I MHC molecule with a relative frequency of 1% or more is selected depending on the region of the individual to whom the disulfide-linked multivalent multi-function protein is to be administered as follows:

for an individual of European origin the class I MHC molecule is selected from the group comprising HLA-A*0101, HLA-A*0201, HLA-A*0301, HLA-B*0702, HLA-B*0801, HLA-B*4402, HLA-C*0401, HLA-C*0501, HLA-C*0701, and HLA-C*0702, for an individual of Australian origin the class I MHC molecule is selected from the group comprising HLA-A*0201, HLA-A*1101, HLA-A*2402, HLA-A*340101, HLA-B*1301, HLA-B*1521, HLA-B*5601, HLA-B*5602, HLA-C*0102, HLA-C*0401, HLA-C*0403, and HLA-C*1502, for an individual of North American origin the class I MHC molecule is selected from the group comprising HLA-A*0201, HLA-A*2402, HLA-C*0202, HLA-C*0304, HLA-C*0401, and HLA-C*0702, and for an individual of South-East-Asian origin the class I MHC molecule is selected from the group comprising HLA-A*1101, HLA-A*2402, HLA-B*1504, HLA-C*0102, HLA-C*0304, HLA-C*0702, and HLA-C*0801.

In one embodiment the class I MHC molecule with a relative frequency of 1% or more is selected depending on the region of the individual to whom the disulfide-linked multivalent multi-function protein is to be administered as follows:

for an individual of European origin the class I MHC molecule is HLA-A*0201, for an individual of Australian origin the class I MHC molecule is selected from the group comprising HLA-A*2402, HLA-B*1301, HLA-C*0102, and HLA-C*0401, for an individual of North American origin the class I MHC molecule is selected from the group comprising HLA-A*2402, and HLA-C*0304, and for an individual of South-East-Asian origin the class I MHC molecule is HLA-A*2402.

In one embodiment the antigen presenting domain comprises in N- to C-terminal direction a T-cell response eliciting peptide, a β2-microglobulin and the extracellular domains α1, α2 and α3 of a class I MHC molecule with a relative frequency of 1% or more wherein the antigen presenting domain has cysteine residues at least at position 11 and at position 227 and the cysteine residues at position 11 and position 227 form a disulfide bond.

In one embodiment the antigen presenting domain comprises in N- to C-terminal direction a T-cell response eliciting peptide, the extracellular domains α1, α2 and α3 of a class I MHC molecule with a relative frequency of 1% or more and a β2-microglobulin wherein the antigen presenting domain has cysteine residues at least at position 11 and at position 108 and the cysteine residues at position 11 and position 108 form a disulfide bond.

In one embodiment the antigen presenting domain comprises in N- to C-terminal direction a T-cell response eliciting peptide, a β2-microglobulin and the extracellular domains α1, α2 and α3 of a class I MHC molecule with a relative frequency of less than 1% wherein the antigen presenting domain has cysteine residues at least at position 11 and at position 227 and the cysteine residues at position 11 and position 227 form a disulfide bond.

In one embodiment the antigen presenting domain comprises in N- to C-terminal direction a T-cell response eliciting peptide, the extracellular domains α1, α2 and α3 of a class I MHC molecule with a relative frequency of less than 1% and a β2-microglobulin wherein the antigen presenting domain has cysteine residues at least at position 11 and at position 108 and the cysteine residues at position 11 and position 108 form a disulfide bond.

In one embodiment the class I MHC molecule with a relative frequency of less than 1% is selected from the group comprising HLA-B*4201, HLA-B*5901, HLA-B*6701, and HLA-B*7802.

In one embodiment the antigen presenting domain comprises
(i) a virus-derived peptide,
(ii) β2-microglobulin,
(iii) the soluble HLA-A allele A*0201, and
(iv) cysteine residues at least at position 11 and at position 227 and the cysteine residues at position 11 and position 227 form a disulfide bond.

In one embodiment the antigen presenting domain comprises
(i) a virus-derived peptide,
(ii) the soluble HLA-A allele A*0201, and
(iii) β2-microglobulin,
(iv) cysteine residues at least at position 11 and at position 108 and the cysteine residues at position 11 and position 108 form a disulfide bond.

In one embodiment the β2-microglobulin is human β2-microglobulin.

In one embodiment the β2-microglobulin is wild-type human β2-microglobulin.

In one embodiment the β2-microglobulin is consisting of the amino acid sequence of SEQ ID NO: 71 or is a variant thereof comprising of from 1 to 10 amino acid exchanges, additions, and/or deletions.

In one embodiment the β2-microglobulin is human β2-microglobulin and the class I MHC molecule with a relative frequency of 10% or more is human HLA-A*0201.

In one embodiment the extracellular domains α1, α2 and α3 of a class I MHC molecule is consisting of the amino acid sequence of SEQ ID NO: 140 or is a variant thereof comprising of from 1 to 10 amino acid exchanges, additions, and/or deletions.

In one embodiment the antigen presenting domain comprises in N- to C-terminal direction a β2-microglobulin and the extracellular domains α1, α2 and α3 of a class I MHC molecule that has a relative frequency of occurrence of less than 1% wherein the antigen presenting domain has cysteine residues at least at position 11 and at position 227 and the cysteine residues at position 11 and position 227 form a disulfide bond.

In one embodiment the antigen presenting domain comprises in N- to C-terminal direction the extracellular domains α1, α2 and α3 of a class I MHC molecule that has a relative frequency of occurrence of less than 1% and a β2-microglobulin wherein the antigen presenting domain has cysteine residues at least at position 11 and at position 108 and the cysteine residues at position 11 and position 108 form a disulfide bond.

In one embodiment the virus-derived peptide is fused to the β2-microglobulin via a first linker peptide.

In one embodiment the virus-derived peptide is fused to the N-terminus of the β2-microglobulin.

In one embodiment the β2-microglobulin is fused to the extracellular domain α1 of a class I MHC molecule via a second linker peptide.

In one embodiment the extracellular domains α3 of a class I MHC molecule is fused to one of the disulfide-linked polypeptide chains via a third linker peptide.

In one embodiment the first, second, and third linker peptide is the same or different.

In one embodiment the first linker peptide, the second linker peptide, and the third linker peptide are selected independently from each other from the amino acid sequences GS (SEQ ID NO: 73), GGS (SEQ ID NO: 74), GSG (SEQ ID NO: 136), GGGS (SEQ ID NO: 75), GGGSGGGS (SEQ ID NO: 76), GGGSGGGSGOGS (SEQ ID NO: 77), GGGSGGGSGGGSGGGS (SEQ ID NO: 78), GGGSGGGSGGGSGGGSGGGS (SEQ ID NO: 79), GGGGS (SEQ ID NO: 80), GGGGSGGGGS (SEQ ID NO: 81), GGGGSGGGGSGGGGS (SEQ ID NO: 82), GGGGSGGGGSGGGGSGGGGS (SEQ ID NO: 83), GGGGSGGGGSGGGGSGGGGSGGGGS (SEQ ID NO: 84), and GCGGSGGGGSGGGGS (SEQ ID NO: 139).

In one embodiment of all aspects the first linker peptide comprises the amino acid sequence of SEQ ID NO: 139.

In one embodiment of all aspects the second linker peptide comprises the amino acid sequence of SEQ ID NO: 83.

In one embodiment of all aspects the third linker peptide comprises the amino acid sequence of SEQ ID NO: 136.

In one embodiment the antigen presenting domain comprises in N- to C-terminal direction
(i) a virus-derived peptide that has an amino acid sequence selected from the group comprising SEQ ID NO: 01 to SEQ ID NO: 70, (ii) a first linker peptide that has an amino acid sequence selected from the group comprising SEQ ID NO: 77, 78, 79, 82, 83, 84, and 139,
(iii) a β2-microglobulin that has an amino acid sequence of SEQ ID NO: 71,
(iv) a second linker peptide that has an amino acid sequence selected from the group comprising SEQ ID NO: 77, 78, 79, 82, 83, and 84,
(v) the extracellular domains α1, α2, and α3 of a class I MHC molecule that has an amino acid sequence of SEQ ID NO: 140,
(vi) a third linker peptide that has an amino acid sequence selected from the group comprising SEQ ID NO: 73, 77, 78, 79, 82, 83, 84, and 136, and
(vii) cysteine residues at least at position 11 and at position 227 and a disulfide bond between the cysteine residues at position 11 and position 227.

In one embodiment the antigen presenting domain comprises in N- to C-terminal direction
(i) a virus-derived peptide that has an amino acid sequence selected from the group comprising SEQ ID NO: 01 to SEQ ID NO: 70,
(ii) a first linker peptide that has an amino acid sequence selected from the group comprising SEQ ID NO: 77, 78, 79, 82, 83, 84, and 139,
(iii) the extracellular domains α1, α2, and α3 of a class I MHC molecule that has an amino acid sequence of SEQ ID NO: 140,
(iv) a β2-microglobulin that has an amino acid sequence of SEQ ID NO: 71,
(v) a second linker peptide that has an amino acid sequence selected from the group comprising SEQ ID NO: 77, 78, 79, 82, 83, and 84,
(vi) a third linker peptide that has an amino acid sequence selected from the group comprising SEQ ID NO: 73, 77, 78, 79, 82, 83, 84, and 136, and
(vii) cysteine residues at least at position 11 and at position 108 and a disulfide bond between the cysteine residues at position 11 and position 108.

In one embodiment
the first linker peptide has the amino acid sequence of SEQ ID NO: 139, and/or
the second linker peptide has the amino acid sequence of SEQ ID NO: 83, and/or
the third linker peptide has the amino acid sequence of SEQ ID NO: 136.

In one embodiment the disulfide-linked multivalent multi-function protein is characterized in that the antigen presenting domain comprises in N- to C-terminal direction
(i) a virus-derived peptide that has an amino acid sequence selected from the group comprising SEQ ID NO: 01 to SEQ ID NO: 70,
(ii) a first linker peptide that has an amino acid sequence selected from the group comprising SEQ ID NO: 77, 78, 79, 82, 83, 84, and 139,
(iii) a β2-microglobulin that has an amino acid sequence of SEQ ID NO: 71 or is a variant thereof comprising of from 1 to 10 amino acid exchanges, additions, and/or deletions,
(iv) a second linker peptide that has an amino acid sequence selected from the group comprising SEQ ID NO: 77, 78, 79, 82, 83, and 84,
(v) the extracellular domains α1, α2 and α3 of a class I MHC molecule that has an amino acid sequence of SEQ ID NO: 140 or is a variant thereof comprising of from 1 to 10 amino acid exchanges, additions, and/or deletions,
(vi) a third linker peptide that has an amino acid sequence selected from the group comprising SEQ ID NO: 73, 77, 78, 79, 82, 83, 84, and 136, and
(vii) cysteine residues at least at position 11 and at position 227 and a disulfide bond between the cysteine residues at position 11 and position 227.

In one embodiment the disulfide-linked multivalent multi-function protein is characterized in that the antigen presenting domain comprises in N- to C-terminal direction
(i) a virus-derived peptide that has an amino acid sequence selected from the group comprising SEQ ID NO: 01 to SEQ ID NO: 70,
(ii) a first linker peptide that has an amino acid sequence selected from the group comprising SEQ ID NO: 77, 78, 79, 82, 83, 84, and 139,
(iii) the extracellular domains α1, α2 and α3 of a class I MHC molecule that has an amino acid sequence of SEQ ID NO: 140 or is a variant thereof comprising of from 1 to 10 amino acid exchanges, additions, and/or deletions,
(iv) a β2-microglobulin that has an amino acid sequence of SEQ ID NO: 71 or is a variant thereof comprising of from 1 to 10 amino acid exchanges, additions, and/or deletions,
(v) a second linker peptide that has an amino acid sequence selected from the group comprising SEQ ID NO: 77, 78, 79, 82, 83, and 84,
(vi) a third linker peptide that has an amino acid sequence selected from the group comprising SEQ ID NO: 73, 77, 78, 79, 82, 83, 84, and 136, and
(vii) cysteine residues at least at position 11 and at position 108 and a disulfide bond between the cysteine residues at position 11 and position 108.

In one embodiment the antibody Fc-region is selected from an antibody Fc-region of a human antibody of the class IgG or the class IgE.

In one embodiment the antibody Fc-region is selected from an antibody Fc-region of a human antibody of the subclass IgG, or IgG2, or IgG3, or IgG4.

In one embodiment the antibody Fc-region is of a human antibody of the subclass IgG1 or IgG2 and comprises at least one mutation in E233, L234, L235, G236, D265, D270, N297, E318, K320, K322, A327, P329, A330, and/or P331 (numbering according to the EU index of Kabat).

In one embodiment the antibody Fc-region is of a human antibody of the subclass IgG1 or the human subclass IgG2 with the mutations L234A and L235A, and/or the mutations D265A and N297A, and/or contains the PVA236 mutation, and/or contains the mutation P329G.

In one embodiment the antibody Fc-region is of a human antibody of the subclass IgG1 with the mutations L234A and L235A and/or P329G.

In one embodiment the antibody Fc-region is of a human antibody of the subclass IgG4 with the mutation S228P and/or L235E.

In one embodiment the first and second antibody Fc-region polypeptide is selected independently of each other from the group comprising SEQ ID NO: 87 to 101.

In one embodiment the antibody Fc-region comprises two Fc-region polypeptides with the amino acid sequence of SEQ ID NO: 94.

In one embodiment the antibody Fc-region comprises two Fc-region polypeptides with the amino acid sequence of SEQ ID NO: 100.

In one embodiment the antibody Fc-region comprises two Fc-region polypeptides with the amino acid sequence of SEQ ID NO: 101.

In one embodiment the antibody Fc-region comprises a first Fc-region polypeptide with the amino acid sequence of SEQ ID NO: 89 and a second Fc-region polypeptide with the amino acid sequence of SEQ ID NO: 90.

In one embodiment the antibody Fc-region comprises a first Fc-region polypeptide with the amino acid sequence of SEQ ID NO: 97 and a second Fc-region polypeptide with the amino acid sequence of SEQ ID NO: 98.

In one embodiment the antibody Fc-region comprises a first Fc-region polypeptide with the amino acid sequence of SEQ ID NO: 102 and a second Fc-region polypeptide with the amino acid sequence of SEQ ID NO: 103.

One aspect as reported herein is a disulfide-linked multivalent multi-function protein, characterized in that it comprises
- one or two antigen presenting domains, which comprise independently of each other in N- to C-terminal direction
  either
    - (i) a β2-microglobulin, and
    - (ii) the extracellular domains α1, α2, and α3 of a class I MHC molecule with a relative frequency of less than 1%,
  or
    - (i) the extracellular domains α1, α2, and α3 of a class I MHC molecule with a relative frequency of less than 1%, and
    - (ii) a β2-microglobulin,
  or
    - (i) a T-cell response eliciting peptide,
    - (ii) a β2-microglobulin, and
    - (iii) the extracellular domains α1, α2, and α3 of a class I MHC molecule with a relative frequency of 1% or more,
  or
    - (i) a T-cell response eliciting peptide,
    - (ii) the extracellular domains α1, cα2, and α3 of a class I MHC molecule with a relative frequency of 1% or more, and
    - (iii) a β2-microglobulin,
  wherein the antigen presenting domain has cysteine residues at least at position 11 and at position 108 or position 227 and the cysteine residues at position 11 and position 108 or 227 form a disulfide bond,
- exactly one antibody Fc-region, and
- one or more antigen binding sites.

One aspect as reported herein is a disulfide-linked multivalent multi-function protein, characterized in that it comprises
- one or two antigen presenting domains, which comprise in N- to C-terminal direction
  - (i) a T-cell response eliciting peptide,
  - (ii) a β2-microglobulin, and
  - (iii) the extracellular domains α1, α2, and α3 of a class I MHC molecule with a relative frequency of 1% or more,
  wherein the antigen presenting domain has cysteine residues at least at position 11 and at position 227 and the cysteine residues at position 11 and position 227 form a disulfide bond,
- exactly one antibody Fc-region, and
- one or more antigen binding sites.

One aspect as reported herein is a disulfide-linked multivalent multi-function protein, characterized in that it comprises
- one or two antigen presenting domains, which comprise in N- to C-terminal direction
  - (i) a T-cell response eliciting peptide,
  - (iii) the extracellular domains α1, α2, and α3 of a class I MHC molecule with a relative frequency of 1% or more, and
  - (ii) a β2-microglobulin,
  wherein the antigen presenting domain has cysteine residues at least at position 11 and at position 108 and the cysteine residues at position 11 and position 108 form a disulfide bond,
- exactly one antibody Fc-region, and
- one or more antigen binding sites.

One aspect as reported herein is a disulfide-linked multivalent multi-function protein, characterized in that it comprises
- one or two antigen presenting domains, which comprises in N- to C-terminal direction
  - (i) a T-cell response eliciting peptide of SEQ ID NO: 01,
  - (ii) a β2-microglobulin of SEQ ID NO: 71, and
  - (iii) the extracellular domains α1, α2, and α3 of a class I MHC molecule of SEQ ID NO: 72,
  wherein the antigen presenting domain has cysteine residues at least at position 11 and at position 227 and the cysteine residues at position 11 and position 227 form a disulfide bond,
- exactly one antibody Fc-region, and
- one or more antigen binding sites.

One aspect as reported herein is a disulfide-linked multivalent multi-function protein, characterized in that it comprises
- one or two antigen presenting domains, which comprises in N- to C-terminal direction
  - (i) a T-cell response eliciting peptide of SEQ ID NO: 01,
  - (ii) the extracellular domains α1, α2, and α3 of a class I MHC molecule of SEQ ID NO: 72, and
  - (ii) a β2-microglobulin of SEQ ID NO: 71, and
  wherein the antigen presenting domain has cysteine residues at least at position 11 and at position 108 and the cysteine residues at position 11 and position 108 form a disulfide bond,
- exactly one antibody Fc-region, and
- one or more antigen binding sites.

One aspect as reported herein is a disulfide-linked multivalent multi-function protein, characterized in that it comprises
- one or two antigen presenting domains, which comprise in N- to C-terminal direction
  - (i) a T-cell response eliciting peptide of SEQ ID NO: 01,
  - (ii) a β2-microglobulin of SEQ ID NO: 71, and
  - (iii) the extracellular domains α1, α2, and α3 of a class I MHC molecule of SEQ ID NO: 72,
  wherein the antigen presenting domain has cysteine residues at least at position 11 and at position 227 and the cysteine residues at position 11 and position 227 form a disulfide bond,
- exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and
- one or more antigen binding sites.

One aspect as reported herein is a disulfide-linked multivalent multi-function protein, characterized in that it comprises one or two antigen presenting domains, which comprise in N- to C-terminal direction
  (i) a T-cell response eliciting peptide of SEQ ID NO: 01,
  (ii) the extracellular domains α1, α2, and α3 of a class I MHC molecule of SEQ ID NO: 72,
  (iii) a β2-microglobulin of SEQ ID NO: 71, and
  wherein the antigen presenting domain has cysteine residues at least at position 11 and at position 108 and the cysteine residues at position 11 and position 108 form a disulfide bond,
exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and
one or more antigen binding sites.

One aspect as reported herein is a disulfide-linked multivalent multi-function protein, characterized in that it comprises
  one or two antigen presenting domains, which comprises in N- to C-terminal direction
  (i) a T-cell response eliciting peptide of SEQ ID NO: 01,
  (ii) a β2-microglobulin of SEQ ID NO: 71, and
  (iii) the extracellular domains α1, α2, and α3 of a class I MHC molecule of SEQ ID NO: 72,
  wherein the antigen presenting domain has cysteine residues at least at position 11 and at position 227 and the cysteine residues at position 11 and position 227 form a disulfide bond,
exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and
one or more antigen binding sites.

One aspect as reported herein is a disulfide-linked multivalent multi-function protein, characterized in that it comprises
  one or two antigen presenting domains, which comprise in N- to C-terminal direction
  (i) a T-cell response eliciting peptide of SEQ ID NO: 01,
  (ii) the extracellular domains α1, α2, and α3 of a class I MHC molecule of SEQ ID NO: 72,
  (iii) a β2-microglobulin of SEQ ID NO: 71, and
  wherein the antigen presenting domain has cysteine residues at least at position 11 and at position 108 and the cysteine residues at position 11 and position 108 form a disulfide bond,
exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and
one or more antigen binding sites.

One aspect as reported herein is a disulfide-linked multivalent multi-function protein, characterized in that it comprises
  one or two antigen presenting domains, which comprise in N- to C-terminal direction
  (i) a T-cell response eliciting peptide of SEQ ID NO: 01,
  (ii) a β2-microglobulin of SEQ ID NO: 71, and
  (iii) the extracellular domains α1, α2, and α3 of a class I MHC molecule of SEQ ID NO: 72,
  wherein the antigen presenting domain has cysteine residues at least at position 11 and at position 227 and the cysteine residues at position 11 and position 227 form a disulfide bond,
exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and
one or more antigen binding sites, which comprise an antibody light chain variable domain comprising an amino acid sequence selected from SEQ ID NO: 104 to 106, and an antibody heavy chain variable domain comprising SEQ ID NO: 108 to 110, which specifically bind to melanoma-associated chondroitin sulfate proteoglycan (MCSP).

One aspect as reported herein is a disulfide-linked multivalent multi-function protein, characterized in that it comprises
  one or two antigen presenting domains, which comprise in N- to C-terminal direction
  (i) a T-cell response eliciting peptide of SEQ ID NO: 01,
  (ii) a β2-microglobulin of SEQ ID NO: 71, and
  (iii) the extracellular domains α1, α2, and α3 of a class I MHC molecule of SEQ ID NO: 72,
  wherein the antigen presenting domain has cysteine residues at least at position 11 and at position 227 and the cysteine residues at position 11 and position 227 form a disulfide bond,
exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and
one or more antigen binding sites, which specifically bind to melanoma-associated chondroitin sulfate proteoglycan (MCSP), and which comprises an antibody light chain with a variable domain comprising SEQ ID NO: 104 to 106 and an antibody heavy chain with a variable domain comprising SEQ ID NO: 108 to 110.

One aspect as reported herein is a disulfide-linked multivalent multi-function protein, characterized in that it comprises
  one or two antigen presenting domain, which comprises in N- to C-terminal direction
  (i) a T-cell response eliciting peptide of SEQ ID NO: 01,
  (ii) a β2-microglobulin of SEQ ID NO: 71, and
  (iii) the extracellular domains α1, α2, and α3 of a class I MHC molecule of SEQ ID NO: 72,
  wherein the antigen presenting domain has cysteine residues at least at position 11 and at position 227 and the cysteine residues at position 11 and position 227 form a disulfide bond,
exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and two antigen binding sites, which specifically bind to melanoma-associated chondroitin sulfate proteoglycan (MCSP), and which each comprise an antibody light chain with a variable domain comprising SEQ ID NO: 105 to 107 and an antibody heavy chain with a variable domain comprising SEQ ID NO: 110 to 112.

One aspect as reported herein is a disulfide-linked multivalent multi-function protein, characterized in that it comprises one or two antigen presenting domains, which comprise in N- to C-terminal direction
(i) a T-cell response eliciting peptide of SEQ ID NO: 01,
(ii) a β2-microglobulin of SEQ ID NO: 71, and
(iii) the extracellular domains α1, α2, and α3 of a class I MHC molecule of SEQ ID NO: 72,
wherein the antigen presenting domain has cysteine residues at least at position 11 and at position 227 and the cysteine residues at position 11 and position 227 form a disulfide bond,
exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and
one or more antigen binding sites, which specifically bind to melanoma-associated chondroitin sulfate proteoglycan (MCSP), and which comprises an antibody light chain with a variable domain comprising SEQ ID NO: 105 to 107 and an antibody heavy chain with a variable domain comprising SEQ ID NO: 110 to 112, whereby the Fc-region of the antibody heavy chain is one of the disulfide-linked Fc-region polypeptides.

One aspect as reported herein is a disulfide-linked multivalent multi-function protein, characterized in that it comprises one or two antigen presenting domains, which comprise in N- to C-terminal direction
(i) a T-cell response eliciting peptide of SEQ ID NO: 01,
(ii) a β2-microglobulin of SEQ ID NO: 71, and
(iii) the extracellular domains α1, α2, and α3 of a class I MHC molecule of SEQ ID NO: 72,
wherein the antigen presenting domain has cysteine residues at least at position 11 and at position 227 and the cysteine residues at position 11 and position 227 form a disulfide bond,
exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and
one or more antigen binding sites, which specifically bind to melanoma-associated chondroitin sulfate proteoglycan (MCSP), and which comprise an antibody light chain with a variable domain comprising SEQ ID NO: 104 to 106 and an antibody heavy chain with a variable domain comprising SEQ ID NO: 108 to 110, whereby the Fc-region of the antibody heavy chain is one of the disulfide-linked Fc-region polypeptides,
wherein the antigen presenting domain is linked to the N-terminus of one of the variable domains.

One aspect as reported herein is a disulfide-linked multivalent multi-function protein, characterized in that it comprises one or two antigen presenting domains, which comprise in N- to C-terminal direction
(i) a T-cell response eliciting peptide of SEQ ID NO: 01,
(ii) a β2-microglobulin of SEQ ID NO: 71, and
(iii) the extracellular domains α1, α2, and α3 of a class I MHC molecule of SEQ ID NO: 72,
wherein the antigen presenting domain has cysteine residues at least at position 11 and at position 227 and the cysteine residues at position 11 and position 227 form a disulfide bond,
exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and
two antigen binding sites, which specifically bind to melanoma-associated chondroitin sulfate proteoglycan (MCSP), and which each comprise an antibody light chain with a variable domain comprising SEQ ID NO: 104 to 106 and an antibody heavy chain with a variable domain comprising SEQ ID NO: 108 to 110, whereby the Fc-regions of the antibody heavy chains are the disulfide-linked Fc-region polypeptides,
wherein the antigen presenting domain is linked to the N-terminus of one of the variable domains.

One aspect as reported herein is a disulfide-linked multivalent multi-function protein, characterized in that it comprises one or two antigen presenting domains, which comprise in N- to C-terminal direction
(i) a T-cell response eliciting peptide of SEQ ID NO: 01,
(ii) a β2-microglobulin of SEQ ID NO: 71, and
(iii) the extracellular domains α1, α2, and α3 of a class I MHC molecule of SEQ ID NO: 72,
wherein the antigen presenting domain has cysteine residues at least at position 11 and at position 227 and the cysteine residues at position 11 and position 227 form a disulfide bond,
exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and
two antigen binding sites, which specifically bind to melanoma-associated chondroitin sulfate proteoglycan (MCSP), and which each comprise an antibody light chain with a variable domain comprising SEQ ID NO: 105 to 107 and an antibody heavy chain with a variable domain comprising SEQ ID NO: 110 to 112, whereby the Fc-regions of the antibody heavy chains are the disulfide-linked Fc-region polypeptides,
wherein the antigen presenting domain is linked to the N-terminus of one of the heavy chain variable domains.

One aspect as reported herein is a disulfide-linked multivalent multi-function protein, characterized in that it comprises one or two antigen presenting domains, which comprise in N- to C-terminal direction
(i) a T-cell response eliciting peptide of SEQ ID NO: 01,
(ii) a β2-microglobulin of SEQ ID NO: 71, and
(iii) the extracellular domains α1, α2, and α3 of a class I MHC molecule of SEQ ID NO: 72, wherein the antigen presenting domain has cysteine residues at least at position 11 and at position 227 and the cysteine residues at position 11 and position 227 form a disulfide bond, exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and two antigen binding sites, which specifically bind to melanoma-associated chondroitin sulfate proteoglycan (MCSP), and which each comprise an antibody light chain with a variable domain comprising SEQ ID NO: 105 to 107 and an antibody heavy chain with a variable domain comprising SEQ ID NO: 110 to 112, whereby the Fc-regions of the antibody heavy chains are the disulfide-linked Fc-region polypeptides, wherein the antigen presenting domain is linked to the N-terminus of one of the heavy chain variable domains.

One aspect as reported herein is a disulfide-linked multivalent multi-function protein, characterized in that it comprises one polypeptide chain of SEQ ID NO: 117,
one polypeptide chain of SEQ ID NO: 118,
two polypeptide chains each of SEQ ID NO: 119,
wherein the antigen presenting domain has cysteine residues at least at position 11 and at position 227 and the cysteine residues at position 11 and position 227 form a disulfide bond.

One aspect as reported herein is a disulfide-linked multivalent multi-function protein, characterized in that it comprises one polypeptide chain of SEQ ID NO: 137,
one polypeptide chain of SEQ ID NO: 118,
two polypeptide chains each of SEQ ID NO: 119,
wherein the antigen presenting domain has cysteine residues at least at position 11 and at position 227 and the cysteine residues at position 11 and position 227 form a disulfide bond.

One aspect as reported herein is a disulfide-linked multivalent multi-function protein, characterized in that it comprises one polypeptide chain of SEQ ID NO: 117,
one polypeptide chain of SEQ ID NO: 118,
two polypeptide chains each of SEQ ID NO: 119,
wherein the antigen presenting domain has cysteine residues at least at position 11 and at position 108 and the cysteine residues at position 11 and position 108 form a disulfide bond.

One aspect as reported herein is a disulfide-linked multivalent multi-function protein, characterized in that it comprises one polypeptide chain of SEQ ID NO: 137,
one polypeptide chain of SEQ ID NO: 118,
two polypeptide chains each of SEQ ID NO: 119,
wherein the antigen presenting domain has cysteine residues at least at position 11 and at position 108 and the cysteine residues at position 11 and position 108 form a disulfide bond.

One aspect as reported herein is a disulfide-linked multivalent multi-function protein, characterized in that it comprises two polypeptide chains of SEQ ID NO: 117,
two polypeptide chains each of SEQ ID NO: 119,
wherein the antigen presenting domain has cysteine residues at least at position 11 and at position 227 and the cysteine residues at position 11 and position 227 form a disulfide bond.

One aspect as reported herein is a disulfide-linked multivalent multi-function protein, characterized in that it comprises two polypeptide chains of SEQ ID NO: 137,
two polypeptide chains each of SEQ ID NO: 119,
wherein the antigen presenting domain has cysteine residues at least at position 11 and at position 227 and the cysteine residues at position 11 and position 227 form a disulfide bond.

One aspect as reported herein is a disulfide-linked multivalent multi-function protein, characterized in that it comprises two polypeptide chains of SEQ ID NO: 117,
two polypeptide chains each of SEQ ID NO: 119,
wherein the antigen presenting domain has cysteine residues at least at position 11 and at position 108 and the cysteine residues at position 11 and position 108 form a disulfide bond.

One aspect as reported herein is a disulfide-linked multivalent multi-function protein, characterized in that it comprises two polypeptide chains of SEQ ID NO: 137,
two polypeptide chains each of SEQ ID NO: 119,
wherein the antigen presenting domain has cysteine residues at least at position 11 and at position 108 and the cysteine residues at position 11 and position 108 form a disulfide bond.

In one embodiment the MCSP binding site comprises an antibody heavy chain variable domain comprising an HVR-H1 comprising the amino acid sequence of SEQ ID NO: 108, an HVR-H2 comprising the amino acid sequence of SEQ ID NO: 109, and an HVR-H3 comprising the amino acid sequence of SEQ ID NO: 110.

In one embodiment the MCSP binding site comprises an antibody light chain variable domain comprising an HVR-L1 comprising the amino acid sequence of SEQ ID NO: 104; an HVR-L2 comprising the amino acid sequence of SEQ ID NO: 105; and an HVR-L3 comprising the amino acid sequence of SEQ ID NO: 106.

In one embodiment the MCSP binding site comprises an antibody heavy chain variable domain comprising an HVR-H1 comprising the amino acid sequence of SEQ ID NO: 108; an HVR-H2 comprising the amino acid sequence of SEQ ID NO: 109; an HVR-H3 comprising the amino acid sequence of SEQ ID NO: 110; and an antibody light chain variable domain comprising an HVR-L1 comprising the amino acid sequence of SEQ ID NO: 104; an HVR-L2 comprising the amino acid sequence of SEQ ID NO: 105; and an HVR-L3 comprising the amino acid sequence of SEQ ID NO: 106.

In one embodiment the MCSP binding site comprises an antibody heavy chain variable domain comprising an HVR-H1 comprising the amino acid sequence of SEQ ID NO: 111, an HVR-H2 comprising the amino acid sequence of SEQ ID NO: 112, and an HVR-H3 comprising the amino acid sequence of SEQ ID NO: 110.

In one embodiment the MCSP binding site comprises an antibody light chain variable domain comprising an HVR-L1 comprising the amino acid sequence of SEQ ID NO: 107; an HVR-L2 comprising the amino acid sequence of SEQ ID NO: 105; and an HVR-L3 comprising the amino acid sequence of SEQ ID NO: 106.

In one embodiment the MCSP binding site comprises an antibody heavy chain variable domain comprising an HVR-H1 comprising the amino acid sequence of SEQ ID NO: 111; an HVR-H2 comprising the amino acid sequence of SEQ ID NO: 112; an HVR-H3 comprising the amino acid sequence of SEQ ID NO: 110; and an antibody light chain variable domain comprising an HVR-L1 comprising the amino acid sequence of SEQ ID NO: 107; an HVR-L2 comprising the amino acid sequence of SEQ ID NO: 105; and an HVR-L3 comprising the amino acid sequence of SEQ ID NO: 106.

In one embodiment the MCSP binding site comprises an antibody heavy chain variable domain having at least 95% sequence identity to the amino acid sequence of SEQ ID NO: 114; and an antibody light chain variable domain having at least 95% sequence identity to the amino acid sequence of SEQ ID NO: 113.

In one embodiment the MCSP binding site comprises an antibody heavy chain variable domain of SEQ ID NO: 114 and an antibody light chain variable domain of SEQ ID NO: 113.

In one embodiment the MCSP binding site comprises SEQ ID NO: 114 and SEQ ID NO: 113.

In one embodiment the MCSP binding site comprises an antibody heavy chain variable domain having at least 95% sequence identity to the amino acid sequence of SEQ ID NO: 116; and an antibody light chain variable domain having at least 95% sequence identity to the amino acid sequence of SEQ ID NO: 115.

In one embodiment the MCSP binding site comprises an antibody heavy chain variable domain of SEQ ID NO: 116; and an antibody light chain variable domain of SEQ ID NO: 115.

In one embodiment the MCSP binding site comprises SEQ ID NO: 116 and SEQ ID NO: 115.

In one aspect, the invention provides disulfide-linked multivalent multi-function proteins comprising the binding specificity, i.e. HVRs or variable domains, of isolated antibodies that bind to MCSP. In particular, the anti-MCSP antibody binding specificity, i.e. HVRs or variable domains, comprised in the disulfide-linked multivalent multi-function proteins as provided herein bind to a membrane proximal epitope of human MCSP. As discussed in Staub, E., et al. (FEBS Lett. 527 (2002) 114-118), the membrane proximal region of MCSP is comprised of multiple novel repeated domains, referred to as CSPG repeat domains.

One aspect as reported herein is a nucleic acid encoding the disulfide-linked multivalent multi-function protein as reported herein.

In one embodiment the nucleic acid comprises two to four expression cassettes comprising structural genes encoding polypeptides with different amino acid sequence.

One aspect as reported herein is a host cell comprising the nucleic acid as reported herein.

One aspect as reported herein is a method of producing a disulfide-linked multivalent multi-function protein as reported herein comprising culturing the host cell as reported herein so that the disulfide-linked multivalent multi-function protein is produced.

In one embodiment the disulfide-linked multivalent multi-function protein is recovered from the cells or the cultivation medium and thereby the disulfide-linked multivalent multi-function protein is produced.

One aspect as reported herein is a pharmaceutical formulation comprising the disulfide-linked multivalent multi-function protein as reported herein and optionally a pharmaceutically acceptable carrier.

In one embodiment the pharmaceutical formulation further comprises an additional therapeutic agent.

One aspect as reported herein is the disulfide-linked multivalent multi-function protein as reported herein for use as a medicament.

One aspect as reported herein is the disulfide-linked multivalent multi-function protein as reported herein for use in treating cancer.

One aspect as reported herein is the disulfide-linked multivalent multi-function protein as reported herein for use in treating a virus infection.

One aspect as reported herein is the disulfide-linked multivalent multi-function protein as reported herein for use in attracting virus-specific cytotoxic T-cells of an individual to a target.

One aspect as reported herein is the disulfide-linked multivalent multi-function protein as reported herein for use in elimination (removal) of cancer cells.

One aspect as reported herein is the disulfide-linked multivalent multi-function protein as reported herein for use in elimination (removal) of virus-infected cells.

One aspect as reported herein is the use of the disulfide-linked multivalent multi-function protein as reported herein in the manufacture of a medicament.

In one embodiment the medicament is for treatment of cancer.

In one embodiment the medicament is for treatment of a viral infection.

In one embodiment the medicament is for attracting virus-specific cytotoxic T-cells of an individual to a target.

In one embodiment the medicament is for elimination (removal) of cancer cells.

In one embodiment the medicament is for elimination (removal) of virus infected cells.

One aspect as reported herein is a method of treating an individual having cancer comprising administering to the individual an effective amount of the disulfide-linked multivalent multi-function protein as reported herein.

In one embodiment the method further comprises administering an additional therapeutic agent to the individual.

One aspect as reported herein is a method of treating an individual having a viral infection comprising administering to the individual an effective amount of the disulfide-linked multivalent multi-function protein as reported herein.

In one embodiment the method further comprises administering an additional therapeutic agent to the individual.

One aspect as reported herein is a method of attracting virus-specific cytotoxic T-cells of an individual to a target in an individual comprising administering to the individual an effective amount of the disulfide-linked multivalent multi-function protein as reported herein to attract virus-specific cytotoxic T-cells of an individual to a target.

One aspect as reported herein is a method of removal of cancer cells in an individual comprising administering to the individual an effective amount of the disulfide-linked multivalent multi-function protein as reported herein to remove/disintegrate cancer cells.

One aspect as reported herein is a method of removal of virus-infected cells in an individual comprising administering to the individual an effective amount of the disulfide-linked multivalent multi-function protein as reported herein to remove/disintegrate virus-infected cells.

One aspect as reported herein is a method for the recombinant production of a disulfide-linked multivalent multi-function protein comprising i) a fusion polypeptide of β2-microglobulin and the extracellular domains α1, α2 and α3 of a class I MHC molecule, ii) a pair of disulfide-linked polypeptide chains each comprising an antibody hinge region, and iii) at least one pair of an antibody light chain variable domain and an antibody heavy chain variable domain in a eukaryotic cell, comprising the steps of i) cultivating a eukaryotic cell comprising one or more nucleic acids encoding the disulfide-linked multivalent multi-function protein, and ii) recovering the disulfide-linked multivalent multi-function protein from the cell or the cultivation medium, wherein the disulfide-linked multivalent multi-function protein comprises one, two or more disulfide-linked fusion polypeptides of β2-microglobulin and the extracellular domains α1, α2 and α3 of a class I MHC molecule, wherein the disulfide bind is between residues 11 and 227.

In one embodiment the disulfide-linked multivalent multi-function protein comprises one MHC-derived polypeptide or one fusion polypeptide comprising an MHC-derived molecule.

In one embodiment the disulfide-linked multivalent multi-function protein comprises two MHC-derived polypeptides or two fusion polypeptides comprising an MHC-derived molecule.

In one embodiment the disulfide-linked multivalent multi-function protein is obtained with a concentration of 1 mg/L or more in the cultivation medium. In one embodiment the disulfide-linked multivalent multi-function protein is obtained with a concentration of 4 mg/L or more in the cultivation medium.

In one embodiment the eukaryotic cell is a mammalian cell. In one embodiment the mammalian cell is a human embryonic kidney cell, or a chinese hamster ovary cell, or a baby hamster kidney cell, or a mouse myeloma cell.

The following embodiments can be combined with any of the aspects as reported herein. Also any embodiment as reported herein can be combined with any other embodiment or combination of embodiments as reported herein.

DETAILED DESCRIPTION OF THE INVENTION

Short Description of the Figures

FIG. 1 Annotated scheme of an exemplary disulfide-linked bivalent disulfide-linked multivalent multi-function protein as reported herein; HLA-Fc-region fusion polypeptide N- to C-terminal sequence: 1-2-3-4-5-6-(3-6 disulfide bond)-7-8-9-12-13-14 (with II); HLA-heavy chain fusion polypeptide N- to C-terminal sequence: 1-2-3-4-5-6-(3-6 disulfide bond)-7-8-9-10-11-12-13-14 (with I); light chain: a-b.

Figures 1, 2, 6A:
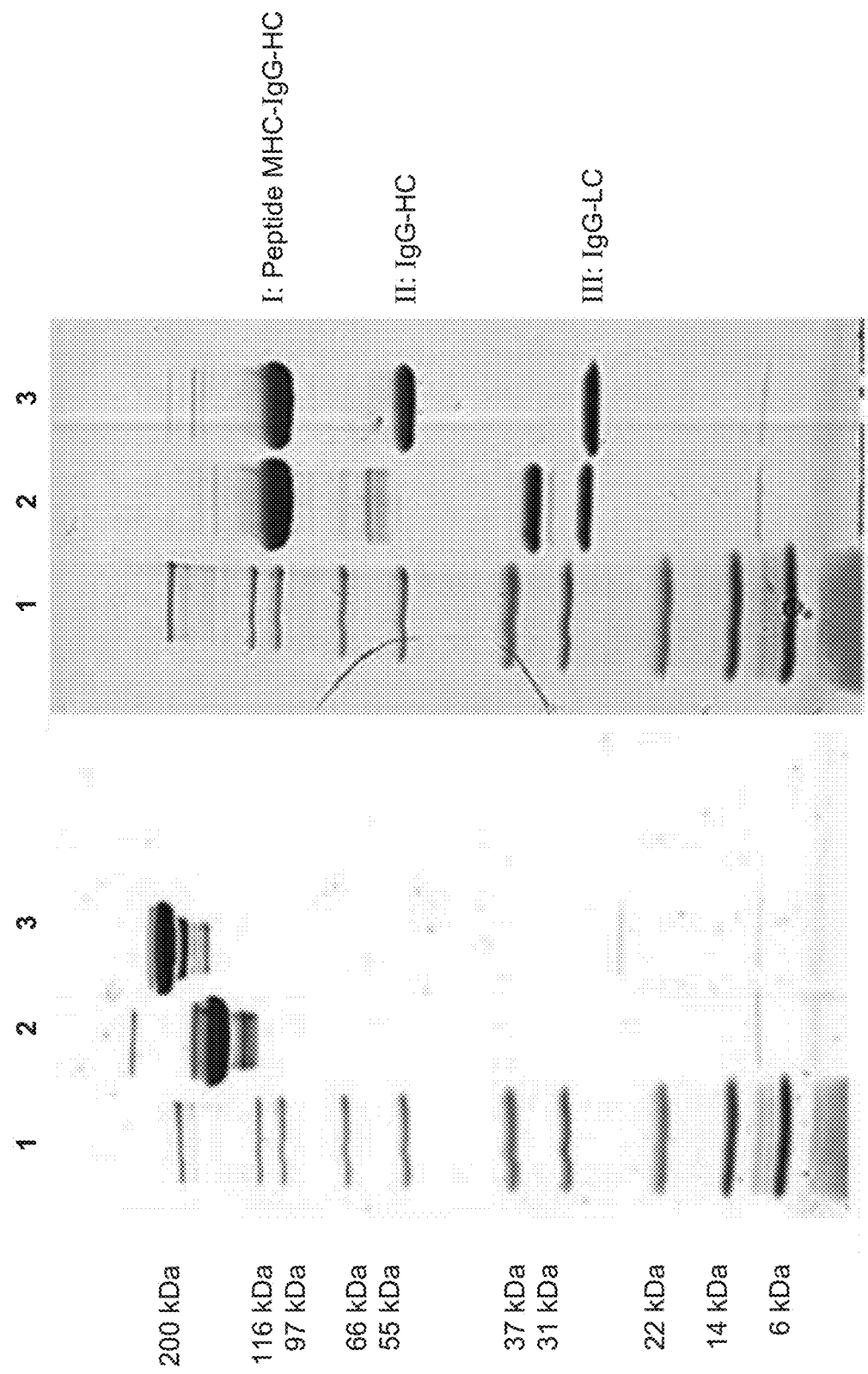

FIG. 2 Exemplary polypeptides comprised in the multi-function protein as reported herein: fusion polypeptides were N-terminally fused to either an antibody light chain or to an antibody heavy chain hinge region comprising polypeptide.

FIG. 3 Western blot of a SDS polyacrylamide gel of cell culture supernatant of HEK 293 cells transfected with the corresponding expression plasmids. Staining was performed with peroxidase conjugated polyclonal rabbit anti-human κ-light chain antibody and polyclonal rabbit anti-human IgG antibody conjugated to horseradish peroxidase.

Lanes: 1: two-armed peptide-β2-microglobulin-HLA-A0201-IgG-Fc; 2: one-armed peptide-β2-microglobulin-HLA-A0201-IgG-Fc+IgG-Fc; 3: one-armed peptide-β2-microglobulin-HLA-A0201-IgG-heavy chain+IgG-light chain+IgG-Fc; 4: one-armed peptide-β2-microglobulin-HLA-A0201-IgG-heavy chain+IgG-heavy chain+IgG-light chain; 5: two-armed β2-microglobulin-HLA-A0201-IgG-light chain+IgG-heavy chain; 6: two-armed peptide-β2-microglobulin-HLA-A0201-IgG-light chain+IgG-heavy chain; 7: two-armed peptide-β2-microglobulin-HLA-A0201-IgG-heavy chain+IgG-light chain; 8: two-armed peptide-β2-microglobulin-HLA-A0201-IgG-Fc-scFv; 9: one-armed peptide-β2-microglobulin-HLA-A0201-IgG-Fc+one-armed IgG (heavy and light chain); 10: molecular weight marker, 11: reference standard IgG1 antibody.

Figure 4A:
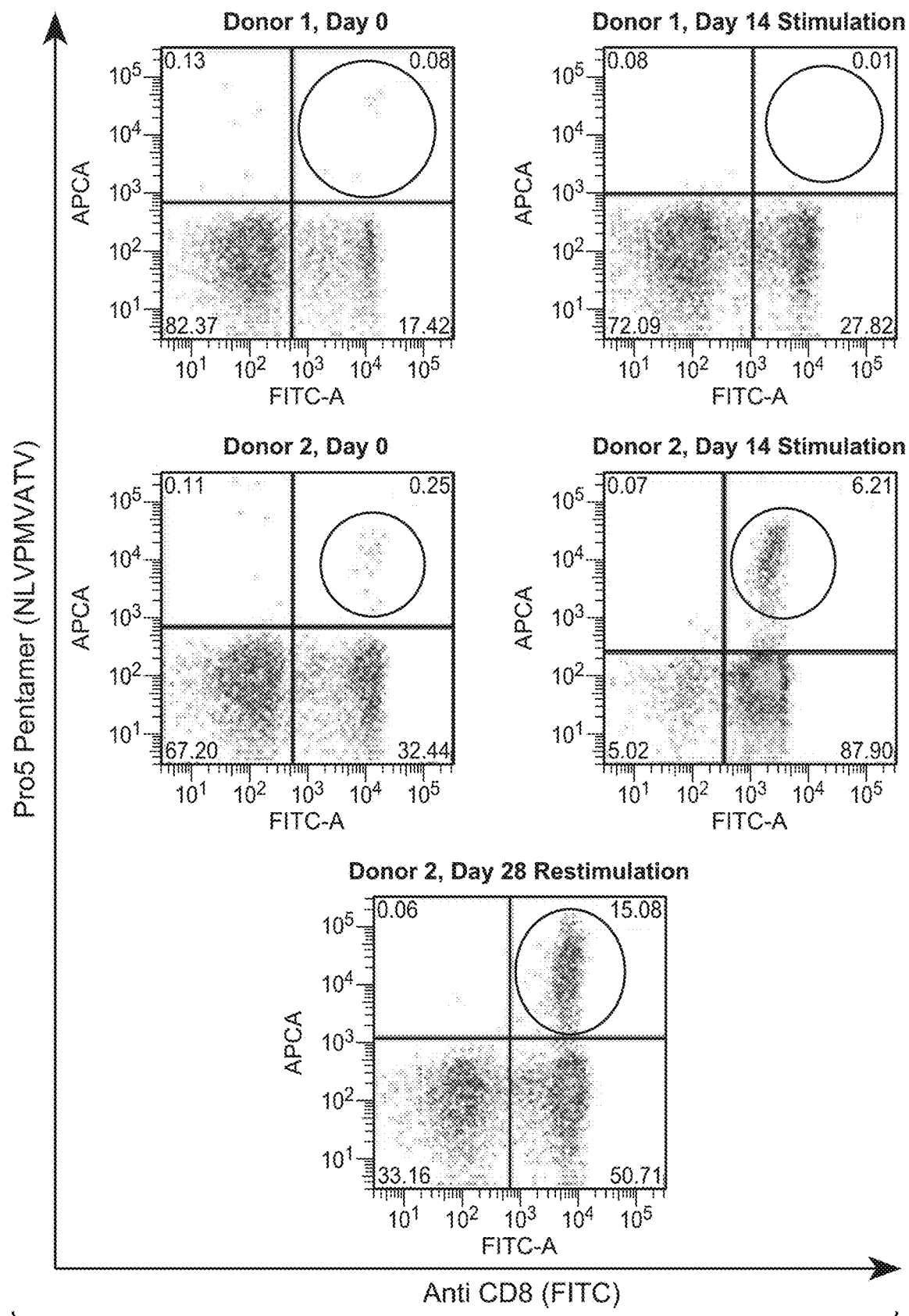
Figure 4B:
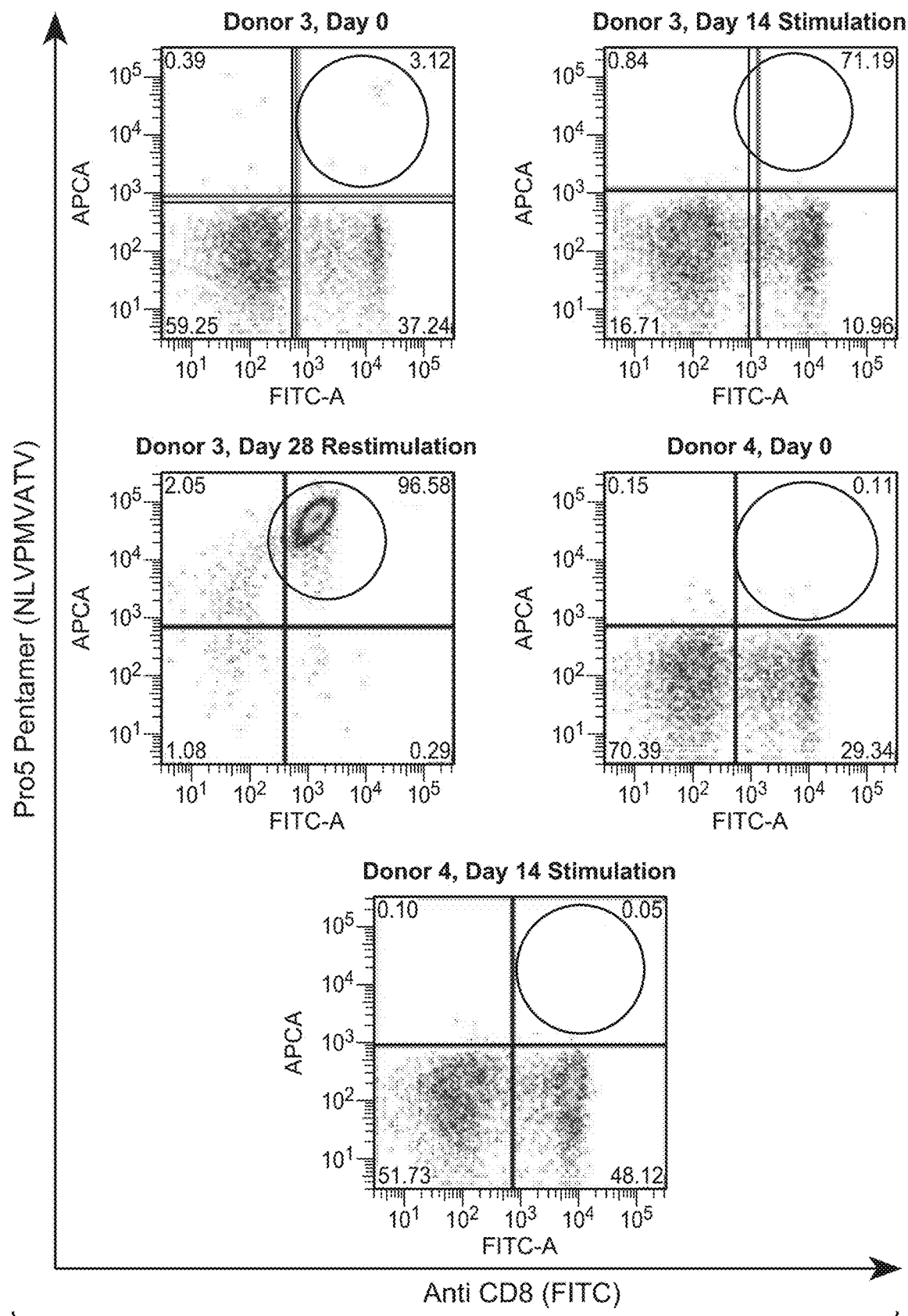

FIGS. 4A-B Flow cytometric analysis to determine the number of CMV-specific cytolytic T-cells from different donors before and after in vitro stimulation with specific peptide: Analysis of 4 human donor derived peripheral blood lymphocytes (PBLs); anti-CD8 antibody conjugated to FITC label staining (BD, Cat. No. 345772) combined with Pro5 pentamer APC (ProImmune, Cat No. F008-4A-E) stained TCR recognizing MHC-class I (HLA-A*0201) loaded with CMV-derived peptide (NLVPMVATV, SEQ ID NO: 01); circle: CMV-specific CD8$^+$-T-cells; FIG. 4A: Donor 1; FIG. 4B: Donor 3.

Figure 5A:
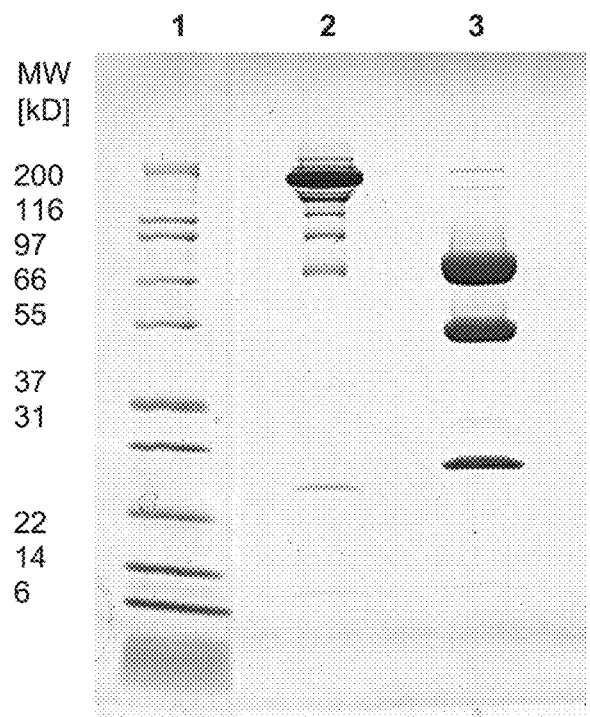
Figure 5C:
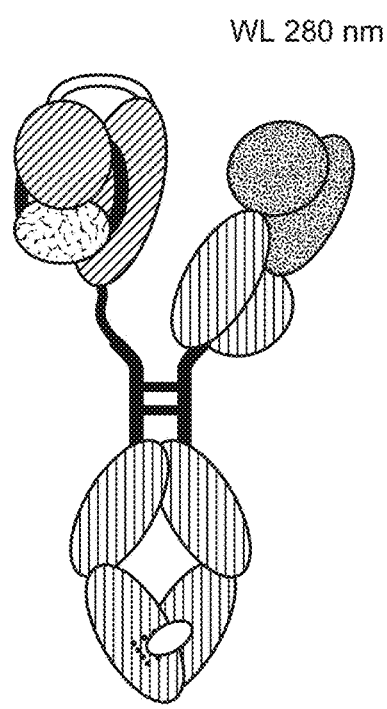
Figure 5B:
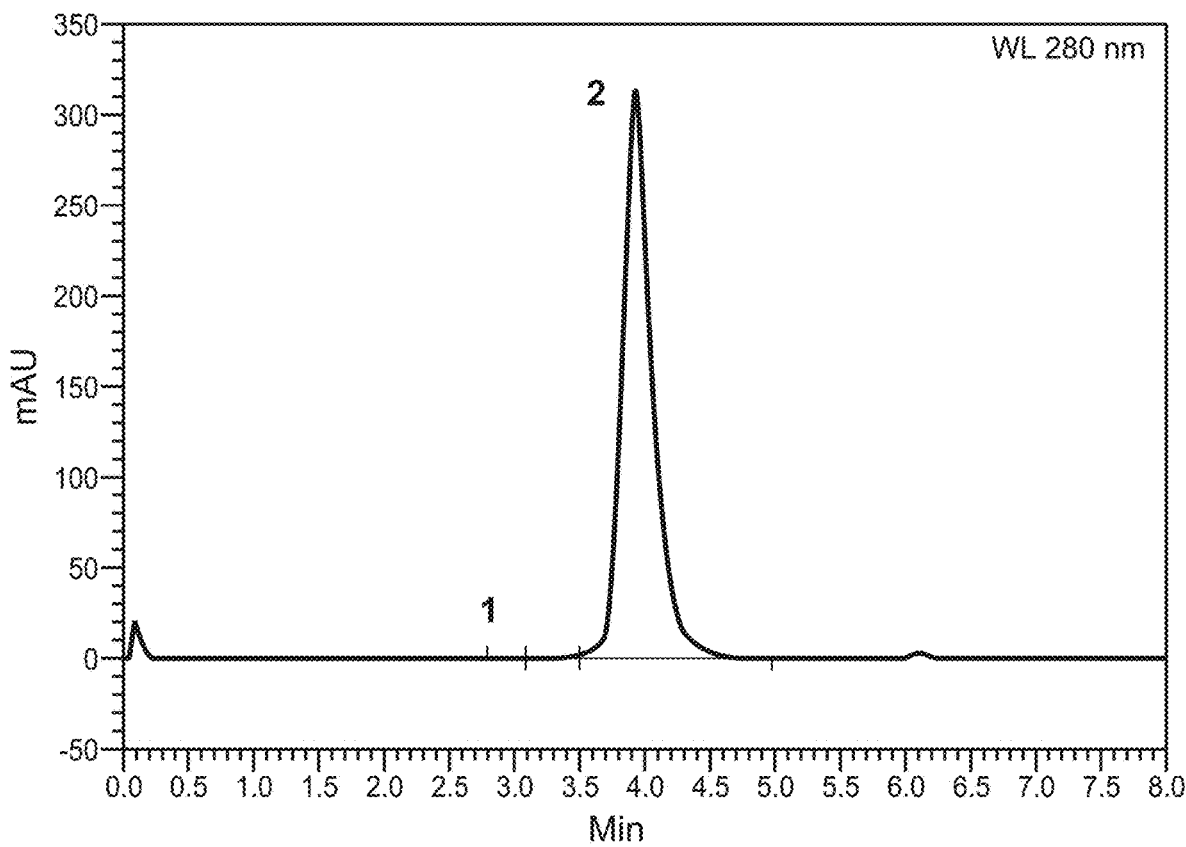

FIGS. 5A-C FIG. 5A: SDS-PAGE gel with Coomassie staining: lane 1: molecular weight standard, lane 2: one-armed peptide-42-microglobulin-HLA-A0201-IgG-Fc+one-armed IgG (heavy and light chain), non-reducing conditions; lane 3: one-armed peptide-β2-microglobulin-HLA-A0201-IgG-Fc+one-armed IgG multi-function protein (heavy and light chain), reducing conditions.

FIG. 5B: Size exclusion chromatography chromatogram; 1: high molecular weight forms (0.7 area %); 2: monomeric multi-function protein (99.3 area %).

FIG. 5C: schematic molecule.

FIGS. 6A-C FIG. 6A-1: SDS-PAGE gel with Coomassie staining after protein A HPLC and SEC; non-reducing conditions; lane 1: molecular weight standard, lane 2: peptide-β2-microglobulin-HLA-A0201-HC+LC+IgG-Fc, lane 3: peptide-β2-microglobulin-HLA-A0201-HC+LC+one-armed IgG (heavy and light chain).

FIG. 6A-2: SDS-PAGE gel with Coomassie staining after protein A HPLC and SEC; reducing conditions; lane 1: molecular weight standard, lane 2: peptide-β2-microglobulin-HLA-A0201-HC+LC+IgG-Fc, lane 3: peptide-β2-microglobulin-HLA-A0201-HC+LC+one-armed IgG (heavy and light chain).

Figures 2, 6B:
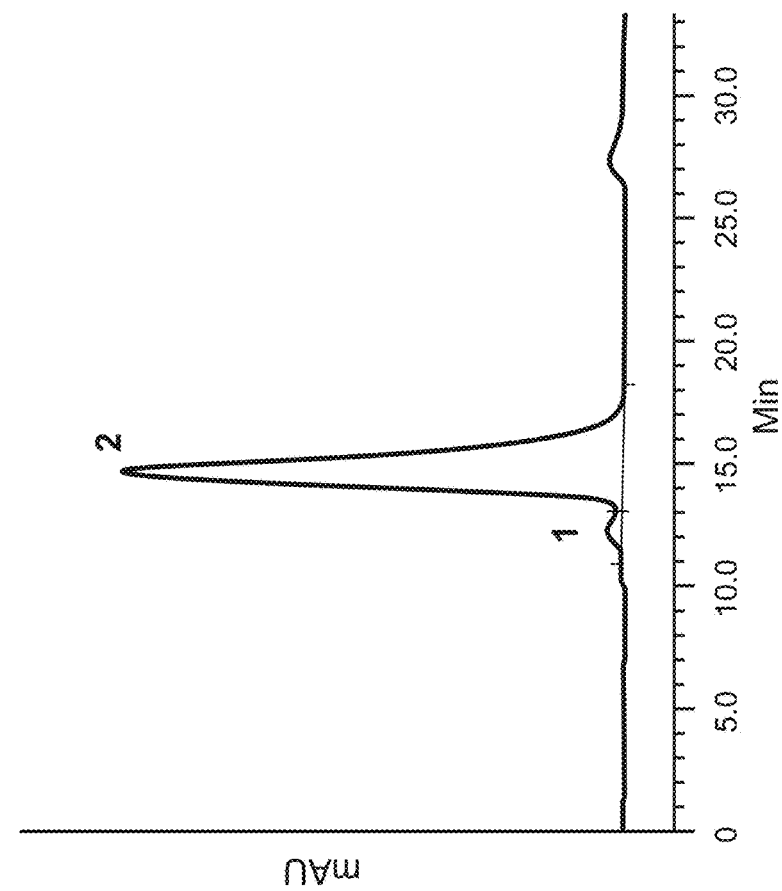
Figures 1, 6B:
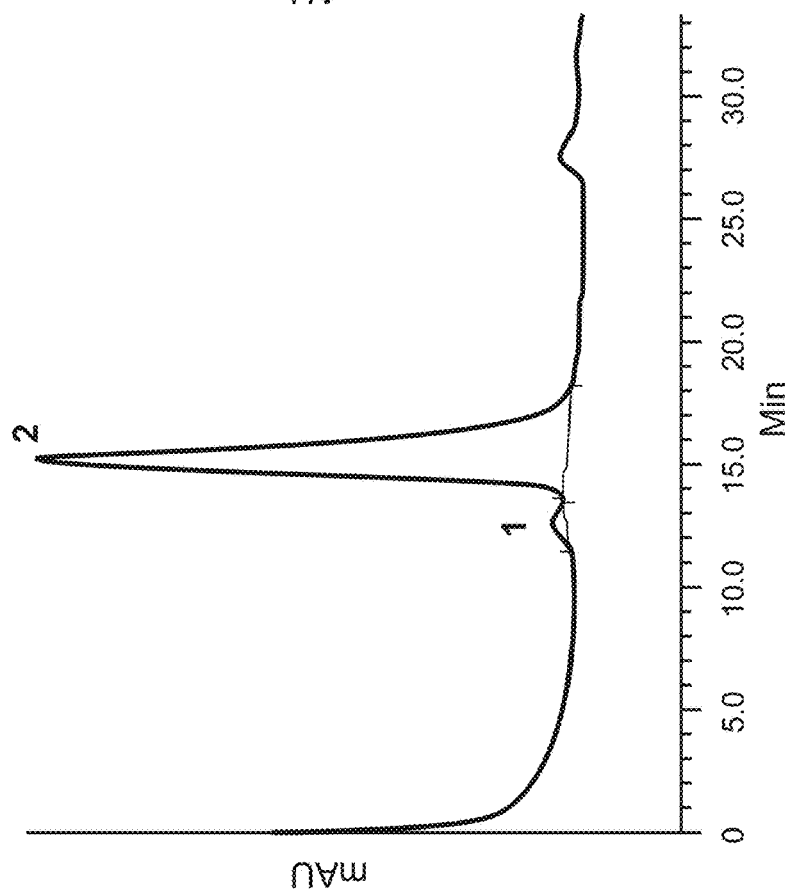

FIG. 6B-1: Size exclusion chromatography chromatogram of peptide-β2-microglobulin-HLA-A0201-HC+LC+IgG-Fc; 1: high molecular weight forms (1.9 area %); 2: monomeric multi-function protein (98.1 area %).

FIG. 6B-2 Size exclusion chromatography chromatogram of peptide-β2-microglobulin-HLA-A0201-HC+LC+one-armed IgG (heavy and light chain); 1: high molecular weight forms (2.1 area %); 2: monomeric multi-function protein (97.9 area %)

Figures 2, 6C:
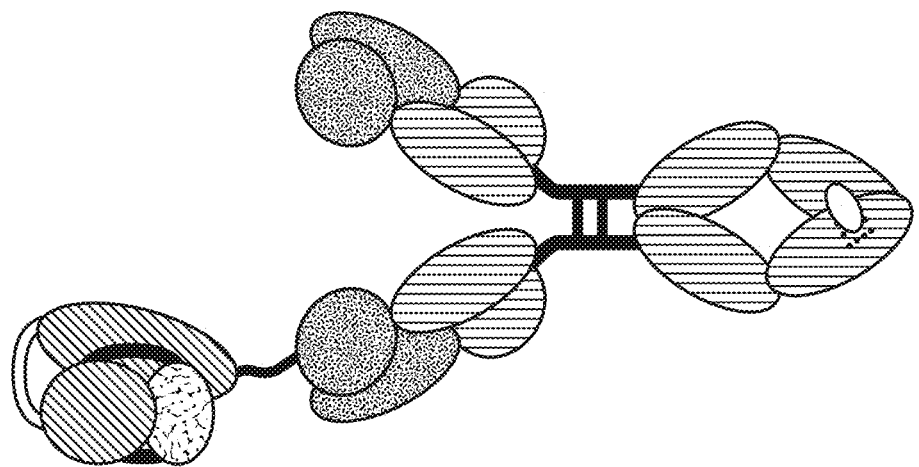
Figures 1, 6C:
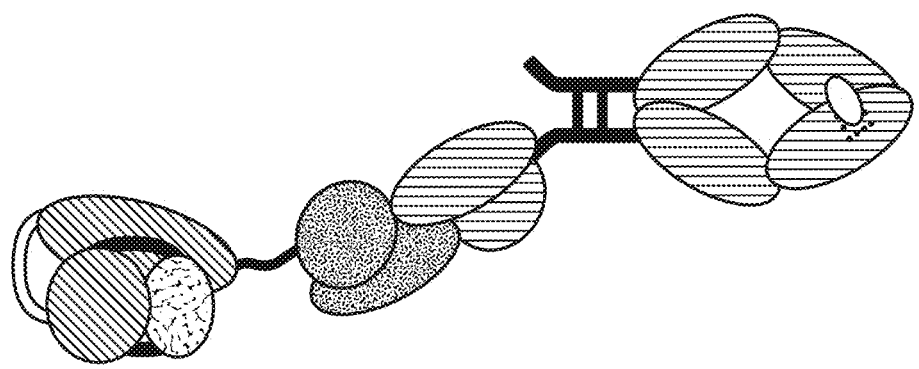

FIG. 6C-1 and FIG. 6C-2: schematic molecules. FIG. 6C-1: peptide-β2-microglobulin-HLA-A0201-HC+LC+IgG-Fc, FIG. 6C-2: peptide-β2-microglobulin-HLA-A0201-HC+LC+one-armed IgG.

Figure 7:
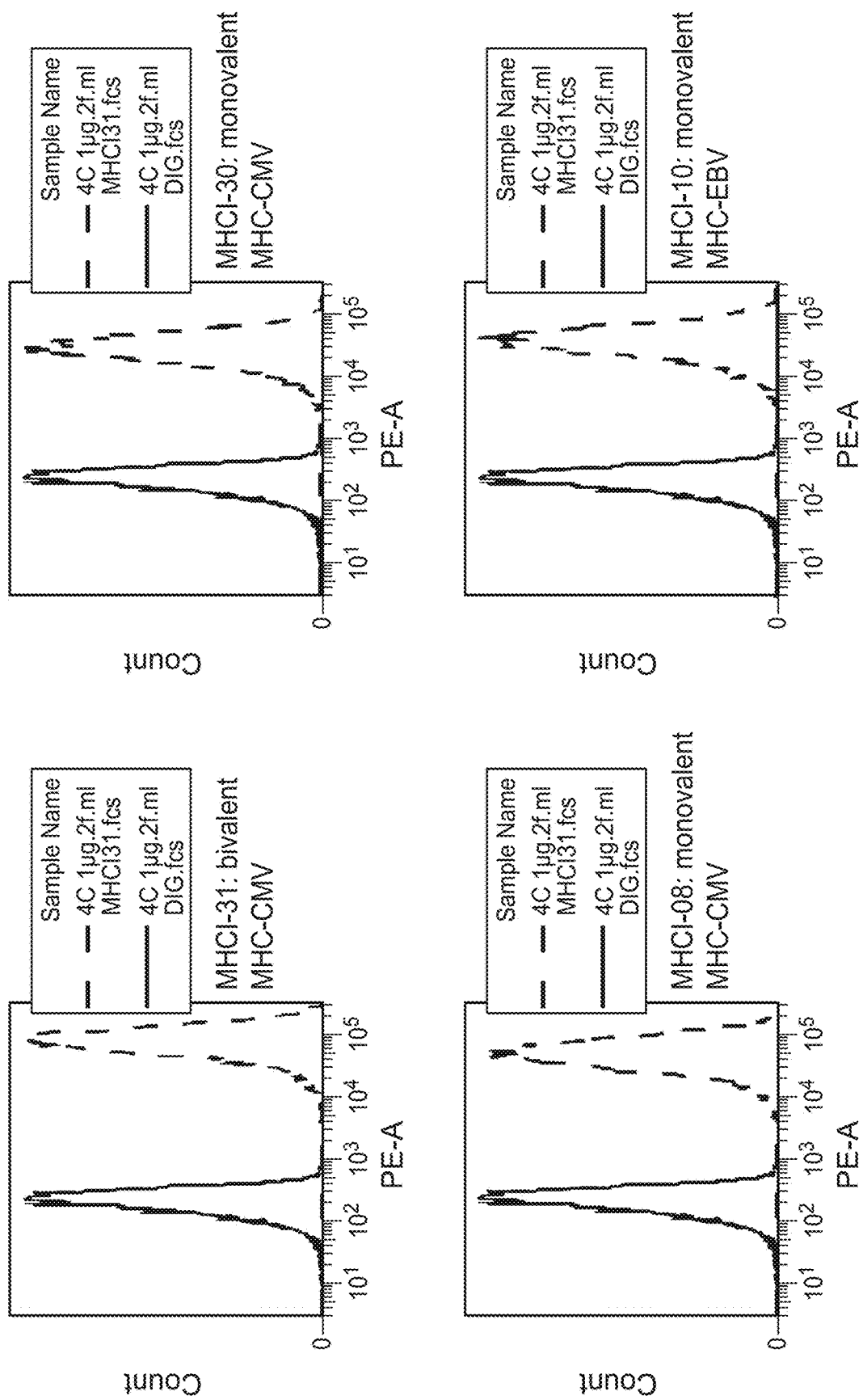

FIG. 7 Binding of different MHC-I-multi function proteins on MCSP+target cells (Colo38): Colo38 cells were incubated for 5 min. with Accutase (PAA, Cat. # L11-007) to obtain a single cell suspension. 2×10$^5$ cells per vial were incubated with 1 μg/ml MHC-I-multi function protein in 10011 PBS/2% FCS for 45 min. at 4° C. After incubation cells were washed with 1 ml cold PBS/2% FCS and centrifuged for 7 min. with 910 rpm. Cells were resuspended in 100 μl PBS/2% FCS with secondary antibody (goat anti-human IgG antibody PE conjugate, Jackson, Cat. # 109-116-088) (2 µg/ml) and incubated for another 45 min. at 4° C. Cells were washed twice with 1 ml PBS %2% FCS and measured with BD Canto II Flow Cytometer.

Figure 8A:
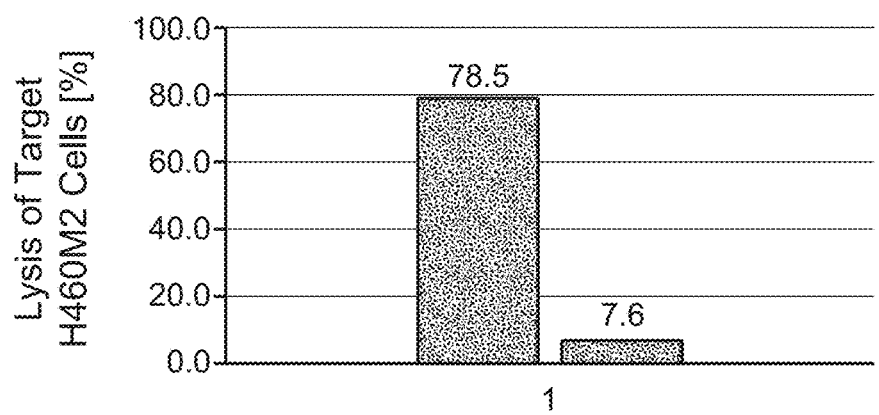
Figure 8B:
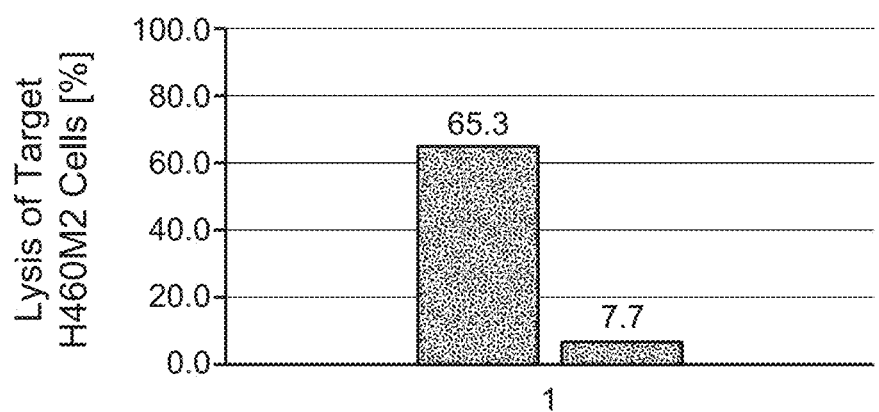
Figure 8C:
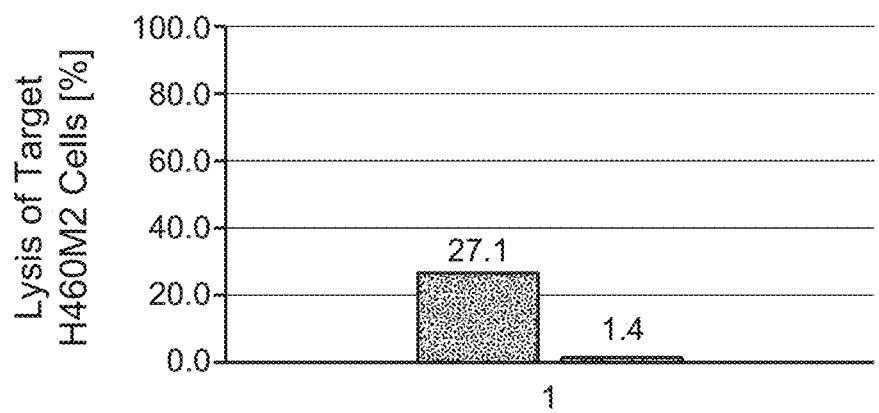

FIGS. 8A-C Cytotoxicity assay: antigen binding multi-function protein as reported herein triggers lysis of H460M2 tumor cells through human CMV-specific T-cells. FIG. 8A (6h) target Cells: CMV-specific effector T-cells 1:1.5; FIG. 8B (6h) target cells: CMV-specific effector T-cells 1:0.75; FIG. 8C (6h) target cells: CMV-specific effector T-cells 1:0.5; left bar: multi-function protein as reported herein; right bar MAB IGF-1R-afucosylated.

Figure 9A:
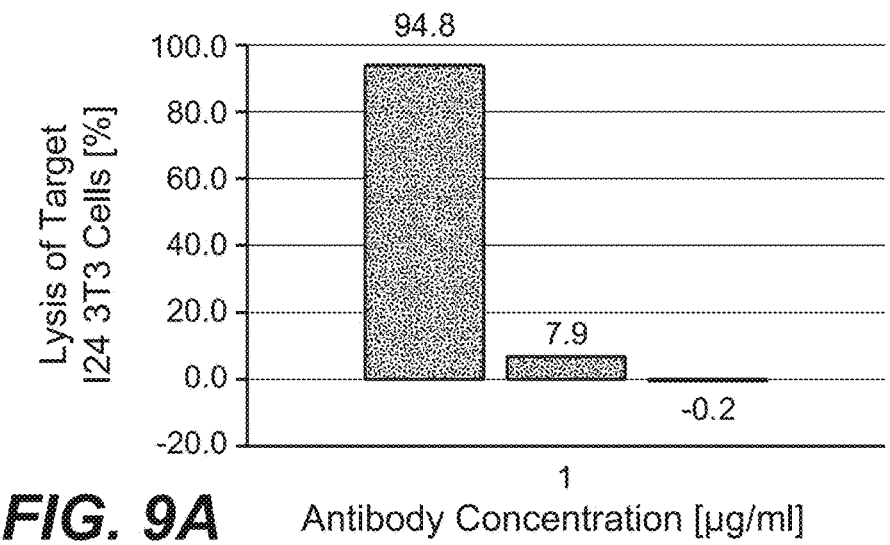
Figure 9B:
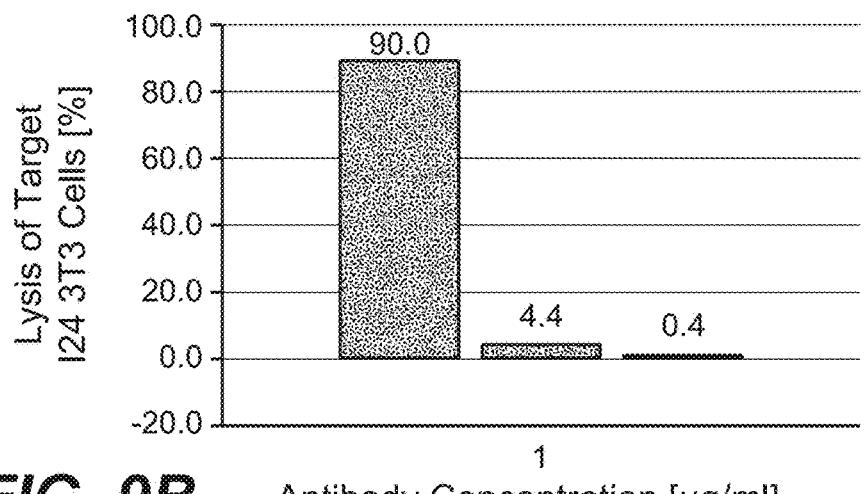
Figure 9C:
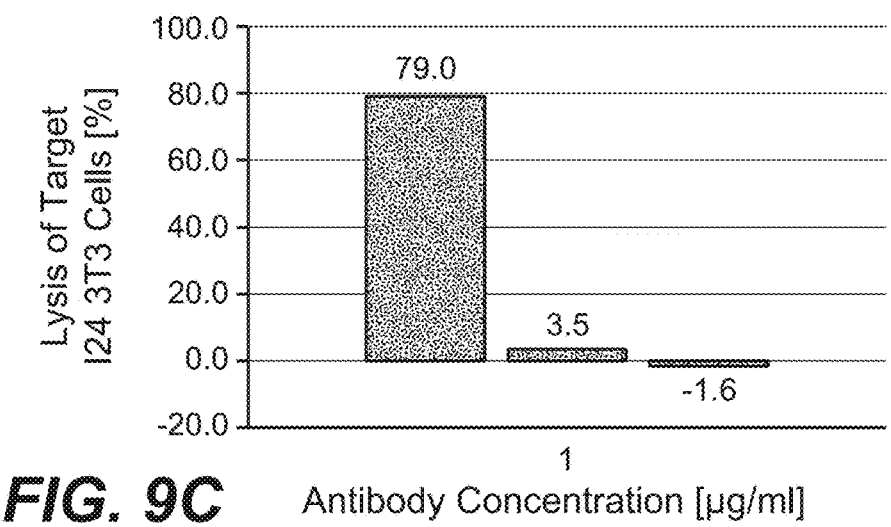

FIGS. 9A-C Cytotoxicity assay: antigen binding multi-function protein as reported herein triggers lysis of I24 3T3 tumor cells through human CMV-specific T-cells; FIG. 9A (9h) Target Cells: CMV-specific Effector T-cells 1:1.5; FIG. 9B (9h) Target Cells: CMV-specific Effector T-cells 1:0.75; FIG. 9C 9h) Target Cells: CMV-specific Effector T-cells 1:0.5; left bar: multi-function protein as reported herein; middle bar MAB IGF-1R-afu; right bar: anti-digoxigenin antibody.

Figure 10A:
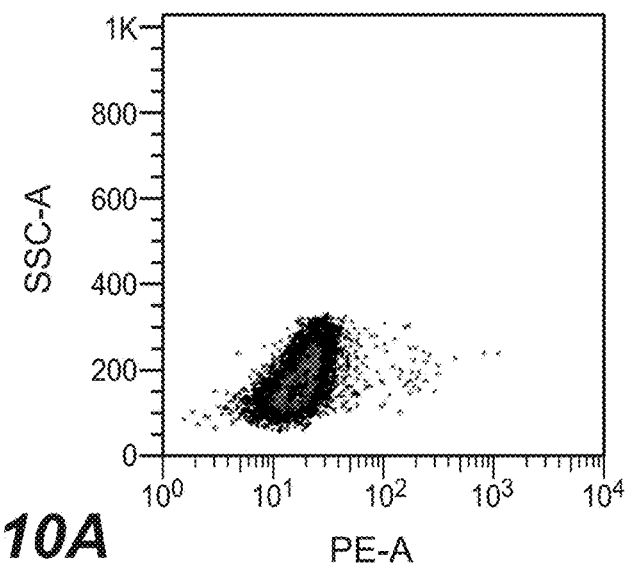
Figure 10B:
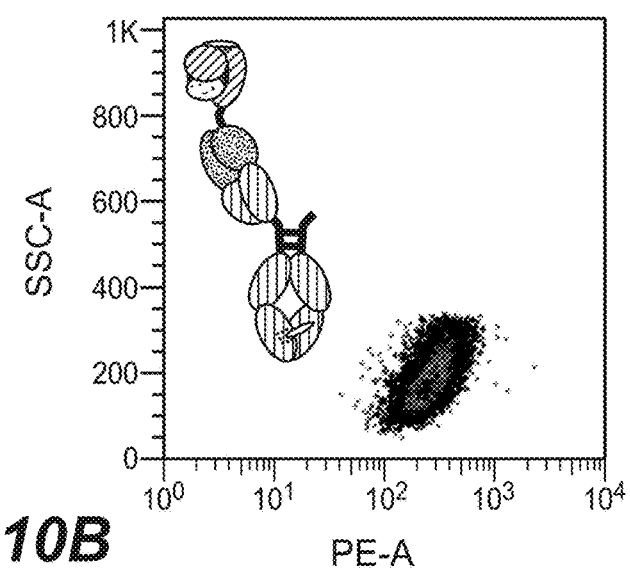
Figure 10C:
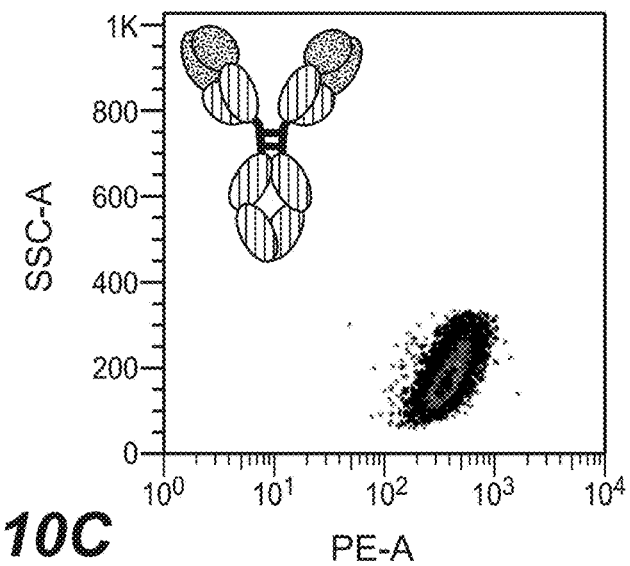

FIGS. 10A-C FACS analysis of binding of anti-IGF-1R antibody and multi-function proteins as reported herein to lung adenocarcinoma cell line H460M2; FIG. 10A secondary antibody only (goat anti-human IgG(H+L) (Jackson Laboratories, Cat #109-116-088)); FIG. 10B multi-function protein as reported herein wherein the fusion polypeptide is fused to the N-terminus of the heavy chain of an anti-IGF-1R antibody comprising only one pair of variable domains; FIG. 10C) anti-IGF-1R antibody.

Figure 11:
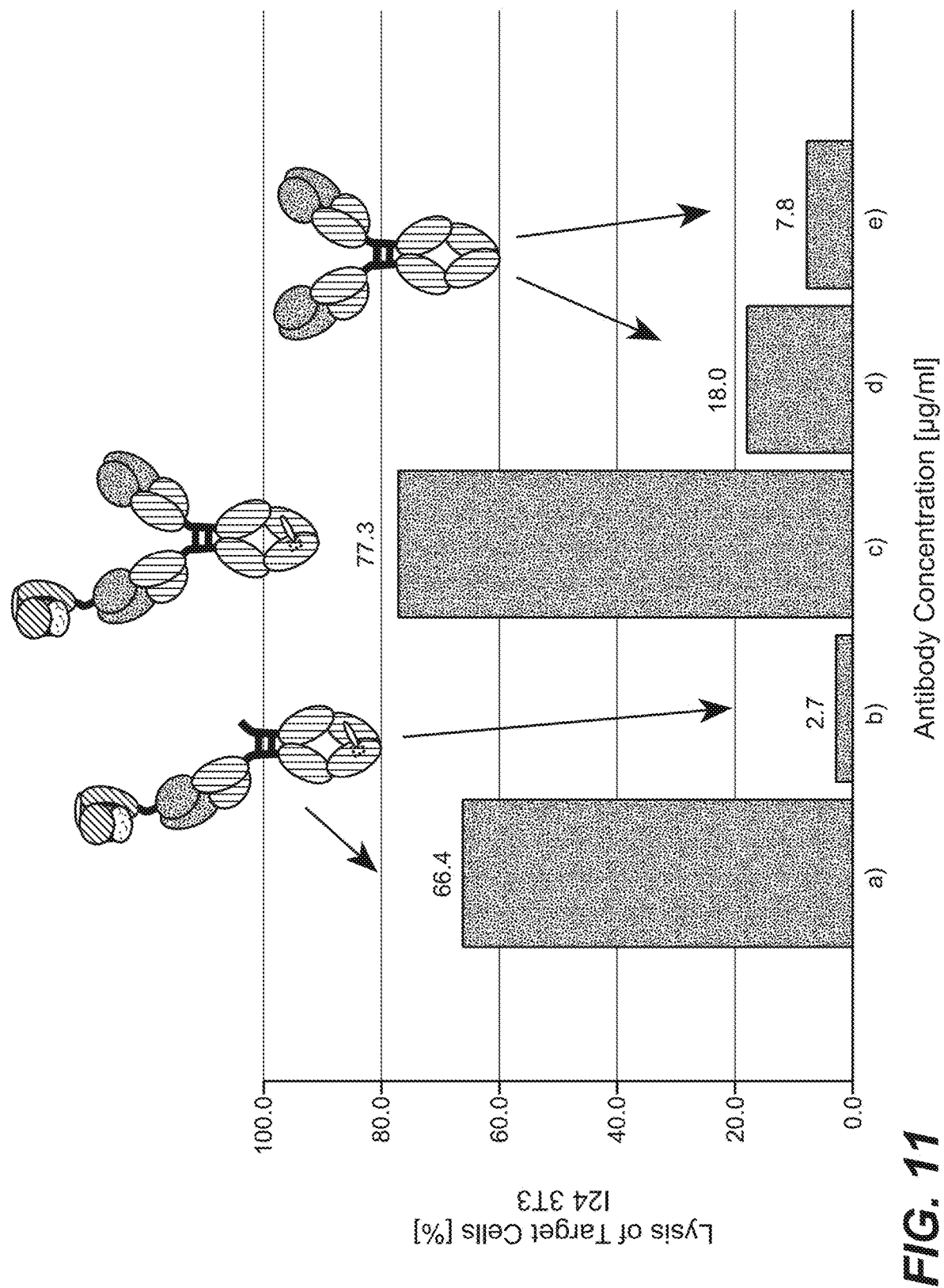

FIG. 11 In vitro efficacy and specificity (cytotoxicity assay) of different multi-function proteins as reported herein; a) multi-function protein comprising a monovalent anti-IGF1R antibody and a CMV-derived peptide; b) multi-function protein comprising a monovalent anti-IGF1R antibody and an EBV-derived peptide (control); c) multi-function protein comprising a bivalent anti-IGF1R antibody and a CMV-derived peptide; d) anti-IGF-1R antibody (control); e) anti-digoxigenin antibody (control).

Figure 12:
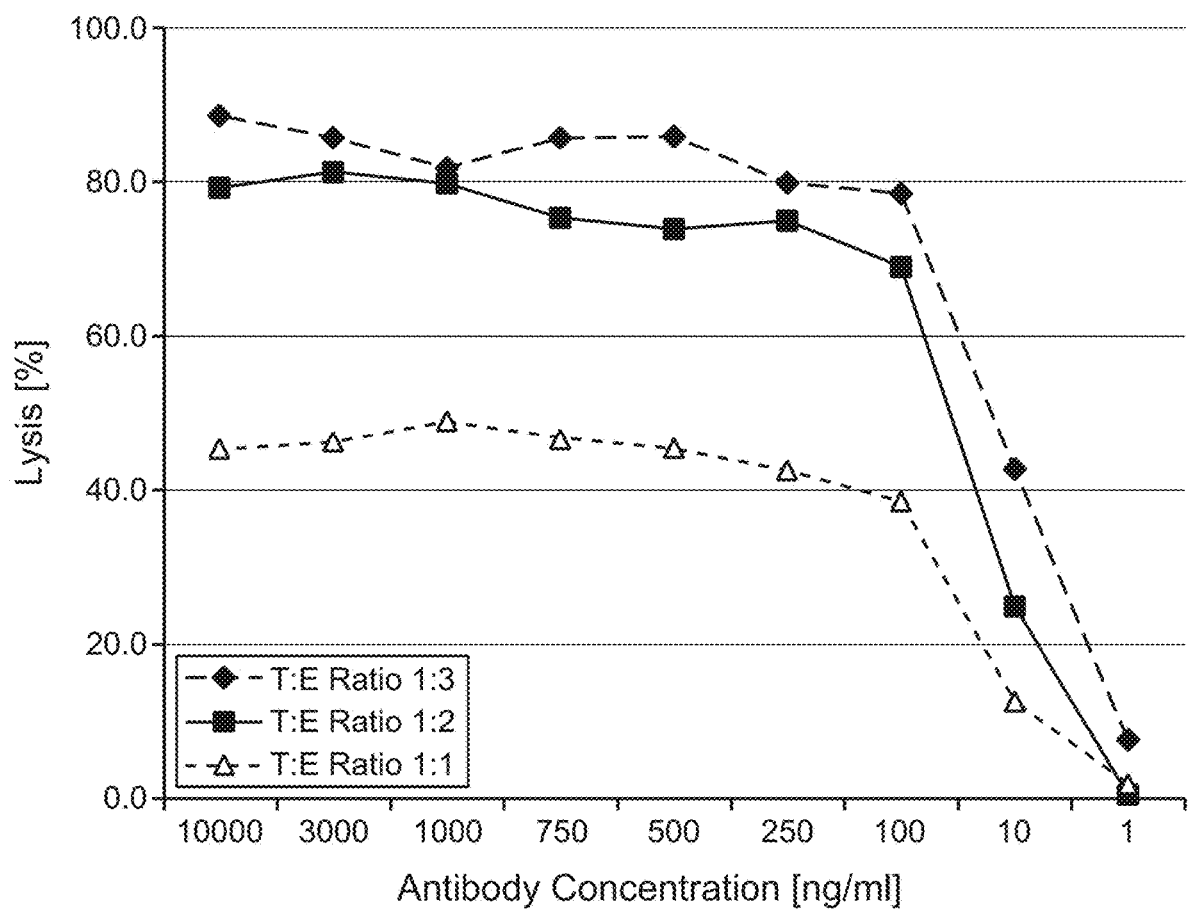

FIG. 12 In vitro efficacy and specificity (EC50 value) of a multi-function protein as reported herein wherein the fusion polypeptide is fused to the N-terminus of the heavy chain of a complete anti-IGF-1R antibody determined at different target (T) to effector (E) cell ratios.

Figure 13:
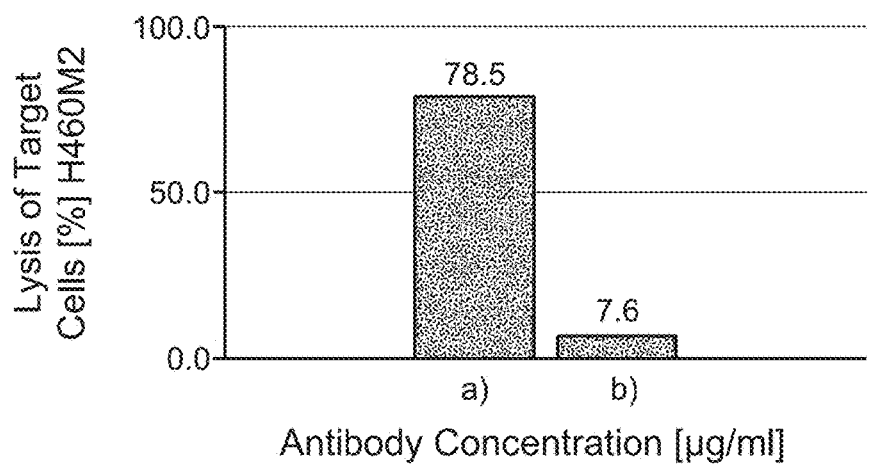

FIG. 13 Lysis of target cells after 6 hours incubation with a) a multi-function protein comprising a monovalent anti-IGF1R antibody and a fusion polypeptide comprising a CMV-derived peptide and b) an anti-IGF-1R antibody at a ratio of target to effector cells of 1:1.5.

Figure 14:
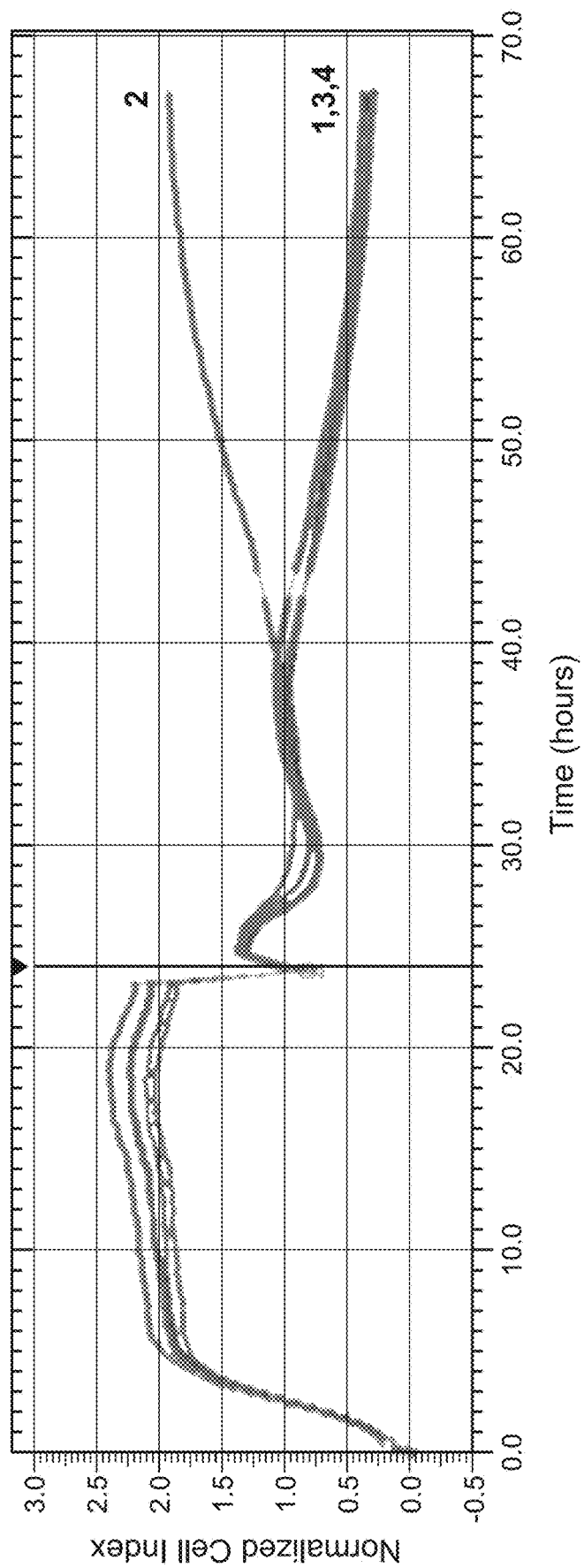

FIG. 14 Course of normalized cell index for Colo38 cells incubated with MHC-I-anti-MCSP multi-function proteins; 1 µg/ml multi-function protein concentration (MHCI-0008 (1), MHCI-0010 (2), MHCI-0030 (3), MHCI-0031 (4)), effector to target cell ratio of 10:1; PBMCs from Donor 3 (200.000 cells, Donor 3 is CMV-positive but EBV negative) and melanoma tumor cell line Colo38 (20.000 cells) and per 96 well, data are triplicates.

Figure 15A:
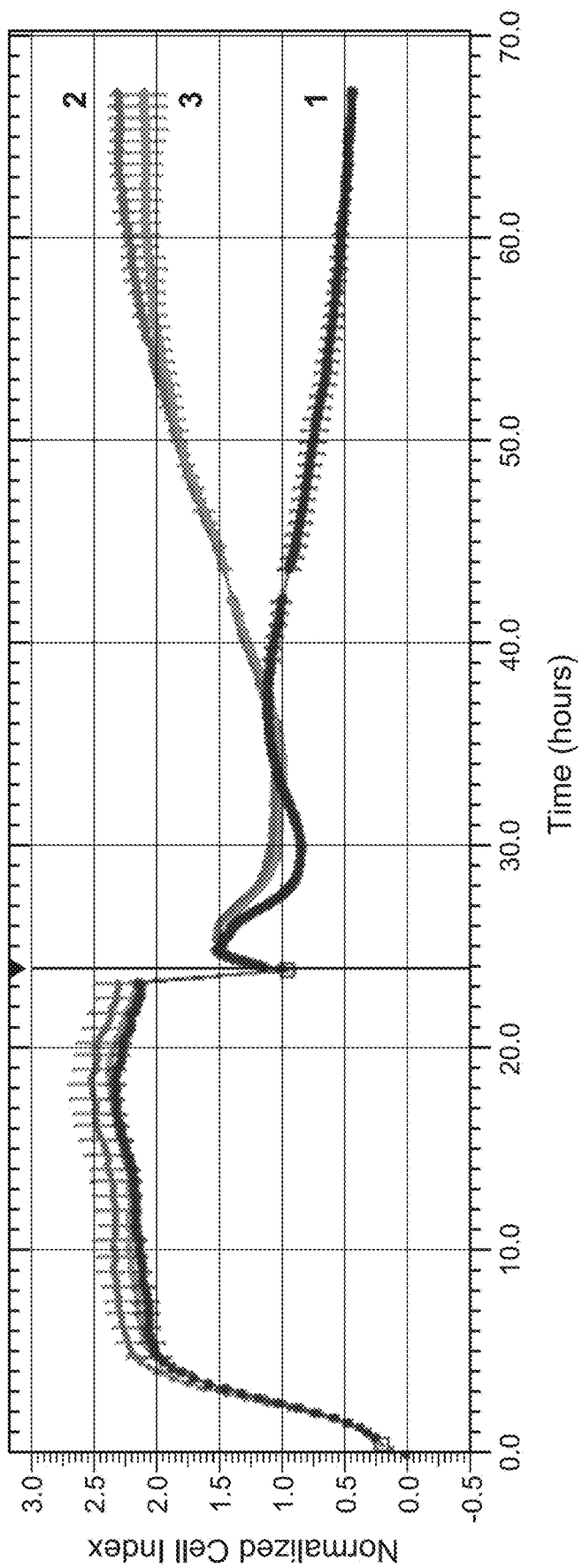
Figure 15B:
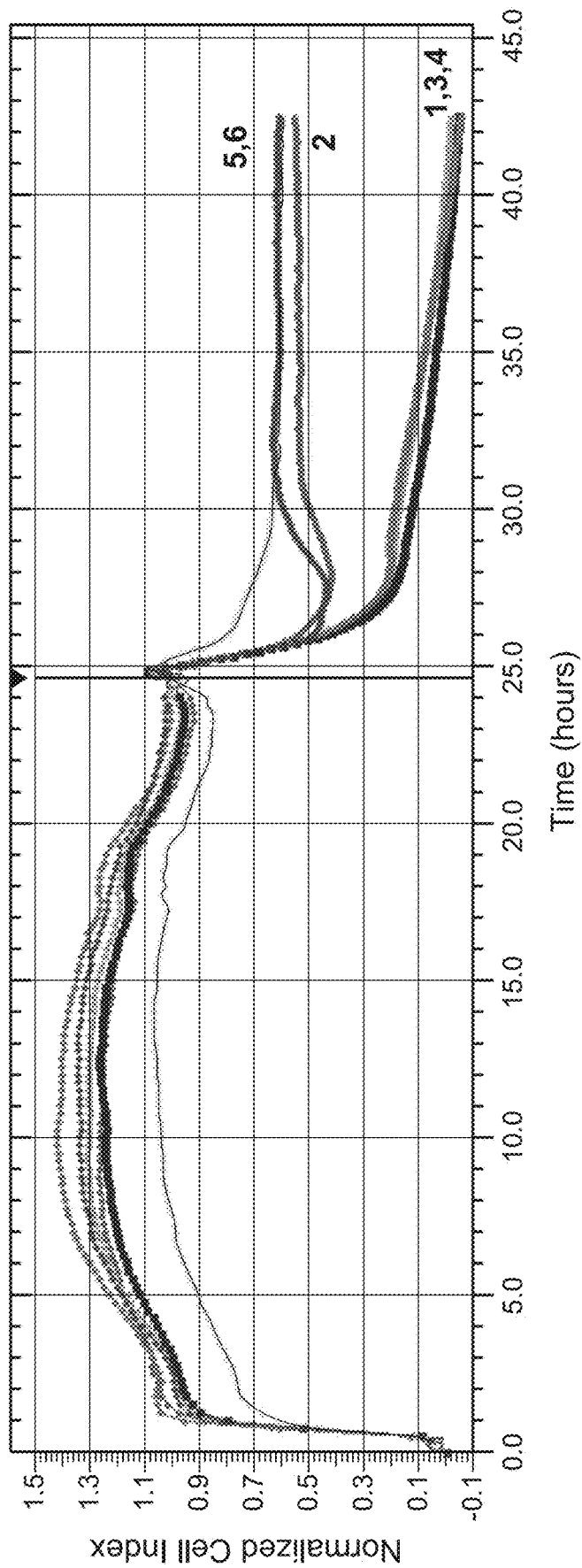

FIGS. 15A-B FIG. 15A: Course of normalized cell index for Colo38 cells incubated with MHCI-anti-MCSP multi-function proteins; 1 µg/ml multi-function protein concentration (MHCI-0008 (1), MHCI-0010 (2), PBMCs only (3)), effector to target cell ratio of 10:1; PBMCs from Donor 3 (200.000 cells, Donor 3 is CMV-positive but EBV negative) and melanoma tumor cell line Colo38 (20.000 cells) and per 96 well, data are triplicates.

FIG. 15B: Course of normalized cell index for WM266 cells incubated with MHC-I-anti-MCSP multi-function proteins; 1 µg/ml multi-function protein concentration (MHCI-0008 (1), MHCI-0010 (2), MHCI-0030 (3), MHCI-0031 (4), target cells alone (5), target cells+T-cells (6)), effector to target cell ratio of 10:1; PBMCs from Donor 3 (200.000 cells, Donor 3 is CMV-positive but EBV negative) and melanoma tumor cell line MW266 (20.000 cells) and per 96 well, data are triplicates.

Figure 16:
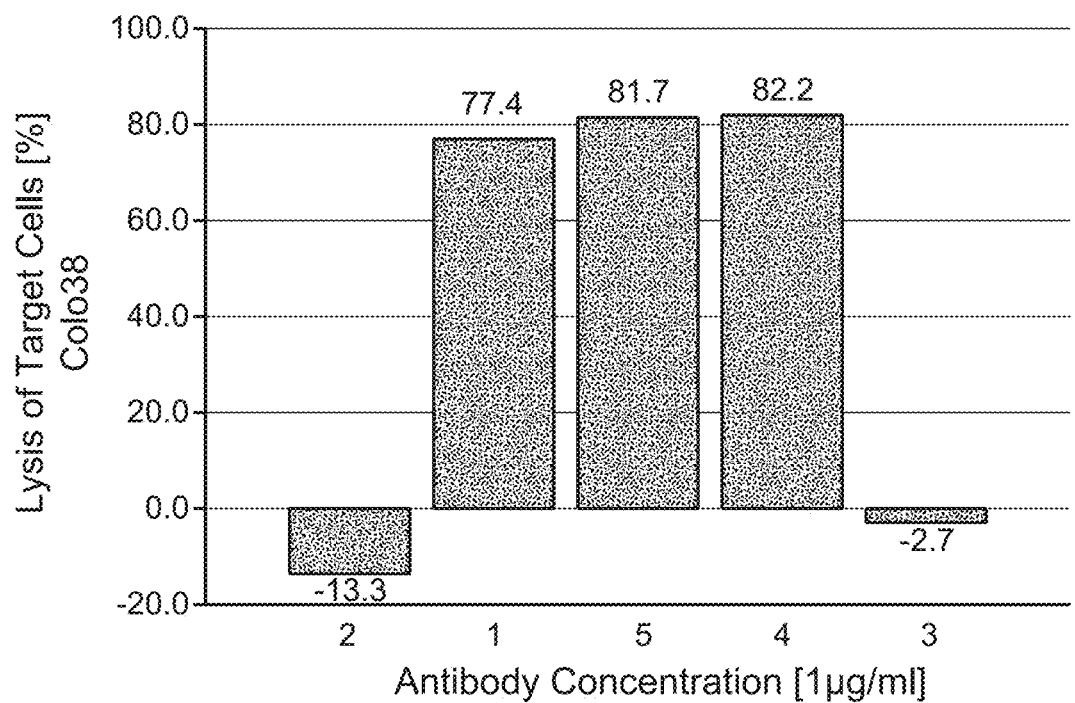

FIG. 16 Lysis of target cells after 42 hours of incubation with multi-function protein in the presence of non-stimulated PBMCs by the multi-function proteins MHCI-0008 (monovalent, CMV peptide loaded, 1), MHCI-0010 (monovalent, EBV peptide loaded control, 2), MHC-0026 (bivalent, CMV peptide loaded, non-binding control, 3), MHCI-0030 (monovalent, CMV peptide loaded, active, 4) and MHCI-0031 (bivalent, CMV peptide loaded, active, 5).

Figure 17:
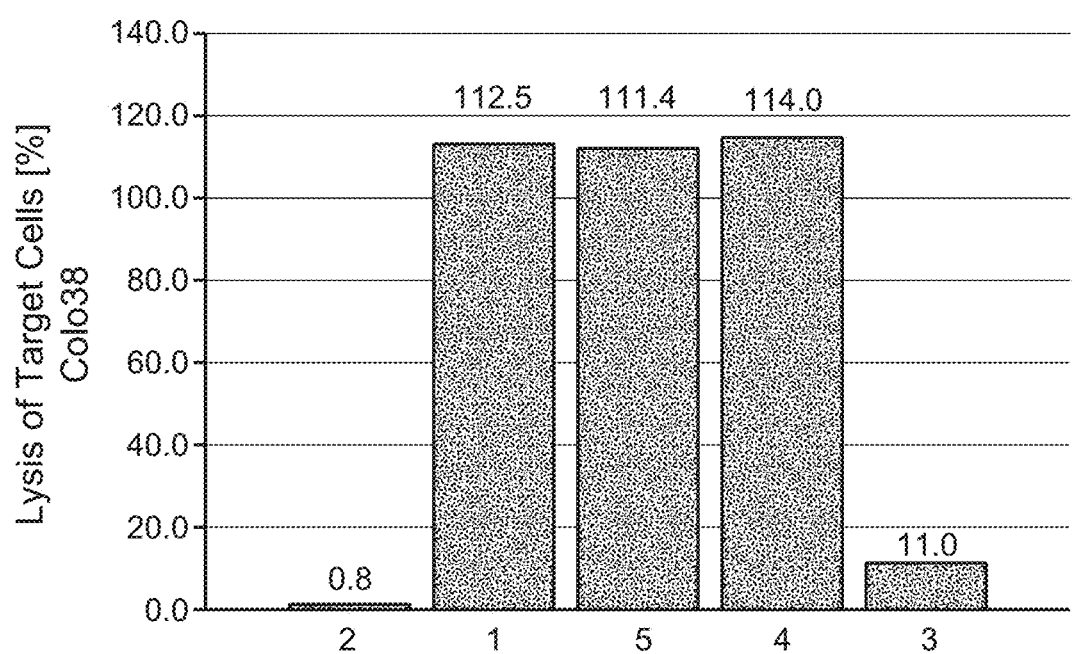

FIG. 17 LDH release after 48 hours of incubation with multi-function protein effected in the presence of non-stimulated PBMCs by the multi-function proteins MHCI-0008 (monovalent, CMV peptide loaded, 1), MHCI-0010 (monovalent, EBV peptide loaded control, 2), MHC-0026 (bivalent, CMV peptide loaded, non-binding control, 3), MHCI-0030 (monovalent, CMV peptide loaded, active, 4) and MHCI-0031 (bivalent, CMV peptide loaded, active, 5).

Figure 18A:
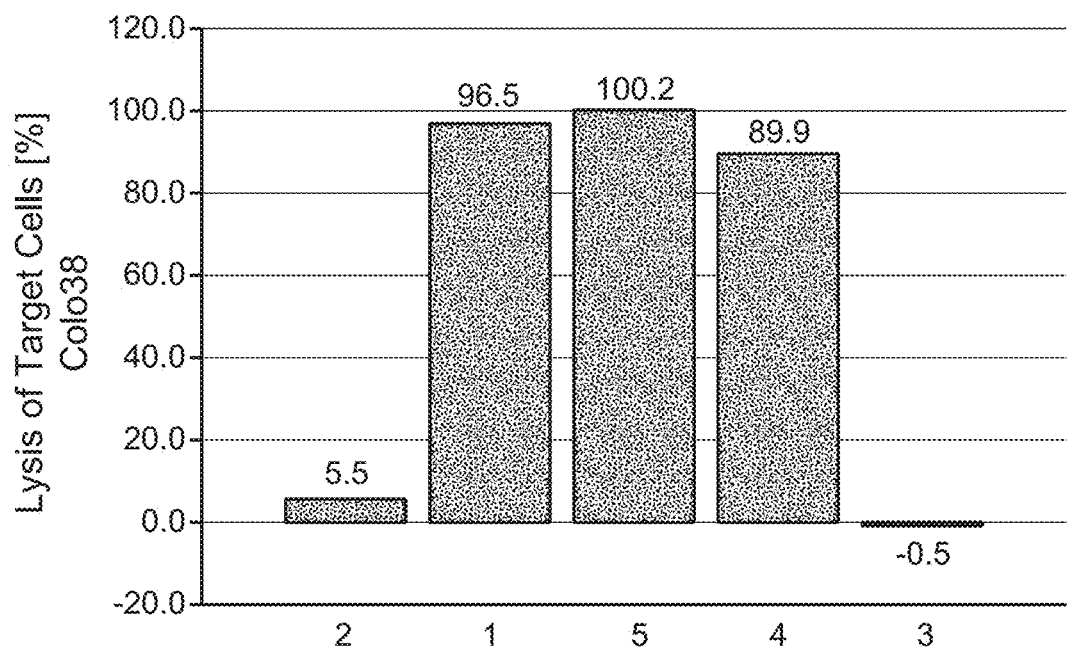
Figure 18B:
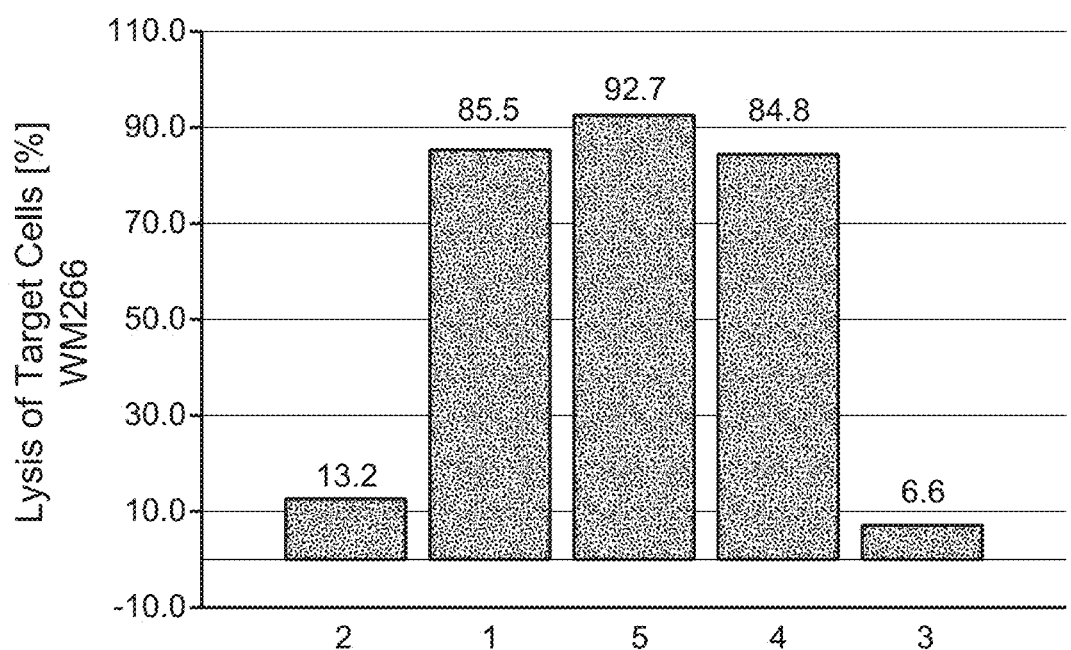

FIGS. 18A-B FIG. 18A: Lysis of Colo38 cells after 10 hours of incubation with multi-function protein in the presence of stimulated PBMCs by the multi-function proteins MHCI-0008 (monovalent, CMV peptide loaded, 1), MHCI-0010 (monovalent, EBV peptide loaded control, 2), MHC-0026 (bivalent, CMV peptide loaded, non-binding control, 3), MHCI-0030 (monovalent, CMV peptide loaded, active, 4) and MHCI-0031 (bivalent, CMV peptide loaded, active, 5) at a concentration of 1 µg/ml.

FIG. 18B: Lysis of WM266 cells after 10 hours of incubation with multi-function protein in the presence of stimulated PBMCs by the multi-function proteins MHCI-0008 (monovalent, CMV peptide loaded, 1), MHCI-0010 (monovalent, EBV peptide loaded control, 2), MHC-0026 (bivalent, CMV peptide loaded, non-binding control, 3), MHCI-0030 (monovalent, CMV peptide loaded, active, 4) and MHCI-0031 (bivalent, CMV peptide loaded, active, 5) at a concentration of 1 µg/ml.

Figures 2, 19A:
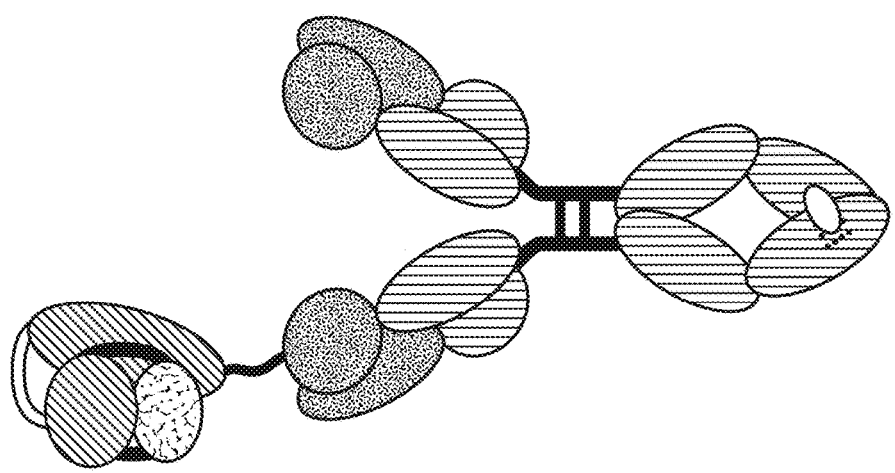
Figures 1, 19A:
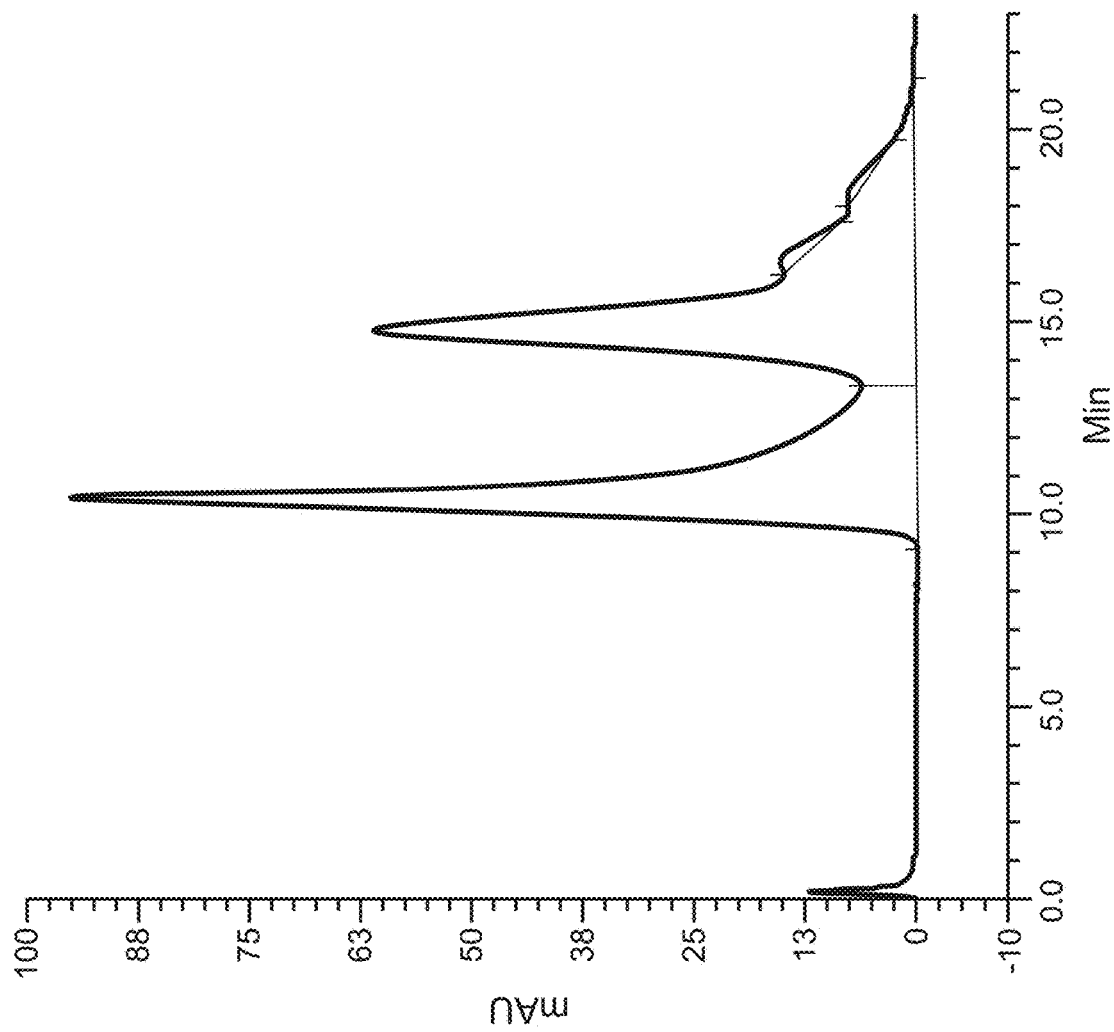
Figures 1, 2, 19B:
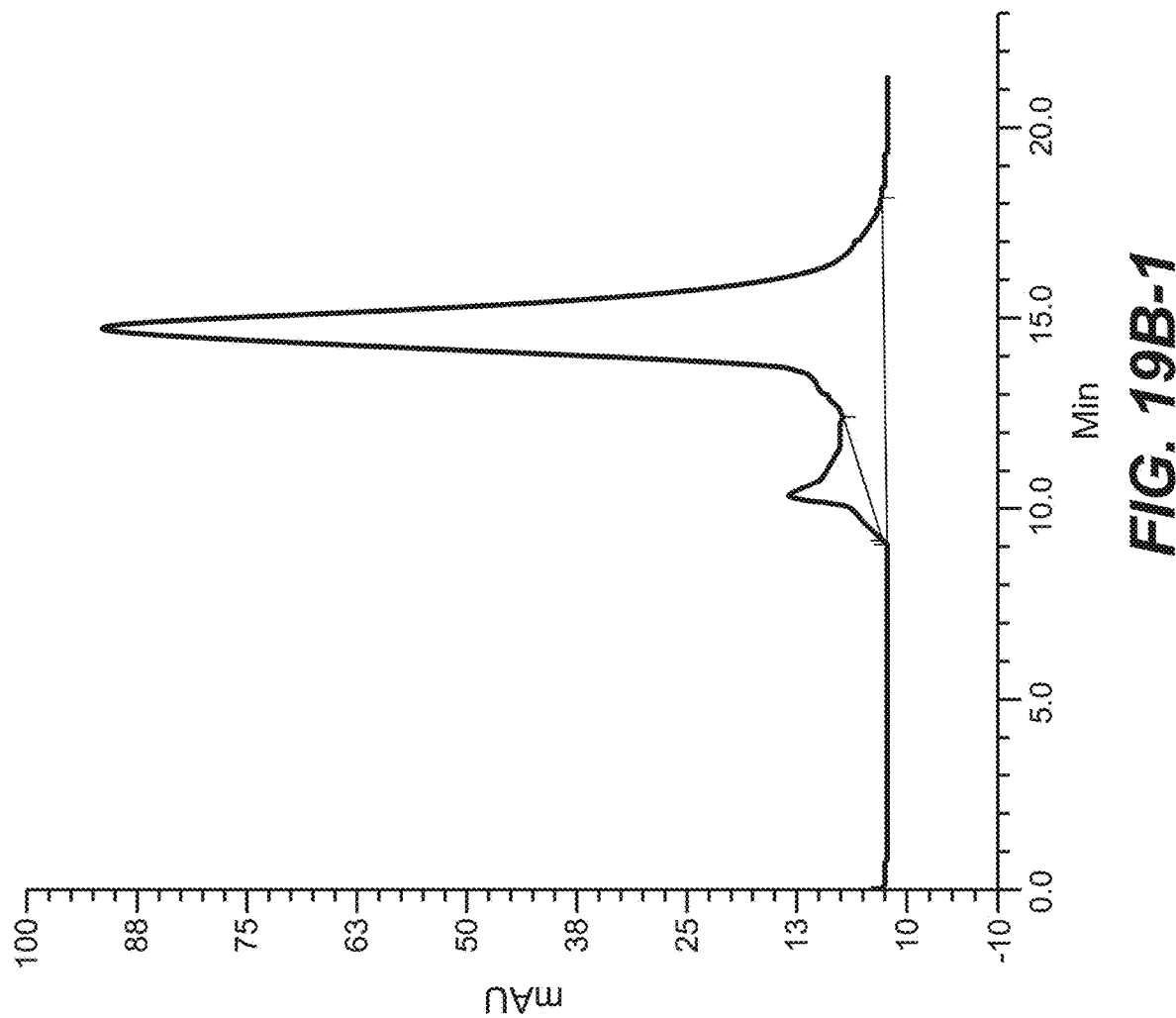

FIGS. 19A-B Analytical size exclusion chromatogram after protein A affinity chromatography but prior to preparative size exclusion chromatography of a non-disulfide stabilized multi-function protein (FIGS. 19A-1 and 19A-2) and a disulfide stabilized multi-function protein (FIGS. 19B-1 and 19B-2).

Figure 20:
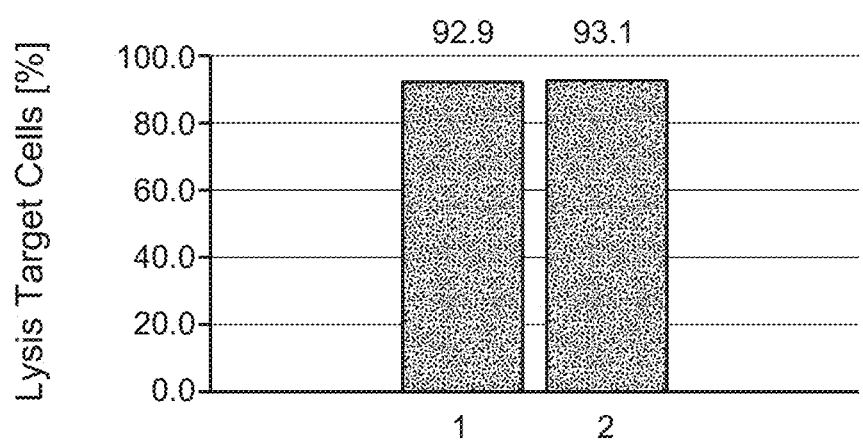

FIG. 20 Lysis of Colo38 cells with in the presence of stimulated PBMCs by the multi-function proteins MHCI-0031 (bivalent, CMV peptide loaded, active, non-disulfide-linked, 1) and MHCI-0054 (bivalent, CMV peptide loaded, active, disulfide-linked version of MHCI-0031, 2) at a concentration of 1 µg/ml.

Figure 21:
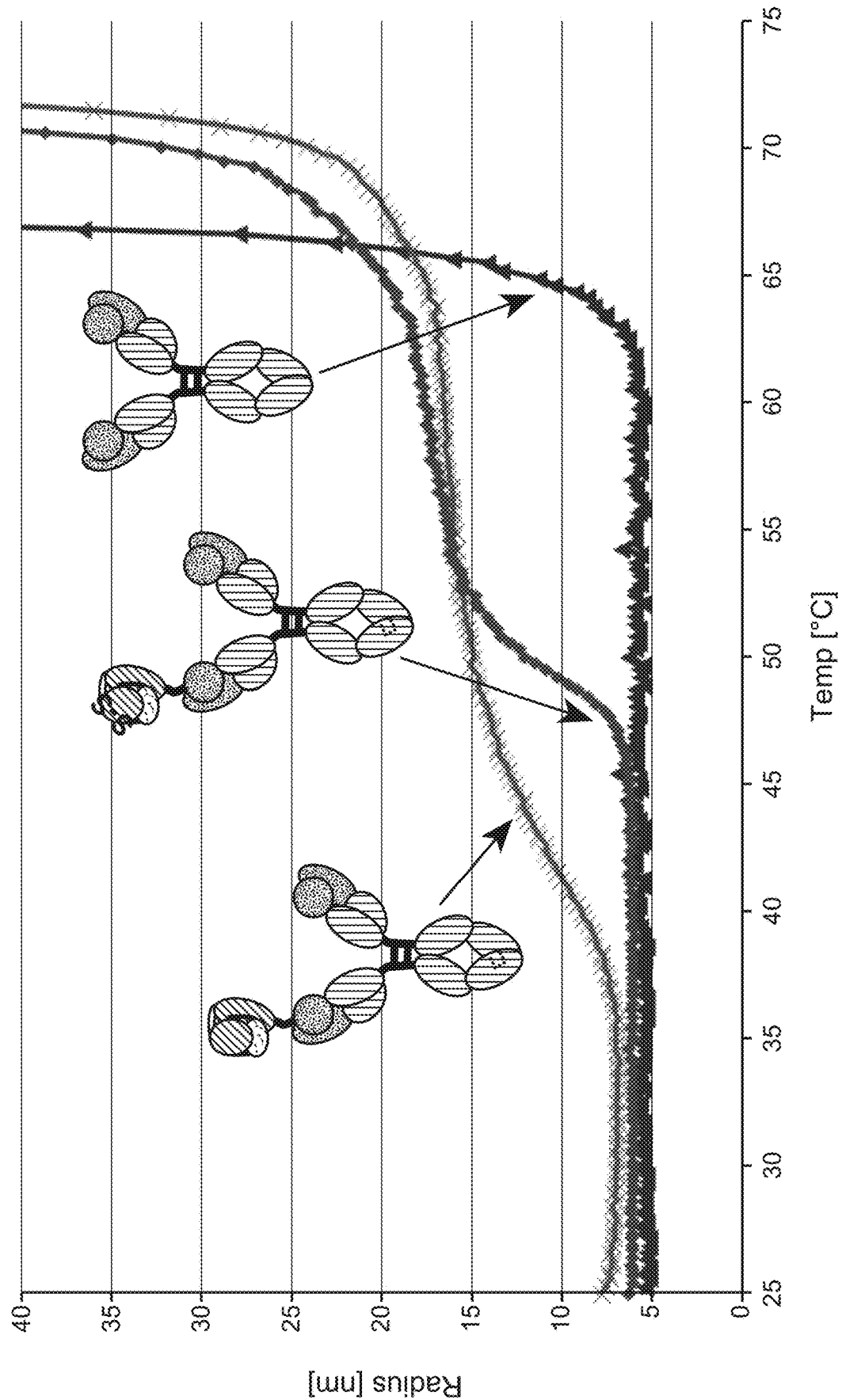

FIG. 21 Thermal stability of wild-type full length IgG (triangles), exemplary disulfide-linked multivalent multi-function proteins as reported herein (diamonds), multivalent multi-function proteins without disulfide bond stabilization (asterix).

Figure 22A:
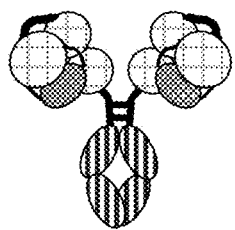
Figure 22B:
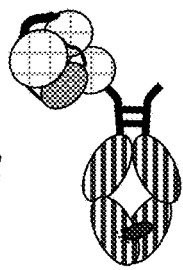
Figure 22C:
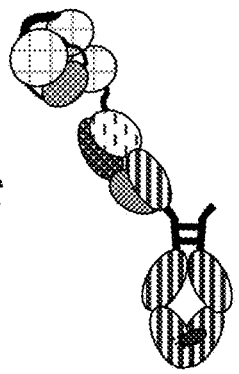
Figure 22D:
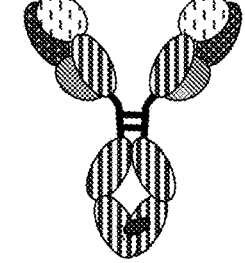
Figure 22E:
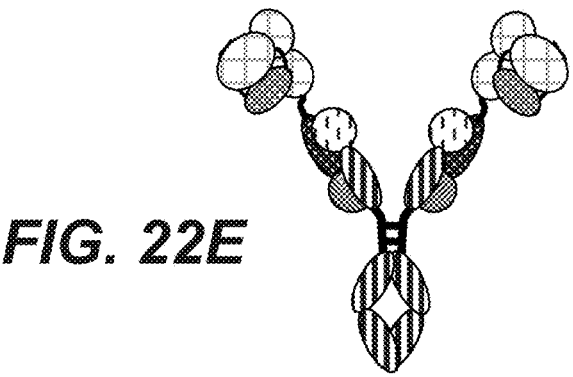
Figure 22F:
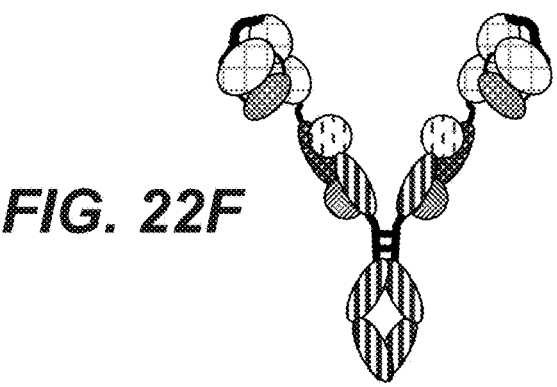
Figure 22G:
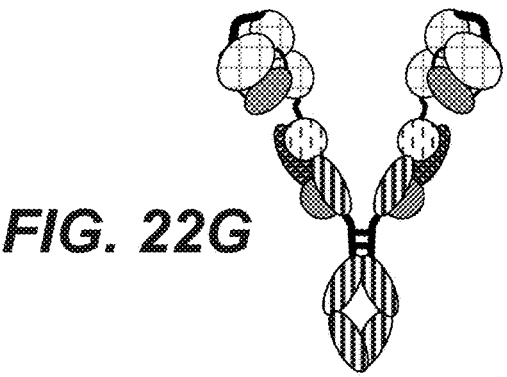
Figure 22H:
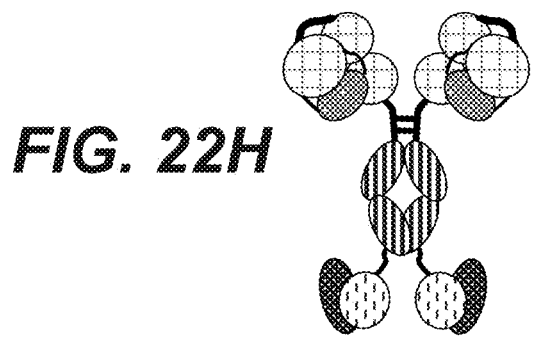
Figure 22I:
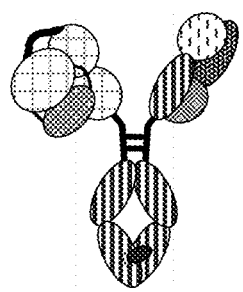
Figure 22J:
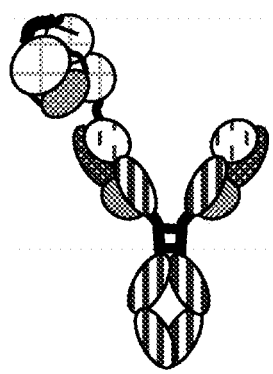
Figure 22K:
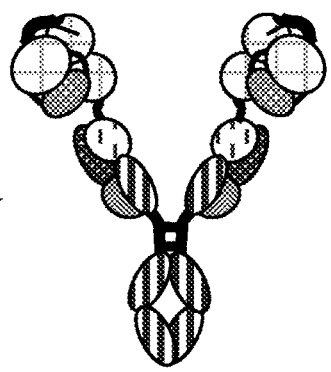

FIGS. 22A-K Multi-function proteins comprising one, two or more antigen presenting domains containing an MHC-I protein complex can be expressed in the presence of variable antibody domain and antibody hinge region derived polypeptides when the antigen presenting domains are disulfide-linked. Further the obtainable yield is increased. FIG. 22A depicts two virus-derived peptide-class I MHC fusion polypeptides, no variable domains or constant domains, no disulfide-linked antigen presenting domain, and contains an antibody heavy chain hinge region comprising polypeptide. FIG. 22B depicts one virus-derived peptide-class I MHC fusion polypeptide, no variable domains or constant domains, no disulfide-linked antigen presenting domain, and contains an antibody heavy chain hinge region comprising polypeptide. FIG. 22C depicts one virus-derived peptide-class I MHC fusion polypeptide, one variable domain and one constant domain, no disulfide-linked antigen presenting domain, and contains an antibody heavy chain hinge region comprising polypeptide. FIG. 22D depicts one virus-derived peptide-class I MHC fusion polypeptide, two variable domains and two constant domains, no disulfide-linked antigen presenting domain, and contains an antibody heavy chain hinge region comprising polypeptide. FIG. 22E depicts two virus-derived peptide-class I MHC fusion polypeptides, two variable domains and two constant domains, no disulfide-linked antigen presenting domain, and contains an antibody heavy chain hinge region comprising polypeptide. FIG. 22F depicts two virus-derived peptide-class I MHC fusion polypeptides, two variable domains and two constant domains, no disulfide-linked antigen presenting domain, and contains an antibody heavy chain hinge region comprising polypeptide. FIG. 22G depicts two virus-derived peptide-class I MHC fusion polypeptides, two variable domains and two constant domains, no disulfide-linked antigen presenting domain, and contains an antibody heavy chain hinge region comprising polypeptide. FIG. 22H depicts two virus-derived peptide-class I MHC fusion polypeptides, two variable domains and no constant domains, no disulfide-linked antigen presenting domain, and contains an antibody heavy chain hinge region comprising polypeptide. FIG. 22I depicts one virus-derived peptide-class I MHC fusion polypeptide, one variable domain and one constant domain, no disulfide-linked antigen presenting domain, and contains an antibody heavy chain hinge region comprising polypeptide. FIG. 22J depicts one virus-derived peptide-class I MHC fusion polypeptide, one variable domain and one constant domain, a disulfide-linked antigen presenting domain, and contains an antibody heavy chain hinge region comprising polypeptide. FIG. 22K depicts two virus-derived peptide-class I MHC fusion polypeptides, two variable domains and two constant domains, a disulfide-linked antigen presenting domain, and contains an antibody heavy chain hinge region comprising polypeptide.

Figure 23A:
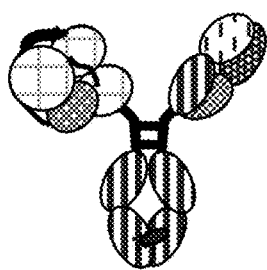
Figure 23D:
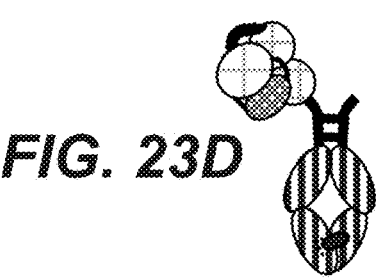
Figures 1, 23B:
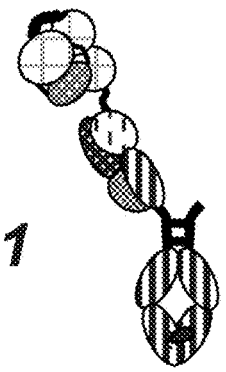
Figure 23E:
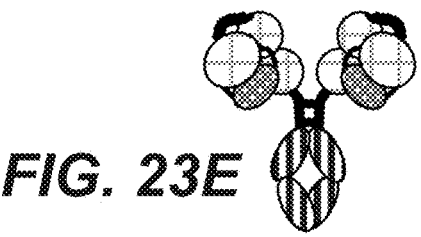
Figures 2, 23B:
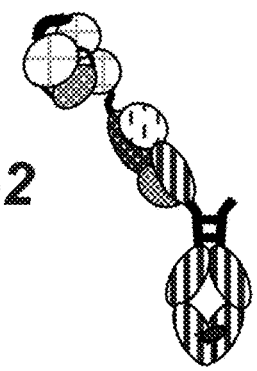
Figure 23F:
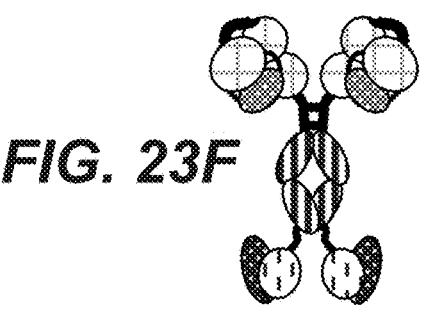
Figures 1, 23C:
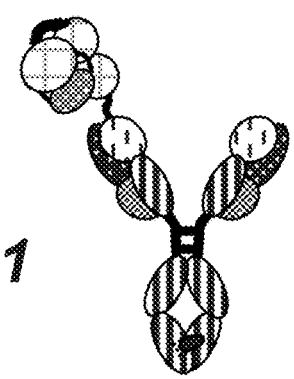
Figures 1, 23G:
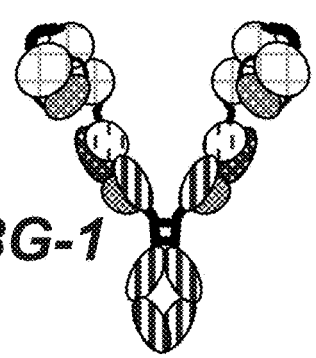
Figures 2, 23C:
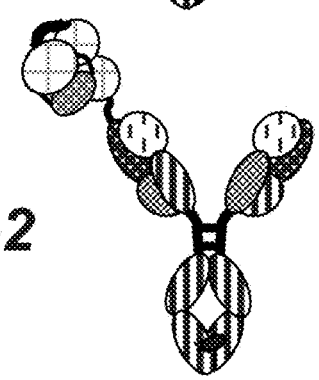
Figures 2, 23G:
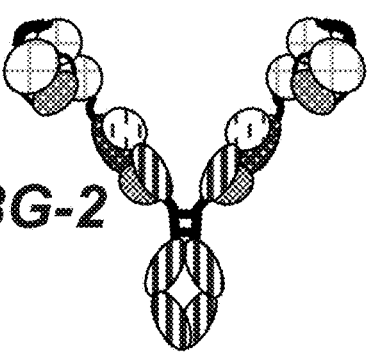

FIGS. 23A-G Multi-function proteins of the invention comprising a CMV-derived peptide with IGF-1R binding specificity, as generated and tested in Example 3. FIG. 23A depicts a [CMV-pp65-peptide]-[linker 1]-[β2-microglobulin]-[linker 2]-[HLA-A-α1-α2-α3]-[linker 3]-[IgG1-L234A, L235A mutant with hole variation], an Ig heavy chain (IgG1-L234A, L235A mutant with knob variation), and an Ig light chain. FIG. 23B-1 depicts a [CMV-pp65-peptide]-[linker 1]-[β2-microglobulin]-[linker 2]-[HLA-A-α1-α2-α3]-[linker 3]-[IgG1-L234A, L235A mutant with hole variation], an IgG1-L234A, L235A mutant Fc-region knob variant, and an Ig light chain; FIG. 23B-2 is the same as in FIG. 23B-1 but with the fusion to the Ig light chain. FIG. 23C-1 depicts a [CMV-pp65-peptide]-[linker 1]-[β2-microglobulin]-[linker 2]-[HLA-A-α1-α2-α3]-[linker 3]-[IgG1-L234A, L235A mutant with hole variation], an IgG1-L234A, L235A mutant with knob variation, and an Ig light chain; FIG. 23C-2 is the same as in FIG. 23C-1 but with the fusion to the Ig light chain. FIG. 23D depicts a [CMV-pp65-Peptide]-[Linker 1]-[β2-microglobulin]-[Linker 2]-[HLA-A-α1-α2-α3]-[Linker 3]-[IgG1-L234A, L235A mutant with hole variation], an IgG1-L234A, L235A mutant with knob variation. FIG. 23E depicts a [CMV-pp65-peptide]-[linker 1]-[β2-microglobulin]-[linker 2]-[HLA-A-α1-α2-α3]-[linker 3]-[IgG1-L234A, L235 A-Fc-region]. FIG. 23F depicts a [CMV-pp65-peptide]-[linker]-[β2-microglobulin]-[linker 2]-[HLA-A-α1-α2-α3]-[linker 3]-[IgG1-L234A, L235A mutant Fc-region]-[linker 4]-[scFv]. FIG. 23G-1 depicts a [CMV-pp65-peptide]-[linker 1]-[β2-microglobulin]-[linker 2]-[HLA-A-α1-α2-α3]-[linker 3]-[IgG1-L234A, L235A mutant], and an Ig light chain; and FIG. 23G-2 is the same as in FIG. 23G-1 but with a fusion to the Ig light chain.

Figure 24A:
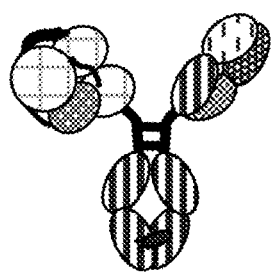
Figure 24B:
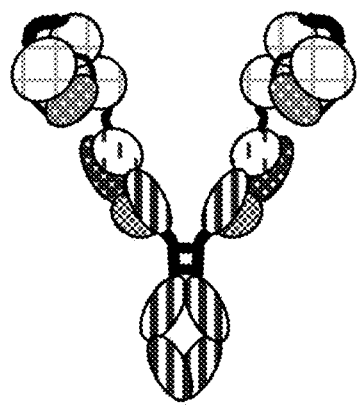
Figure 24C:
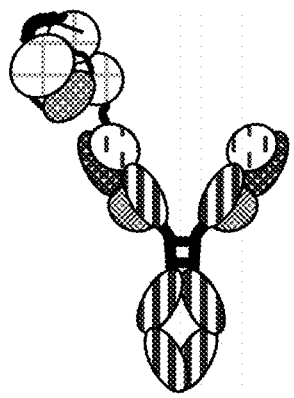
Figure 24D:
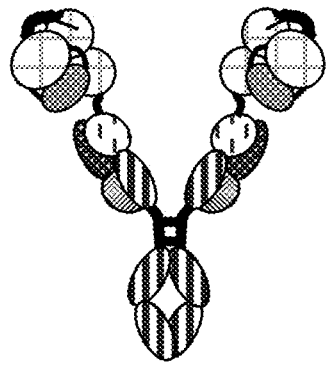

FIGS. 24A-D Multi-function proteins of the invention comprising a CMV-derived peptide and MCSP binding specificity, as generated and tested in Example 14. FIG. 24A depicts a [CMV-pp65-peptide]-[linker 1]-[β2-microglobulin]-[linker 2]-[HLA-A-α1-α2-α3]-[linker 3]-[IgG1-L234A, L235A mutant with hole variation], an Ig heavy chain (IgG1-L234A, L235A mutant with knob variation), and an Ig light chain. FIG. 24B depicts a [CMV-pp65-peptide]-[linker 1]-[β2-microglobulin]-[linker 2]-[HLA-A-α1-α2-α3]-[linker 3]-[IgG1-L234A, L235A mutant], and an Ig light chain. FIG. 24C depicts a [CMV-pp65-peptide]-[disulfide linker]-[β2-microglobulin]-[linker 2]-[disulfide HLA-A-α1-α2-α3]-[linker 3]-[IgG1-L234A, L235A, P329G mutant with hole variation], an Ig heavy chain (IgG1-L234A, L235A mutant with knob variation), and an Ig light chain. FIG. 24D depicts a [CMV-pp65-peptide]-[disulfide linker]-[β2-microglobulin]-[linker 2]-[disulfide HLA-A-α1-α2-α3]-[linker 3]-[IgG1-L234A, L235A, P329G mutant], and an Ig light chain.

| | Short description of the sequences |
|---|---|
| SEQ ID NO: 01 to 47 | Human cytomegalovirus-derived peptides. |
| SEQ ID NO: 48 | Human immunodeficiency virus-derived peptide. |
| SEQ ID NO: 49 | Human herpesvirus 4 derived peptide. |
| SEQ ID NO: 50 | Influenza A virus-derived peptide. |
| SEQ ID NO: 51 | Hepatitis-B-virus-derived peptide. |
| SEQ ID NO: 52 | Human T-cell lymphotropic virus type 1 derived peptide. |
| SEQ ID NO: 53 | V-jun Sarcoma Virus 17 Oncogene Homolog (JUN) derived peptide. |
| SEQ ID NO: 54 | Human adenovirus type 3-derived peptide. |
| SEQ ID NO: 55 | Hepatitis-C-virus-derived peptide. |
| SEQ ID NO: 56 to 70 | Dengue virus-derived peptides. |
| SEQ ID NO: 71 | Human β2-microglobulin amino acid sequence. |
| SEQ ID NO: 72 | Human HLA-A*0201 α1-α3 chain amino acid sequence. |
| SEQ ID NO: 73-84 | Linker peptide amino acid sequences. |
| SEQ ID NO: 85 | Human IgG1 CH2 domain amino acid sequence. |
| SEQ ID NO: 86 | Human IgG1 CH2 domain amino acid sequence. |
| SEQ ID NO: 87 | Human IgG1 Fc-region amino acid sequence. |
| SEQ ID NO: 88 | Human IgG1 Fc-region L234A, L235A mutant amino acid sequence. |
| SEQ ID NO: 89 | Human IgG1 Fc-region T366S, L368A, Y407V mutant amino acid sequence. |
| SEQ ID NO: 90 | Human IgG1 Fc-region T366W mutant amino acid sequence. |
| SEQ ID NO: 91 | Human IgG1 Fc-region L234A, L235A, T366S, L368A, Y407V mutant amino acid sequence. |
| SEQ ID NO: 92 | Human IgG1 Fc-region L234A, L235A, T366W mutant amino acid sequence. |
| SEQ ID NO: 93 | Human IgG1 Fc-region P329G mutant amino acid sequence. |
| SEQ ID NO: 94 | Human IgG1 Fc-region L234A, L235A, P329G mutant amino acid sequence. |
| SEQ ID NO: 95 | Human IgG1 Fc-region P329G, T366S, L368A, Y407V mutant amino acid sequence. |
| SEQ ID NO: 96 | Human IgG1 Fc-region P329G, T366W mutant amino acid sequence. |

-continued

| | Short description of the sequences |
|---|---|
| SEQ ID NO: 97 | Human IgG1 Fc-region L234A, L235A, P329G, T366S, L368A, Y407V mutant amino acid sequence. |
| SEQ ID NO: 98 | Human IgG1 Fc-region L234A, L235A, P329G, T366W mutant amino acid sequence. |
| SEQ ID NO: 99 | Human IgG4 Fc-region amino acid sequence. |
| SEQ ID NO: 100 | Human IgG4 Fc-region S228P, L235E mutant amino acid sequence. |
| SEQ ID NO: 101 | Human IgG4 Fc-region S228P, L235E, P329G mutant amino acid sequence. |
| SEQ ID NO: 102 | Human IgG4 Fc-region S228P, L235E, P329G, T366S, L368A, Y407V mutant amino acid sequence. |
| SEQ ID NO: 103 | Human IgG4 Fc-region S228P, L235E, P329G, T366W mutant amino acid sequence. |
| SEQ ID NO: 104 | HVR-L1 |
| SEQ ID NO: 105 | HVR-L2 |
| SEQ ID NO: 106 | HVR-L3 |
| SEQ ID NO: 107 | HVR-L1 |
| SEQ ID NO: 108 | HVR-H1 |
| SEQ ID NO: 109 | HVR-H2 |
| SEQ ID NO: 110 | HVR-H3 |
| SEQ ID NO: 111 | HVR-H1 |
| SEQ ID NO: 112 | HVR-H2 |
| SEQ ID NO: 113 | VL |
| SEQ ID NO: 114 | VH |
| SEQ ID NO: 115 | VL |
| SEQ ID NO: 116 | VH |
| SEQ ID NO: 117 | MHC-I-VH (MCSP)-IgG1 Fc-region L234A, L235A, P329G, T366S, L368A, Y407V mutant amino acid sequence. |
| SEQ ID NO: 118 | VH(MCSP)-IgG1 Fc-region L234A, L235A, P329G, T366W mutant amino acid sequence. |
| SEQ ID NO: 119 | VL(MCSP)-CL amino acid sequence. |
| SEQ ID NO: 120 | Humanized anti-IGF-1R monoclonal light chain antibody amino acid sequence (kappa). |
| SEQ ID NO: 121 | Humanized anti-IGF-1R monoclonal heavy chain antibody amino acid sequence (IgG1 L234A, L235A mutant). |
| SEQ ID NO: 122 | Humanized anti-IGF-1R monoclonal heavy chain antibody amino acid sequence (IgG1 L234A, L235A mutant and knob variant). |
| SEQ ID NO: 123 | Humanized anti-IGF-1R monoclonal heavy chain antibody amino acid sequence (IgG1 L234A, L235A mutant and hole variant). |
| SEQ ID NO: 124 | Human IgG1 Fc-region mutant hinge region and L234A, L235A mutant and knob variant. |
| SEQ ID NO: 125 | Disulfide-stabilized single chain Fv of humanized anti-IGF-1R monoclonal antibody. |
| SEQ ID NO: 126 | Murine anti-MCSP monoclonal light chain antibody amino acid sequence (kappa). |
| SEQ ID NO: 127 | Humanized anti-MCSP monoclonal light chain antibody amino acid sequence (kappa). |
| SEQ ID NO: 128 | Murine anti-MCSP monoclonal heavy chain antibody amino acid sequence (IgG1 L234A, L235A mutant). |
| SEQ ID NO: 129 | Humanized anti-MCSP monoclonal heavy chain antibody amino acid sequence (IgG1 L234A, L235A mutant). |
| SEQ ID NO: 130 | Murine anti-MCSP monoclonal heavy chain antibody amino acid sequence (IgG1 L234A, L235A mutant and knob variant). |
| SEQ ID NO: 131 | Humanized anti-MCSP monoclonal heavy chain antibody amino acid sequence (IgG1 L234A, L235A mutant and knob variant). |
| SEQ ID NO: 132 | Murine anti-MCSP monoclonal heavy chain antibody amino acid sequence (IgG1 L234A, L235A mutant and hole variant). |
| SEQ ID NO: 133 | Humanized anti-MCSP monoclonal heavy chain antibody amino acid sequence (IgG1 L234A, L235A mutant and hole variant). |
| SEQ ID NO: 134 | Disulfide-stabilized single chain Fv of murine anti-MCSP monoclonal antibody. |
| SEQ ID NO: 135 | Disulfide-stabilized single chain Fv of humanized anti-MCSP monoclonal antibody. |
| SEQ ID NO: 136 | Linker peptide 13. |
| SEQ ID NO: 137 | Disulfide-stabilized MHC-I-VH (MCSP)-IgG1 Fc-region L234A, L235A, P329G, T366S, L368A, Y407V mutant amino acid sequence. |
| SEQ ID NO: 138 | Amino acid sequence of human MCSP. |
| SEQ ID NO: 139 | Linker for disulfide-linked multi-function proteins. |
| SEQ ID NO: 140 | Modified human HLA-A*0201 α1-α3 chain amino acid sequence for disulfide-linked multi-function proteins. |
| SEQ ID NO: 141 | VH (MCSP)-IgG1 Fc-region L234A, L235A, P329G, T366S, L368A, Y407V mutant amino acid sequence. |
| SEQ ID NO: 142 | VH (MCSP)-IgG1 Fc-region L234A, L235A, P329G, T366W mutant amino acid sequence. |

I. DEFINITIONS

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "amino acid" as used within this application denotes the group of carboxy α-amino acids, which directly or in form of a precursor can be encoded by a nucleic acid. The individual amino acids are encoded by nucleic acids consisting of three nucleotides, so called codons or base-triplets. Each amino acid is encoded by at least one codon. This is known as "degeneration of the genetic code". The term "amino acid" as used within this application denotes the naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The terms "anti-target antibody" and "an antibody that binds to a target" refer to an antibody that is capable of binding a target with sufficient affinity such that the antibody is useful as a diagnostic and/or therapeutic agent in targeting the target. In certain embodiments, an antibody that binds to the target has a dissociation constant (Kd) of ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); single domain antibodies; and multispecific antibodies formed from antibody fragments.

The term "antigen binding site" denotes a proteinaceous moiety that can specifically bind to a target. Exemplary antigen binding sites are peptides, antibody fragments, domain antibodies, or variable domains of single chain antibodies (e.g. camel or shark antibodies). The antigen binding site can be a naturally occurring antigen binding site or an engineered antigen binding site. Exemplary engineered antigen binding sites are DARPINs, domain exchanged antibodies or domain exchanged antibody fragments, and dual variable domain antibodies.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called $\alpha$, $\delta$, $\epsilon$, $\gamma$, and $\mu$, respectively.

The term "class I MHC molecule with a relative frequency of" denotes that the respective class I MHC molecule has a frequency of occurrence in a specific population of humans or within all humans of the given relative frequency. That is a class I MHC molecule with a relative frequency of 10% or more can be found in 10% or more of all humans of a specific population, such as e.g. in 27.2% of all humans of European origin.

The "conjugation" of a multi-function protein to its conjugation partner can be performed by different methods, such as chemical binding, or binding via a specific binding pair, or via genetic fusion. The term "conjugation partner" denotes e.g. polypeptides, detectable labels, members of specific binding pairs. In one embodiment the conjugation of disulfide-linked multivalent multi-function protein to its conjugation partner is performed by chemically binding via N-terminal and/or $\epsilon$-amino groups (lysine), $\epsilon$-amino groups of different lysins, carboxy-, sulfhydryl-, hydroxyl-, and/or phenolic functional groups of the amino acid sequence of the parts of the disulfide-linked multivalent multi-function protein, and/or sugar alcohol groups of the carbohydrate structure of the disulfide-linked multivalent multi-function protein. In one embodiment the disulfide-linked multivalent multi-function protein is conjugated to its conjugation partner via a specific binding pair.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents.

Chromogens (fluorescent or luminescent groups and dyes), enzymes, NMR-active groups or metal particles, haptens, e.g. digoxigenin, are examples of "detectable labels". The detectable label can also be a photoactivatable crosslinking group, e.g. an azido or an azirine group. Metal chelates which can be detected by electrochemiluminescense are also suitable signal-emitting groups, with particular interest being given to ruthenium chelates, e.g. a ruthenium (bispyridyl)$_3^{2+}$ chelate. Suitable ruthenium labeling groups are described, for example, in EP 0 580 979, WO 90/05301, WO 90/11511, and WO 92/14138. For direct detection the labeling group can be selected from any known detectable marker groups, such as dyes, luminescent labeling groups such as chemiluminescent groups, e.g. acridinium esters or dioxetanes, or fluorescent dyes, e.g. fluorescein, coumarin, rhodamine, oxazine, resorufin, cyanine and derivatives thereof. Other examples of labeling groups are luminescent metal complexes, such as ruthenium or europium complexes, enzymes, e.g. as used for ELISA or for CEDIA (Cloned Enzyme Donor Immunoassay, e.g. EP-A-0 061 888), and radioisotopes.

"Effector functions" refer to those biological activities attributable to the Fc-region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "expression" as used herein refers to transcription and/or translation and secretion processes occurring within a cell. The level of transcription of a nucleic acid sequence of interest in a cell can be determined on the basis of the amount of corresponding mRNA that is present in the cell. For example, mRNA transcribed from a sequence of interest can be quantitated by RT-PCR or by Northern hybridization (see Sambrook, et al., Molecular Cloning: A Laboratory Manual, Second Edition, Cold Spring Harbor Laboratory Press, Cold Spring Harbor, N.Y. (1989)). Polypeptides encoded by a nucleic acid can be quantitated by various methods, e.g. by ELISA, by assaying for the biological activity of the polypeptide, or by employing assays that are independent of such activity, such as Western blotting or radioimmunoassay, using immunoglobulins that recognize and bind to the polypeptide (see Sambrook, et al., (1989), supra).

An "expression cassette" denotes a construct that contains the necessary regulatory elements, such as promoter and polyadenylation site, for expression of at least the contained nucleic acid in a cell.

The term "expression machinery" denotes the sum of the enzymes, cofactors, etc. of a cell that is involved in the steps beginning with the transcription step of a nucleic acid or gene (i.e. also called "gene expression machinery") to the post-translational modification of the polypeptide encoded by the nucleic acid. The expression machinery e.g. comprises the steps of transcription of DNA into pre-mRNA, pre-mRNA splicing to mature mRNA, translation into a polypeptide of the mRNA, and post translational modification of the polypeptide.

An "expression plasmid" is a nucleic acid providing all required elements for the expression of the comprised structural gene(s) in a host cell. Typically, an expression plasmid comprises a prokaryotic plasmid propagation unit, e.g. for *E. coli*, comprising an origin of replication, and a selectable marker, an eukaryotic selection marker, and one or more expression cassettes for the expression of the structural gene(s) of interest each comprising a promoter, a structural gene, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

The term "Fc-region" denotes the C-terminal region of an immunoglobulin heavy chain. The Fc-region is a dimeric molecule comprising two disulfide-linked antibody heavy chain polypeptides. An Fc-region can be generated by papain digestion, or IdeS digestion, or trypsin digestion of an intact (full length) antibody or can be produced recombinantly.

The Fc-region obtainable from a full length antibody or immunoglobulin comprises at least residues 226 (Cys) to the C-terminus of the full length heavy chain and, thus, comprises a part of the hinge region and two or three constant domains, i.e. a CH2 domain, a CH3 domain, and an additional/extra CH4 domain in case of IgE and IgM class antibodies. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A., et al., Sequences of Proteins of Immunological Interest, 5th ed., Public Health Service, National Institutes of Health, Bethesda, Md. (1991), NIH Publication 91-3242.

The formation of the dimeric Fc-region comprising two identical or non-identical antibody heavy chain Fc-region polypeptides is mediated by the non-covalent dimerization of the comprised CH3 domains (for involved amino acid residues see e.g. Dall'Acqua, Biochem. 37 (1998) 9266-9273). The Fc-region is covalently stabilized by the formation of disulfide bonds in the hinge region (see e.g. Huber, et al., Nature 264 (1976) 415-420; Thies, et al., J. Mol. Biol. 293 (1999) 67-79).

It is known from U.S. Pat. No. 5,648,260 and U.S. Pat. No. 5,624,821 that the modification of defined amino acid residues in the Fc-region results in phenotypic effects.

The disulfide-linked multivalent multi-function protein as reported herein may comprise in one embodiment as antibody heavy chain hinge region polypeptide a human Fc-region or an Fc-region derived from human origin. In a further embodiment the Fc-region is either an Fc-region of a human antibody of the subclass IgG4 or an Fc-region of a human antibody of the subclass IgG1, IgG2, or IgG3, which is modified in such a way that no Fcγ receptor (e.g. FcγRIIIa) binding and/or no C1q binding can be detected. In one embodiment the Fc-region is a human Fc-region and especially either from human IgG4 subclass or a mutated Fc-region from human IgG1 subclass. In one embodiment the Fc-region is from human IgG1 subclass with mutations L234A and L235A and P329G. While IgG4 shows reduced Fcγ receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, or/and His435 are residues which, if altered, provide also reduced Fcγ receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434). In one embodiment a disulfide-linked multivalent multi-function protein as reported herein is in regard to Fcγ receptor binding of IgG4 subclass or of IgG1 or IgG2 subclass, with a mutation in L234, L235, P329 and/or D265, and/or contains the PVA236 mutation. In one embodiment the mutations are S228P, L234A, L235A, L235E, PVA236 (PVA236 denotes that the amino acid sequence ELLG (given in one letter amino acid code) from amino acid position 233 to 236 of IgG1 or EFLG of IgG4 is replaced by PVA) and/or P329G. In one embodiment the mutations are S228P and P329G of IgG4, and L234A, L235A and P329G of IgG1. The Fc-region of an antibody is directly involved in ADCC (antibody-dependent cell-mediated cytotoxicity) and CDC (complement-dependent cytotoxicity). A disulfide-linked multivalent multi-function protein which does not bind Fcγ receptor and/or complement factor C1q does not elicit antibody-dependent cellular cytotoxicity (ADCC) and/or complement dependent cytotoxicity (CDC).

A polypeptide chain of a wild-type human Fc-region of the IgG1 isotype has the following amino acid sequence:

```
                                          (SEQ ID NO: 87)
EPKSADKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK.
```

A polypeptide chain of a variant human Fc-region of the IgG1 isotype with the mutations L234A, L235A has the following amino acid sequence:

```
                                          (SEQ ID NO: 88)
EPKSADKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVD

KSRWQQGNVFSCSVMHEALHNHYTQKSLSLSPGK.
```

A polypeptide chain of a variant human Fc-region of the IgG1 isotype with T366S, L368A and Y407V mutations has the following amino acid sequence:

```
                                          (SEQ ID NO: 89)
EPKSADKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVCTLPPSRDELTKNQVSL

SCAVKGFYPSDIAVEWESNGQPENNYKTTPPVLDSDGSFFLVSKLTVDKS

RWQQGNVFSCSVMHEALHNHYTQKSLSLSPGK.
```

A polypeptide chain of a variant human Fc-region of the IgG1 isotype with a T366W mutation has the following amino acid sequence:

```
                                          (SEQ ID NO: 90)
EPKSADKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPCRDELTKNQVSL

WCLVKGFYPSDIAVEWESNGQPENNYKTTPPVLDSDGSFFLYSKLTVDKS

RWQQGNVFSCSVMHEALHNHYTQKSLSLSPGK.
```

A polypeptide chain of a variant human Fc-region of the IgG1 isotype with a L234A, L235A and T366S, L368A and Y407V mutations has the following amino acid sequence:

(SEQ ID NO: 91)
EPKSADKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVCTLPPSRDELTKNQVSL
SCAVKGFYPSDIAVEWESNGQPENNYKTTPPVLDSDGSFFLVSKLTVDKS
RWQQGNVFSCSVMHEALHNHYTQKSLSLSPGK.

A polypeptide chain of a variant human Fc-region of the IgG1 isotype with a L234A, L235A and T366W mutation has the following amino acid sequence:

(SEQ ID NO: 92)
EPKSADKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPCRDELTKNQVSL
WCLVKGFYPSDIAVEWESNGQPENNYKTTPPVLDSDGSFFLYSKLTVDKS
RWQQGNVFSCSVMHEALHNHYTQKSLSLSPGK.

A polypeptide chain of a variant human Fc-region of the IgG1 isotype with a P329G mutation has the following amino acid sequence:

(SEQ ID NO: 93)
EPKSADKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALGAPIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPGK.

A polypeptide chain of a variant human Fc-region of the IgG1 isotype with a L234A, L235A and P329G mutation has the following amino acid sequence:

(SEQ ID NO: 94)
EPKSADKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALGAPIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPGK.

A polypeptide chain of a variant human Fc-region of the IgG1 isotype with a P239G and T366S, L368A and Y407V mutation has the following amino acid sequence:

(SEQ ID NO: 95)
EPKSADKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALGAPIEKTISKAKGQPREPQVCTLPPSRDELTKNQVSL
SCAVKGFYPSDIAVEWESNGQPENNYKTTPPVLDSDGSFFLVSKLTVDKS
RWQQGNVFSCSVMHEALHNHYTQKSLSLSPGK.

A polypeptide chain of a variant human Fc-region of the IgG isotype with a P329G and T366W mutation has the following amino acid sequence:

(SEQ ID NO: 96)
EPKSADKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALGAPIEKTISKAKGQPREPQVYTLPPCRDELTKNQVSL
WCLVKGFYPSDIAVEWESNGQPENNYKTTPPVLDSDGSFFLYSKLTVDKS
RWQQGNVFSCSVMHEALHNHYTQKSLSLSPGK.

A polypeptide chain of a variant human Fc-region of the IgG1 isotype with a L234A, L235A, P329G and T366S, L368A and Y407V mutation has the following amino acid sequence:

(SEQ ID NO: 97)
EPKSADKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALGAPIEKTISKAKGQPREPQVCTLPPSRDELTKNQVSL
SCAVKGFYPSDIAVEWESNGQPENNYKTTPPVLDSDGSFFLVSKLTVDKS
RWQQGNVFSCSVMHEALHNHYTQKSLSLSPGK.

A polypeptide chain of a variant human Fc-region of the IgG isotype with a L234A, L235A, P329G and T366W mutation has the following amino acid sequence:

(SEQ ID NO: 98)
EPKSADKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALGAPIEKTISKAKGQPREPQVYTLPPCRDELTKNQVSL
WCLVKGFYPSDIAVEWESNGQPENNYKTTPPVLDSDGSFFLYSKLTVDKS
RWQQGNVFSCSVMHEALHNHYTQKSLSLSPGK.

A polypeptide chain of a wild-type human Fc-region of the IgG4 isotype has the following amino acid sequence:

(SEQ ID NO: 99)
ESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGK.

A polypeptide chain of a variant human Fc-region of the IgG4 isotype with a S228P and L235E mutation has the following amino acid sequence:

(SEQ ID NO: 100)
ESKYGPPCPPCPAPEFEGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGK.

A polypeptide chain of a variant human Fc-region of the IgG4 isotype with a S228P, L235E and P329G mutation has the following amino acid sequence:

(SEQ ID NO: 101)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK.

A polypeptide chain of a variant human Fc-region of the IgG4 isotype with a S228P, L235E, P329G and T366S, L368A and Y407V mutation has the following amino acid sequence:

(SEQ ID NO: 102)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLSCA

VKGFYPSDIAVEWESNGQPENNYKTTPPVLDSDGSFFLVSRLTVDKSRWQ

EGNVFSCSVMHEALHNHYTQKSLSLSLGK.

A polypeptide chain of a variant human Fc-region of the IgG4 isotype with a S228P, L235E, P329G and T366W mutation has the following amino acid sequence:

(SEQ ID NO: 103)
ESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLGSSIEKTISKAKGQPREPQVYTLPPSQEEMTKNQVSLWCL

VKGFYPSDIAVEWESNGQPENNYKTTPPVLDSDGSFFLYSRLTVDKSRWQ

EGNVFSCSVMHEALHNHYTQKSLSLSLGK.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "cell" includes both prokaryotic cells, which are used for propagation of plasmids, and eukaryotic cells, which are used for the expression of a nucleic acid. In one embodiment the eukaryotic cell is a mammalian cell. In one embodiment the mammalian cell is selected from the group of mammalian cells comprising CHO cells (e.g. CHO K1, CHO DG44), BHK cells, NS0 cells, Sp2/0 cells, HEK 293 cells, HEK 293 EBNA cells, PER.C6® cells, and COS cells.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

An "immunoconjugate" denotes a disulfide-linked multivalent multi-function protein as reported herein conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" disulfide-linked multivalent multi-function protein is one which has been separated from a component of its natural environment. In some embodiments, a disulfide-linked multivalent multi-function protein is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "MCSP", as used herein, refers to any native MCSP (Melanoma Chondroitin Sulfate Proteoglycan) from any vertebrate source, including mammals such as primates (e.g. humans) and rodents (e.g., mice and rats), unless otherwise indicated. The term encompasses "full-length", unprocessed MCSP as well as any form of MCSP that results from processing in the cell. The term also encompasses naturally occurring variants of MCSP, e.g., splice variants or allelic variants. MCSP is also known as chondroitin sulfate proteoglycan 4 (CSPG4), chondroitin sulfate proteoglycan NG2, high molecular weight-melanoma associated antigen (HMW-MAA), and melanoma chondroitin sulfate proteoglycan. The amino acid sequence of an exemplary human MCSP is shown in SEQ ID NO: 1. See also Pluschke, G., et al., Proc. Natl. Acad. Sci. USA 93 (1996) 9710-9715, Staub, E., et al., FEBS Lett. 527 (2002) 114-118, and GenBank Accession No: NP_001888.

The term "one antigen presenting domain" denotes exactly one, i.e. a single, antigen presenting domain as defined and excludes the presence of a further, i.e. second, antigen presenting domains defined. The term "one" denotes "exactly one" or "a single".

The term "two antigen presenting domains" denotes the presence of exactly two antigen presenting domains as defined and excludes the presence of only a single, i.e. one, antigen presenting domain.

"Operably linked" refers to a juxtaposition of two or more components, wherein the components so described are in a relationship permitting them to function in their intended manner. For example, a promoter and/or enhancer are operably linked to a coding sequence, if it acts in cis to control or modulate the transcription of the linked sequence. Generally, but not necessarily, the DNA sequences that are "operably linked" are contiguous and, where necessary to join two protein encoding regions such as a secretory leader and a polypeptide, contiguous and in (reading) frame. However, although an operably linked promoter is generally located upstream of the coding sequence, it is not necessarily contiguous with it. Enhancers do not have to be contiguous. An enhancer is operably linked to a coding sequence if the enhancer increases transcription of the coding sequence. Operably linked enhancers can be located upstream, within or downstream of coding sequences and at considerable distance from the promoter. A polyadenylation site is operably linked to a coding sequence if it is located at the downstream end of the coding sequence such that transcription proceeds through the coding sequence into the polyadenylation sequence. A translation stop codon is operably linked to an exonic nucleic acid sequence if it is located at the downstream end (3' end) of the coding sequence such that translation proceeds through the coding sequence to the stop codon and is terminated there. Linking is accomplished by recombinant methods known in the art, e.g., using PCR methodology and/or by ligation at convenient restriction sites. If convenient restriction sites do not exist, then synthetic oligonucleotide adaptors or linkers are used in accord with conventional practice.

The term "package insert" is used to refer to instructions customarily included in commercial packages of therapeutic products, that contain information about the indications, usage, dosage, administration, combination therapy, contraindications and/or warnings concerning the use of such therapeutic products.

The term "peptide linker" denotes amino acid sequences of natural and/or synthetic origin. They consist of a linear amino acid chain wherein the 20 naturally occurring amino acids are the monomeric building blocks. The peptide linker has a length of from 1 to 50 amino acids, in one embodiment between 1 and 28 amino acids, in a further embodiment between 2 and 25 amino acids. The peptide linker may contain repetitive amino acid sequences or sequences of naturally occurring polypeptides. The linker has the function to ensure that polypeptides conjugated to each other can perform their biological activity by allowing the polypeptides to fold correctly and to be presented properly. In one embodiment the peptide linker is rich in glycine, glutamine, and/or serine residues. These residues are arranged e.g. in small repetitive units of up to five amino acids, such as GS (SEQ ID NO: 73), GGS (SEQ ID NO: 74), GGGS (SEQ ID NO: 75), and GGGGS (SEQ ID NO: 80). This small repetitive unit may be repeated for one to five times. At the amino- and/or carboxy-terminal ends of the multimeric unit up to six additional arbitrary, naturally occurring amino acids may be added. Other synthetic peptidic linkers are composed of a single amino acid, which is repeated between 10 to 20 times and may comprise at the amino- and/or carboxy-terminal end up to six additional arbitrary, naturally occurring amino acids. All peptidic linkers can be encoded by a nucleic acid molecule and therefore can be recombinantly expressed. As the linkers are themselves peptides, the polypeptide connected by the linker are connected to the linker via a peptide bond that is formed between two amino acids.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

A "polypeptide" is a polymer consisting of amino acids joined by peptide bonds, whether produced naturally or synthetically. Polypeptides of less than about 25 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell.

Polypeptides are defined herein in terms of their amino acid backbone structure or the nucleic acid encoding the same. Additions such as carbohydrate groups are generally not specified, but may be present nonetheless.

A "structural gene" denotes the region of a gene without a signal sequence, i.e. the coding region.

The term "T-cell response eliciting peptide" denotes a peptide that is presented in the peptide-binding grove of a class I MHC multi-function protein and which is recognized by circulating memory or effector T-cells. Recognition of the peptide results in an immune response effecting the removal of the cell presenting such a peptide-class I MHC multi-function protein.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J., et al., Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S., et al., J. Immunol. 150 (1993) 880-887; Clackson, T., et al., Nature 352 (1991) 624-628).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. COMPOSITIONS AND METHODS

A. Exemplary Disulfide-Linked Multivalent Multi-Function Protein

Herein is reported an antigen binding disulfide-linked multivalent multi-function protein comprising as first part an antibody derived part that specifically binds to a target antigen, and as second part a virus-derived peptide linked to a MHC class I protein complex.

With the disulfide-linked multivalent multi-function protein as reported herein existing virus-specific circulating cytotoxic T-cells (T-memory-cells and/or T-effector-cells) of an individual can be directed to cells expressing the target antigen, to which the antibody derived part of the disulfide-linked multivalent multi-function protein specifically binds to, by dressing these cells with MHC class I multi-function complexes mimicking an acute viral infection.

In one aspect, the invention is based, in part, on the finding that a disulfide-linked multivalent multi-function protein as reported herein, which comprises as first part a virus-derived peptide linked to a MHC class I protein and as second part an antibody derived disulfide-linked molecule, can be used to direct existing virus-specific cytotoxic T-cells of an individual to cells expressing a target antigen mimicking an acute viral infection and thereby elimination (removal) of the cells expressing the target antigen can be initiated.

It has been found that in contrast to non-disulfide-linked MHC class I comprising multi-function proteins, in which at most a single MHC class I unit in combination with an antibody hinge region can be present to allow recombinant production, in disulfide-linked MHC class I comprising multi-function proteins one, two or more disulfide-linked MHC class I units can be present without hampering recombinant production in combination with an antibody hinge region in the multivalent multi-function protein.

By using a disulfide-linked multivalent multi-function protein as reported herein comprising one, i.e. a single, antigen presenting domain, some modes of action of the disulfide-linked multivalent multi-function protein as reported herein comprising two or more antigen presenting domains are no longer possible, such as cross-linking of T-cell receptors. Additionally disulfide-linked multivalent multi-function proteins as reported herein comprising one antigen presenting domain con be produced with improved yields and have an improve thermal stability. Further without being bound by this theory disulfide-linked multivalent multi-function proteins as reported herein comprising one antigen presenting domain are more specific with respect to T-cell activation (see Example 15).

In certain embodiments a disulfide-linked multivalent multi-function protein comprising one, two or more antigen presenting domains each comprising (i) a virus-derived peptide, (ii) the soluble HLA-A allele A*0201, and (iii) beta-2-microglobulin, wherein the antigen presenting domain has cysteine residues at least at position 11 and at position 227 and the cysteine residues at position 11 and position 227 form a disulfide bond, is provided.

In certain embodiments a disulfide-linked multivalent multi-function protein comprising one, two or more antigen presenting domains each comprising (i) a virus-derived peptide, (ii) the soluble HLA-A allele A*0201, and (iii) beta-2-microglobulin, wherein the antigen presenting domain has cysteine residues at least at position 11 and at position 108 and the cysteine residues at position 11 and position 108 form a disulfide bond, is provided.

Disulfide-linked multivalent multi-function proteins as reported herein are useful, e.g., for the diagnosis or treatment of various diseases like cancer or viral infections.

In one aspect, the invention provides a multi-functions protein that hinds (i) to a cell surface antigen and (ii) to cytotoxic T-cells.

The disulfide-linked multivalent multi-function proteins as reported herein exploit a naturally occurring, highly effective anti-viral immune response to eliminate/remove/disintegrate target cells, e.g. tumor cells or virus infected cells. The cell elimination is achieved by using an individual's own very powerful circulating T-cells that do not need any co-stimulation for their activation. Additionally a small number of therapeutic molecules are needed on the cell surface for this mechanism of action (see e.g. Mottez et al., J. Exp. Med. 181 (1995) 493-502).

During the treatment the disulfide-linked multivalent multi-function protein can trigger the anti-viral immune response of the individual similar to an immunization. Thereby multiple treatments/applications can enhance the efficacy of the treatment. Thus, an immunization as pretreatment can be used in order to enhance efficacy.

Also an allotype can be used whose frequency within the population is very low, as in one embodiment below I %. The use of such an allotype may make an immunization step obsolete as the allotype will be recognized by the individual's immune system as foreign and an immune response will be initiated.

The targeting antigen binding site needs to be highly cell or antigen specific to limit toxicity and side effects.

Thus by using a disulfide-linked multivalent multi-function protein as reported herein (i) only a highly specific T-cell population is activated (CD8 positive effector/memory cells specific for a single virus-derived peptide displayed in the MHC-I protein complex of the disulfide-linked multivalent multi-function protein), all other $CD3^+$-cells are not affected ($CD4^+$-T-cells: TH1, TH2, TH17, regulatory T-cells);

(ii) the natural response of the individual's immune system is mimicked (normal removal of virus-infected cells); and (iii) the response to the application/treatment of/with the disulfide-linked multivalent multi-function protein will be low at the beginning but can boost during treatment (specific T-cells will be activated and expand in number), therewith initially infusion reactions and initial cytokine release can be reduced.

In one embodiment the method comprises the step of stimulating CD8-positive cytotoxic T-cell by application of a selected virus-derived peptide, e.g. a human cytomegalovirus (huCMV) derived peptide. In one preferred embodiment the peptide has the amino acid sequence of SEQ ID NO: 01.

It has been shown that the activated CMV-peptide specific T-cells mediate effective tumor cell removal in vitro (tumor cells loaded with the CMV-derived peptide in vitro).

Virus-infected cells present a complex of virus-derived peptides with MHC class I proteins on their cell surface. These are recognized by specific $CD8^+$ T-cells which remove/deplete the virus-derived peptide presenting cells. Cytolytic (cytotoxic) $CD8^+$-T-cells (CTL) recognize peptides in MHC class I proteins by their specific T-cell-receptor. The CTLs trigger removal of virus infected cells without the requirement of a co-stimulating signal.

Effector cells, e.g. peripheral blood mononuclear cells (PBMC) or FACS-sorted $CD8^+$-T-cells, which can be prestimulated with the CMV-derived peptide as comprised in the fusion polypeptide as reported herein can be used.

The HLA-allotype of an individual to be treated has to be recognized.

According to NCBI the HLA-allotypes with a frequency of 10% or more are distributed as it is shown in the following table.

TABLE

| HLA- | HLA-allotype | | | |
|---|---|---|---|---|
| | Australian frequency [%] | European frequency [%] | North American frequency [%] | South-East Asian frequency [%] |
| A*01:01 | | 16.4 | | |
| A*02:01 | 12.7 | 27.2 | 19.7 | |
| A*02:04 | | | | |
| A*03:01 | | 14.1 | | |
| A*11:01 | 13.5 | | | 20.4 |
| A*24:02 | 25.9 | | 37.7 | 29.9 |
| A*31:01:02 | | | | |
| A*34:01:01 | 40.1 | | | |
| B*07:02 | | 13.9 | | |
| B*08:01 | | 11.8 | | |
| B*13:01 | 23.8 | | | |
| B*15:04 | | | | 11.7 |
| B*15:21 | 10.6 | | | |
| B*44:02 | | 10.6 | | |
| B*56:01 | 16.1 | | | |
| B*56:02 | 10.3 | | | |
| C*01:02 | 24.6 | | | 13.3 |
| C*02:02 | | | 12.7 | |
| C*03:03 | | | | |
| C*03:04 | | | 20.4 | 17.3 |
| C*04:01 | 26.0 | 10.1 | 15.0 | |
| C*04:03 | 13.9 | | | |
| C*05:01 | | 10.6 | | |
| C*06:02 | | | | |
| C*07:01 | | 17.0 | | |
| C*07:02 | | 15.9 | 10.2 | 18.9 |
| C*08:01 | | | | 12.8 |
| C*15:02 | 16.5 | | | |

Thus, one aspect as reported herein is an antigen binding disulfide-linked multivalent multi-function protein, characterized in that it comprises
one, two or more antigen presenting domains,
one antibody Fc-region, and
one or more antigen binding sites,
wherein the antigen presenting domains comprise independently of each other in N- to C-terminal direction either
  (i) a β2-microglobulin, and
  (ii) the extracellular domains α1, α2, and α3 of a class I MHC molecule with a relative frequency of less than 1%,
or
  (i) the extracellular domains α1, α2, and α3 of a class I MHC molecule with a relative frequency of less than 1%, and
  (ii) a β2-microglobulin,
or
  (i) a T-cell response eliciting peptide,
  (ii) a β2-microglobulin, and
  (iii) the extracellular domains α1, α2, and α3 of a class I MHC molecule with a relative frequency of 1% or more,
or
  (i) a T-cell response eliciting peptide,
  (ii) the extracellular domains α1, α2, and α3 of a class I MHC molecule with a relative frequency of 1 % or more, and
  (iii) a β2-microglobulin,
wherein the antigen binding site binds to a cancer cell surface antigen,
wherein the antigen presenting domain has cysteine residues at least at position 11 and at position 227 and the cysteine residues at position 11 and position 227 form a disulfide bond.

In one embodiment an antigen presenting domain that comprises in N- to C-terminal direction a β2-microglobulin and the extracellular domains α1, α2, and α3 of a class I MHC molecule with a relative frequency of less than 1% further comprises at its N-terminus a peptide binding to the MHC-peptide binding grove, wherein the antigen presenting domain has cysteine residues at least at position 11 and at position 227 and the cysteine residues at position 11 and position 227 form a disulfide bond. In one embodiment the peptide is a T-cell-response eliciting peptide.

In one embodiment the T-cell-response eliciting peptide is a virus-derived peptide. In one embodiment the virus is selected from adenovirus, human herpesvirus 1, human herpesvirus 2, human herpesvirus 4 (Epstein-Barr virus), hepatitis-B-virus, hepatitis-C-virus, human cytomegalovirus, human immunodeficiency virus, human papillomavirus type 16, human papillomavirus type 18, human papillomavirus type 31, human papillomavirus type 33, human papillomavirus type 35, human papillomavirus type 39, human papillomavirus type 45, human papillomavirus type 51, human papillomavirus type 52, human papillomavirus type 56, human papillomavirus type 58, human papillomavirus type 59, human papillomavirus type 68, human papillomavirus type 73, human papillomavirus type 82, human T-cell lymphotropic virus type I, human influenza A virus, human influenza B virus, or vaccinia virus.

In one embodiment the virus-derived peptide is selected from NLVPMVATV (SEQ ID NO: 01), SLYNTVATL (SEQ ID NO: 48), GLCTLVAML (SEQ ID NO: 49), GILGFVFTL (SEQ ID NO: 50), STNRQSGRQ (SEQ ID NO: 51), LLFGYPVYV (SEQ ID NO: 52), FAEGFVRAL (SEQ ID NO: 53), LIVIGILIL (SEQ ID NO: 54), or ILHTPGCV (SEQ ID NO: 55).

In one embodiment the β2-microglobulin is human β2-microglobulin. In one embodiment the β2-microglobulin is consisting of the amino acid sequence of SEQ ID NO: 71.

In one embodiment the class I MHC molecule with a relative frequency of I % or more is human HLA-A*0201. In one embodiment the extracellular domains α1, α2, and α3 of a class I MHC molecule is consisting of the amino acid sequence of SEQ ID NO: 140.

In one embodiment the virus-derived peptide is fused to the β2-microglobulin via a first linker peptide.

In one embodiment the β2-microglobulin is fused to the extracellular domain α1 of a class I MHC molecule via a second linker peptide.

In one embodiment the extracellular domain α3 of a class I MHC molecule is fused to the polypeptide (either disulfide-linked or not disulfide-linked) via a third linker peptide.

In one embodiment the first, second, and third linker peptide is the same or different.

In one embodiment the first linker peptide, the second linker peptide, and the third linker peptide are selected independently from each other from the amino acid sequences GS (SEQ ID NO: 73), GGS (SEQ ID NO: 74), GGGS (SEQ ID NO: 75), GGGSGGS (SEQ ID NO: 76), GGGSGGGSGGGS (SEQ ID NO: 77), GGGSGGGSGGGSGGGS (SEQ ID NO: 78), GGGSGGGSGGGSGGGSGGGS (SEQ ID NO: 79), GGGGS (SEQ ID NO: 80), GGGGSGGGGS (SEQ ID NO: 81), GGGGSGGGGSGGGGS (SEQ ID NO: 82), GGGGSGGGGSGGGGSGGGGS (SEQ ID NO: 83), GGGGSGGGGSGGGGSGGGGSGGGGS (SEQ ID NO: 84), and GCGGSGGGGSGGGGS (SEQ ID NO: 139).

In one embodiment the first linker peptide comprises the amino acid sequence of SEQ ID NO: 82.

In one embodiment the second linker peptide comprises the amino acid sequence of SEQ ID NO: 83.

In one embodiment the third linker peptide comprises the amino acid sequence of SEQ ID NO: 73.

In one embodiment the antibody Fc-region is selected from an antibody Fc-region of a human antibody of the class IgG or the class IgE.

In one embodiment the antibody Fc-region is selected from an antibody Fc-region of a human antibody of the subclass IgG1, or IgG2, or IgG3, or IgG4.

In one embodiment the first disulfide-linked polypeptide and the second disulfide-linked polypeptide comprises a CH2 domain and a CH3 domain of human origin. In one embodiment the CH2 domain and the CH3 of human origin is of a human antibody of the class IgG or IgE. In one embodiment the CH2 domain and the CH3 domain is of a human antibody of the subclass IgG1, or IgG2, or IgG3, or IgG4. In one embodiment the CH2 domain comprises the amino acid sequence of SEQ ID NO: 85. In one embodiment the CH2 domain is of a human antibody of the subclass IgG1 or IgG2 and comprises at least one mutation of E233, L234, L235, G236, D265, D270, N297, E318, K320, K322, A327, P329, A330, and/or P331 (numbering according to the EU index of Kabat). In one embodiment the CH2 domain is of a human antibody of the subclass IgG1 or the human subclass IgG2 with the mutations L234A and L235A, and/or the mutations D265A and N297A, and/or contains the PVA236 mutation, and/or contains the mutation P329G. In one embodiment the CH2 domain is of a human antibody of the subclass IgG1 with the mutations L234A and L235A, and/or P329G. In one embodiment the CH2 domain is of a human antibody of the subclass IgG4 with the mutations S228P and/or L235E.

In one embodiment the first disulfide-linked polypeptide comprises the amino acid sequence of SEQ ID NO: 89 and the second disulfide-linked polypeptide comprises the amino acid sequence of SEQ ID NO: 90.

In one embodiment the first and the second disulfide-linked polypeptide comprise the amino acid sequence of SEQ ID NO: 94 or SEQ ID NO: 101.

In one embodiment the first disulfide-linked polypeptide or the second disulfide-linked polypeptide is consisting of the amino acid sequence of SEQ ID NO: 97 or SEQ ID NO: 98.

In one embodiment the first disulfide-linked polypeptide comprises the amino acid sequence of SEQ ID NO: 102 and the second disulfide-linked polypeptide comprises the amino acid sequence of SEQ ID NO: 103.

In one embodiment the disulfide-linked polypeptides are linked by two, or three, or four disulfide bonds.

In one embodiment the antigen presenting domain is characterized in that it comprises in N- to C-terminal direction
(i) a virus-derived peptide that has an amino acid sequence of SEQ ID NO: 01,
(ii) a first linker peptide that has an amino acid sequence of SEQ ID NO: 139.
(iii) a β2-microglobulin that has an amino acid sequence of SEQ ID NO: 71,
(iv) a second linker peptide that has an amino acid sequence of SEQ ID NO: 83,
(v) the extracellular domains α1, α2, and α3 of a class I MHC molecule that has an amino acid sequence of SEQ ID NO: 140,
(vi) a third linker peptide that has an amino acid sequence of SEQ ID NO: 136, and
(vii) a cysteine residues at least at position 11 and at position 227 and the cysteine residues at position 11 and position 227 form a disulfide bond.

In one embodiment the antigen presenting domain is characterized in that it comprises in N- to C-terminal direction
(i) a virus-derived peptide that has an amino acid sequence of SEQ ID NO: 01,
(ii) a first linker peptide that has an amino acid sequence of SEQ ID NO: 139.
(iii) a β2-microglobulin that has an amino acid sequence of SEQ ID NO: 71,
(iv) a second linker peptide that has an amino acid sequence of SEQ ID NO: 83,
(v) the extracellular domains α1, α2, and α3 of a class I MHC molecule that has an amino acid sequence of SEQ ID NO: 140,
(vi) a third linker peptide that has an amino acid sequence of SEQ ID NO: 136, and
(vii) a cysteine residues at least at position 11 and at position 108 and the cysteine residues at position 11 and position 108 form a disulfide bond.

From FIGS. 10A-C it can be seen that a multi-function protein maintains the binding properties of the antigen binding site with which it is combined (FIG. 10 B and C).

In FIGS. 11 and 13 the in vitro efficacy and specificity of a multi-function protein is shown.

The cytotoxicity assay was performed in the presence of CMV-specific CD8$^+$ T-cells. It can be seen that a multi-function protein comprising a CMV-derived virus peptide induce the lysis/removal/disintegration/elimination of the target cells (see FIG. 11 *a*) for monovalent antibody, FIG. 11 *b*) for bivalent antibody). It can further be seen that the lysis of the target cells is highly specific as the incubation with the multi-function protein comprising an EBV-derived viral peptide (FIG. 11 *b*)) and control antibodies (FIG. 11 *d*) and *e*)) do not result in extensive cell lysis (the spontaneous lysis is about 3.5%).

In FIG. 13 the lysis of IGF-1R positive lung adenocarcinoma cell line H460M2 is shown.

The EC$_{50}$ value for a multi-function protein comprising a CMV-derived peptide and a bivalent antibody is about 10 ng/ml corresponding to about 50 pM. The determined EC$_{50}$ value is independent from the target cell to effector cell ratio (see FIG. 12; target cell to effector cell ratio from 1:3 to 1:1 corresponding to an effective ratio of 1:0.44 to 1:0.14 (76% of effector cells are CD8 positive and 19% are CMV specific)).

1. Affinity

In certain embodiments, a disulfide-linked multivalent multi-function protein as provided herein comprises an antigen binding site derived from an antibody, e.g. a pair of antibody variable domains or a single domain antibody. In certain embodiments the antigen binding site has a dissociation constant (Kd) of ≤10 nM, ≤1 nM, ≤0.1 nM, ≤0.01 nM, or ≤0.001 nM (e.g. $10^{-8}$ or less, e.g. from $10^{-8}$ M to $10^{-13}$ M, e.g., from $10^{-9}$ M to $10^{-13}$ M) with respect to its antigen.

In one embodiment, Kd is measured using surface plasmon resonance assays.

For example this can be done by using a BIACORE®-2000 or a BIACORE®-3000 instrument (BIAcore, Inc., Piscataway, N.J.) at 25° C. with immobilized antigen CM5 chips at ~10 response units (RU). Briefly, carboxymethylated dextran biosensor chips (CM5, BIAcore, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon. See, e.g., Chen, Y., et al., J. Mol. Biol. 293 (1999) 865-881.

2. Expression

Expression of different non-disulfide-linked bivalent multi-function proteins (different linker, different combinations of HLA and β2-microglobulin) in HEK 293 and CHO cells led to an accumulation of the non-disulfide-linked bivalent multi-function protein, if detectable at all, within the endoplasmatic reticulum, i.e. isolation and secretion of the non-disulfide-linked bivalent multi-function protein was strongly impaired if detectable at all.

No secretion of a non-disulfide-linked multi-function protein to the cultivation medium could be detected when the multi-function protein was intended to comprise one of the polypeptides as outlined in the following tables.

virus-derived peptide linked to a MHC class I protein complex, and at least one variable domain and one constant domain of an antibody is possible in eukaryotic cells. Additionally the expression yield is increased compared to the non-disulfide-linked complexes.

Thus, in a multi-function protein as reported herein one, two or more disulfide-linked antigen presenting domains comprising a virus-derived peptide linked to a MHC class I protein and one or more antibody variable domain and one antibody constant domain can be present still allowing for the recombinant production and the secretion of the disulfide-linked multivalent multi-function protein using eukaryotic cells.

Thus, a multi-function protein comprising one, two or more disulfide-linked antigen presenting domains of a virus-derived peptide linked to a MHC class I protein, an antibody heavy chain hinge region, and one or more antibody variable domains and one antibody constant domain can be recombinantly produced in and secreted from eukaryotic cells.

Thus, a multi-function protein comprising an antibody heavy chain hinge region, at least one pair of antibody variable domains, optionally an antibody constant domain, and one, two or more disulfide-linked antigen presenting domains of a virus-derived peptide linked to a MHC class I protein can be recombinantly produced in and secreted from eukaryotic cells.

Various combinations were tested. Secreted expression of multi-function proteins can be accomplished by e.g. N-terminal fusion of an immunoglobulin-derived signal peptide

TABLE

| signal peptide | CMV-derived peptide | | β2-microglobulin | | α1-α2-α3-chains | | IgG-Fc-region | | scFv |
|---|---|---|---|---|---|---|---|---|---|
| signal peptide | CMV-derived peptide | | β2-microglobulin | | α1-α2-α3-chains | | antibody heavy chain | | |

| signal peptide | CMV-derived peptide | $G_4S(G_3S)_2$-linker | β2-microglobulin | $(G_4S)_3$-linker | α1-α2-α3-chains | $(G_4S)_2$-linker | antibody light chain | | |
| signal peptide | β2-microglobulin | $(G_4S)_3$-linker | α1-α2-α3-chains | $(G_4S)_2$-linker | antibody light chain | | | | |
| signal peptide | CMV-derived peptide | $(G_3S)_2GG$-linker | α1-α2-α3-chains | $(G_4S)_3$-linker | β2-microglobulin | $(G_4S)_2$-linker | antibody light chain | | |
| signal peptide | CMV-derived peptide | GGPGGGSGGG-linker | α1-α2-α3-chains | $(G_4S)_3$-linker | β2-microglobulin | $(G_4S)_2$-linker | antibody light chain | | |
| signal peptide | α1-α2-α3-chains | $(G_4S)_3$-linker | β2-microglobulin | $(G_4S)_2$-linker | antibody light chain | | | | |
| signal peptide | CMV-derived peptide | $(G_3S)_2GG$-linker | α1-α2-α3-chains | $(G_4S)_3$-linker | antibody light chain | | | | |
| signal peptide | CMV-derived peptide | GGPGGGSGGG-linker | α1-α2-α3-chains | $(G_4S)_3$-linker | antibody light chain | | | | |
| signal peptide | CMV-derived peptide | $(G_3S)_2GG$-linker | α1-α2-α3-chains | $(G_4S)_3$-linker | β2-microglobulin | $(G_4S)_2$-linker | antibody heavy chain | | |

It has been found that the expression, and especially the secretion, of multi-function proteins comprising two non-disulfide-linked antigen presenting domains formed of a virus-derived peptide linked to a MHC class I protein complex, and at least one variable domain and one constant domain of an antibody is not possible in eukaryotic cells.

Further it has been found that the expression, and especially the secretion, of multi-function proteins comprising two non-disulfide-linked antigen presenting domains formed of a virus-derived peptide linked to a MHC class I protein multi-function protein, at least one variable domain, and an antibody hinge region is not possible in eukaryotic cells.

But it has been found that the expression, and especially the secretion, of multi-function proteins comprising one or two disulfide-linked antigen presenting domains formed of a wherein the virus-derived peptide is fused N-terminally to the class I MHC molecule. Class I MHC molecule heavy chain (α1-α2-α3 lacking the transmembrane and the cytoplasmatic domain) and light chain (β2-microglobulin) can be changed in order. The different antigen presenting domains were N-terminally fused to either an antibody light chain or an antibody heavy chain hinge region comprising polypeptide. Exemplary combinations are shown in FIG. 2.

As can be seen from the following Table multi-function proteins comprising one, two or more antigen presenting domains containing an MHC-I protein complex can be expressed in the presence of variable antibody domain and antibody hinge region derived polypeptides when the antigen presenting domains are disulfide-linked. Further the obtainable yield is increased.

TABLE

| FIG. | number of virus-derived peptide-class I MHC fusion polypeptide | number of variable domains | number of constant domains | disulfide-linked antigen presenting domain | contains antibody heavy chain hinge region comprising polypeptide | expression Level | lane in FIG. 3 |
|---|---|---|---|---|---|---|---|
| FIG. 22A | 2 | 0 | 0 | no | yes | high | 1 |
| FIG. 22B | 1 | 0 | 0 | no | yes | high | 2 |
| FIG. 22C | 1 | 1 | 1 | no | yes | high | 3 |
| FIG. 22D | 1 | 2 | 2 | no | yes | high | 4 |
| FIG. 22E | 2 | 2 | 2 | no | yes | no expression | 5 |
| FIG. 22F | 2 | 2 | 2 | no | yes | no expression | 6 |
| FIG. 22G | 2 | 2 | 2 | no | yes | very low | 7 |
| FIG. 22H | 2 | 2 | 0 | no | yes | no expression | 8 |
| FIG. 22I | 1 | 1 | 1 | no | yes | high | 9 |
| FIG. 22J | 1 | 1 | 1 | yes | yes | high | n.a. |
| FIG. 22K | 2 | 2 | 2 | yes | yes | high | n.a. |

In some embodiments the disulfide-linked multivalent multi-function protein as reported herein comprises different pairs of polypeptides. In order to allow proper pairing of the polypeptides the knobs-into-holes technology or the cross-mAb technology can be used in order to reduce the amount of not correctly associated multi-function protein.

The knob modification denotes the mutation T366W in the CH3 domain of an antibody (numbering according to EU index of Kabat).

The hole-modification denotes the mutations T366S, L368A and Y407V in the CH3 domain of an antibody (numbering according to EU index of Kabat).

In addition to the knob and hole modification the mutation S354C in the one CH3 domain and the mutation Y349C in the other CH3 domain can be present.

The cross-mAb technology is reported e.g. in WO 2009/080251, WO 2009/080252, WO 2009/080254, WO 2009/080253, WO 2010/112193, WO 2010/115589, WO 2010/136172, WO 2010/145792, and WO 2010/145793.

3. Variants

In certain embodiments, amino acid sequence variants of the disulfide-linked multivalent multi-function protein provided herein are contemplated. For example, it may be desirable to improve the binding affinity and/or other biological properties of the disulfide-linked multivalent multi-function protein. Amino acid sequence variants of the disulfide-linked multivalent multi-function protein may be prepared by introducing appropriate modifications into the nucleotide sequence encoding the polypeptide chains of the disulfide-linked multivalent multi-function protein, or by peptide synthesis. Such modifications include, for example, deletions from, and/or insertions into and/or substitutions of residues within the amino acid sequences of the polypeptides of the disulfide-linked multivalent multi-function protein. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, disulfide-linked multivalent multi-function protein variants having one or more amino acid substitutions in one or more of the polypeptide chains are provided. Exemplary changes are provided in the following table under the heading of "exemplary substitutions", and as further described below in reference to amino acid side chain classes. Conservative substitutions are shown in the following Table under the heading of "preferred substitutions". Amino acid substitutions may be introduced into a disulfide-linked multivalent multi-function protein of interest and the products screened for a desired activity, e.g., retained/improved antigen binding, decreased immunogenicity, or improved ADCC or CDC.

TABLE

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

Non-conservative substitutions will entail exchanging a member of one of these classes for another class.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a disulfide-linked multivalent multi-function protein comprising a polypeptide with an N-terminal methionyl residue. Other insertional variants include the fusion to the N- or C-terminus of the polypeptide chains of the disulfide-linked multivalent multi-function protein to an enzyme.

b) Glycosylation Variants

In certain embodiments, one or more polypeptides of the disulfide-linked multivalent multi-function protein provided herein can be altered to increase or decrease the extent to which the polypeptide(s) is(are) glycosylated. Addition or deletion of glycosylation sites to a polypeptide may be conveniently accomplished by altering the amino acid sequence such that one or more glycosylation sites is created or removed.

The disulfide-linked multivalent multi-function protein comprises an antibody Fc-region and the carbohydrate attached thereto may be altered. Native Fc-regions produced by mammalian cells typically comprise a branched, biantennary oligosaccharide that is generally attached by an N-linkage to Asn297 of the CH2 domain of the Fc-region. See, e.g., Wright, A. and Morrison, S. L, TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in a disulfide-linked multivalent multi-function protein as reported herein may be made in order to create variants with certain improved properties.

In one embodiment, disulfide-linked multivalent multi-function protein comprising polypeptide variants are provided having a carbohydrate structure that lacks fucose attached (directly or indirectly) to the Fc-region. For example, the amount of fucose in such Fc-region may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. disulfide-linked multivalent multi-function protein, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A., et al., J. Mol. Biol. 336 (2004) 1239-1249; Yamane-Ohnuki, N., et al., Biotech. Bioeng. 87 (2004) 614-622. Examples of cell lines capable of producing defucosylated antibodies include Lec13 CHO cells deficient in protein fucosylation (Ripka, J., et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N., et al., Biotech. Bioeng. 87 (2004) 614-622; Kanda, Y., et al., Biotechnol. Bioeng. 94 (2006) 680-688; and WO 2003/085107).

Disulfide-linked multivalent multi-function proteins comprising Fc-region variants are further provided with bisected oligosaccharides, e.g., in which a biantennary oligosaccharide attached to the Fc-region is bisected by GlcNAc. Such variants may have reduced fucosylation and/or improved ADCC function. Examples of such antibody variants are described, e.g., in WO 2003/011878; U.S. Pat. No. 6,602,684; and US 2005/0123546. Fc-region variants with at least one galactose residue in the oligosaccharide attached to the Fc-region are also provided. Such Fc-region variants may have improved CDC function. Corresponding antibody variants are described, e.g., in WO 97/30087; WO 98/58964; and WO 99/22764.

c) Fc-Region Variants

In certain embodiments, one or more amino acid modifications may be introduced into the Fc-region of the disulfide-linked multivalent multi-function protein provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, the invention contemplates an Fc-region variant that possesses some but not all effector functions, which make it a desirable candidate for applications in which the half-life of the disulfide-linked multivalent multi-function protein in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the disulfide-linked multivalent multi-function protein lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I., et al., Proc. Natl. Acad. Sci. USA 83 (1986) 7059-7063; and Hellstrom, I., et al., Proc. Natl. Acad. Sci. USA 82 (1985) 1499-1502); U.S. Pat. No. 5,821,337 (see Bruggemann, M., et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R., et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H., et al., J. Immunol. Methods 202 (1996) 163-171; Cragg, M. S., et al., Blood 101 (2003) 1045-1052; and Cragg, M. S. and Glennie, M. J., Blood 103 (2004) 2738-2743). FcRn binding and in vivo clearance/half-life determinations can also be performed using methods known in the art (see, e.g., Petkova, S. B., et al., Int. Immunol. 18 (2006) 1759-1769).

Fc-regions with reduced effector function include those with substitution of one or more of Fc-region residues 234, 235, 238, 265, 269, 270, 297, 327 and 329 (see e.g. U.S. Pat. No. 6,737,056). Such Fc-region mutants include Fc-region mutants with substitutions at two or more of amino acid positions 265, 269, 270, 297 and 327, including the so-called "DANA" Fc-region mutant with substitution of residues 265 and 297 to alanine (U.S. Pat. No. 7,332,581).

Certain Fc-region variants with improved or diminished binding to FcRs are described. (See, e.g., U.S. Pat. No. 6,737,056; WO 2004/056312, and Shields, R. L, et al., J. Biol. Chem. 276 (2001) 6591-6604).

In certain embodiments, a disulfide-linked multivalent multi-function protein variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E., et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L., et al., J. Immunol. 117 (1976) 587-593, and Kim, J. K., et al., J. Immunol. 24 (1994) 2429-2434), are described in US 2005/0014934. Those antibodies comprise an Fc-region with one or more substitutions therein which improve binding of the Fc-region to FcRn. Such Fc-region variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. No. 5,648,260; U.S. Pat. No. 5,624,821; and WO 94/29351 concerning other examples of Fc-region variants.

B. Recombinant Methods and Compositions

Disulfide-linked multivalent multi-function proteins as reported herein may be produced using recombinant methods and compositions, e.g., as described in U.S. Pat. No. 4,816,567. In one embodiment, isolated nucleic acids encoding the polypeptides of the disulfide-linked multivalent multi-function protein described herein are provided. In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp2/0 cell). In one embodiment, a method of making a disulfide-linked multivalent multi-function protein as reported herein is provided, wherein the method comprises culturing a host cell comprising a nucleic acid encoding the polypeptides of the disulfide-linked multivalent multi-function protein, as provided above, under conditions suitable for expression of the polypeptides and formation of the disulfide-linked multivalent multi-function protein, and optionally recovering the disulfide-linked multivalent multi-function protein from the host cell (or host cell culture medium).

For recombinant production of a disulfide-linked multivalent multi-function protein, nucleic acid encoding the polypeptides of the disulfide-linked multivalent multi-function protein, e.g., as described above, are isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression vectors include prokaryotic or eukaryotic cells described herein. For example, disulfide-linked multivalent multi-function proteins may be produced in bacteria, in particular when glycosylation and Fc effector function are not needed. For expression of antibody fragments and polypeptides in bacteria, see, e.g., U.S. Pat. No. 5,648,237, U.S. Pat. No. 5,789,199, and U.S. Pat. No. 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the disulfide-linked multivalent multi-function protein may be isolated from the bacterial cell paste in a soluble fraction and can be further purified.

In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of an antibody with a partially or fully human glycosylation pattern. See Gerngross, T. U., Nat. Biotech. 22 (2004) 1409-1414; and Li, H., et al., Nat. Biotech. 24 (2006) 210-215.

Suitable host cells for the expression of glycosylated disulfide-linked multivalent multi-function proteins are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. No. 5,959,177, U.S. Pat. No. 6,040,498, U.S. Pat. No. 6,420,548, U.S. Pat. No. 7,125,978, and U.S. Pat. No. 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (HEK 293 or 293 cells as described, e.g., in Graham, F. L., et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P., et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G., et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Pharmaceutical Formulations

Pharmaceutical formulations of a disulfide-linked multivalent multi-function protein as described herein are prepared by mixing such disulfide-linked multivalent multi-function protein having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

D. Therapeutic Methods and Compositions

Any of the disulfide-linked multivalent multi-function proteins provided herein may be used in therapeutic methods.

In one aspect, a disulfide-linked multivalent multi-function protein as reported herein for use as a medicament is provided.

In further aspects, a disulfide-linked multivalent multi-function protein as reported herein for use in treating cancer is provided.

In certain embodiments, a disulfide-linked multivalent multi-function protein as reported herein for use in a method of treatment is provided.

In certain embodiments, the invention provides a disulfide-linked multivalent multi-function protein as reported herein for use in a method of treating an individual having cancer or a viral infection comprising administering to the individual an effective amount of the disulfide-linked multivalent multi-function protein as reported herein. In one such embodiment, the method further comprises administering to the individual an effective amount of at least one additional therapeutic agent, e.g., as described below.

In further embodiments, the invention provides a disulfide-linked multivalent multi-function protein as reported herein for use in removal of cancer cells or virus infected cells. In certain embodiments, the invention provides a disulfide-linked multivalent multi-function protein as reported herein for use in a method of removal of cancer cells or virus-infected cells in an individual comprising administering to the individual an effective of the disulfide-linked multivalent multi-function protein as reported herein to remove cancer cells. An "individual" according to any of the above embodiments may be a human.

In a further aspect, the invention provides for the use of a disulfide-linked multivalent multi-function protein as reported herein in the manufacture or preparation of a medicament. In one embodiment, the medicament is for treatment of cancer or a viral infection. In a further embodiment, the medicament is for use in a method of treating cancer or a viral infection comprising administering to an individual having cancer or a viral infection an effective amount of the medicament. In one such embodiment, the method further comprises administering to the individual an effective amount of at least one additional therapeutic agent. In a further embodiment, the medicament is for the removal of cancer cells or virus infected cells. In a further embodiment, the medicament is for use in a method of removal of cancer cells or virus infected cells in an individual comprising administering to the individual an amount effective of the medicament to remove cancer cells or virus infected cells. An "individual" according to any of the above embodiments may be a human.

In a further aspect, the invention provides a method for treating cancer or a viral infection. In one embodiment, the method comprises administering to an individual having such cancer or viral infection an effective amount of a disulfide-linked multivalent multi-function protein as reported herein. In one such embodiment, the method further comprises administering to the individual an effective amount of at least one additional therapeutic agent. An "individual" according to any of the above embodiments may be a human.

In a further aspect, the invention provides a method for removal of cancer cells or virus infected cells in an individual. In one embodiment, the method comprises administering to the individual an effective amount of a disulfide-linked multivalent multi-function protein as reported herein to remove cancer cells or virus infected cells. In one embodiment, an "individual" is a human.

In a further aspect, the invention provides pharmaceutical formulations comprising any of the disulfide-linked multivalent multi-function proteins as reported herein, e.g., for use in any of the above therapeutic methods. In one embodiment, a pharmaceutical formulation comprises any of the disulfide-linked multivalent multi-function proteins as reported herein and a pharmaceutically acceptable carrier. In another embodiment, a pharmaceutical formulation comprises any of the disulfide-linked multivalent multi-function proteins as reported herein and at least one additional therapeutic agent.

Disulfide-linked multivalent multi-function proteins of the invention can be used either alone or in combination with other agents in a therapy. For instance, a disulfide-linked multivalent multi-function protein of the invention may be co-administered with at least one additional therapeutic agent.

Such combination therapies noted above encompass combined administration (where two or more therapeutic agents are included in the same or separate formulations), and separate administration, in which case, administration of the multi-function protein of the invention can occur prior to, simultaneously, and/or following, administration of the additional therapeutic agent and/or adjuvant. Multi-function proteins of the invention can also be used in combination with radiation therapy.

A disulfide-linked multivalent multi-function protein of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Disulfide-linked multivalent multi-function proteins of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The disulfide-linked multivalent multi-function protein need not be, but is optionally formulated with one or more agents currently used to prevent or treat the disorder in question. The effective amount of such other agents depends on the amount of disulfide-linked multivalent multi-function protein present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a disulfide-linked multivalent multi-function protein of the invention (when used alone or in combination with one or more other additional therapeutic agents) will depend on the type of disease to be treated, the type of disulfide-linked multivalent multi-function protein, the severity and course of the disease, whether the disulfide-linked multivalent multi-function protein is administered for preventive or therapeutic purposes, previous therapy, the patient's clinical history and response to the disulfide-linked multivalent multi-function protein, and the discretion of the attending physician. The disulfide-linked multivalent multi-function protein is suitably administered to the patient at one time or over a series of treatments.

Depending on the type and severity of the disease, about 1 µg/kg to 15 mg/kg (e.g. 0.5 mg/kg-10 mg/kg) of disulfide-linked multivalent multi-function protein can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the disulfide-linked multivalent multi-function protein would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to a disulfide-linked multivalent multi-function protein as reported herein.

One aspect as reported herein is the disulfide-linked multivalent multi-function protein as reported herein for use in a method of treating a cancer or a viral infection in a patient, wherein the disulfide-linked multivalent multi-function protein is to be administered before, simultaneously or after the immunization of the patient with the virus-derived peptide comprised in the disulfide-linked multivalent multi-function protein.

One aspect as reported herein is the use of a disulfide-linked multivalent multi-function protein as reported herein for the manufacture of a medicament for the treatment of cancer or a viral infection in combination with immunization against the virus-derived peptide comprised in the disulfide-linked multivalent multi-function protein.

In the first step the virus-derived peptide as contained in the disulfide-linked multivalent multi-function protein is administered first to the individual to be treated. At a certain time span later, i.e. between 4 days and 28 days, the disulfide-linked multivalent multi-function protein as reported herein is administered to the individual.

By this successive and separated application of the virus-derived polypeptide, in the first step alone and in the second step in the disulfide-linked multivalent multi-function protein as reported herein, it is possible to increase the number of virus-derived peptide specific T-cell and, thus, to increase the efficacy of the treatment.

III. ARTICLES OF MANUFACTURE

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a multi-function protein of the invention. The label or package insert indicates that the composition is used for treating the condition of choice. Moreover, the article of manufacture may comprise (a) a first container with a composition contained therein, wherein the composition comprises a multi-function protein of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to a multi-function protein as reported herein.

IV. SPECIFIC EMBODIMENTS

1. A disulfide-linked multivalent multi-function protein, characterized in that it comprises
   two or more antigen presenting domains,
   one antibody Fc-region, and
   one or more antigen binding sites,
   wherein each of the antigen presenting domains comprises independently of each other in N- to C-terminal direction
   either
      (i) a β2-microglobulin, and
      (ii) the extracellular domains α1, α2, and α3 of a class I MHC molecule with a relative frequency of less than 1%,
   or
      (i) the extracellular domains α1, α2, and α3 of a class I MHC molecule with a relative frequency of less than 1%, and
      (ii) a β2-microglobulin,
   or
      (i) a T-cell response eliciting peptide,
      (ii) a β2-microglobulin, and
      (iii) the extracellular domains α1, α2, and α3 of a class I MHC molecule with a relative frequency of I % or more,
   or
      (i) a T-cell response eliciting peptide,
      (ii) the extracellular domains α1, α2, and α3 of a class I MHC molecule with a relative frequency of 1% or more, and
      (iii) a β2-microglobulin,
   wherein the antigen binding site or sites bind to a cancer cell surface antigen or a virus-infected cell surface antigen, and
   wherein one or more of the antigen presenting domains has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond.

2. A disulfide-linked multivalent multi-function protein, characterized in that it comprises
   one antigen presenting domain,
   one antibody Fc-region, and
   one or more antigen binding sites,
   wherein the antigen presenting domain comprises in N- to C-terminal direction
   either
      (i) a β2-microglobulin, and
      (ii) the extracellular domains α1, α2, and α3 of a class I MHC molecule with a relative frequency of less than 1%,
   or
      (i) the extracellular domains α1, α2, and α3 of a class I MHC molecule with a relative frequency of less than 1%, and
      (ii) a β2-microglobulin,
   or
      (i) a T-cell response eliciting peptide,
      (ii) a β2-microglobulin, and
      (iii) the extracellular domains α1, α2, and α3 of a class I MHC molecule with a relative frequency of I % or more,
   or
      (i) a T-cell response eliciting peptide,
      (ii) the extracellular domains α1, α2, and α3 of a class I MHC molecule with a relative frequency of 1% or more, and
      (iii) a β2-microglobulin,
   wherein the antigen binding site or sites bind to a cancer cell surface antigen or a virus-infected cell surface antigen, and
   wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond.

3. The multi-function protein according to any one of items 1 to 2, characterized in that antibody Fc-region comprises a first and second disulfide-linked Fc-region polypeptide, whereby the antigen binding site or one of the antigen binding sites comprises the first Fc-region polypeptide and the second antigen binding site, if present, comprises the second Fc-region polypeptide.

4. The multi-function protein according to any one of items 1 to 3, characterized in that the antigen binding sites comprise independently of each other i) a pair of an antibody heavy chain and an antibody light chain, or ii) a scFv fusion polypeptide comprising in N- to C-terminal direction a scFv antibody fragment and an antibody Fc-region polypeptide, or iii) a scFab fusion polypeptide comprising in N- to C-terminal direction a scFab and an antibody Fc-region polypeptide.

5. The multi-function protein according to any one of items 1 to 4, characterized in that i) an antigen presenting domain is linked to the N-terminus of the heavy chain or to the N-terminus of the light chain of an antigen binding site, or ii) one antigen presenting domain is linked to each N-terminus of the heavy chain or to each N-terminus of the light chain of each antigen binding site, or iii) an antigen presenting domain is linked to the C-terminus of the heavy chain or to the C-terminus of the light chain of the antigen binding site, or vi) one antigen presenting domain is linked to each C-terminus of the heavy chain or to each C-terminus of the light chain of each antigen binding site, or v) an antigen presenting domain is linked to the N- or C-terminus of an scFv fusion polypeptide, or vi) one antigen presenting domain is linked to each N- or C-terminus of each scFv fusion polypeptide, or vii) an antigen presenting domain is linked to the N- or C-terminus of a scFab fusion polypeptide, or viii) one antigen presenting domain is linked to each N- or C-terminus of each scFab fusion polypeptide, or ix) an antigen presenting domain is linked to the N- or C-terminus of the second Fc-region polypeptide, or x) one antigen presenting domain is linked to the N- or C-terminus of the first Fc-region polypeptide and one antigen presenting domain is linked to the N- or C-terminus of the second Fc-region polypeptide.

6. The multi-function protein according to any one of items 1 to 5, characterized in that the cancer cell surface antigen is melanoma-associated chondroitin sulfate proteoglycan (MCSP).

7. The multi-function protein according to any one of items 1 to 6, characterized in that the T-cell response eliciting peptide is a virus-derived peptide.

8. The multi-function protein according to any one of items 1 to 7, characterized in that the T-cell response eliciting peptide is a CD8$^+$-T-cell response eliciting peptide.

9. The multi-function protein according to any one of items 7 to 8, characterized in that the virus-derived peptide is a human cytomegalovirus-derived peptide.

10. The multi-function protein according to any one of items 1 to 9, characterized in that the virus-derived peptide has an amino acid sequence selected from the group of SEQ ID NO: 01 to SEQ ID NO: 70.

11. The multi-function protein according to any one of items 1 to 10, characterized in that the virus-derived peptide has the amino acid sequence of SEQ ID NO: 01.

12. The multi-function protein according to any one of items 1 to 11, characterized in that the class I MHC molecule with a relative frequency of 1% or more is selected from the group comprising HLA-A*0201, HLA-A*1101, HLA-A*2402, HLA-A*340101, HLA-C*0304, HLA-C*0401, and HLA-C*0702.

13. The multi-function protein according to any one of items 1 to 12, characterized in that the class I MHC molecule with a relative frequency of 1% or more is selected depending on the region of the individual to whom the multi-function protein is to be administered as follows:
for an individual of European origin the class I MHC molecule is selected from the group comprising HLA-A*0101, HLA-A*0201, HLA-A*0301, HLA-B*0702, HLA-B*0801, HLA-B*4402, HLA-C*0401, HLA-C*0501, HLA-C*0701, and HLA-C*0702,
for an individual of Australian origin the class I MHC molecule is selected from the group comprising HLA-A*0201, HLA-A*1101, HLA-A*2402, HLA-A*340101, HLA-B*1301, HLA-B*1521, HLA-B*5601, HLA-B*5602, HLA-C*0102, HLA-C*0401, HLA-C*0403, and HLA-C*1502,
for an individual of North American origin the class I MHC molecule is selected from the group comprising HLA-A*0201, HLA-A*2402, HLA-C*0202, HLA-C*0304, HLA-C*0401, and HLA-C*0702, and
for an individual of South-East-Asian origin the class I MHC molecule is selected from the group comprising HLA-A*1101, HLA-A*2402, HLA-B*1504, HLA-C*0102, HLA-C*0304, HLA-C*0702, and HLA-C*0801.

14. The multi-function protein according to any one of items 1 to 13, characterized in that the class I MHC molecule with a relative frequency of 1% or more is selected depending on the region of the individual to whom the multi-function protein is to be administered as follows:
for an individual of European origin the class I MHC molecule is HLA-A*0201,
for an individual of Australian origin the class I MHC molecule is selected from the group comprising HLA-A*2402, HLA-B*1301, HLA-C*0102, and HLA-C*0401,
for an individual of North American origin the class I MHC molecule is selected from the group comprising HLA-A*2402, and HLA-C*0304, and
for an individual of South-East-Asian origin the class I MHC molecule is HLA-A*2402.

15. The multi-function protein according to any one of items 1 to 14, characterized in that the class I MHC molecule with a relative frequency of less than 1% is selected from the group comprising HLA-B*4201, HLA-B*5901, HLA-B*6701, and HLA-B*7802.

16. The multi-function protein according to any one of items 1 to 15, characterized in that the β2-microglobulin is human β2-microglobulin and the class I MHC molecule with a relative frequency of 10% or more is human HLA-A*0201.

17. The multi-function protein according to any one of items 1 to 16, characterized in that the antigen presenting domain comprises
(i) a virus-derived peptide,
(ii) β2-microglobulin,
(iii) the soluble HLA-A allele A*0201, and
(iv) cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond
or
(i) a virus-derived peptide,
(ii) the soluble HLA-A allele A*0201,
(iii) β2-microglobulin, and
(iv) cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond.

18. The multi-function protein according to any one of items 1 to 17, characterized in that the β2-microglobulin is consisting of the amino acid sequence of SEQ ID NO: 71 or is a variant thereof comprising of from 1 to 10 amino acid exchanges, additions, and/or deletions.
19. The multi-function protein according to any one of items 1 to 18, characterized in that the extracellular domains α1, α2 and α3 of a class I MHC molecule is consisting of the amino acid sequence of SEQ ID NO: 72 or SEQ ID NO: 140 or is a variant thereof comprising of from 1 to 10 amino acid exchanges, additions, and/or deletions.
20. The multi-function protein according to any one of items 1 to 19, characterized in that the antigen presenting domain comprises in N- to C-terminal direction
    (i) a virus-derived peptide that has an amino acid sequence selected from the group comprising SEQ ID NO: 01 to SEQ ID NO: 70,
    (ii) a first linker peptide that has an amino acid sequence selected from the group comprising SEQ ID NO: 77, 78, 79, 82, 83, 84, and 139,
    (iii) a β2-microglobulin that has an amino acid sequence of SEQ ID NO: 71,
    (iv) a second linker peptide that has an amino acid sequence selected from the group comprising SEQ ID NO: 77, 78, 79, 82, 83, and 84,
    (v) the extracellular domains α1, α2, and α3 of a class 1 MHC molecule that has an amino acid sequence of SEQ ID NO: 140,
    (vi) a third linker peptide that has an amino acid sequence selected from the group comprising SEQ ID NO: 73, 77, 78, 79, 82, 83, 84, and 136, and
    (vii) the antigen presenting domain has cysteine residues at least at position 11 and at position 227 and the cysteine residues at position 11 and position 227 form a disulfide bond.
21. The multi-function protein according to any one of items 1 to 20, characterized in that the multi-function protein is characterized in that the antigen presenting domain comprises in N- to C-terminal direction
    (i) a virus-derived peptide that has an amino acid sequence selected from the group comprising SEQ ID NO: 01 to SEQ ID NO: 70,
    (ii) a first linker peptide that has an amino acid sequence selected from the group comprising SEQ ID NO: 77, 78, 79, 82, 83, 84, and 139
    (iii) a β2-microglobulin that has an amino acid sequence of SEQ ID NO: 71 or is a variant thereof comprising of from 1 to 10 amino acid exchanges, additions, and/or deletions,
    (iv) a second linker peptide that has an amino acid sequence selected from the group comprising SEQ ID NO: 77, 78, 79, 82, 83, and 84,
    (v) the extracellular domains α1, α2 and α3 of a class I MHC molecule that has an amino acid sequence of SEQ ID NO: 140 or is a variant thereof comprising of from 1 to 10 amino acid exchanges, additions, and/or deletions,
    (vi) a third linker peptide that has an amino acid sequence selected from the group comprising SEQ ID NO: 73, 77, 78, 79, 82, 83, 84, 136, and
    (vii) the antigen presenting domain has cysteine residues at least at position 11 and at position 227 and the cysteine residues at position 11 and position 227 form a disulfide bond.
22. The multi-function protein according to item 21, characterized in that
    the first linker peptide has the amino acid sequence of SEQ ID NO: 139, and/or
    the second linker peptide has the amino acid sequence of SEQ ID NO: 83, and/or
    the third linker peptide has the amino acid sequence of SEQ ID NO: 136.
23. The multi-function protein according to any one of items 1 to 22, characterized in that the antibody Fc-region is selected from an antibody Fc-region of a human antibody of the class IgG or the class IgE.
24. The multi-function protein according to any one of items 1 to 23, characterized in that the antibody Fc-region is selected from an antibody Fc-region of a human antibody of the subclass IgG1, or IgG2, or IgG3, or IgG4.
25. The multi-function protein according to any one of items 1 to 24, characterized in that the antibody Fc-region is of a human antibody of the subclass IgG1 or IgG2 and comprises at least one mutation in E233, L234, L235, G236, D265, D270, N297, E318, K320, K322, A327, P329, A330, and/or P331 (numbering according to the EU index of Kabat).
26. The multi-function protein according to any one of items 1 to 25, characterized in that the antibody Fc-region is of a human antibody of the subclass IgG1 or the human subclass IgG2 with the mutations L234A and L235A, and/or the mutations D265A and N297A, and/or contains the PVA236 mutation, and/or contains the mutation P329G.
27. The multi-function protein according to any one of items 1 to 26, characterized in that the antibody Fc-region is of a human antibody of the subclass IgG1 with the mutations L234A and L235A and/or P329G.
28. The multi-function protein according to any one of items 1 to 26, characterized in that the antibody Fc-region is of a human antibody of the subclass IgG4 with the mutation S228P and/or L235E.
29. The multi-function protein according to any one of items 1 to 26, characterized in that the first and second antibody Fc-region polypeptide is selected independently of each other from the group comprising SEQ ID NO: 87 to 103.
30. The multi-function protein according to any one of items 1 to 26, characterized in that the antibody Fc-region comprises two Fc-region polypeptides with the amino acid sequence of SEQ ID NO: 94.
31. The multi-function protein according to any one of items 1 to 26, characterized in that the antibody Fc-region comprises two Fc-region polypeptides with the amino acid sequence of SEQ ID NO: 100.
32. The multi-function protein according to any one of items 1 to 26, characterized in that the antibody Fc-region comprises two Fc-region polypeptides with the amino acid sequence of SEQ ID NO: 101.
33. The multi-function protein according to any one of items 1 to 26, characterized in that the antibody Fc-region comprises a first Fc-region polypeptide with the amino acid sequence of SEQ ID NO: 89 and a second Fc-region polypeptide with the amino acid sequence of SEQ ID NO: 90.
34. The multi-function protein according to any one of items 1 to 26, characterized in that the antibody Fc-region comprises a first Fc-region polypeptide with the amino acid sequence of SEQ ID NO: 97 and a second Fc-region polypeptide with the amino acid sequence of SEQ ID NO: 98.
35. The multi-function protein according to any one of items 1 to 26, characterized in that the antibody Fc-region comprises a first Fc-region polypeptide with the amino acid sequence of SEQ ID NO: 102 and a second Fc-region polypeptide with the amino acid sequence of SEQ ID NO: 103.

36. A disulfide-linked multivalent multi-function protein, characterized in that it comprises
    two antigen presenting domains, which comprise in N- to C-terminal direction
        either
            (i) a β2-microglobulin, and
            (ii) the extracellular domains α1, α2, and α3 of a class I MHC molecule with a relative frequency of less than 1%,
        or
            (i) the extracellular domains α1, α2, and α3 of a class I MHC molecule with a relative frequency of less than 1%, and
            (ii) a β2-microglobulin,
        or
            (i) a T-cell response eliciting peptide,
            (ii) a β2-microglobulin, and
            (iii) the extracellular domains α1, α2, and α3 of a class I MHC molecule with a relative frequency of 1% or more,
        or
            (i) a T-cell response eliciting peptide,
            (ii) the extracellular domains α1, α2, and α3 of a class I MHC molecule with a relative frequency of 1% or more, and
            (iii) a β2-microglobulin,
        wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
    exactly one antibody Fc-region, and
    one or more antigen binding sites.

37. A disulfide-linked multivalent multi-function protein, characterized in that it comprises
    two antigen presenting domains, which comprise in N- to C-terminal direction
        (i) a T-cell response eliciting peptide,
        (ii) a β2-microglobulin, and
        (iii) the extracellular domains α1, α2, and α3 of a class I MHC molecule with a relative frequency of 1% or more,
    wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
    exactly one antibody Fc-region, and
    one or more antigen binding sites.

38. A disulfide-linked multivalent multi-function protein, characterized in that it comprises
    two antigen presenting domains, which comprise in N- to C-terminal direction
        (i) a T-cell response eliciting peptide of SEQ ID NO: 01,
        (ii) a β2-microglobulin of SEQ ID NO: 71, and
        (iii) the extracellular domains α1, α2, and α3 of a class I MHC molecule of SEQ ID NO: 72,
    wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
    exactly one antibody Fc-region, and
    one or more antigen binding sites.

39. A disulfide-linked multivalent multi-function protein, characterized in that it comprises
    two antigen presenting domains, which comprise in N- to C-terminal direction
        (i) a T-cell response eliciting peptide of SEQ ID NO: 01,
        (ii) a β2-microglobulin of SEQ ID NO: 71, and
        (iii) the extracellular domains α1, α2, and α3 of a class I MHC molecule of SEQ ID NO: 72,
    wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
    exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and
    one or more antigen binding sites.

40. A disulfide-linked multivalent multi-function protein, characterized in that it comprises
    two antigen presenting domains, which comprise in N- to C-terminal direction
        (i) a T-cell response eliciting peptide of SEQ ID NO: 01,
        (ii) a β2-microglobulin of SEQ ID NO: 71, and
        (iii) the extracellular domains α1, α2, and α3 of a class I MHC molecule of SEQ ID NO: 72,
    wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
    exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and
    one or more antigen binding sites.

41. A disulfide-linked multivalent multi-function protein, characterized in that it comprises
    two antigen presenting domains, which comprise in N- to C-terminal direction
        (i) a T-cell response eliciting peptide of SEQ ID NO: 01,
        (ii) a β2-microglobulin of SEQ ID NO: 71, and
        (iii) the extracellular domains α1, α2, and α3 of a class I MHC molecule of SEQ ID NO: 72,
    wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and
one or more antigen binding sites, which comprise an antibody light chain variable domain comprising SEQ ID NO: 104 to 106 and an antibody heavy chain variable domain comprising SEQ ID NO: 108 to 110, which specifically bind to melanoma-associated chondroitin sulfate proteoglycan (MCSP).

42. A disulfide-linked multivalent multi-function protein, characterized in that it comprises
two antigen presenting domains, which comprise in N- to C-terminal direction
(i) a T-cell response eliciting peptide of SEQ ID NO: 01,
(ii) a β2-microglobulin of SEQ ID NO: 71, and
(iii) the extracellular domains α1, α2, and α3 of a class I MHC molecule of SEQ ID NO: 72,
wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and
one or more antigen binding sites, which specifically bind to melanoma-associated chondroitin sulfate proteoglycan (MCSP), and which comprises an antibody light chain with a variable domain comprising SEQ ID NO: 104 to 106 and an antibody heavy chain with a variable domain comprising SEQ ID NO: 108 to 110.

43. A disulfide-linked multivalent multi-function protein, characterized in that it comprises
two antigen presenting domains, which comprise in N- to C-terminal direction
(i) a T-cell response eliciting peptide of SEQ ID NO: 01,
(ii) a β2-microglobulin of SEQ ID NO: 71, and
(iii) the extracellular domains α1, α2, and α3 of a class I MHC molecule of SEQ ID NO: 72,
wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and
two antigen binding sites, which specifically bind to melanoma-associated chondroitin sulfate proteoglycan (MCSP), and which each comprise an antibody light chain with a variable domain comprising SEQ ID NO: 105 to 107 and an antibody heavy chain with a variable domain comprising SEQ ID NO: 110 to 112.

44. A disulfide-linked multivalent multi-function protein, characterized in that it comprises
two antigen presenting domains, which comprise in N- to C-terminal direction
(i) a T-cell response eliciting peptide of SEQ ID NO: 01,
(ii) a β2-microglobulin of SEQ ID NO: 71, and
(iii) the extracellular domains α1, α2, and α3 of a class I MHC molecule of SEQ ID NO: 72,
wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and
one or more antigen binding sites, which specifically bind to melanoma-associated chondroitin sulfate proteoglycan (MCSP), and which comprises an antibody light chain with a variable domain comprising SEQ ID NO: 105 to 107 and an antibody heavy chain with a variable domain comprising SEQ ID NO: 110 to 112, whereby the Fc-region of the antibody heavy chain is one of the disulfide-linked Fc-region polypeptides.

45. A disulfide-linked multivalent multi-function protein, characterized in that it comprises
two antigen presenting domains, which comprise in N- to C-terminal direction
(i) a T-cell response eliciting peptide of SEQ ID NO: 01,
(ii) a β2-microglobulin of SEQ ID NO: 71, and
(iii) the extracellular domains α1, α2, and α3 of a class I MHC molecule of SEQ ID NO: 72,
wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and
one or more antigen binding sites, which specifically bind to melanoma-associated chondroitin sulfate proteoglycan (MCSP), and which comprise an antibody light chain with a variable domain comprising SEQ ID NO: 104 to 106 and an antibody heavy chain with a variable domain comprising SEQ ID NO: 108 to 110, whereby the Fc-region of the antibody heavy chain is one of the disulfide-linked Fc-region polypeptides,
wherein the antigen presenting domain is linked to the N-terminus of one of the variable domains.

46. A disulfide-linked multivalent multi-function protein, characterized in that it comprises
   two antigen presenting domains, which comprise in N- to C-terminal direction
      (i) a T-cell response eliciting peptide of SEQ ID NO: 01,
      (ii) a β2-microglobulin of SEQ ID NO: 71, and
      (iii) the extracellular domains α1, α2, and α3 of a class I MHC molecule of SEQ ID NO: 72,
      wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
   exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and
   two antigen binding site, which specifically bind to melanoma-associated chondroitin sulfate proteoglycan (MCSP), and which each comprise an antibody light chain with a variable domain comprising SEQ ID NO: 104 to 106 and an antibody heavy chain with a variable domain comprising SEQ ID NO: 108 to 110, whereby the Fc-regions of the antibody heavy chains are the disulfide-linked Fc-region polypeptides,
   wherein the antigen presenting domain is linked to the N-terminus of one of the variable domains.

47. A disulfide-linked multivalent multi-function protein, characterized in that it comprises
   two antigen presenting domains, which comprise in N- to C-terminal direction
      (i) a T-cell response eliciting peptide of SEQ ID NO: 01,
      (ii) a β2-microglobulin of SEQ ID NO: 71, and
      (iii) the extracellular domains α1, α2, and α3 of a class I MHC molecule of SEQ ID NO: 72,
      wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
   exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and
   two antigen binding site, which specifically bind to melanoma-associated chondroitin sulfate proteoglycan (MCSP), and which each comprise an antibody light chain with a variable domain comprising SEQ ID NO: 105 to 107 and an antibody heavy chain with a variable domain comprising SEQ ID NO: 110 to 112, whereby the Fc-regions of the antibody heavy chains are the disulfide-linked Fc-region polypeptides,
   wherein the antigen presenting domain is linked to the N-terminus of one of the heavy chain variable domains.

48. A disulfide-linked multivalent multi-function protein, characterized in that it comprises
   two antigen presenting domains, which comprise in N- to C-terminal direction
      (i) a T-cell response eliciting peptide of SEQ ID NO: 01,
      (ii) a β2-microglobulin of SEQ ID NO: 71, and
      (iii) the extracellular domains α1, α2, and α3 of a class I MHC molecule of SEQ ID NO: 72,
      wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
   exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and
   two antigen binding site, which specifically bind to melanoma-associated chondroitin sulfate proteoglycan (MCSP), and which each comprise an antibody light chain with a variable domain comprising SEQ ID NO: 105 to 107 and an antibody heavy chain with a variable domain comprising SEQ ID NO: 110 to 112, whereby the Fc-regions of the antibody heavy chains are the disulfide-linked Fc-region polypeptides,
   wherein the antigen presenting domain is linked to the N-terminus of one of the heavy chain variable domains.

49. A disulfide-linked multivalent multi-function protein, characterized in that it comprises
   one polypeptide chain of SEQ ID NO: 117 or 137,
   one polypeptide chain of SEQ ID NO: 118,
   two polypeptide chains each of SEQ ID NO: 119,
   wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond.

50. A disulfide-linked multivalent multi-function protein, characterized in that it comprises
   two polypeptide chains of SEQ ID NO: 117 or 137,
   two polypeptide chains each of SEQ ID NO: 119,
   wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond.

51. A disulfide-linked multivalent multi-function protein, characterized in that it comprises
   one antigen presenting domain, which comprises in N- to C-terminal direction
      either
         (i) a β2-microglobulin, and
         (ii) the extracellular domains α1, α2, and α3 of a class I MHC molecule with a relative frequency of less than 1%,
      or
         (i) the extracellular domains α1, α2, and α3 of a class I MHC molecule with a relative frequency of less than 1%, and
         (ii) a β2-microglobulin, or
  (i) a T-cell response eliciting peptide,
  (ii) a β2-microglobulin, and
  (iii) the extracellular domains α1, α2, and α3 of a class I MHC molecule with a relative frequency of 1% or more,
or
  (i) a T-cell response eliciting peptide,
  (ii) the extracellular domains α1, α2, and α3 of a class I MHC molecule with a relative frequency of 1 % or more, and
  (iii) a β2-microglobulin,
  wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
exactly one antibody Fc-region, and
one or more antigen binding sites.

52. A disulfide-linked multivalent multi-function protein, characterized in that it comprises
one antigen presenting domain, which comprises in N- to C-terminal direction
  (i) a T-cell response eliciting peptide,
  (ii) a β2-microglobulin, and
  (iii) the extracellular domains α1, α2, and α3 of a class I MHC molecule with a relative frequency of 1% or more,
  wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
exactly one antibody Fc-region, and
one or more antigen binding sites.

53. A disulfide-linked multivalent multi-function protein, characterized in that it comprises
one antigen presenting domain, which comprise in N- to C-terminal direction
  (i) a T-cell response eliciting peptide of SEQ ID NO: 01,
  (ii) a β2-microglobulin of SEQ ID NO: 71, and
  (iii) the extracellular domains α1, α2, and α3 of a class I MHC molecule of SEQ ID NO: 72,
  wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond.
exactly one antibody Fc-region, and
one or more antigen binding sites.

54. A disulfide-linked multivalent multi-function protein, characterized in that it comprises
one antigen presenting domain, which comprises in N- to C-terminal direction
  (i) a T-cell response eliciting peptide of SEQ ID NO: 01,
  (ii) a β2-microglobulin of SEQ ID NO: 71, and
  (iii) the extracellular domains α1, α2, and α3 of a class I MHC molecule of SEQ ID NO: 72,
  wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and
one or more antigen binding sites.

55. A disulfide-linked multivalent multi-function protein, characterized in that it comprises
one antigen presenting domain, which comprises in N- to C-terminal direction
  (i) a T-cell response eliciting peptide of SEQ ID NO: 01,
  (ii) a β2-microglobulin of SEQ ID NO: 71, and
  (iii) the extracellular domains cal, α2, and α3 of a class I MHC molecule of SEQ ID NO: 72,
  wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and
one or more antigen binding sites.

56. A disulfide-linked multivalent multi-function protein, characterized in that it comprises
one antigen presenting domain, which comprises in N- to C-terminal direction
  (i) a T-cell response eliciting peptide of SEQ ID NO: 01,
  (ii) a β2-microglobulin of SEQ ID NO: 71, and
  (iii) the extracellular domains α1, α2, and α3 of a class I MHC molecule of SEQ ID NO: 72,
  wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and
one or more antigen binding sites, which comprise an antibody light chain variable domain comprising SEQ ID NO: 104 to 106 and an antibody heavy chain variable domain comprising SEQ ID NO: 108 to 110, which specifically bind to melanoma-associated chondroitin sulfate proteoglycan (MCSP).

57. A disulfide-linked multivalent multi-function protein, characterized in that it comprises one antigen presenting domain, which comprises in N- to C-terminal direction
(i) a T-cell response eliciting peptide of SEQ ID NO: 01,
(ii) a β2-microglobulin of SEQ ID NO: 71, and
(iii) the extracellular domains α1, α2, and α3 of a class I MHC molecule of SEQ ID NO: 72,
wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and
one or more antigen binding sites, which specifically bind to melanoma-associated chondroitin sulfate proteoglycan (MCSP), and which comprises an antibody light chain with a variable domain comprising SEQ ID NO: 104 to 106 and an antibody heavy chain with a variable domain comprising SEQ ID NO: 108 to 110.

58. A disulfide-linked multivalent multi-function protein, characterized in that it comprises
one antigen presenting domain, which comprises in N- to C-terminal direction
(i) a T-cell response eliciting peptide of SEQ ID NO: 01,
(ii) a β2-microglobulin of SEQ ID NO: 71, and
(iii) the extracellular domains α1, α2, and α3 of a class I MHC molecule of SEQ ID NO: 72,
wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and
two antigen binding sites, which specifically bind to melanoma-associated chondroitin sulfate proteoglycan (MCSP), and which each comprise an antibody light chain with a variable domain comprising SEQ ID NO: 105 to 107 and an antibody heavy chain with a variable domain comprising SEQ ID NO: 110 to 112.

59. A disulfide-linked multivalent multi-function protein, characterized in that it comprises
one antigen presenting domain, which comprises in N- to C-terminal direction
(i) a T-cell response eliciting peptide of SEQ ID NO: 01,
(ii) a β2-microglobulin of SEQ ID NO: 71, and
(iii) the extracellular domains α1, α2, and α3 of a class I MHC molecule of SEQ ID NO: 72,
wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and
one or more antigen binding sites, which specifically bind to melanoma-associated chondroitin sulfate proteoglycan (MCSP), and which comprises an antibody light chain with a variable domain comprising SEQ ID NO: 105 to 107 and an antibody heavy chain with a variable domain comprising SEQ ID NO: 110 to 112, whereby the Fc-region of the antibody heavy chain is one of the disulfide-linked Fc-region polypeptides.

60. A disulfide-linked multivalent multi-function protein, characterized in that it comprises
one antigen presenting domains, which comprises in N- to C-terminal direction
(i) a T-cell response eliciting peptide of SEQ ID NO: 01,
(ii) a β2-microglobulin of SEQ ID NO: 71, and
(iii) the extracellular domains α1, α2, and α3 of a class I MHC molecule of SEQ ID NO: 72,
wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and
one or more antigen binding sites, which specifically bind to melanoma-associated chondroitin sulfate proteoglycan (MCSP), and which comprise an antibody light chain with a variable domain comprising SEQ ID NO: 104 to 106 and an antibody heavy chain with a variable domain comprising SEQ ID NO: 108 to 110, whereby the Fc-region of the antibody heavy chain is one of the disulfide-linked Fc-region polypeptides,
wherein the antigen presenting domain is linked to the N-terminus of one of the variable domains.

61. A disulfide-linked multivalent multi-function protein, characterized in that it comprises
one antigen presenting domain, which comprises in N- to C-terminal direction
(i) a T-cell response eliciting peptide of SEQ ID NO: 01,
(ii) a β2-microglobulin of SEQ ID NO: 71, and
(iii) the extracellular domains α1, α2, and α3 of a class I MHC molecule of SEQ ID NO: 72,
wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond,
exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and two antigen binding site, which specifically bind to melanoma-associated chondroitin sulfate proteoglycan (MCSP), and which each comprise an antibody light chain with a variable domain comprising SEQ ID NO: 104 to 106 and an antibody heavy chain with a variable domain comprising SEQ ID NO: 108 to 110, whereby the Fc-regions of the antibody heavy chains are the disulfide-linked Fc-region polypeptides, wherein the antigen presenting domain is linked to the N-terminus of one of the variable domains.

62. A disulfide-linked multivalent multi-function protein, characterized in that it comprises one antigen presenting domain, which comprises in N- to C-terminal direction
  (i) a T-cell response eliciting peptide of SEQ ID NO: 01,
  (ii) a β2-microglobulin of SEQ ID NO: 71, and
  (iii) the extracellular domains α1, α2, and α3 of a class I MHC molecule of SEQ ID NO: 72,
  wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond, exactly one antibody Fc-region, which comprises two disulfide-linked Fc-region polypeptides, whereof the first disulfide-linked Fc-region polypeptide has the amino acid sequence of SEQ ID NO: 97 and the second disulfide-linked Fc-region polypeptide has the amino acid sequence of SEQ ID NO: 98, and two antigen binding site, which specifically bind to melanoma-associated chondroitin sulfate proteoglycan (MCSP), and which each comprise an antibody light chain with a variable domain comprising SEQ ID NO: 105 to 107 and an antibody heavy chain with a variable domain comprising SEQ ID NO: 110 to 112, whereby the Fc-regions of the antibody heavy chains are the disulfide-linked Fc-region polypeptides, wherein the antigen presenting domain is linked to the N-terminus of one of the heavy chain variable domains.

63. A disulfide-linked multivalent multi-function protein, characterized in that it comprises one antigen presenting domain, which comprises in N- to C-terminal direction
  (i) a T-cell response eliciting peptide of SEQ ID NO: 01,
  (ii) a β2-microglobulin of SEQ ID NO: 71, and
  (iii) the extracellular domains α1, α2, and α3 of a class I MHC molecule of SEQ ID NO: 72,
  wherein the antigen presenting domain has cysteine residues at least at position 11 and at position 227 and the cysteine residues at position 11 and position 227 form a disulfide bond or cysteine residues at least at position 11 and at position 108 and the cysteine residues at position 11 and position 108 form a disulfide bond, exactly one antibody Fc-region, which comprises two disulfide-linked Fc-region polypeptides, whereof the first disulfide-linked Fc-region polypeptide has the amino acid sequence of SEQ ID NO: 102 and the second disulfide-linked Fc-region polypeptide has the amino acid sequence of SEQ ID NO: 103, and two antigen binding site, which specifically bind to melanoma-associated chondroitin sulfate proteoglycan (MCSP), and which each comprise an antibody light chain with a variable domain comprising SEQ ID NO: 105 to 107 and an antibody heavy chain with a variable domain comprising SEQ ID NO: 110 to 112, whereby the Fc-regions of the antibody heavy chains are the disulfide-linked Fc-region polypeptides, wherein the antigen presenting domain is linked to the N-terminus of one of the heavy chain variable domains.

64. The multi-function protein according to any one of items 1 to 63, characterized in that the MCSP binding site comprises an antibody heavy chain variable domain comprising an HVR-H1 comprising the amino acid sequence of SEQ ID NO: 108, an HVR-H2 comprising the amino acid sequence of SEQ ID NO: 109, and an HVR-H3 comprising the amino acid sequence of SEQ ID NO: 110.

65. The multi-function protein according to any one of items 1 to 63, characterized in that the MCSP binding site comprises an antibody light chain variable domain comprising an HVR-L1 comprising the amino acid sequence of SEQ ID NO: 104; an HVR-L2 comprising the amino acid sequence of SEQ ID NO: 105; and an HVR-L3 comprising the amino acid sequence of SEQ ID NO: 106.

66. The multi-function protein according to any one of items 1 to 63, characterized in that the MCSP binding site comprises an antibody heavy chain variable domain comprising an HVR-H1 comprising the amino acid sequence of SEQ ID NO: 108; an HVR-H2 comprising the amino acid sequence of SEQ ID NO: 109; an HVR-H3 comprising the amino acid sequence of SEQ ID NO: 110; and an antibody light chain variable domain comprising an HVR-L1 comprising the amino acid sequence of SEQ ID NO: 104; an HVR-L2 comprising the amino acid sequence of SEQ ID NO: 105; and an HVR-L3 comprising the amino acid sequence of SEQ ID NO: 106.

67. The multi-function protein according to any one of items 1 to 63, characterized in that the MCSP binding site comprises an antibody heavy chain variable domain comprising an HVR-H1 comprising the amino acid sequence of SEQ ID NO: 111, an HVR-H2 comprising the amino acid sequence of SEQ ID NO: 112, and an HVR-H3 comprising the amino acid sequence of SEQ ID NO: 110.

68. The multi-function protein according to any one of items 1 to 63, characterized in that the MCSP binding site comprises an antibody light chain variable domain comprising an HVR-L1 comprising the amino acid sequence of SEQ ID NO: 107; an HVR-L2 comprising the amino acid sequence of SEQ ID NO: 105; and an HVR-L3 comprising the amino acid sequence of SEQ ID NO: 106.

69. The multi-function protein according to any one of items 1 to 63, characterized in that the MCSP binding site comprises an antibody heavy chain variable domain comprising an HVR-H1 comprising the amino acid sequence of SEQ ID NO: 111; an HVR-H2 comprising the amino acid sequence of SEQ ID NO: 112; an HVR-H3 comprising the amino acid sequence of SEQ ID NO: 110; and an antibody light chain variable domain comprising an HVR-L1 comprising the amino acid sequence of SEQ ID NO: 107; an HVR-L2 comprising the amino acid sequence of SEQ ID NO: 105; and an HVR-L3 comprising the amino acid sequence of SEQ ID NO: 106.

70. The multi-function protein according to any one of items 1 to 63, characterized in that the MCSP binding site comprises an antibody heavy chain variable domain having at least 95% sequence identity to the amino acid sequence of SEQ ID NO: 114; and an antibody light chain variable domain having at least 95% sequence identity to the amino acid sequence of SEQ ID NO: 113.
71. The multi-function protein according to any one of items 1 to 63, characterized in that the MCSP binding site comprises an antibody heavy chain variable domain of SEQ ID NO: 114; and an antibody light chain variable domain of SEQ ID NO: 113.
72. The multi-function protein according to any one of items 1 to 63, characterized in that the MCSP binding site comprises SEQ ID NO: 114 and SEQ ID NO: 113.
73. The multi-function protein according to any one of items 1 to 63, characterized in that the MCSP binding site comprises an antibody heavy chain variable domain having at least 95% sequence identity to the amino acid sequence of SEQ ID NO: 116; and an antibody light chain variable domain having at least 95% sequence identity to the amino acid sequence of SEQ ID NO: 115.
74. The multi-function protein according to any one of items 1 to 63, characterized in that the MCSP binding site comprises an antibody heavy chain variable domain of SEQ ID NO: 116; and an antibody light chain variable domain of SEQ ID NO: 115.
75. The multi-function protein according to any one of items 1 to 63, characterized in that the MCSP binding site comprises SEQ ID NO: 116 and SEQ ID NO: 115.
76. A nucleic acid encoding the disulfide-linked multivalent multi-function protein of any one of items 1 to 75.
77. A host cell comprising the nucleic acid of item 76.
78. A pharmaceutical formulation comprising the disulfide-linked multivalent multi-function protein according to any one of items 1 to 75 and optionally a pharmaceutically acceptable carrier.
79. The multi-function protein according to any one of items 1 to 75 for use as a medicament.
80. The multi-function protein according to any one of items 1 to 75 for use in treating cancer or a viral infection.
81. The multi-function protein according to any one of items 1 to 75 for use in attracting virus-specific cytotoxic T-cells of an individual to a target.
82. The multi-function protein according to any one of items 1 to 75 for use in removal of cancer cells or virus infected cells.
83. A method for the recombinant production of a disulfide-linked multivalent multi-function protein according to item 1 comprising the following steps:
  cultivating a eukaryotic cell comprising a nucleic acid according to item 76, and
  recovering the disulfide-linked multivalent multi-function protein from the cell or the cultivation medium,
  wherein the disulfide-linked multivalent multi-function protein comprises exactly two or more antigen presenting domains comprising a β2-microglobulin and the extracellular domains α1, α2 and α3 of a class I MHC molecule, wherein the antigen presenting domain has cysteine residues at least at position 11 and at position 227 and the cysteine residues at position 11 and position 227 form a disulfide bond or the antigen presenting domain has cysteine residues at least at position 11 and at position 108 and the cysteine residues at position 11 and position 108 form a disulfide bond.
84. Use of the multi-function protein according to any one of items 1 to 75 in the manufacture of a medicament.
85. The use according to item 84, wherein the medicament is for treatment of cancer or a viral infection.
86. The use according to item 84, wherein the medicament is for attracting virus-specific cytotoxic T-cells of an individual to a target.
87. The use according to item 84, wherein the medicament is for removal cancer cells or virus-infected cells.
88. A method of attracting virus-specific cytotoxic T-cells of an individual to a target in an individual comprising administering to the individual an effective amount of the disulfide-linked multivalent multi-function protein according to any one of items 1 to 75 to attract virus-specific cytotoxic T-cells of an individual to a target.
89. A method of removal of cancer cells or virus-infected cells in an individual comprising administering to the individual an effective amount of the disulfide-linked multivalent multi-function protein according to any one of items 1 to 75 to remove cancer cells or virus-infected cells.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

V. EXAMPLES

The following are examples of methods and compositions of the invention. It is understood that various other embodiments may be practiced, given the general description provided above.

Example 1

Procedure for Isolation and Stimulation of CMV-Specific CD8 Positive T-Cells from Human Donors Isolation of PBLs PBL were isolated by Ficoll gradient centrifugation from human donor blood (Greiner bio-one, Cat. No. 227290). PBLs were cultured in RPMI supplemented with 5% human serum (Sigma Cat. No. H2520), 2 mM L-glutamine (PAN Biotech, Cat. No. P04-80100), 100 µg/ml Penicillin/Streptomycin (Roche Diagnostics GmbH, Mannheim, Germany, Cat. No. 14001100).

Stimulation of PBLs

Cells ($2 \times 10^7$ cells/ml) were cultured in cell culture medium supplemented with 50 µg/ml CMV pp65-derived peptide (SEQ ID NO: 01) for two hours under cell culture conditions (37° C., 5% $CO_2$, 80% humidity). Thereafter the cell suspension was 20-fold diluted with culture medium and further cultured in flat-bottom 96-well plates at a seeding density of $2 \times 10^5$ cells per 96 well. After 4 to 5 days, 20 U/ml IL-2 (Roche, Cat. No. 11011456001), 25 ng/ml IL-7 (Peprotech, Cat. No. 200-01) and 25 ng/ml IL-15 (Peprotech, Cat. No. 200-15) were added and the cells were cultured for another 7 to 8 days. Stimulation of T-cells is visible under the microscope as cell clusters.

Re-Stimulation of PBLs

T-cells were co-cultured with stimulator cells, which are peptide-pulsed autologous primary PBLs of the same donor (either freshly prepared or derived from frozen stocks). The stimulator cells were pulsed with the peptide as described above. After the two hours of peptide incubation the PBLs were irradiated (4000 rad; STS GmbH OB29 Nr.9510-5) and washed twice in culture medium without peptide. The re-stimulation was carried out in 96 well plates round bottom plates. $8 \times 10^4$ to $1 \times 10^5$ stimulator cells were used per 96 well. Cells from the primary culture were washed twice with culture medium, resuspended in 200 µl culture medium and 80 µl were transferred to each well of the stimulator cells. After 3 days 20 U/ml IL-2, 25 ng/ml IL-7 and 25 ng/ml IL-15 were added. Cells did proliferate and were expanded every 2 to 3 days in new wells with fresh medium.

Analysis of T-Cells

Cells were stained for CD8 expression (BD, Cat. No. 345772) and CMV-specific T-cell receptors (ProImmune, Cat. No. F008-4A-E) and analyzed in FACS.

Cell Culture Medium

RPMI1640 (PAN Biotech, Cat No. P04-17500), 5% Human Serum (HS; Sigma Cat. No. H2520), 2 mM L-glutamine (PAN Biotech, Cat. No. P04-80100), 100 µg/ml Penicillin/Streptomycin (Roche Diagnostics GmbH, Mannheim, Germany, Cat. No. 14001100).

Results

FACS analysis of four human donor derived peripheral blood lymphocytes (PBLs) was performed. The cells were labeled with a FITC-conjugated anti-CD8 antibody (BD, Cat. No. 345772) combined with APC-conjugated Pro5 pentamer (ProImmune, Cat. No. F008-4A-E) to stain T-cells which carry a T-cell receptor (TCR) recognizing MHC-class I (HLA-A*0201) loaded with CMV-derived peptide (NLVP-MVATV (SEQ ID NO: 01)). For results see FIGS. 4A-B. At day 0 donor 1 and 4 carry low numbers of CMV-specific CD8 T-cells (0.08% and 0.1%, respectively). Donor 2 and 3 carry a higher number of CMV-specific CD8 T cells in their peripheral blood (0.25% and 3.12%, respectively). Fourteen days later after stimulation with CMV-derived peptide pulsed autologous cells only donors 2 and 3 show a significant increase in CMV-specific CD8 T cells (6.2% and 71.2%, respectively) whereas donors 1 and 4 do not show increased numbers of CMV-specific CD8 T cells (0.01% and 0.05%, respectively). Another 14 days later after a second stimulation with CMV-derived peptide pulsed autologous cells donors 2 and 3 show a further increase in CMV-specific CD8 T cells (15.1% and 96.6%, respectively).

Example 2

Cytotoxicity Assay

Acute lymphoblastic leukemia cells MN60 carry the A*0201 HLA-A allele. MN60 cells ($1 \times 10^6$ cells/ml) were incubated with 50 µg/ml CMV pp65 peptide (SEQ ID NO: 01) for 45 minutes under cell culture conditions (37° C., 5% $CO_2$, 80% humidity). The incubation results in a peptide exchange in the HLA-A*0201 peptide binding groove. The peptide exchanged MN60 cells were centrifuged and diluted to a density of $1 \times 10^6$ cells/ml with PBS (PanBiotech, Cat. No. P04-36500) and stained with 1 µM of the cell tracer carboxyfluorescein succinimidyl ester (CFSE, Invitrogen, Cat. No. 34554) 15 minutes at room temperature (RT). Cells were washed thereafter once with PBS and diluted to $1 \times 10^3$ cells/ml with AIM-V media (Gibco, Cat. No. 0870112DK). For the assay MN60 cells (target cells) were co-cultured in 96-well round bottom plates with CMV-specific human donor 3 derived CD8+ T-cells (effector cells, see example 1) for four hours under cell culture conditions. The effector to target cell ratio of was 4:1. Dead cells are stained with 1 µl/100 µl propidium iodide (PI, Sigma, Cat. No. P-4864) and were FACS analyzed.

Results

Flow Cytometric Analysis was performed to analyze the cytolytic capability of stimulated CTLs through lysis of MN60 tumor cells loaded with CMV peptide:

A co-culture of MN60 cells not loaded with the CMV-derived peptide was performed. MN60 cells are FITC-positive. Effector cells are FITC-negative. Dead cells are PI positive, alive cells are PI-negative. More than 85% of the MN60 cells are alive when they are not loaded with the CMV-derived peptide (Q2 and Q4).

A co-culture of MN60 cells loaded with the CMV-derived peptide was performed. More than 80% of the MN60 cells are dead (Q2 and Q4) whereas the ratio of alive and dead effector cells is not remarkably altered between the FACS analysis indicating a specific lysis of CMV-peptide-loaded target cells.

Flow Cytometric Analysis to analyze the cytolytic capability of stimulated CTLs through lysis of MN60 tumor cells loaded with CMV peptide depending on the effector to target cell ratio:

The cytotoxic assay was performed as described above. Different effector cell to target cell ratios were applied ranging from 0.5 effector cells per target cell to four effector cells per target cell. Incubation time was four hours. MN60 cells which were not loaded with the CMV-derived peptide do not show an increased number of dead cells with an increased effector to target ratio, i.e. ranging from 8% to 13% with ratio 0.5:1 to 4:1.

Almost 20% of the MN60 cells loaded with CMV-derived peptide are already killed with a low effector to target ratio of 0.5:1 within four hours. The number of dead cells increases steeply with an increase in effector to target ratio reaching up to 83% at a ratio of 4:1 effector cells per target cell.

Example 3

DNA Preparation, Transfection, Expression, Purification and Analysis

DNA Preparation 250 ml of overnight bacterial LB culture were harvested and plasmid DNA was extracted according to the manufacturer's protocol (High speed Maxi kit, Qiagen, Cat. No. 12663). The resulting plasmid DNA was eluted in 1 ml TE buffer and DNA concentration was determined by spectrophotometric measurement (Epoch, BioTek).

The final expression vector comprised the following elements:

the endonucleolytic restriction sites HindIII, NheI,
a CMV-promoter,
an 5'UTR 1 (derived from the human CMV),
Intron A,
a 5'UTR 2,
an ampicillin-resistance gene,
a BGH poly A site (bovine growth hormone polyadenylation signal),
pUC Ori.

Amino acid sequences of the elements of the multi-function protein comprising a CMV-derived peptide and IGF1R binding specificity (anti-IGF1R antibody):

CMV pp65 Peptide:
SEQ ID NO: 01
NLVPMVATV

Linker 1:
SEQ ID NO: 82
GGGGSGGGGSGGGGS

β2-microglobulin:
SEQ ID NO: 71
IQRTPKIQVYSRHPAENGKSNFLNCYVSGFHPSDIEVD
LLKNGERIEKVEHSDLSFSKDWSFYLLYYTEFTPTEKD
EYACRVNHVTLSQPKIVKWDRDM Linker 2:
SEQ ID NO: 83
GGGGSGGGGSGGGGSGGGGS HLA-A*0201 α1-α3:
SEQ ID NO: 72
GSHSMRYFFTSVSRPGRGEPRFIAVGYVDDTQFVRFDS
DAASQRMEPRAPWIEQEGPEYWDGETRKVKAHSQTH
RVDLGTLRGYYNQSEAGSHTVQRMYGCDVGSDWRF
LRGYHQYAYDGKDYIALKEDLRSWTAADMAAQTTK
HKWEAAHVAEQLRAYLEGTCVEWLRRYLENGKETL
QRTDAPKTHMTHHAVSDHEATLRCWALSFYPAEITLT
WQRDGEDQTQDTELVETRPAGDGTFQKWAAVVVPS
GQEQRYTCHVQHEGLPKPLTLRW Linker 3:
SEQ ID NO: 73
GS Linker 4:
SEQ ID NO: 83
GGGGSGGGGSGGGGSGGGGS Linker 13:
SEQ ID NO: 136
GSG Ig light chain:
SEQ ID NO: 120
EIVLTQSPATLSLSPGERATLSCRASQSVSSYLAWYQQ
KPGQAPRLLIYDASKRATGIPARFSGSGSGTDFTLTISS
LEPEDFAVYYCQQRSKWPPWTFGQGTKVESKRTVAA
PSVFIFPPSDEQLKSGTASVVCLLNNFYPREAKVQWKV
DNALQSGNSQESVTEQDSKDSTYSLSSTLTLSKADYE
KHKVYACEVTHQGLSSPVTKSFNRGEC Ig heavy chain (IgG1-L234A, L235A mutant):
SEQ ID NO: 121
QVELVESGGGVVQPGRSQRLSCAASGFTFSSYGMHW
VRQAPGKGLEWVAIIWFDGSSTYYADSVRGRFTISRD
NSKNTLYLQMNSLRAEDTAVYFCARELGRRYFDLWG
RGTLVSVSSASTKGPSVFPLAPSSKSTSGGTAALGCLV
KDYFPEPVTVSWNSGALTSGVHTFPAVLQSSGLYSLSS
VVTVPSSSLGTQTYICNVNHKPSNTKVDKKVEPKSCD
KTHTCPPCPAPEAAGGPSVFLFPPKPKDTLMISRTPEVT
CVVVDVSHEDPEVKFNWYVDGVEVHNAKTKPREEQ
YNSTYRVVSVLTVLHQDWLNGKEYKCKVSNKALPAP
IEKTISKAKGQPREPQVYTLPPSRDELTKNQVSLTCLV
KGFYPSDIAVEWESNGQPENNYKTTPPVLDSDGSFFLY
SKLTVDKSRWQQGNVFSCSVMHEALHNHYTQKSLSL
SPGK Ig heavy chain (IgG1-L234A, L235A mutant with knob variation):
SEQ ID NO: 122
QVELVESGGGVVQPGRSQRLSCAASGFTFSSYGMHW
VRQAPGKGLEWVAIIWFDGSSTYYADSVRGRFTISRD
NSKNTLYLQMNSLRAEDTAVYFCARELGRRYFDLWG
RGTLVSVSSASTKGPSVFPLAPSSKSTSGGTAALGCLV
KDYFPEPVTVSWNSGALTSGVHTFPAVLQSSGLYSLSS
VVTVPSSSLGTQTYICNVNHKPSNTKVDKKVEPKSCD
KTHTCPPCPAPEAAGGPSVFLFPPKPKDTLMISRTPEVT
CVVVDVSHEDPEVKFNWYVDGVEVHNAKTKPREEQ
YNSTYRVVSVLTVLHQDWLNGKEYKCKVSNKALPAP
IEKTISKAKGQPREPQVYTLPPCRDELTKNQVSLWCLV
KGFYPSDIAVEWESNGQPENNYKTTPPVLDSDGSFFLY
SKLTVDKSRWQQGNVFSCSVMHEALHNHYTQKSLSL
SPGK Ig heavy chain (IgG1-L234A, L235A mutant with hole variation):
SEQ ID NO: 123
QVELVESGGGVVQPGRSQRLSCAASGFTFSSYGMHW
VRQAPGKGLEWVAIIWFDGSSTYYADSVRGRFTISRD
NSKNTLYLQMNSLRAEDTAVYFCARELGRRYFDLWG
RGTLVSVSSASTKGPSVFPLAPSSKSTSGGTAALGCLV
KDYFPEPVTVSWNSGALTSGVHTFPAVLQSSGLYSLSS
VVTVPSSSLGTQTYICNVNHKPSNTKVDKKVEPKSCD
KTHTCPPCPAPEAAGGPSVFLFPPKPKDTLMISRTPEVT
CVVVDVSHEDPEVKFNWYVDGVEVHNAKTKPREEQ
YNSTYRVVSVLTVLHQDWLNGKEYKCKVSNKALPAP
IEKTISKAKGQPREPQVCTLPPSRDELTKNQVSLSCAV
KGFYPSDIAVEWESNGQPENNYKTTPPVLDSDGSFFLV
SKLTVDKSRWQQGNVFSCSVMHEALHNHYTQKSLSL
SPGK Ig heavy chain Fc-region
(IgG1-L234A, L235A mutant Fc-region knob variant):
SEQ ID NO: 124
EPKSADKTHTCPPCPAPEAAGGPSVFLFPPKPKDTLMI
SRTPEVTCVVVDVSHEDPEVKFNWYVDGVEVHNAKT
KPREEQYNSTYRVVSVLTVLHQDWLNGKEYKCKVSN
KALPAPIEKTISKAKGQPREPQVYTLPPCRDELTKNQV
SLWCLVKGFYPSDIAVEWESNGQPENNYKTTPPVLDS
DGSFFLYSKLTVDKSRWQQGNVFSCSVMHEALHNHY
TQKSLSLSPGK scFv:
SEQ ID NO: 125
QVELVESGGGVVQPGRSQRLSCAASGFTFSSYGMHW
VRQAPGKCLEWVAIIWFDGSSTYYADSVRGRFTISRD
NSKNTLYLQMNSLRAEDTAVYFCARELGRRYFDLWG
RGTLVSVSSGGGGSGGGGSGGGGSGGGGSEIVLTQSP
ATLSLSPGERATLSCRASQSVSSYLAWYQQKPGQAPR
LLIYDASKRATGIPARFSGSGSGTDFTLTISSLEPEDFAV
YYCQQRSKWPPWTFGCGTKVESK Amino acid sequences of the elements of the multi-function protein comprising a CMV-derived peptide and M -continued Ig heavy chain (IgG1-L234A, L235A mutant with knob variation):
MHCI-0008
SEQ ID NO: 130
EVQLQESGPGLVKPSQSLSLTCSVTGYSITSGYYWNWI
RQFPGNKLEWMGYITYDGSNNYNPSLKNRISITRDTSK
NQFFLKLNSVTTEDTATYYCADFDYWGQGTTLTVSSA
STKGPSVFPLAPSSKSTSGGTAALGCLVKDYFPEPVTV
SWNSGALTSGVHTFPAVLQSSGLYSLSSVVTVPSSSLG
TQTYICNVNHKPSNTKVDKKVEPKSCDKTHTCPPCPA
PEAAGGPSVFLFPPKPKDTLMISRTPEVTCVVVDVSHE
DPEVKFNWYVDGVEVHNAKTKPREEQYNSTYRVVSV
LTVLHQDWLNGKEYKCKVSNKALPAPIEKTISKAKGQ
PREPQVYTLPPCRDELTKNQVSLWCLVKGFYPSDIAV
EWESNGQPENNYKTTPPVLDSDGSFFLYSKLTVDKSR
WQQGNVFSCSVMHEALHNHYTQKSLSLSPGK Ig heavy chain (IgG1-L234A, L235A mutant with knob variation):
MHCI-0030 and MHCI-0031
SEQ ID NO: 131
QVQLQESGPGLVKPSQTLSLTCTVSGGSITSGYYWNW
IRQHPGKGLEWIGYITYDGSNNYNPSLKSRVTISRDTS
KNQFSLKLSSVTAADTAVYYCADFDYWGQGTLVTVS
SASTKGPSVFPLAPSSKSTSGGTAALGCLVKDYFPEPV
TVSWNSGALTSGVHTFPAVLQSSGLYSLSSVVTVPSSS
LGTQTYICNVNHKPSNTKVDKKVEPKSCDKTHTCPPC
PAPEAAGGPSVFLFPPKPKDTLMISRTPEVTCVVVDVS
HEDPEVKFNWYVDGVEVHNAKTKPREEQYNSTYRVV
SVLTVLHQDWLNGKEYKCKVSNKALPAPIEKTISKAK
GQPREPQVYTLPPCRDELTKNQVSLWCLVKGFYPSDI
AVEWESNGQPENNYKTTPPVLDSDGSFFLYSKLTVDK
SRWQQGNVFSCSVMHEALHNHYTQKSLSLSPGK Ig heavy chain (IgG1-L234A, L235A mutant with hole variation):
MHCI-0008
SEQ ID NO: 132
EVQLQESGPGLVKPSQSLSLTCSVTGYSITSGYYWNWI
RQFPGNKLEWMGYITYDGSNNYNPSLKNRISITRDTSK
NQFFLKLNSVTTEDTATYYCADFDYWGQGTTLTVSSA
STKGPSVFPLAPSSKSTSGGTAALGCLVKDYFPEPVTV
SWNSGALTSGVHTFPAVLQSSGLYSLSSVVTVPSSSLG
TQTYICNVNHKPSNTKVDKKVEPKSCDKTHTCPPCPA
PEAAGGPSVFLFPPKPKDTLMISRTPEVTCVVVDVSHE
DPEVKFNWYVDGVEVHNAKTKPREEQYNSTYRVVSV
LTVLHQDWLNGKEYKCKVSNKALPAPIEKTISKAKGQ
PREPQVCTLPPSRDELTKNQVSLSCAVKGFYPSDIAVE
WESNGQPENNYKTTPPVLDSDGSFFLVSKLTVDKSRW
QQGNVFSCSVMHEALHNHYTQKSLSLSPGK Ig heavy chain (IgG1-L234A, L235A mutant with hole variation):
MHCI-0030 and MHCI-0031
SEQ ID NO: 133
QVQLQESGPGLVKPSQTLSLTCTVSGGSITSGYYWNW
IRQHPGKGLEWIGYITYDGSNNYNPSLKSRVTISRDTS
KNQFSLKLSSVTAADTAVYYCADFDYWGQGTLVTVS
SASTKGPSVFPLAPSSKSTSGGTAALGCLVKDYFPEPV
TVSWNSGALTSGVHTFPAVLQSSGLYSLSSVVTVPSSS
LGTQTYICNVNHKPSNTKVDKKVEPKSCDKTHTCPPC
PAPEAAGGPSVFLFPPKPKDTLMISRTPEVTCVVVDVS
HEDPEVKFNWYVDGVEVHNAKTKPREEQYNSTYRVV
SVLTVLHQDWLNGKEYKCKVSNKALPAPIEKTISKAK
GQPREPQVCTLPPSRDELTKNQVSLSCAVKGFYPSDIA
VEWESNGQPENNYKTTPPVLDSDGSFFLVSKLTVDKS
RWQQGNVFSCSVMHEALHNHYTQKSLSLSPGK Ig heavy chain Fc-region (IgG1-L234A, L235A mutant Fc-region knob variant):
SEQ ID NO: 124
EPKSADKTHTCPPCPAPEAAGGPSVFLFPPKPKDTLMI
SRTPEVTCVVVDVSHEDPEVKFNWYVDGVEVHNAKT
KPREEQYNSTYRVVSVLTVLHQDWLNGKEYKCKVSN
KALPAPIEKTISKAKGQPREPQVYTLPPCRDELTKNQV
SLWCLVKGFYPSDIAVEWESNGQPENNYKTTPPVLDS
DGSFFLYSKLTVDKSRWQQGNVFSCSVMHEALHNHY
TQKSLSLSPGK scFv:
MHCI-0008
SEQ ID NO: 134
EVQLQESGPGLVKPSQSLSLTCSVTGYSITSGYYWNWI
RQFPGNKLEWMGYITYDGSNNYNPSLKNRISITRDTSK
NQFFLKLNSVTTEDTATYYCADFDYWGQGTTLTVSSG
GGGSGGGGSGGGGSGGGGSDIVLTQSPSSLSASLGDR
VTISCSASQGIRNYLNWYQQRPDGTVKLLIYYTSSLHS
GVPSRFSGSGSGTDYSLTISNLEPEDIATYYCQQYSKLP
WTFGGGTKLEIK scFv:
MHCI-0030 and MHCI-0031
SEQ ID NO: 135
QVQLQESGPGLVKPSQTLSLTCTVSGGSITSGYYWNW
IRQHPGKGLEWIGYITYDGSNNYNPSLKSRVTISRDTS
KNQFSLKLSSVTAADTAVYYCADFDYWGQGTLVTVS
SGGGGSGGGGSGGGGSGGGGSDIQMTQSPSSLSASVG
DRVTITCRASQGIRNYLNWYQQKPGKAPKLLIYYTSSL -continued

HSGVPSRFSGSGSGTDFTLTISSLQPEDFATYYCQQYS

KLPWTFGQGTKVEIK

Transfection

HEK 293 cells were diluted to 8×10$^5$ cells/ml the day before transfection. About 1 to 1.6×10$^6$ cells/ml were transfected according to the manufacturer's protocol. For a final transfection volume of 30 ml, 30 μg DNA were diluted to a final volume of 1 ml with Opti-MEM® I Reduced Serum Medium (Gibco, Cat. No. 31985070). 2 μl of 293Fectin™ Reagent (Invitrogen, Cat. No. 12347019) per 1 μg DNA were equally diluted to a final volume of 1 ml with Opti-MEM® medium and incubated for 5 minutes. After incubation the diluted DNA was added to the diluted 293Fectin™ Reagent, gently mixed, incubated for another 20-30 minutes and afterwards drop wise pipetted to 28 ml of the HEK 293 cells to obtain a final volume of 30 ml. The cells were incubated under cell culture condition (37° C., 8% $CO_2$, 80% humidity) on an orbital shaker rotating at 125 rpm and harvested after 72 hours. The harvest was centrifuged for 10 minutes at 1000 rpm, for 10 minutes at 3000 rpm and filtered through a 22 μm sterile filter (Millipore, Cat. No. SCGPU05RE).

Western Blotting

500 μl of cell culture supernatant was concentrated with Pall Nanosep Omega-Membrane 30KD Centrifugal Devices (Pall, Cat. No. OD030C33) to a volume of 50 μl. 17.5 μl of each concentrate was diluted to a final volume of 25 μl with 4× XT Sample Buffer (Bio Rad, Cat. No. 161-0791) and 20× XT Reducing Agent (BioRad, Cat. No. 161-0792), heated for 8 minutes at 96° C. and applied on a 4-12% Criterion XT Precast Gel (Cat. No. 345-0124). Blotting was performed with Trans-Blot SD semi-dry Transfer Cell (BioRad) at 20 V for 30 minutes on a Trans-blot Pure Nitrocellulose membrane (0.45 μm) (BioRad, Cat. No. 162-0117). Blocking of the membrane was performed with 1× Western Blocking Reagent (Roche, Cat. No. 11921681001) for one hour at room temperature. Staining was performed with peroxidase conjugated polyclonal rabbit anti-human κ-light chain (DAKO, Cat. No. P0129, diluted 1:3000) and polyclonal rabbit anti-human IgG antibody HRP conjugate (DAKO, Cat. No. P0214, diluted 1:5000) for one hour at room temperature. Luminescence detection was carried out with LUMI-Imager F1 (Roche).

Purification

Cells were removed from culture medium by centrifugation. Multi-function proteins were purified from supernatants by protein A affinity chromatography (MabSelect-Sepharose on an ÄKTA-Avant). Eluted multi-function proteins were concentrated with Amicon centrifugation tubes to a protein concentration of 3 mg/ml. An aliquot was analyzed on a size exclusion chromatography (HPLC TSK-gel GFC300 Sys89). Preparative SEC on a Superdex 200 was performed to remove aggregates and buffer the fusion proteins in 20 mM histidine, 140 mM NaCl, pH 6.0. Eluted multi-function proteins were concentrated with Amicon centrifugation tube to a protein concentration of 1 mg/ml and sterile filtered (0.2 μm pore size).

Analytics

Multi-function protein samples were analyzed by OD280 using a UV spectrophotometer to determine the protein concentration in solution. The extinction coefficient required for this was calculated from the amino acid sequence according to Pace (Pace, et al., Protein Science 4 (1995) 2411-2423). Size-exclusion chromatography (SE-HPLC) was performed on TSK-Gel300SWXL or Superdex 200 columns with a 0.2 M potassium phosphate buffer, comprising 0.25 M KCl, pH 7.0 as mobile phase in order to determine the content of monomeric, aggregated and degraded species in the samples. Sodium dodecyl sulfate (SDS) polyacrylamide gel electrophoresis (reducing and non-reducing) was performed to analyze the purity of the multi-function protein preparations with regard to product-related degradation products and unrelated impurities. Electrospray ionization mass spectrometry (ESI-MS) was performed with reduced (TCEP) and deglycosylated (N-glycosidase F) samples to confirm the correct mass/identity of each chain and detect chemical modifications. ESI-MS of the deglycosylated samples was carried out to analyze the nature and quality of the fully assembled protein and detect potential product-related side products.

Method SDS-PAGE and Coomassie Staining

| Method SDS-PAGE and Coomassie Staining | |
|---|---|
| Device: | Invitrogen XCell Sure Lock Mini-Cell |
| Gel: | 4-20% Tris-Glycine Gel, Invitrogen EC6025BOX |
| Buffer: | Tris-Glycine SDS Running Buffer (10x), Invitrogen LC2675-5 |
| Sample buffer: | Tris-Glycine SDS Sample Buffer (2x), Invitrogen LC2676 |
| Reducing buffer: | NuPAGE Sample Reducing Agent (10x), Invitrogen NP0004 |
| Molecular Weight Marker: | Mark 12, MW Standard, Invitrogen LC5677 |

Protein Sample Preparation

The sample was adjusted to a protein concentration of 1 mg/ml with buffer. For sample reduction the following procedure was carried out:

reduction buffer: 4 ml Sample buffer (2×) and 1 ml reducing buffer (10×)

dilute sample 1:1 with reduction buffer incubate for 5 minutes at 70° C.

The gel electrophoresis was carried out at 125 V for 90 minutes. The gels were stained with Simply Blue Safe Stain (Invitrogen. Cat. No. LC6065).

Results

TABLE

| No. | polypeptides comprised in the multi-function protein with IGF-1R binding specificity | FIG. | yield |
|---|---|---|---|
| 1 | 1. [CMV-pp65-peptide]-[linker 1]-[β2-microglobulin]-[linker 2]-[HLA-A-α1-α2-α3]-[linker 3]-[IgG1-L234A, L235A mutant with hole variation]<br>2. Ig heavy chain (IgG1-L234A, L235A mutant with knob variation)<br>3. Ig light chain | FIG. 23A | 5 mg/l |
| 2 | 1. [CMV-pp65-peptide]-[linker 1]-[β2-microglobulin]-[linker 2]-[HLA-A-α1-α2-α3]-[linker 3]-[IgG1-L234A, L235A mutant with hole variation]<br>2. IgG1-L234A, L235A mutant Fc-region knob variant<br>3. Ig light chain Fusion to the Ig light chain | FIG. 22B-1<br><br><br><br><br><br>FIG. 22B-2 | A: 5-18 mg/l |

TABLE-continued

| No. | polypeptides comprised in the multi-function protein with IGF-1R binding specificity | FIG. | yield |
|---|---|---|---|
| 3 | 1. [CMV-pp65-peptide]-[linker 1]-[β2-microglobulin]-[linker 2]-[HLA-A-α1-α2-α3]-[linker 3]-[IgG1-L234A, L235A mutant with hole variation] 2. IgG1-L234A, L235A mutant with knob variation 3. Ig light chain Fusion to the Ig light chain | FIG. 23C-1 FIG. 23C-2 | A: 4-23 mg/l |
| 4 | 1. [CMV-pp65-peptide]-[Linker 1]-[β2-microglobulin]-[Linker 2]-[HLA-A-α1-α2-α3]-[Linker 3]-[IgG1-L234A, L235A mutant with hole variation] 2. IgG1-L234A, L235A mutant with knob variation | FIG. 23D | 4 mg/l |
| 5 | 1. [CMV-pp65-peptide]-[linker 1]-[β2-microglobulin]-[linker 2]-[HLA-A-α1-α2-α3]-[linker 3]-[IgG1-L234A, L235 A-Fc-region] | FIG. 23E | 4 mg/l |
| 6 | 1. [CMV-pp65-peptide]-[linker 1]-[β2-microglobulin]-[linker 2]-[HLA-A-α1-α2-α3]-[linker 3]-[IgG1-L234A, L235A mutant Fc-region]-[linker 4]-[scFv] | FIG. 23F | <1 µg/l |
| 7 | 1. [CMV-pp65-peptide]-[linker 1]-[β2-microglobulin]-[linker 2]-[HLA-A-α1-α2-α3]-[linker 3]-[IgG1-L234A, L235A mutant] 2. Ig light chain Fusion to the Ig light chain | FIG. 23G-1 FIG. 23G-2 | <1 µg/l |

The SDS gel with Coomassie staining and the corresponding SEC chromatograms of selected multi-function proteins with a structure corresponding to number 1, 2A and 3A according to the previous table are shown in FIGS. 5A-C and 6A-C. It can be seen that defined multi-function proteins can be obtained.

Example 4

Binding of MHC-I-Anti-IGF-1R Multi-Function Protein to Human IGF-1R Positive Cell Line H460M2 cells were diluted to 8×10$^5$ cells/ml in AIM-V medium (Gibco, Cat. No. 0870112DK). 500 µl of the cell suspension was stained with 10 µg of a MHC-I-anti-IGF-1R multi-function protein as reported herein either at 4° C. or 37° C. for one hour. Thereafter cells were washed once with ice-cold AIM-V medium and stained with a second antibody, which was a goat F(ab')$_2$ anti-human IgG (H+L) antibody conjugated to R-PE (Dianova, Cat. No. 109-116-088, dilution 1:50) for 30 minutes at 4° C. Thereafter cells were washed once with ice-cold AIM-V medium and fluorescence was measured via FACS Canto II (BD Bioscience) with gating on living cells. A bispecific antibody served as Isotype control, an anti IGF-1R antibody (see e.g. WO 2004/087756 and WO 2007/115814) served as positive control.

Results

Considering the shift in the PE-fluorescence measurement (X-axis), the MHC-I-anti-IGF-1R multi-function protein shows no visible difference in binding to H460M2 target cells in comparison to the control antibody. There is also no difference whether the incubation with the MHC-I-anti-IGF-1R multi-function protein is accomplished at 4° C. or 37° C. Neither the incubation with the isotype control nor with the fluorescence labeled secondary antibody alone shows any shift in the PE fluorescence measurement. Despite the fusion of the class I MHC molecule the antibody variable domain of the MHC-I-anti-IGF-1R multi-function protein herein still binds to the H460M2 target cells.

Example 5

In Vitro Removal of Antigen Expressing Cells

I24 target cells (1×10$^5$ cells/ml) were seeded in cell culture media (RPMI 1640 supplemented with 2 mM L-glutamine, 1 mM sodium pyruvate, 0.1 mM NEAA, and 10% (v/w) FCS) on WillCo Glass Bottom Dishes (FA. WillCo Wells BV, REF GWST-3522) for 24 to 48 hours. WillCo Glass Bottom Dishes were pre-coated with 50 µg/ml poly-L-lysine hydrochloride (Sigma Aldrich, Cat # P2658) per dish for 30 min. After coating the dishes were thoroughly rinsed with sterile tissue culture grade water and dried for two hours.

After the cultivation cell culture media was removed and the IGF-1R binding multi-function protein comprising one [CMV-pp65-peptide]-[linker 1]-[β2-microglobulin]-[linker 2]-[HLA-A-α1-α2-α3]-[linker 3]-[IgG1-L234A, L235A mutant with hole variation] fusion polypeptide, one IgG1-L234A, L235A mutant Fc-region knob variant disulfide-linked polypeptide and one Ig light chain, wherein the multi-function protein specifically binds to human IGF-1R as reported herein (see e.g. Example 3) was added in a final concentration of 5 µg/ml in 3 mM K$^+$ Krebs Ringer HEPES Buffer pH 7.3 (supplemented with 0.5 mM DL-dithiothreitol, 1 mM ascorbic acid, and 4 mM glutathione).

T-cells were added in a target cell to effector cell ration of 1:10. Imaging was performed for 4 hours with a Zeiss Axiovert 135 microscope.

Results

The IGF-1R binding multi-function protein mediated lysis of human IGF-1R expressing I24 3T3 cells (large adherently growing cells). Lysis is mediated by human CMV-specific T-cells (small cells either round shaped or amoeboid migrating cells). I24 cells are incubated with the multi-function protein at a concentration of 5 µg/ml and human CMV-specific T-cells (pre-activated with HLA-A0201$^+$/CMV peptide pulsed APCs). Note the interaction of the I24 cells with the T-cells at 56 min and 76 min and subsequently the collapse of the I24 cell after 125 min.

A control showing the absence of lysis of I24 3T3 cells (large adherently growing cells, white arrowhead) through human CMV-specific T-cells (small cells either round shaped or amoeboid migrating cells) in the absence of an antigen binding multi-function protein as reported herein was performed. I24 cells are incubated with specific cytotoxic T-cells (pre-activated with HLA-A0201$^+$/CMV peptide pulsed APCs). Time lapse is indicated below the respective picture.

Example 6

Cytotoxicity Assay

Cell culture medium (50 µl) was pipetted into each well of an Xcelligence 96well E-plate (Roche, Cat #05232368001) to perform background measurement.

I24 cells were diluted to 1×10$^6$ cells/ml in cell culture media (RPMI 1640, 2 mM L-glutamine, 1 mM Sodium pyruvate, 0.1 mM NEAA, 10% (v/w) FCS) and 50 µl (2×10$^4$ cells/well) were pipetted in each well of an Xcelligence 96well plate to a final volume of 100 µl and cultivated for 24 hours (37° C., 8% CO$_2$, 80% humidity). After 24 hours the medium was removed and the cells were washed with 200 µl AIM-V (Serum Free Medium (Invitrogen) T-cell medium (Cat-No): 12055-083) medium. The IGF-1R binding multi-function protein comprising one [CMV-pp65-peptide]-[linker 1]-[β2-microglobulin]-[linker 2]-[HLA-A-α1-α2-α3]-[linker 3]-[IgG1-L234A, L235A mutant with hole variation] fusion polypeptide, one IgG1-L234A, L235A mutant Fc-region knob variant disulfide-linked polypeptide and one Ig light chain, wherein the multi-function protein specifically binds to human IGF-1R, was added to the washed target cells in a final concentration of 1 µg/ml in AIM-V medium. Effector cells in the respectable ratio were added in AIM-V media to a final volume of 150 µl. Afucosylated IgG1 monoclonal antibody directed against human IGF-1R (anti-IGF-1R antibody-afucosylated) and non-binding human anti-digoxinenin antibody (anti-digoxygenin antibody) served as Isotype control and specific antibody control, respectively. Measurement was performed for 6 to 9 hours respectively with the Xcelligence System (Roche).

Results

The IGF-1R binding multi-function protein triggers lysis of H460M2 tumor cells through human CMV-specific T-cells.

Tumor cells were incubated for 4 hours with 1 µg/ml of the multi-function protein comprising one [CMV-pp65-peptide]-[linker 1]-[β2-microglobulin]-[linker 2]-[HLA-A-α1-α2-α3]-[linker 3]-[IgG1-L234A, L235A mutant with hole variation] fusion polypeptide, one IgG1-L234A, L235A mutant Fc-region knob variant disulfide-linked polypeptide and one Ig light chain, wherein the multi-function protein specifically binds to human IGF-1R, and specific T-cells in the respective ratio (1:1.5 to 1:0.5) (see FIGS. 8A-C). Percentage of lysis is denoted above the respective bars. Afucosylated IgG1 monoclonal antibody directed against human IGF-1R (MAB IGF-1R-afu) did not trigger a significant tumor cell lysis.

The multi-function protein as reported herein triggers lysis of I24 3T3 target cells through human CMV-specific T-cells.

Target cells were incubated for 4 hours with 1 µg/ml of an antigen binding multi-function protein comprising one [CMV-pp65-peptide]-[linker 1]-[β2-microglobulin]-[linker 2]-[HLA-A-α1-α2-α3]-[linker 3]-[IgG1-L234A, L235A mutant with hole variation] fusion polypeptide, one IgG1-L234A, L235A mutant Fc-region knob variant disulfide-linked polypeptide and one Ig light chain, wherein the multi-function protein specifically binds to human IGF-1R, and specific T-cells in the respective ratio (1:1.5 to 1:0.5) (see FIGS. 9A-C). Percentage of lysis is denoted above the respective bars. Afucosylated IgG1 monoclonal antibody directed against human IGF-1R (anti-IGF-1R antibody-afucosylated) and non-binding human anti-Digoxigenin antibody (anti-digoxygenin antibody) did not trigger a significant target cell lysis.

Example 7

In Vitro Efficacy

IGF-1R positive lung adenocarcinoma cell line H460M2 was incubated with 1 µg/ml of a multi-function protein comprising an hCMV-derived peptide and an anti-IGF-1R antibody and human CMV-specific CD8-positive T-cells at a low effector cell to target cell ratio (1.5 to 0.5 specific T-cells per tumor cell). Control antibody was a glycoengineered anti-IGF-1R antibody. The incubation time was 6 hours. The incubation with multi-function protein results in a potent removal of H460M2 tumor cells.

Example 8

Binding of Different MHC-I-Anti-MCSP Multi-Function Protein to MCSP Positive Target Cells Colo38 cells were incubated for 5 min. with Accutase (PAA, Cat. # L11-007) to obtain a single cell suspension. $2 \times 10^5$ cells per vial were incubated with 1 µg/ml MHC-I-anti-MCSP multi-function protein construct in 100 µl PBS/2% FCS for 45 min. at 4° C. After incubation cells were washed with 1 ml cold PBS/2% FCS and centrifuged for 7 min. with 910 rpm. Cells were resuspended in 100 µl PBS/2% FCS with secondary antibody (goat anti-human IgG1 antibody-PE conjugate, Jackson Lab., Cat. #109-116-088) at 2 µg/ml and incubated for another 45 min. at 4° C. Cells were washed twice with 1 ml PBS %2% FCS and measured with BD Canto II Flow Cytometer. The results are shown in FIG. 7.

Example 9

Incubation of MCSP Positive Cells with MHC-I-Anti-MCSP Multi-Function Proteins

Colo38 or WM266-4 cells were incubated for 5 min. with Accutase (PAA, Cat. # L11-007) to obtain a single cell suspension. $2 \times 10^4$ cells of the Colo38 cell line or $1 \times 10^4$ cells of the WM266-4 cell line per well were incubated for 24 h in Eplates96 (Roche, Cat. #05232368001) in 100 µl of the respective cell culture medium (Colo38 cell line: RPMI1640 supplemented with 2 mM glutamine, 10% FCS; WM-266-4 cell line: RPMI1640 supplemented with 2 mM glutamine, 10% FKS, 2 mM sodium pyruvate, 2 mM NEAA) and adherence (impedance) was measured every 15 min with ACEA technology (Xcelligence RTCA). After 24h (undisturbed growth phase) the cells were washed with 200 µl of AIMV-medium (Gibco, Cat. #0870112DK). MHC-I-anti-MCSP multi-function proteins were added in a final concentration of 1 µg/ml together with stimulated T-cells or PBMCs in different ratios to a final volume of 150 µl in AIMV-medium to the cells. Incubation was continued for another 4 to 48 hours with simultaneous ACEA measurement every 5 minutes. The read-out is based on impedance measurement, detecting lysed or collapsed cells as detached from the Eplate bottom. The cell index has been normalized to 1 at the first measurement point after addition of the multi-function protein. The results for 1 µg/ml multi-function protein concentration (MHCI-0008 (1), MHCI-0010 (2), MHCI-0030 (3), MHCI-0031 (4)), effector to target cell ratio of 10:1; PBMCs from Donor 3 (200.000 cells, Donor 3 is CMV-positive but EBV negative) and melanoma tumor cell line Colo38 (20.000 cells) and per 96 well, data are triplicates is shown in FIG. 14. The results for 1 µg/ml multi-function protein concentration (MHCI-0008 (1), MHCI-0010 (2), PBMCs only (3)), effector to target cell ratio of 10:1; PBMCs from Donor 3 (200.000 cells, Donor 3 is CMV-positive but EBV negative) and melanoma tumor cell line Colo38 (20.000 cells) and per 96 well, data are triplicates is shown in FIGS. 15A (Colo38) and 15B (WM266).

Example 10

Cytotoxicity Assay

Cell culture medium (50 µl) was pipetted into each well of an Xcelligence 96well E-plate (Roche, Cat # 05232368001) to perform background measurement.

Colo38 cells were diluted to $1\times10^6$ cells/ml in cell culture media (RPMI1640 supplemented with 2 mM glutamine, 10% FCS) and 50 µl ($2\times10^4$ cells/well) were pipetted in each well of an Xcelligence 96well plate to a final volume of 100 µl and cultivated for 24 hours (37° C., 8% $CO_2$, 80% humidity). After 24 hours the medium was removed and the cells were washed with 200 µl AIM-V (Serum Free Medium (Invitrogen) T-cell medium (Cat-No): 12055-083) medium. The MCSP binding multi-function proteins MHCI-0008 (monovalent, CMV peptide loaded), MHCI-0010 (monovalent, EBV peptide loaded control), MHC-0026 (bivalent, CMV peptide loaded, non-binding control), MHCI-0030 (monovalent, CMV peptide loaded, active) and MHCI-0031 (bivalent, CMV peptide loaded, active) were individually added to the washed target cells in a final concentration of 1 µg/ml in AIM-V medium. Effector cells in the respectable ratio of 10:1 (E:T) were added in AIM-V media to a final volume of 150 µl. Measurement was performed 42 hours post addition with the Xcelligence System (Roche).

The results obtained for 200.000 PBMCs (effector cells) freshly isolated from Donor 3 co-cultured with 20.000 adherent Colo38 cells (96 well plates in triplicates) are shown in FIG. 16 (lysis of cells after 42 hours of incubation with multi-function protein). 25% of the PBMCs are CD8-positive T cells of which in turn 3% are CMV-pp65-peptide specific resulting in approx. 1.500 CMV-pp65-peptide-specific CD8+ T cells per 20.000 Colo38 target cells (real E:T (Effector to Target Cell Ratio)=1:13).

Results

The MCSP binding multi-function protein triggers lysis of Colo38 tumor cells through human CMV-specific T-cells.

Example 11

LDH Release Assay

ACEA plates were centrifuged for 7 min. at 910 rpm. 50 µl of ACEA supernatants were transferred in another 96well flat bottom plate (Costar). LDH reagent (Cytotoxicity Detection Kit, Roche, Cat. # 11644793001) 1 and 2 are diluted according to the manufacturer's instructions and 50 µl of the solution were added to the supernatant. Absorption was detected after an incubation period of 5 to 25 minutes in Tecan Reader Sunrise (Tecan). Total lysis is detected through addition of 1% Triton X-100 (Sigma, Cat. # T-8787) to the target cells before centrifugation.

The results obtained for 200.000 PBMCs (effector cells) freshly isolated from Donor 3 co-cultured with 20.000 adherent Colo38 cells (96 well plates in triplicates) are shown in FIG. 17 (LDH release after 48 hours of incubation with multi-function protein). 200.000 PBMCs freshly isolated from Donor 3 were co-cultured with 20.000 adherent Colo38 cells (96 well plates in triplicates). 25% of the PBMCs are CD8-positive T cells of which in turn 3% are CMV-pp65-peptide specific resulting in approx. 1.500 CMV-pp65-peptide-specific CD8+ T cells per 20.000 Colo38 target cells (E:T (Effector to Target Cell Ratio)=1:13)

Results

The MCSP binding multi-function protein triggers lysis of Colo38 tumor cells through human CMV-specific T-cells.

Example 12

Cytotoxicity Assay

PBMCs were obtained from whole blood via Ficoll centrifugation. $1\times10^7$ PBMCs per ml were diluted in T-cell medium (RPMI 1640 supplemented with 10% HS, 2 mM glutamine) and peptide exchange on HLA-A0201 molecules was accomplished by addition of 50 µg/ml CMV pp65 peptide to the suspension. After 2-3 h incubation the PBMCs were diluted 1:10 and plated á 200 µl in 96well round bottom plates. On day 3 20 U/ml IL-2, 25 ng/ml IL-7 and IL-15 were added. After 14 d a re-stimulation was performed.

The stimulated T-cells were washed two times in the 96well plates and diluted in 200 µl T-cell medium from which 80 µl were transferred in new 96well round bottom plates.

PBMCs were stimulated according to the protocol above. Stimulated PBMCs were irradiated after peptide exchange with 4000 Gray, washed with T-cell medium twice and $1\times10^5$ PBMCs were pipetted to the 80 µl of T-cells. On day 3 20 U/ml IL-2, 25 ng/ml IL-7 and IL-15 were added. An Xcelligence cytotoxicity assay was performed with re-stimulated T-cells on day 11.

63% of the effector cells are CMV-pp65-peptide specific CD8+ T-cells.

The target cell to effector cell ratio was 1:3.5. Cell lysis was determined 10 hours after addition of the respective multi-function protein. The multi-function fusion protein was added to a final concentration of 1 µg/ml.

The results are shown in FIG. 18A for Colo38 cells and in FIG. 18B for WM266 cells.

Example 13

Disulfide-Stabilized Multi-Function Proteins A disulfide-bridge between position 11 and 227 of the antigen presenting domain in the multi-function protein as reported herein has been introduced.

The amino acid sequence of the disulfide stabilized antigen presenting domain is:

```
                                         (SEQ ID NO: 137)
NLVPMVATVGCGGSGGGGSGGGGSIQRTPKIQVYSRHPAENGKSNFLNCY

VSGFHPSDIEVDLLKNGERIEKVEHSDLSFSKDWSFYLLYYTEFTPTEKD

EYACRVNHVTLSQPKIVKWDRDMGGGGSGGGGSGGGGSGGGGSGSHSMRY

FFTSVSRPGRGEPRFIAVGYVDDTQFVRFDSDAASQRMEPRAPWIEQEGP

EYWDGETRKVKAHSQTHRVDLGTLRGCYNQSEAGSHTVQRMYGCDVGSD

WRFLRGYHQYAYDGKDYIALKEDLRSWTAADMAAQTTKHKWEAAHVA

EQLRAYLEGTCVEWLRRYLENGKETLQRTDAPKTHMTHHAVSDHEATLR

CWALSFYPAEITLTWQRDGEDQTQDTELVETRPAGDGTFQKWAAVVVPS

GQEQRYTCHVQHEGLPKPLTLRWGSGQVQLQESGPGLVKPSQTLSLTCTV

SGGSITSGYYWNWIRQHPGKGLEWIGYITYDGSNNYNPSLKSRVTISRDT

SKNQFSLKLSSVTAADTAVYYCADFDYWGQGTLVTVSSASTKGPSVFPLA

PSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPC
```

-continued

PAPEAAGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALG

APIEKTISKAKGQPREPQVCTLPPSRDELTKNQVSLSCAVKGFYPSDIAV

EWESNGQPENNYKTTPPVLDSDGSFFLVSKLTVDKSRWQQGNVFSCSVMH

EALHNHYTQKSLSLSPGK.

Without disulfide stabilization 6.4 mg of multi-function protein can be obtained from 1 l cultivation supernatant after protein A affinity purification. The final yield after size exclusion chromatography to separate aggregates was 2.2 mg.

With disulfide stabilization 17.8 mg of multi-function protein can be obtained from 1 l cultivation supernatant after protein A affinity purification. The final yield after size exclusion chromatography was 11.4 mg due to a lower amount of aggregates due to increased thermal stability by the introduced disulfide bridge.

The analytical size exclusion chromatograms after protein A affinity chromatography but prior to aggregate removal by preparative size exclusion chromatography are shown in FIG. 19.

The disulfide-linked multi-function proteins show the same functionality as the non-disulfide-linked multi-function proteins (see FIG. 20).

PBMCs were obtained from whole blood via Ficoll centrifugation. 1×10⁷ PBMCs per ml were diluted in T-cell medium (RPMI 1640, supplemented with 10% HS, 2 mM glutamine) and peptide exchange on HLA-A0201 molecules was accomplished by addition of 50 µg/ml CMV pp65 peptide to the suspension. After 2-3 h incubation the PBMCs are diluted 1:10 and plated á 200 µl in 96well round bottom plates. On day 3 20 U/ml IL-2, 25 ng/ml IL-7 and IL-15S were added. Cell were taken 11 d after primary stimulation; 45% of the cells were CMV specific. The results for a target cell to effector cell ration of 1:3 are shown in FIG. 20.

The disulfide-linked multi-function proteins show an increased thermal stability (FIG. 21).

Example 14

DNA Preparation, Transfection, Expression, Purification and Analysis

DNA Preparation 250 ml of overnight bacterial LB culture were harvested and plasmid DNA was extracted according to the manufacturer's protocol (High speed Maxi kit, Qiagen, Cat. No. 12663). The resulting plasmid DNA was eluted in 1 ml TE buffer and DNA concentration was determined by spectrophotometric measurement (Epoch, BioTek).

The final expression vector comprised the following elements:
the endonucleolytic restriction sites HindIII, NheI,
a CMV-promoter,
a 5'UTR 1 (derived from the human CMV),
Intron A,
a 5'UTR 2,
an ampicillin-resistance gene,
a BGH poly A site (bovine growth hormone polyadenylation signal),
pUC Ori.

Amino acid sequences of the elements of an exemplary monovalent disulfide-linked multi-function protein comprising a CMV-derived peptide and MCSP binding specificity (anti-MCSP antibody):

CMV pp65 Peptide:
SEQ ID NO: 01
NLVPMVATV

Linker 1:
SEQ ID NO: 139
GCGGSGGGGSGGGGS

β2-microglobulin:
SEQ ID NO: 71
IQRTPKIQVYSRHPAENGKSNFLNCYVSGFHPSDIEVD

LLKNGERIEKVEHSDLSFSKDWSFYLLYYTEFTPTEKD

EYACRVNHVTLSQPKIVKWDRDM

Linker 2:
SEQ ID NO: 83
GGGGSGGGGSGGGGSGGGGS

HLA-A*0201 α1-α3:
SEQ ID NO: 140
GSHSMRYFFTSVSRPGRGEPRFIAVGYVDDTQFVRFDS

DAASQRMEPRAPWIEQEGPEYWDGETRKVKAHSQTH

RVDLGTLRGCYNQSEAGSHTVQRMYGCDVGSDWRF

LRGYHQYAYDGKDYIALKEDLRSWTAADMAAQTTK

HKWEAAHVAEQLRAYLEGTCVEWLRRYLENGKETL

QRTDAPKTHMTHHAVSDHEATLRCWALSFYPAEITLT

WQRDGEDQTQDTELVETRPAGDGTFQKWAAVVVPS

GQEQRYTCHVQHEGLPKPLTLRW

Linker 13:
SEQ ID NO: 136
GSG

Ig light chain:
SEQ ID NO: 127
DIQMTQSPSSLSASVGDRVTITCRASQGIRNYLNWYQ

QKPGKAPKLLIYYTSSLHSGVPSRFSGSGSGTDFTLTIS

SLQPEDFATYYCQQYSKLPWTFGQGTKVEIKRTVAAP

SVFIFPPSDEQLKSGTASVVCLLNNFYPREAKVQWKV

DNALQSGNSQESVTEQDSKDSTYSLSSTLTLSKADYE

KHKVYACEVTHQGLSSPVTKSFNRGEC

Ig heavy chain (IgG1-L234A, L235A, P329
G mutant with knob variation):
SEQ ID NO: 141
QVQLQESGPGLVKPSQTLSLTCTVSGGSITSGYYWNW

IRQHPGKGLEWIGYITYDGSNNYNPSLKSRVTISRDTS

KNQFSLKLSSVTAADTAVYYCADFDYWGQGTLVTVS

SASTKGPSVFPLAPSSKSTSGGTAALGCLVKDYFPEPV

TVSWNSGALTSGVHTFPAVLQSSGLYSLSSVVTVPSSS

LGTQTYICNVNHKPSNTKVDKKVEPKSCDKTHTCPPC

PAPEAAGGPSVFLFPPKPKDTLMISRTPEVTCVVVDVS

HEDPEVKFNWYVDGVEVHNAKTKPREEQYNSTYRVV

SVLTVLHQDWLNGKEYKCKVSNKALGAPIEKTISKAK

-continued

GQPREPQVYTLPPCRDELTKNQVSLWCLVKGFYPSDI
AVEWESNGQPENNYKTTPPVLDSDGSFFLYSKLTVDK
SRWQQGNVFSCSVMHEALHNHYTQKSLSLSPGK

Ig heavy chain (IgG1-L234A, L235A, P329 G mutant with hole variation):

SEQ ID NO: 142

QVQLQESGPGLVKPSQTLSLTCTVSGGSITSGYYWNW
IRQHPGKGLEWIGYITYDGSNNYNPSLKSRVTISRDTS
KNQFSLKLSSVTAADTAVYYCADFDYWGQGTLVTVS
SASTKGPSVFPLAPSSKSTSGGTAALGCLVKDYFPEPV
TVSWNSGALTSGVHTFPAVLQSSGLYSLSSVVTVPSSS
LGTQTYICNVNHKPSNTKVDKKVEPKSCDKTHTCPPC
PAPEAAGGPSVFLFPPKPKDTLMISRTPEVTCVVVDVS
HEDPEVKFNWYVDGVEVHNAKTKPREEQYNSTYRVV
SVLTVLHQDWLNGKEYKCKVSNKALGAPIEKTISKAK
GQPREPQVCTLPPSRDELTKNQVSLSCAVKGFYPSDIA
VEWESNGQPENNYKTTPPVLDSDGSFFLVSKLTVDKS

RWQQGNVFSCSVMHEALHNHYTQKSLSLSPGK

Ig heavy chain Fc-region (IgG1-L234A, L235A, P329G mutant Fc-region knob variant):

SEQ ID NO: 98

EPKSADKTHTCPPCPAPEAAGGPSVFLFPPKPKDTLMI
SRTPEVTCVVVDVSHEDPEVKFNWYVDGVEVHNAKT
KPREEQYNSTYRVVSVLTVLHQDWLNGKEYKCKVSN
KALGAPIEKTISKAKGQPREPQVYTLPPCRDELTKNQV
SLWCLVKGFYPSDIAVEWESNGQPENNYKTTPPVLDS
DGSFFLYSKLTVDKSRWQQGNVFSCSVMHEALHNHY
TQKSLSLSPGK

Amino acid sequences of the elements of an exemplary divalent disulfide-linked multi-function protein comprising a CMV-derived peptide and MCSP binding specificity (anti-MCSP antibody):

CMV pp65 Peptide:

SEQ ID NO: 01

NLVPMVATV

Linker 1:

SEQ ID NO: 139

GCGGSGGGGSGGGGS

β2-microglobulin:

SEQ ID NO: 71

IQRTPKIQVYSRHPAENGKSNFLNCYVSGFHPSDIEVD
LLKNGERIEKVEHSDLSFSKDWSFYLLYYTEFTPTEKD

EYACRVNHVTLSQPKIVKWDRDM

Linker 2:

SEQ ID NO: 83

GGGGSGGGGSGGGGSGGGGS

HLA-A*0201 α1-α3:

SEQ ID NO: 140

GSHSMRYFFTSVSRPGRGEPRFIAVGYVDDTQFVRFDS
DAASQRMEPRAPWIEQEGPEYWDGETRKVKAHSQTH
RVDLGTLRGCYNQSEAGSHTVQRMYGCDVGSDWRF
LRGYHQYAYDGKDYIALKEDLRSWTAADMAAQTTK

HKWEAAHVAEQLRAYLEGTCVEWLRRYLENGKETL

QRTDAPKTHMTHHAVSDHEATLRCWALSFYPAEITLT

WQRDGEDQTQDTELVETRPAGDGTFQKWAAVVVPS

GQEQRYTCHVQHEGLPKPLTLRW

Linker 13:

SEQ ID NO: 136

GSG

Ig light chain:

SEQ ID NO: 127

DIQMTQSPSSLSASVGDRVTITCRASQGIRNYLNWYQ

QKPGKAPKLLIYYTSSLHSGVPSRFSGSGSGTDFTLTIS

SLQPEDFATYYCQQYSKLPWTFGQGTKVEIKRTVAAP

SVFIFPPSDEQLKSGTASVVCLLNNFYPREAKVQWKV

DNALQSGNSQESVTEQDSKDSTYSLSSTLTLSKADYE

KHKVYACEVTHQGLSSPVTKSFNRGEC

Ig heavy chain (IgG1-L234A, L235A, P329 G mutant with knob variation):

SEQ ID NO: 142

QVQLQESGPGLVKPSQTLSLTCTVSGGSITSGYYWNW

IRQHPGKGLEWIGYITYDGSNNYNPSLKSRVTISRDTS

KNQFSLKLSSVTAADTAVYYCADFDYWGQGTLVTVS

SASTKGPSVFPLAPSSKSTSGGTAALGCLVKDYFPEPV

TVSWNSGALTSGVHTFPAVLQSSGLYSLSSVVTVPSSS

LGTQTYICNVNHKPSNTKVDKKVEPKSCDKTHTCPPC

PAPEAAGGPSVFLFPPKPKDTLMISRTPEVTCVVVDVS

HEDPEVKFNWYVDGVEVHNAKTKPREEQYNSTYRVV

SVLTVLHQDWLNGKEYKCKVSNKALGAPIEKTISKAK

GQPREPQVYTLPPCRDELTKNQVSLWCLVKGFYPSDI

AVEWESNGQPENNYKTTPPVLDSDGSFFLYSKLTVDK

SRWQQGNVFSCSVMHEALHNHYTQKSLSLSPGK

Ig heavy chain (IgG1-L234A, L235A, P329 G mutant with hole mutation):

SEQ ID NO: 141

QVQLQESGPGLVKPSQTLSLTCTVSGGSITSGYYWNW

IRQHPGKGLEWIGYITYDGSNNYNPSLKSRVTISRDTS

KNQFSLKLSSVTAADTAVYYCADFDYWGQGTLVTVS

SASTKGPSVFPLAPSSKSTSGGTAALGCLVKDYFPEPV

TVSWNSGALTSGVHTFPAVLQSSGLYSLSSVVTVPSSS

LGTQTYICNVNHKPSNTKVDKKVEPKSCDKTHTCPPC

PAPEAAGGPSVFLFPPKPKDTLMISRTPEVTCVVVDVS

HEDPEVKFNWYVDGVEVHNAKTKPREEQYNSTYRVV

-continued

```
SVLTVLHQDWLNGKEYKCKVSNKALGAPIEKTISKAK

GQPREPQVCTLPPSRDELTKNQVSLSCAVKGFYPSDIA

VEWESNGQPENNYKTTPPVLDSDGSFFLVSKLTVDKS

RWQQGNVFSCSVMHEALHNHYTQKSLSLSPGK
```

Amino acid sequences of the elements of a further exemplary divalent disulfide-linked multi-function protein comprising a CMV-derived peptide and MCSP binding specificity (anti-MCSP antibody):

```
CMV pp65 Peptide:
                              SEQ ID NO: 01
NLVPMVATV

Linker 1:
                              SEQ ID NO: 139
GCGGSGGGGSGGGGS

HLA-A*0201 α1-α3:
                              SEQ ID NO: 140
GSHSMRYFFTSVSRPGRGEPRFIAVGYVDDTQFVRFDS

DAASQRMEPRAPWIEQEGPEYWDGETRKVKAHSQTH

RVDLGTLRGCYNQSEAGSHTVQRMYGCDVGSDWRF

LRGYHQYAYDGKDYIALKEDLRSWTAADMAAQTTK

HKWEAAHVAEQLRAYLEGTCVEWLRRYLENGKETL

QRTDAPKTHMTHHAVSDHEATLRCWALSFYPAEITLT

WQRDGEDQTQDTELVETRPAGDGTFQKWAAVVVPS

GQEQRYTCHVQHEGLPKPLTLRW

Linker 2:
                              SEQ ID NO: 77
GGGGSGGGGSGGGGS

β2-microglobulin:
                              SEQ ID NO: 71
IQRTPKIQVYSRHPAENGKSNFLNCYVSGFHPSDIEVD

LLKNGERIEKVEHSDLSFSKDWSFYLLYYTEFTPTEKD

EYACRVNHVTLSQPKIVKWDRDM

Linker 13:
                              SEQ ID NO: 81
GGGGSGGGGS

Ig light chain:
                              SEQ ID NO: 127
DIQMTQSPSSLSASVGDRVTITCRASQGIRNYLNWYQ

QKPGKAPKLLIYYTSSLHSGVPSRFSGSGSGTDFTLTIS

SLQPEDFATYYCQQYSKLPWTFGQGTKVEIKRTVAAP

SVFIFPPSDEQLKSGTASVVCLLNNFYPREAKVQWKV

DNALQSGNSQESVTEQDSKDSTYSLSSTLTLSKADYE

KHKVYACEVTHQGLSSPVTKSFNRGEC

Ig heavy chain (IgG1-L234A, L235A, P329
G mutant with knob variation):
                              SEQ ID NO: 142
QVQLQESGPGLVKPSQTLSLTCTVSGGSITSGYYWNW

IRQHPGKGLEWIGYITYDGSNNYNPSLKSRVTISRDTS

KNQFSLKLSSVTAADTAVYYCADFDYWGQGTLVTVS

SASTKGPSVFPLAPSSKSTSGGTAALGCLVKDYFPEPV

TVSWNSGALTSGVHTFPAVLQSSGLYSLSSVVTVPSSS

LGTQTYICNVNHKPSNTKVDKKVEPKSCDKTHTCPPC

PAPEAAGGPSVFLFPPKPKDTLMISRTPEVTCVVVDVS

HEDPEVKFNWYVDGVEVHNAKTKPREEQYNSTYRVV

SVLTVLHQDWLNGKEYKCKVSNKALGAPIEKTISKAK

GQPREPQVYTLPPCRDELTKNQVSLWCLVKGFYPSDI

AVEWESNGQPENNYKTTPPVLDSDGSFFLYSKLTVDK

SRWQQGNVFSCSVMHEALHNHYTQKSLSLSPGK

Ig heavy chain (IgG1-L234A, L235A, P329
G mutant with hole mutation):
                              SEQ ID NO: 141
QVQLQESGPGLVKPSQTLSLTCTVSGGSITSGYYWNW

IRQHPGKGLEWIGYITYDGSNNYNPSLKSRVTISRDTS

KNQFSLKLSSVTAADTAVYYCADFDYWGQGTLVTVS

SASTKGPSVFPLAPSSKSTSGGTAALGCLVKDYFPEPV

TVSWNSGALTSGVHTFPAVLQSSGLYSLSSVVTVPSSS

LGTQTYICNVNHKPSNTKVDKKVEPKSCDKTHTCPPC

PAPEAAGGPSVFLFPPKPKDTLMISRTPEVTCVVVDVS

HEDPEVKFNWYVDGVEVHNAKTKPREEQYNSTYRVV

SVLTVLHQDWLNGKEYKCKVSNKALGAPIEKTISKAK

GQPREPQVCTLPPSRDELTKNQVSLSCAVKGFYPSDIA

VEWESNGQPENNYKTTPPVLDSDGSFFLVSKLTVDKS

RWQQGNVFSCSVMHEALHNHYTQKSLSLSPGK
```

Transfection

HEK 293 cells were diluted to $8 \times 10^5$ cells/ml the day before transfection. About 1 to $1.6 \times 10^6$ cells/ml were transfected according to the manufacturer's protocol. For a final transfection volume of 30 ml, 30 μg DNA were diluted to a final volume of 1 ml with Opti-MEM® I Reduced Serum Medium (Gibco, Cat. No. 31985070). 2 μl of 293Fectin™ M Reagent (Invitrogen, Cat. No. 12347019) per 1 μg DNA were equally diluted to a final volume of 1 ml with Opti-MEM® medium and incubated for 5 minutes. After incubation the diluted DNA was added to the diluted 293Fectin™ Reagent, gently mixed, incubated for another 20-30 minutes and afterwards drop wise pipetted to 28 ml of the HEK 293 cells to obtain a final volume of 30 ml. The cells were incubated under cell culture condition (37° C., 8% $CO_2$, 80% humidity) on an orbital shaker rotating at 125 rpm and harvested after 72 hours. The harvest was centrifuged for 10 minutes at 1000 rpm, for 10 minutes at 3000 rpm and filtered through a 22 μm sterile filter (Millipore, Cat. No. SCGPU05RE).

Western Blotting

500 μl of cell culture supernatant was concentrated with Pall Nanosep Omega-Membrane 30KD Centrifugal Devices (Pall, Cat. No. OD030C33) to a volume of 50 μl. 17.5 μl of each concentrate was diluted to a final volume of 25 μl with 4× XT Sample Buffer (Bio Rad, Cat. No. 161-0791) and 20× XT Reducing Agent (BioRad, Cat. No. 161-0792), heated for 8 minutes at 96° C. and applied on a 4-12% Criterion XT Precast Gel (Cat. No. 345-0124). Blotting was performed with Trans-Blot SD semi-dry Transfer Cell (BioRad) at 20 V for 30 minutes on a Trans-blot Pure Nitrocellulose membrane (0.45 µm) (BioRad, Cat. No. 162-0117). Blocking of the membrane was performed with 1× Western Blocking Reagent (Roche, Cat. No. 11921681001) for one hour at room temperature. Staining was performed with peroxidase conjugated polyclonal rabbit anti-human κ-light chain (DAKO, Cat. No. P0129, diluted 1:3000) and polyclonal rabbit anti-human IgG antibody HRP conjugate (DAKO, Cat. No. P0214, diluted 1:5000) for one hour at room temperature. Luminescence detection was carried out with LUMI-Imager FI (Roche).

Purification

Cells were removed from culture medium by centrifugation. Multi-function proteins were purified from supernatants by protein A affinity chromatography (MabSelect-Sepharose on an ÄKTA-Avant). Eluted multi-function proteins were concentrated with Amicon centrifugation tubes to a protein concentration of 3 mg/ml. An aliquot was analyzed on a size exclusion chromatography (HPLC TSK-gel GFC300 Sys89). Preparative SEC on a Superdex 200 was performed to remove aggregates and buffer the fusion proteins in 20 mM histidine, 140 mM NaCl, pH 6.0. Eluted multi-function proteins were concentrated with Amicon centrifugation tube to a protein concentration of I mg/ml and sterile filtered (0.2 µm pore size).

Analytics

Multi-function protein samples were analyzed by OD280 using a UV spectrophotometer to determine the protein concentration in solution. The extinction coefficient required for this was calculated from the amino acid sequence according to Pace (Pace, et al., Protein Science 4 (1995) 2411-2423). Size-exclusion chromatography (SE-HPLC) was performed on TSK-Gel300SWXL or Superdex 200 columns with a 0.2 M potassium phosphate buffer, comprising 0.25 M KCl, pH 7.0 as mobile phase in order to determine the content of monomeric, aggregated and degraded species in the samples. Sodium dodecyl sulfate (SDS) polyacrylamide gel electrophoresis (reducing and non-reducing) was performed to analyze the purity of the multi-function protein preparations with regard to product-related degradation products and unrelated impurities. Electrospray ionization mass spectrometry (ESI-MS) was performed with reduced (TCEP) and deglycosylated (N-glycosidase F) samples to confirm the correct mass/identity of each chain and detect chemical modifications. ESI-MS of the deglycosylated samples was carried out to analyze the nature and quality of the fully assembled protein and detect potential product-related side products.

Method SDS-PAGE and Coomassie Staining

| Method SDS-PAGE and Coomassie Staining | |
|---|---|
| Device: | Invitrogen XCell Sure Lock Mini-Cell |
| Gel: | 4-20% Tris-Glycine Gel, Invitrogen EC6025BOX |
| Buffer: | Tris-Glycine SDS Running Buffer (10x), Invitrogen LC2675-5 |
| Sample buffer: | Tris-Glycine SDS Sample Buffer (2x), Invitrogen LC2676 |
| Reducing buffer: | NuPAGE Sample Reducing Agent (10x), Invitrogen NP0004 |
| Molecular Weight Marker: | Mark 12, MW Standard, Invitrogen LC5677 |

Protein Sample Preparation

The sample was adjusted to a protein concentration of 1 mg/ml with buffer. For sample reduction the following procedure was carried out:

reduction buffer: 4 ml Sample buffer (2×) and 1 ml reducing buffer (10×)

dilute sample 1:1 with reduction buffer incubate for 5 minutes at 70° C.

The gel electrophoresis was carried out at 125 V for 90 minutes. The gels were stained with Simply Blue Safe Stain (Invitrogen, Cat. No. LC6065).

Results

TABLE

| No. | polypeptides comprised in the multi-function protein with MCSP binding specificity | FIG. | yield |
|---|---|---|---|
| 1 | 1. [CMV-pp65-peptide]-[linker 1]-[β2-microglobulin]-[linker 2]-[ HLA-A-α1-α2-α3]-[linker 3]-[IgG1-L234A, L235A mutant with hole variation]<br>2. Ig heavy chain (IgG1-L234A, L235A mutant with knob variation)<br>3. Ig light chain | FIG. 24A | 2.2 mg/l |
| 2 | A: 1. [CMV-pp65-peptide]-[linker 1]-[β2-microglobulin]-[linker 2]-[HLA-A-α1-α2-α3]-[linker 3]-[IgG1-L234A, L235A mutant]<br>2. Ig light chain | FIG. 24B | <1 µg/l |
| 3 | 1. [CMV-pp65-peptide]-[disulfide linker]-[β2-microglobulin]-[linker 2]-[disulfide HLA-A-α1-α2-α3]-[linker 3]-[IgG1-L234A, L235A, P329G mutant with hole variation]<br>2. Ig heavy chain (IgG1-L234A, L235A mutant with knob variation)<br>3. Ig light chain | FIG. 24C | 11.4 mg/l |
| 4 | 1. [CMV-pp65-peptide]-[disulfide linker]-[β2-microglobulin]-[linker 2]-[disulfide HLA-A-α1-α2-α3]-[linker 3]-[IgG1-L234A, L235A, P329G mutant]<br>2. Ig light chain | FIG. 24D | >20 mg/l |

It can be seen that defined multi-function proteins can be obtained.

Example 15

T-Cell Activation of Complexes Comprising One Antigen Presenting Domain Compared to Complexes Comprising Two Antigen Presenting Domains Twenty thousand PBMCs per well in AIM-V medium (Gibco) were stimulated at a final concentration of 100 µg/ml, 10 µg/ml, 1 µg/ml, 100 ng/ml with MHCI-0054 [bivalent anti-MCSP binder with one-armed, disulfide stabilized CMV-MHCI] or MHCI-0065 [bivalent anti-MCSP binder with two armed, disulfide stabilized CMV-MHCI] constructs in a volume of 150 µl AIM-V medium for 16 hours. PBMCs of four wells were pooled and stained with 1) anti-CD8 antibody labeled with PE-Cy7 (BD #557746) (5 µl/100 µl PBS/2% FCS), or
2) anti-CD4 antibody labeled with FITC (BD #555346) (20 µl/100 µl PBS/2% FCS), or
3) Dextramer CMV APC (Immudex #WB2132) (10 µl/100 µl PBS/2% FCS), or
4) anti-CD25 antibody labeled with PE (BioLegend #302606) (5 µl/100 µl PBS/2% FCS), or 5) anti-CD69 antibody labeled with PezCP/Cy5.5 (BioLegend #310925) (5 μl/100 μl PBS/2% FCS)

on ice for 45 min., washed thereafter twice with PBS/2% FCS (500× g, 10 min.).

For determining T cell activation the following read-outs were used:

1) frequency of CD25+ cells of all CMV-specific (NLVPMVATV pp65) CD8+ cells,
2) frequency of CD69+ cells of CMV-specific (NLVPMVATV pp65) CD8+ cells, and
3) down-regulation of cognate TCR for NLVPMVATV pp65 peptide of CMV (NLVPMVATV pp65) in HLA A*0201 MHC class I complex on CD8+ cells.

Results:

1) CD25 up-regulation on pp65-CMV-HLA A*0201 specific CD8 T cells:

| construct | applied dose | effect |
| --- | --- | --- |
| MHCI-0054 | 100 ng/ml | 0.9% CD25+ |
| MHCI-0054 | 1 μg/ml | 0.7% CD25+ |
| MHCI-0054 | 10 μg/ml | 0.9% CD25+ |
| MHCI-0054 | 100 μg/ml | 13.8% CD25+ |
| MHCI-0065 | 100 ng/ml | 0.6% CD25+ |
| MHCI-0065 | 1 μg/ml | 0.6% CD25+ |
| MHCI-0065 | 10 μg/ml | 3.9% CD25+ |
| MHCI-0065 | 100 μg/ml | 26.6% CD25+ |

Thus, with 10 μg/ml and 100 μg/ml MHCI-0065 an up-regulation of CD25 expression compared to MHCI-0054 can be seen (4.4 times and 1.9 times respectively).

2) CD69 up-regulation on pp65-CMV-HLA A*0201 specific CD8 T cells:

| construct | applied dose | effect |
| --- | --- | --- |
| MHCI-0054 | 100 ng/ml | 0.6% CD69+ |
| MHCI-0054 | 1 μg/ml | 0.9% CD69+ |
| MHCI-0054 | 10 μg/ml | 2.3% CD69+ |
| MHCI-0054 | 100 μg/ml | 36.8% CD69+ |
| MHCI-0065 | 100 ng/ml | 1.3% CD69+ |
| MHCI-0065 | 1 μg/ml | 2.3% CD69+ |
| MHCI-0065 | 10 μg/ml | 20.6% CD69+ |
| MHCI-0065 | 100 μg/ml | 67.1% CD69+ |

Thus, with 10 μg/ml and 100 μg/ml MHCI-0065 an up-regulation of CD69 expression compared to MHCI-0054 can be seen (9.0 times and 1.8 times respectively).

3) TCR down-regulation on pp65-CMV-HLA A*0201 specific CD8 T cells:

| construct | applied dose | effect |
| --- | --- | --- |
| MHCI-0054 | 100 ng/ml | set as 0% down-regulation |
| MHCI-0054 | 1 μg/ml | 0% down-regulation |
| MHCI-0054 | 10 μg/ml | 4.9% down-regulation |
| MHCI-0054 | 100 μg/ml | 43.9% down-regulation |
| MHCI-0065 | 100 ng/ml | 0% down-regulation |
| MHCI-0065 | 1 μg/ml | 5.3% down-regulation |
| MHCI-0065 | 10 μg/ml | 31.5% down-regulation |
| MHCI-0065 | 100 μg/ml | 76.9% down-regulation |

Thus, with 10 μg/ml and 100 μg/ml MHCI-0065 a down-regulation of TCR expression compared to MHCI-0054 can be seen (6.5 times and 1.8 times respectively).

Thus, activation of CMV-specific CD8 T-cells is stronger with the bivalent homodimer antibody fusion carrying two MHC complexes compared to the bivalent heterodimer antibody fusion carrying only a single MHC complex.

The invention claimed is:

1. A disulfide-linked multivalent multi-function protein, comprising:
   two antigen presenting domains,
   one antibody Fc-region, and
   one or more antigen binding sites,
   wherein the antigen presenting domain comprises in an N- to C-terminal direction either:
   (i) a T-cell response eliciting peptide,
   (ii) a β2-microglobulin, and
   (iii) extracellular domains α1, α2, and α3 of a class I MHC molecule with a relative frequency of 1% or more, or (i) a T-cell response eliciting peptide,
   (ii) extracellular domains α1, α2, and α3 of a class I MHC molecule with a relative frequency of 1% or more, and
   (iii) a β2-microglobulin,
   wherein the antigen binding site binds to a cancer cell surface antigen, and
   wherein the antigen presenting domain has at least two non-naturally occurring cysteine residues that form an intrachain/interdomain disulfide bond, wherein one non-naturally occurring cysteine residue in the antigen presenting domain is in a linker between the T-cell response eliciting peptide and either the β2-microglobulin or the α1 domain of the class I MHC molecule, and the other non-naturally occurring cysteine residue is in one of the extracellular domains α1, α2, and α3 of the class I MHC molecule and wherein the at least two non-naturally occuring cysteine residues are at position 11 and at position 227 or at position 11 and at position 108.

2. The disulfide-linked multivalent multi-function protein according to claim 1, wherein the antibody Fc-region comprises a first and second disulfide-linked Fc-region polypeptide, whereby one of the antigen binding sites is linked to the first Fc-region polypeptide and the second antigen binding site is linked to the second Fc-region polypeptide.

3. The disulfide-linked multivalent multi-function protein according to claim 1, wherein the antigen binding site comprises; i) an antibody heavy chain and an antibody light chain, or ii) a scFv fusion polypeptide comprising in an N- to C-terminal direction: a scFv antibody fragment and said antibody Fc-region polypeptide, or iii) a scFab fusion polypeptide comprising in N- to C-terminal direction: a scFab and said antibody Fc-region polypeptide, or the antigen binding sites comprise independently of each other i) an antibody heavy chain and an antibody light chain, whereby the individual chains can be wild-type chains or modified chains, ii) a scFv fusion polypeptide comprising in N- to C-terminal direction: a scFv antibody fragment and said antibody Fc-region polypeptide, or iii) a scFab fusion polypeptide comprising in N- to C terminal direction: a scFab and said antibody Fc-region polypeptide.

4. The disulfide-linked multivalent multi-function protein according to claim 1, wherein the T-cell response eliciting peptide is a human cytomegalovirus-derived peptide.

5. The disulfide-linked multivalent multi-function protein according to claim 4, wherein the human cytomegalovirus-derived peptide has the amino acid sequence of SEQ ID NO: 01.

6. The disulfide-linked multivalent multi-function protein according to claim 1, wherein the class I MHC molecule with a relative frequency of 1% or more is selected from the group consisting of HLA-A*0201, HLA-A*1101, HLA-A*2402, HLA-A*340101, HLA C*0304, HLA-C*0401, and HLA-C*0702.

7. The disulfide-linked multivalent multi-function protein according to claim 1, wherein the two antigen presenting domains comprise:
(i) a virus-derived peptide,
(ii) a β2-microglobulin,
(iii) a soluble HLA-A allele A*0201, and
(iv) cysteine residues at least at position 11 and at position 227 and the cysteine residues at position 11 and position 227 form a disulfide bond.

8. A pharmaceutical formulation comprising the disulfide-linked multivalent multi-function protein according to claim 1, and a pharmaceutically acceptable carrier.

9. The disulfide-linked multivalent multi-function protein according to claim 1, wherein the antigen presenting domain comprises in an N- to C-terminal direction:
(i) a virus-derived peptide having an amino acid sequence of SEQ ID NO: 01,
(ii) a first linker peptide having an amino acid sequence of SEQ ID NO: 139,
(iii) a β2-microglobulin having an amino acid sequence of SEQ ID NO: 71,
(iv) a second linker peptide having an amino acid sequence of SEQ ID NO: 83,
(v) an extracellular domains α1, α2, and α3 of a class I MHC molecule with a relative frequency of 1% or more having an amino acid sequence of SEQ ID NO: 140,
(vi) a third linker peptide having an amino acid sequence of SEQ ID NO: 136, and
(vii) cysteine residues at least at position 11 and at position 227 and the cysteine residues at position 11 and position 227 form a disulfide bond.

* * * * *

SEQUENCE LISTING

```
<160> NUMBER OF SEQ ID NOS: 142

<210> SEQ ID NO 1
<211> LENGTH: 9
<212> TYPE: PRT
<213> ORGANISM: Human cytomegalovirus

<400> SEQUENCE: 1

Asn Leu Val Pro Met Val Ala Thr Val
1               5

<210> SEQ ID NO 2
<211> LENGTH: 9
<212> TYPE: PRT
<213> ORGANISM: Human cytomegalovirus

<400> SEQUENCE: 2

Val Thr Glu His Asp Thr Leu Leu Tyr
1               5

<210> SEQ ID NO 3
<211> LENGTH: 9
<212> TYPE: PRT
<213> ORGANISM: Human cytomegalovirus

<400> SEQUENCE: 3

Asn Thr Asp Phe Arg Val Leu Glu Leu
```

```
1               5

<210> SEQ ID NO 4
<211> LENGTH: 9
<212> TYPE: PRT
<213> ORGANISM: Human cytomegalovirus

<400> SEQUENCE: 4

Cys Val Glu Thr Met Cys Asn Glu Tyr
1               5

<210> SEQ ID NO 5
<211> LENGTH: 9
<212> TYPE: PRT
<213> ORGANISM: Human cytomegalovirus

<400> SEQUENCE: 5

Val Leu Glu Glu Thr Ser Val Met Leu
1               5

<210> SEQ ID NO 6
<211> LENGTH: 9
<212> TYPE: PRT
<213> ORGANISM: Human cytomegalovirus

<400> SEQUENCE: 6

Asn Leu Val Pro Met Val Ala Thr Val
1               5

<210> SEQ ID NO 7
<211> LENGTH: 9
<212> TYPE: PRT
<213> ORGANISM: Human cytomegalovirus

<400> SEQUENCE: 7

Arg Ile Phe Ala Glu Leu Glu Gly Val
1               5

<210> SEQ ID NO 8
<211> LENGTH: 9
<212> TYPE: PRT
<213> ORGANISM: Human cytomegalovirus

<400> SEQUENCE: 8

Ile Ile Tyr Thr Arg Asn His Glu Val
1               5

<210> SEQ ID NO 9
<211> LENGTH: 9
<212> TYPE: PRT
<213> ORGANISM: Human cytomegalovirus

<400> SEQUENCE: 9

Val Leu Ala Glu Leu Val Lys Gln Ile
1               5

<210> SEQ ID NO 10
<211> LENGTH: 9
<212> TYPE: PRT
<213> ORGANISM: Human cytomegalovirus

<400> SEQUENCE: 10

Ala Val Gly Gly Ala Val Ala Ser Val
1               5
```

```
<210> SEQ ID NO 11
<211> LENGTH: 9
<212> TYPE: PRT
<213> ORGANISM: Human cytomegalovirus

<400> SEQUENCE: 11

Thr Val Arg Ser His Cys Val Ser Lys
1               5

<210> SEQ ID NO 12
<211> LENGTH: 9
<212> TYPE: PRT
<213> ORGANISM: Human cytomegalovirus

<400> SEQUENCE: 12

Ile Met Arg Glu Phe Asn Ser Tyr Lys
1               5

<210> SEQ ID NO 13
<211> LENGTH: 10
<212> TYPE: PRT
<213> ORGANISM: Human cytomegalovirus

<400> SEQUENCE: 13

Gly Pro Ile Ser His Gly His Val Leu Lys
1               5                   10

<210> SEQ ID NO 14
<211> LENGTH: 9
<212> TYPE: PRT
<213> ORGANISM: Human cytomegalovirus

<400> SEQUENCE: 14

Ala Thr Val Gln Gly Gln Asn Leu Lys
1               5

<210> SEQ ID NO 15
<211> LENGTH: 9
<212> TYPE: PRT
<213> ORGANISM: Human cytomegalovirus

<400> SEQUENCE: 15

Val Tyr Ala Leu Pro Leu Lys Met Leu
1               5

<210> SEQ ID NO 16
<211> LENGTH: 10
<212> TYPE: PRT
<213> ORGANISM: Human cytomegalovirus

<400> SEQUENCE: 16

Ala Tyr Ala Gln Lys Ile Phe Lys Ile Leu
1               5                   10

<210> SEQ ID NO 17
<211> LENGTH: 9
<212> TYPE: PRT
<213> ORGANISM: Human cytomegalovirus

<400> SEQUENCE: 17

Gln Tyr Asp Pro Val Ala Ala Leu Phe
1               5

<210> SEQ ID NO 18
```

```
<211> LENGTH: 9
<212> TYPE: PRT
<213> ORGANISM: Human cytomegalovirus

<400> SEQUENCE: 18

Tyr Val Lys Val Tyr Leu Glu Ser Phe
1               5

<210> SEQ ID NO 19
<211> LENGTH: 9
<212> TYPE: PRT
<213> ORGANISM: Human cytomegalovirus

<400> SEQUENCE: 19

Asp Ile Tyr Arg Ile Phe Ala Glu Leu
1               5

<210> SEQ ID NO 20
<211> LENGTH: 10
<212> TYPE: PRT
<213> ORGANISM: Human cytomegalovirus

<400> SEQUENCE: 20

Val Phe Glu Thr Ser Gly Gly Leu Val Val
1               5                   10

<210> SEQ ID NO 21
<211> LENGTH: 9
<212> TYPE: PRT
<213> ORGANISM: Human cytomegalovirus

<400> SEQUENCE: 21

Lys Ala Arg Asp His Leu Ala Val Leu
1               5

<210> SEQ ID NO 22
<211> LENGTH: 9
<212> TYPE: PRT
<213> ORGANISM: Human cytomegalovirus

<400> SEQUENCE: 22

Gln Ala Arg Leu Thr Val Ser Gly Leu
1               5

<210> SEQ ID NO 23
<211> LENGTH: 9
<212> TYPE: PRT
<213> ORGANISM: Human cytomegalovirus

<400> SEQUENCE: 23

Lys Ala Arg Ala Lys Lys Asp Glu Leu
1               5

<210> SEQ ID NO 24
<211> LENGTH: 9
<212> TYPE: PRT
<213> ORGANISM: Human cytomegalovirus

<400> SEQUENCE: 24

Gln Ile Lys Val Arg Val Asp Met Val
1               5

<210> SEQ ID NO 25
<211> LENGTH: 9
<212> TYPE: PRT
```

<213> ORGANISM: Human cytomegalovirus

<400> SEQUENCE: 25

Arg Arg Arg His Arg Gln Asp Ala Leu
1               5

<210> SEQ ID NO 26
<211> LENGTH: 9
<212> TYPE: PRT
<213> ORGANISM: Human cytomegalovirus

<400> SEQUENCE: 26

Ala Arg Val Tyr Glu Ile Lys Cys Arg
1               5

<210> SEQ ID NO 27
<211> LENGTH: 9
<212> TYPE: PRT
<213> ORGANISM: Human cytomegalovirus

<400> SEQUENCE: 27

Lys Met Gln Val Ile Gly Asp Gln Tyr
1               5

<210> SEQ ID NO 28
<211> LENGTH: 9
<212> TYPE: PRT
<213> ORGANISM: Human cytomegalovirus

<400> SEQUENCE: 28

Asn Val Arg Arg Ser Trp Glu Glu Leu
1               5

<210> SEQ ID NO 29
<211> LENGTH: 12
<212> TYPE: PRT
<213> ORGANISM: Human cytomegalovirus

<400> SEQUENCE: 29

Cys Pro Ser Gln Glu Pro Met Ser Ile Tyr Val Tyr
1               5                   10

<210> SEQ ID NO 30
<211> LENGTH: 13
<212> TYPE: PRT
<213> ORGANISM: Human cytomegalovirus

<400> SEQUENCE: 30

Lys Pro Gly Lys Ile Ser His Ile Met Leu Asp Val Ala
1               5                   10

<210> SEQ ID NO 31
<211> LENGTH: 9
<212> TYPE: PRT
<213> ORGANISM: Human cytomegalovirus

<400> SEQUENCE: 31

Glu Leu Arg Arg Lys Met Met Tyr Met
1               5

<210> SEQ ID NO 32
<211> LENGTH: 9
<212> TYPE: PRT
<213> ORGANISM: Human cytomegalovirus

```
<400> SEQUENCE: 32

Ile Pro Ser Ile Asn Val His His Tyr
1               5

<210> SEQ ID NO 33
<211> LENGTH: 9
<212> TYPE: PRT
<213> ORGANISM: Human cytomegalovirus

<400> SEQUENCE: 33

Phe Glu Gln Pro Thr Glu Thr Pro Pro
1               5

<210> SEQ ID NO 34
<211> LENGTH: 9
<212> TYPE: PRT
<213> ORGANISM: Human cytomegalovirus

<400> SEQUENCE: 34

Tyr Ala Tyr Ile Tyr Thr Thr Tyr Leu
1               5

<210> SEQ ID NO 35
<211> LENGTH: 11
<212> TYPE: PRT
<213> ORGANISM: Human cytomegalovirus

<400> SEQUENCE: 35

Gln Glu Phe Phe Trp Asp Ala Asn Asp Ile Tyr
1               5                   10

<210> SEQ ID NO 36
<211> LENGTH: 9
<212> TYPE: PRT
<213> ORGANISM: Human cytomegalovirus

<400> SEQUENCE: 36

Tyr Glu Gln His Lys Ile Thr Ser Tyr
1               5

<210> SEQ ID NO 37
<211> LENGTH: 9
<212> TYPE: PRT
<213> ORGANISM: Human cytomegalovirus

<400> SEQUENCE: 37

Gln Glu Pro Met Ser Ile Tyr Val Tyr
1               5

<210> SEQ ID NO 38
<211> LENGTH: 10
<212> TYPE: PRT
<213> ORGANISM: Human cytomegalovirus

<400> SEQUENCE: 38

Ser Glu His Pro Thr Phe Thr Ser Gln Tyr
1               5                   10

<210> SEQ ID NO 39
<211> LENGTH: 9
<212> TYPE: PRT
<213> ORGANISM: Human cytomegalovirus

<400> SEQUENCE: 39
```

-continued

Gln Ala Ile Arg Glu Thr Val Glu Leu
1               5

<210> SEQ ID NO 40
<211> LENGTH: 9
<212> TYPE: PRT
<213> ORGANISM: Human cytomegalovirus

<400> SEQUENCE: 40

Thr Arg Ala Thr Lys Met Gln Val Ile
1               5

<210> SEQ ID NO 41
<211> LENGTH: 8
<212> TYPE: PRT
<213> ORGANISM: Human cytomegalovirus

<400> SEQUENCE: 41

Asp Ala Leu Pro Gly Pro Cys Ile
1               5

<210> SEQ ID NO 42
<211> LENGTH: 9
<212> TYPE: PRT
<213> ORGANISM: Human cytomegalovirus

<400> SEQUENCE: 42

Cys Glu Asp Val Pro Ser Gly Lys Leu
1               5

<210> SEQ ID NO 43
<211> LENGTH: 9
<212> TYPE: PRT
<213> ORGANISM: Human cytomegalovirus

<400> SEQUENCE: 43

His Glu Arg Asn Gly Phe Thr Val Leu
1               5

<210> SEQ ID NO 44
<211> LENGTH: 13
<212> TYPE: PRT
<213> ORGANISM: Human cytomegalovirus

<400> SEQUENCE: 44

Pro Thr Phe Thr Ser Gln Tyr Arg Ile Gln Gly Lys Leu
1               5                   10

<210> SEQ ID NO 45
<211> LENGTH: 9
<212> TYPE: PRT
<213> ORGANISM: Human cytomegalovirus

<400> SEQUENCE: 45

Gln Met Trp Gln Ala Arg Leu Thr Val
1               5

<210> SEQ ID NO 46
<211> LENGTH: 12
<212> TYPE: PRT
<213> ORGANISM: Human cytomegalovirus

<400> SEQUENCE: 46

His Glu Leu Leu Val Leu Val Lys Lys Ala Gln Leu
1               5                   10

```
<210> SEQ ID NO 47
<211> LENGTH: 12
<212> TYPE: PRT
<213> ORGANISM: Human cytomegalovirus

<400> SEQUENCE: 47

Asp Asp Tyr Ser Asn Thr His Ser Thr Arg Tyr Val
1               5                   10

<210> SEQ ID NO 48
<211> LENGTH: 9
<212> TYPE: PRT
<213> ORGANISM: Human immunodeficiency virus

<400> SEQUENCE: 48

Ser Leu Tyr Asn Thr Val Ala Thr Leu
1               5

<210> SEQ ID NO 49
<211> LENGTH: 9
<212> TYPE: PRT
<213> ORGANISM: Human herpesvirus 4

<400> SEQUENCE: 49

Gly Leu Cys Thr Leu Val Ala Met Leu
1               5

<210> SEQ ID NO 50
<211> LENGTH: 9
<212> TYPE: PRT
<213> ORGANISM: Influenza A virus

<400> SEQUENCE: 50

Gly Ile Leu Gly Phe Val Phe Thr Leu
1               5

<210> SEQ ID NO 51
<211> LENGTH: 9
<212> TYPE: PRT
<213> ORGANISM: Hepatitis B virus

<400> SEQUENCE: 51

Ser Thr Asn Arg Gln Ser Gly Arg Gln
1               5

<210> SEQ ID NO 52
<211> LENGTH: 9
<212> TYPE: PRT
<213> ORGANISM: Human T-cell lymphotropic virus type 1

<400> SEQUENCE: 52

Leu Leu Phe Gly Tyr Pro Val Tyr Val
1               5

<210> SEQ ID NO 53
<211> LENGTH: 9
<212> TYPE: PRT
<213> ORGANISM: Artificial Sequence
<220> FEATURE:
<223> OTHER INFORMATION: V-jun Sarcoma Virus 17 Oncogene Homolog (JUN)

<400> SEQUENCE: 53

Phe Ala Glu Gly Phe Val Arg Ala Leu
1               5
```

<210> SEQ ID NO 54
<211> LENGTH: 9
<212> TYPE: PRT
<213> ORGANISM: Human adenovirus type 3

<400> SEQUENCE: 54

Leu Ile Val Ile Gly Ile Leu Ile Leu
1               5

<210> SEQ ID NO 55
<211> LENGTH: 8
<212> TYPE: PRT
<213> ORGANISM: Hepatitis C virus

<400> SEQUENCE: 55

Ile Leu His Thr Pro Gly Cys Val
1               5

<210> SEQ ID NO 56
<211> LENGTH: 9
<212> TYPE: PRT
<213> ORGANISM: Dengue virus

<400> SEQUENCE: 56

Trp Tyr Ala Gln Ile Gln Pro His Trp
1               5

<210> SEQ ID NO 57
<211> LENGTH: 9
<212> TYPE: PRT
<213> ORGANISM: Dengue virus

<400> SEQUENCE: 57

Ala Phe Ser Gly Val Ser Trp Thr Met
1               5

<210> SEQ ID NO 58
<211> LENGTH: 9
<212> TYPE: PRT
<213> ORGANISM: Dengue virus

<400> SEQUENCE: 58

Ile Leu Ile Gly Val Val Ile Thr Trp
1               5

<210> SEQ ID NO 59
<211> LENGTH: 9
<212> TYPE: PRT
<213> ORGANISM: Dengue virus

<400> SEQUENCE: 59

Met Met Ile Pro Thr Val Val Ala Phe
1               5

<210> SEQ ID NO 60
<211> LENGTH: 9
<212> TYPE: PRT
<213> ORGANISM: Dengue virus

<400> SEQUENCE: 60

Pro Phe Pro Gln Ser Asn Ala Pro Ile
1               5

-continued

<210> SEQ ID NO 61
<211> LENGTH: 9
<212> TYPE: PRT
<213> ORGANISM: Dengue virus

<400> SEQUENCE: 61

Leu Leu Leu Thr Leu Leu Ala Thr Val
1               5

<210> SEQ ID NO 62
<211> LENGTH: 9
<212> TYPE: PRT
<213> ORGANISM: Dengue virus

<400> SEQUENCE: 62

Ile Val Leu Glu His Gly Ser Cys Val
1               5

<210> SEQ ID NO 63
<211> LENGTH: 9
<212> TYPE: PRT
<213> ORGANISM: Dengue virus

<400> SEQUENCE: 63

Leu Leu Phe Lys Thr Glu Asn Gly Val
1               5

<210> SEQ ID NO 64
<211> LENGTH: 9
<212> TYPE: PRT
<213> ORGANISM: Dengue virus

<400> SEQUENCE: 64

Pro Leu Asn Glu Ala Ile Met Ala Val
1               5

<210> SEQ ID NO 65
<211> LENGTH: 9
<212> TYPE: PRT
<213> ORGANISM: Dengue virus

<400> SEQUENCE: 65

Asn Leu Val Arg Leu Gln Ser Gly Val
1               5

<210> SEQ ID NO 66
<211> LENGTH: 9
<212> TYPE: PRT
<213> ORGANISM: Dengue virus

<400> SEQUENCE: 66

Leu Val Ile Ser Gly Leu Phe Pro Val
1               5

<210> SEQ ID NO 67
<211> LENGTH: 9
<212> TYPE: PRT
<213> ORGANISM: Dengue virus

<400> SEQUENCE: 67

Leu Leu Leu Val Ala His Tyr Ala Ile
1               5

<210> SEQ ID NO 68
<211> LENGTH: 9

```
<212> TYPE: PRT
<213> ORGANISM: Dengue virus

<400> SEQUENCE: 68

Leu Ala Leu Leu Ala Ala Phe Lys Val
1               5

<210> SEQ ID NO 69
<211> LENGTH: 9
<212> TYPE: PRT
<213> ORGANISM: Dengue virus

<400> SEQUENCE: 69

Val Ile Leu Ala Gly Pro Met Pro Val
1               5

<210> SEQ ID NO 70
<211> LENGTH: 9
<212> TYPE: PRT
<213> ORGANISM: Dengue virus

<400> SEQUENCE: 70

His Val Leu Gly Arg Leu Ile Thr Val
1               5

<210> SEQ ID NO 71
<211> LENGTH: 99
<212> TYPE: PRT
<213> ORGANISM: Homo sapiens

<400> SEQUENCE: 71

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
                20                  25                  30

Ser Asp Ile Glu Val Asp Leu Leu Lys Asn Gly Glu Arg Ile Glu Lys
            35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met

<210> SEQ ID NO 72
<211> LENGTH: 274
<212> TYPE: PRT
<213> ORGANISM: Homo sapiens

<400> SEQUENCE: 72

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
                20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
```

```
                65                  70                  75                  80
Leu Arg Gly Tyr Tyr Asn Gln Ser Glu Ala Gly Ser His Thr Val Gln
                85                  90                  95
Arg Met Tyr Gly Cys Asp Val Gly Ser Asp Trp Arg Phe Leu Arg Gly
               100                 105                 110
Tyr His Gln Tyr Ala Tyr Asp Gly Lys Asp Tyr Ile Ala Leu Lys Glu
               115                 120                 125
Asp Leu Arg Ser Trp Thr Ala Ala Asp Met Ala Gln Thr Thr Lys
130                 135                 140
His Lys Trp Glu Ala Ala His Val Ala Glu Gln Leu Arg Ala Tyr Leu
145                 150                 155                 160
Glu Gly Thr Cys Val Glu Trp Leu Arg Arg Tyr Leu Glu Asn Gly Lys
                165                 170                 175
Glu Thr Leu Gln Arg Thr Asp Ala Pro Lys Thr His Met Thr His His
                180                 185                 190
Ala Val Ser Asp His Glu Ala Thr Leu Arg Cys Trp Ala Leu Ser Phe
                195                 200                 205
Tyr Pro Ala Glu Ile Thr Leu Thr Trp Gln Arg Asp Gly Glu Asp Gln
                210                 215                 220
Thr Gln Asp Thr Glu Leu Val Glu Thr Arg Pro Ala Gly Asp Gly Thr
225                 230                 235                 240
Phe Gln Lys Trp Ala Ala Val Val Val Pro Ser Gly Gln Glu Gln Arg
                245                 250                 255
Tyr Thr Cys His Val Gln His Glu Gly Leu Pro Lys Pro Leu Thr Leu
                260                 265                 270
Arg Trp

<210> SEQ ID NO 73
<211> LENGTH: 2
<212> TYPE: PRT
<213> ORGANISM: Artificial Sequence
<220> FEATURE:
<223> OTHER INFORMATION: linker peptide 1

<400> SEQUENCE: 73

Gly Ser
1

<210> SEQ ID NO 74
<211> LENGTH: 3
<212> TYPE: PRT
<213> ORGANISM: Artificial Sequence
<220> FEATURE:
<223> OTHER INFORMATION: linker peptide 2

<400> SEQUENCE: 74

Gly Gly Ser
1

<210> SEQ ID NO 75
<211> LENGTH: 4
<212> TYPE: PRT
<213> ORGANISM: Artificial Sequence
<220> FEATURE:
<223> OTHER INFORMATION: linker peptide 3

<400> SEQUENCE: 75

Gly Gly Gly Ser
1
```

```
<210> SEQ ID NO 76
<211> LENGTH: 8
<212> TYPE: PRT
<213> ORGANISM: Artificial Sequence
<220> FEATURE:
<223> OTHER INFORMATION: linker peptide 4

<400> SEQUENCE: 76

Gly Gly Gly Ser Gly Gly Gly Ser
1               5

<210> SEQ ID NO 77
<211> LENGTH: 12
<212> TYPE: PRT
<213> ORGANISM: Artificial Sequence
<220> FEATURE:
<223> OTHER INFORMATION: linker peptide 5

<400> SEQUENCE: 77

Gly Gly Gly Ser Gly Gly Gly Ser Gly Gly Gly Ser
1               5                   10

<210> SEQ ID NO 78
<211> LENGTH: 16
<212> TYPE: PRT
<213> ORGANISM: Artificial Sequence
<220> FEATURE:
<223> OTHER INFORMATION: linker peptide 6

<400> SEQUENCE: 78

Gly Gly Gly Ser Gly Gly Gly Ser Gly Gly Gly Ser Gly Gly Gly Ser
1               5                   10                  15

<210> SEQ ID NO 79
<211> LENGTH: 20
<212> TYPE: PRT
<213> ORGANISM: Artificial Sequence
<220> FEATURE:
<223> OTHER INFORMATION: linker peptide 7

<400> SEQUENCE: 79

Gly Gly Gly Ser Gly Gly Gly Ser Gly Gly Gly Ser Gly Gly Gly Ser
1               5                   10                  15

Gly Gly Gly Ser
            20

<210> SEQ ID NO 80
<211> LENGTH: 5
<212> TYPE: PRT
<213> ORGANISM: Artificial Sequence
<220> FEATURE:
<223> OTHER INFORMATION: linker peptide 8

<400> SEQUENCE: 80

Gly Gly Gly Gly Ser
1               5

<210> SEQ ID NO 81
<211> LENGTH: 10
<212> TYPE: PRT
<213> ORGANISM: Artificial Sequence
<220> FEATURE:
<223> OTHER INFORMATION: linker peptide 9

<400> SEQUENCE: 81

Gly Gly Gly Gly Ser Gly Gly Gly Gly Ser
```

```
<210> SEQ ID NO 82
<211> LENGTH: 15
<212> TYPE: PRT
<213> ORGANISM: Artificial Sequence
<220> FEATURE:
<223> OTHER INFORMATION: linker peptide 10

<400> SEQUENCE: 82

Gly Gly Gly Gly Ser Gly Gly Gly Gly Ser Gly Gly Gly Gly Ser
1               5                   10                  15

<210> SEQ ID NO 83
<211> LENGTH: 20
<212> TYPE: PRT
<213> ORGANISM: Artificial Sequence
<220> FEATURE:
<223> OTHER INFORMATION: linker peptide 11

<400> SEQUENCE: 83

Gly Gly Gly Gly Ser Gly Gly Gly Gly Ser Gly Gly Gly Gly Ser Gly
1               5                   10                  15

Gly Gly Gly Ser
            20

<210> SEQ ID NO 84
<211> LENGTH: 25
<212> TYPE: PRT
<213> ORGANISM: Artificial Sequence
<220> FEATURE:
<223> OTHER INFORMATION: linker peptide 12

<400> SEQUENCE: 84

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 85
<211> LENGTH: 107
<212> TYPE: PRT
<213> ORGANISM: Homo sapiens

<400> SEQUENCE: 85

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Trp Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Glu Ser Thr Tyr Arg Trp Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95

Ala Pro Ile Glu Lys Thr Ile Ser Lys Ala Lys
            100                 105

<210> SEQ ID NO 86
<211> LENGTH: 106
```

<212> TYPE: PRT
<213> ORGANISM: Homo sapiens

<400> SEQUENCE: 86

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105
```

<210> SEQ ID NO 87
<211> LENGTH: 232
<212> TYPE: PRT
<213> ORGANISM: Homo sapiens

<400> SEQUENCE: 87

```
Glu Pro Lys Ser Ala Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230
```

-continued

```
<210> SEQ ID NO 88
<211> LENGTH: 232
<212> TYPE: PRT
<213> ORGANISM: Artificial Sequence
<220> FEATURE:
<223> OTHER INFORMATION: variant human Fc-region of the IgG1 isotype
      with the mutations L234A, L235A

<400> SEQUENCE: 88

Glu Pro Lys Ser Ala Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 89
<211> LENGTH: 232
<212> TYPE: PRT
<213> ORGANISM: Artificial Sequence
<220> FEATURE:
<223> OTHER INFORMATION: variant human Fc-region of the IgG1 isotype
      with a hole mutation

<400> SEQUENCE: 89

Glu Pro Lys Ser Ala Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60
```

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Cys Thr Leu Pro Pro Ser Arg Asp Glu Leu Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 90
<211> LENGTH: 232
<212> TYPE: PRT
<213> ORGANISM: Artificial Sequence
<220> FEATURE:
<223> OTHER INFORMATION: variant human Fc-region of the IgG1 isotype
      with a knob mutation

<400> SEQUENCE: 90

Glu Pro Lys Ser Ala Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Cys Arg Asp Glu Leu Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 91
<211> LENGTH: 232
<212> TYPE: PRT
<213> ORGANISM: Artificial Sequence
<220> FEATURE:
<223> OTHER INFORMATION: variant human Fc-region of the IgG1 isotype
      with a L234A, L235A and hole mutation

<400> SEQUENCE: 91

Glu Pro Lys Ser Ala Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Cys Thr Leu Pro Pro Ser Arg Asp Glu Leu Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 92
<211> LENGTH: 232
<212> TYPE: PRT
<213> ORGANISM: Artificial Sequence
<220> FEATURE:
<223> OTHER INFORMATION: variant human Fc-region of the IgG1 isotype
      with a L234A, L235A and knob mutation

<400> SEQUENCE: 92

Glu Pro Lys Ser Ala Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Cys Arg Asp Glu Leu Thr
130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 93
<211> LENGTH: 232
<212> TYPE: PRT
<213> ORGANISM: Artificial Sequence
<220> FEATURE:
<223> OTHER INFORMATION: variant human Fc-region of the IgG1 isotype
      with a P329G mutation

<400> SEQUENCE: 93

Glu Pro Lys Ser Ala Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Gly Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr 130             135             140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
                210                 215                 220

Ser Leu Ser Leu Ser Pro Gly Lys
225                 230

<210> SEQ ID NO 94
<211> LENGTH: 232
<212> TYPE: PRT
<213> ORGANISM: Artificial Sequence
<220> FEATURE:
<223> OTHER INFORMATION: variant human Fc-region of the IgG1 isotype
      with a L234A, L235A and P329G mutation

<400> SEQUENCE: 94

Glu Pro Lys Ser Ala Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
                35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Gly Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
                130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
                210                 215                 220

Ser Leu Ser Leu Ser Pro Gly Lys
225                 230

<210> SEQ ID NO 95
<211> LENGTH: 232

<212> TYPE: PRT
<213> ORGANISM: Artificial Sequence
<220> FEATURE:
<223> OTHER INFORMATION: variant human Fc-region of the IgG1 isotype
      with a P239G and hole mutation

<400> SEQUENCE: 95

```
Glu Pro Lys Ser Ala Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Gly Ala Pro Ile Glu Lys Thr Ile Ser Lys Ala Lys Gly Gln Pro
            115                 120                 125

Arg Glu Pro Gln Val Cys Thr Leu Pro Pro Ser Arg Asp Glu Leu Thr
        130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230
```

<210> SEQ ID NO 96
<211> LENGTH: 232
<212> TYPE: PRT
<213> ORGANISM: Artificial Sequence
<220> FEATURE:
<223> OTHER INFORMATION: variant human Fc-region of the IgG1 isotype
      with a P329G and knob mutation

<400> SEQUENCE: 96

```
Glu Pro Lys Ser Ala Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80
```

```
Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Gly Ala Pro Ile Glu Lys Thr Ile Ser Lys Ala Lys Gly Gln Pro
            115                 120                 125

Arg Glu Pro Gln Val Tyr Thr Leu Pro Pro Cys Arg Asp Glu Leu Thr
130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 97
<211> LENGTH: 232
<212> TYPE: PRT
<213> ORGANISM: Artificial Sequence
<220> FEATURE:
<223> OTHER INFORMATION: variant human Fc-region of the IgG1 isotype
      with a L234A, L235A, P329G and hole mutation

<400> SEQUENCE: 97

Glu Pro Lys Ser Ala Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Gly Ala Pro Ile Glu Lys Thr Ile Ser Lys Ala Lys Gly Gln Pro
            115                 120                 125

Arg Glu Pro Gln Val Cys Thr Leu Pro Pro Ser Arg Asp Glu Leu Thr
130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
            195                 200                 205
```

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 98
<211> LENGTH: 232
<212> TYPE: PRT
<213> ORGANISM: Artificial Sequence
<220> FEATURE:
<223> OTHER INFORMATION: variant human Fc-region of the IgG1 isotype
      with a L234A, L235A, P329G and knob mutation

<400> SEQUENCE: 98

Glu Pro Lys Ser Ala Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Gly Ala Pro Ile Glu Lys Thr Ile Ser Lys Ala Lys Gly Gln Pro
        115                 120                 125

Arg Glu Pro Gln Val Tyr Thr Leu Pro Pro Cys Arg Asp Glu Leu Thr
130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 99
<211> LENGTH: 229
<212> TYPE: PRT
<213> ORGANISM: Homo sapiens

<400> SEQUENCE: 99

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys
225

<210> SEQ ID NO 100
<211> LENGTH: 229
<212> TYPE: PRT
<213> ORGANISM: Artificial Sequence
<220> FEATURE:
<223> OTHER INFORMATION: variant human Fc-region of the IgG4 isotype
      with a S228P and L235E mutation

<400> SEQUENCE: 100

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr

```
                        165                 170                 175
Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 101
<211> LENGTH: 229
<212> TYPE: PRT
<213> ORGANISM: Artificial Sequence
<220> FEATURE:
<223> OTHER INFORMATION: variant human Fc-region of the IgG4 isotype
      with a S228P, L235E and P329G mutation

<400> SEQUENCE: 101

Glu Ser Lys Tyr Gly Pro Pro Cys Pro Pro Cys Pro Ala Pro Glu Phe
1               5                  10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 102
<211> LENGTH: 229
<212> TYPE: PRT
<213> ORGANISM: Artificial Sequence
<220> FEATURE:
<223> OTHER INFORMATION: variant human Fc-region of the IgG4 isotype
      with a S228P and L235E mutation
```

<400> SEQUENCE: 102

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 103
<211> LENGTH: 229
<212> TYPE: PRT
<213> ORGANISM: Artificial Sequence
<220> FEATURE:
<223> OTHER INFORMATION: variant human Fc-region of the IgG4 isotype
with a S228P, L235E and P329G mutation

<400> SEQUENCE: 103

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Gly Ser
            100                 105                 110
```

```
Ser Ile Glu Lys Thr Ile Ser Lys Ala Lys Gly Gln Pro Arg Glu Pro
            115                 120                 125

Gln Val Tyr Thr Leu Pro Pro Ser Gln Glu Met Thr Lys Asn Gln
        130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys
225

<210> SEQ ID NO 104
<211> LENGTH: 11
<212> TYPE: PRT
<213> ORGANISM: Artificial Sequence
<220> FEATURE:
<223> OTHER INFORMATION: HVR-L1

<400> SEQUENCE: 104

Ser Ala Ser Gln Gly Ile Arg Asn Tyr Leu Asn
1               5                   10

<210> SEQ ID NO 105
<211> LENGTH: 7
<212> TYPE: PRT
<213> ORGANISM: Artificial Sequence
<220> FEATURE:
<223> OTHER INFORMATION: HVR-L2

<400> SEQUENCE: 105

Tyr Thr Ser Ser Leu His Ser
1               5

<210> SEQ ID NO 106
<211> LENGTH: 9
<212> TYPE: PRT
<213> ORGANISM: Artificial Sequence
<220> FEATURE:
<223> OTHER INFORMATION: HVR-L3

<400> SEQUENCE: 106

Gln Gln Tyr Ser Lys Leu Pro Trp Thr
1               5

<210> SEQ ID NO 107
<211> LENGTH: 11
<212> TYPE: PRT
<213> ORGANISM: Artificial Sequence
<220> FEATURE:
<223> OTHER INFORMATION: HVR-L1

<400> SEQUENCE: 107

Arg Ala Ser Gln Gly Ile Arg Asn Tyr Leu Asn
1               5                   10

<210> SEQ ID NO 108
<211> LENGTH: 11
```

```
<212> TYPE: PRT
<213> ORGANISM: Artificial Sequence
<220> FEATURE:
<223> OTHER INFORMATION: HVR-H1

<400> SEQUENCE: 108

Gly Tyr Ser Ile Thr Ser Gly Tyr Tyr Trp Asn
1               5                   10

<210> SEQ ID NO 109
<211> LENGTH: 16
<212> TYPE: PRT
<213> ORGANISM: Artificial Sequence
<220> FEATURE:
<223> OTHER INFORMATION: HVR-H2

<400> SEQUENCE: 109

Tyr Ile Thr Tyr Asp Gly Ser Asn Asn Tyr Asn Pro Ser Leu Lys Asn
1               5                   10                  15

<210> SEQ ID NO 110
<211> LENGTH: 3
<212> TYPE: PRT
<213> ORGANISM: Artificial Sequence
<220> FEATURE:
<223> OTHER INFORMATION: HVR-H3

<400> SEQUENCE: 110

Phe Asp Tyr
1

<210> SEQ ID NO 111
<211> LENGTH: 11
<212> TYPE: PRT
<213> ORGANISM: Artificial Sequence
<220> FEATURE:
<223> OTHER INFORMATION: HVR-H1

<400> SEQUENCE: 111

Gly Gly Ser Ile Thr Ser Gly Tyr Tyr Trp Asn
1               5                   10

<210> SEQ ID NO 112
<211> LENGTH: 16
<212> TYPE: PRT
<213> ORGANISM: Artificial Sequence
<220> FEATURE:
<223> OTHER INFORMATION: HVR-H2

<400> SEQUENCE: 112

Tyr Ile Thr Tyr Asp Gly Ser Asn Asn Tyr Asn Pro Ser Leu Lys Ser
1               5                   10                  15

<210> SEQ ID NO 113
<211> LENGTH: 107
<212> TYPE: PRT
<213> ORGANISM: Artificial Sequence
<220> FEATURE:
<223> OTHER INFORMATION: LC007 Chimeric Antibody VL

<400> SEQUENCE: 113

Asp Ile Val Leu Thr Gln Ser Pro Ser Ser Leu Ser Ala Ser Leu Gly
1               5                   10                  15

Asp Arg Val Thr Ile Ser Cys Ser Ala Ser Gln Gly Ile Arg Asn Tyr
            20                  25                  30

Leu Asn Trp Tyr Gln Gln Arg Pro Asp Gly Thr Val Lys Leu Leu Ile
```

```
            35                  40                  45
Tyr Tyr Thr Ser Ser Leu His Ser Gly Val Pro Ser Arg Phe Ser Gly
 50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys
            100                 105

<210> SEQ ID NO 114
<211> LENGTH: 112
<212> TYPE: PRT
<213> ORGANISM: Artificial Sequence
<220> FEATURE:
<223> OTHER INFORMATION: LC007 Chimeric Antibody VH

<400> SEQUENCE: 114

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
                20                  25                  30

Tyr Tyr Trp Asn Trp Ile Arg Gln Phe Pro Gly Asn Lys Leu Glu Trp
            35                  40                  45

Met Gly Tyr Ile Thr Tyr Asp Gly Ser Asn Asn Tyr Asn Pro Ser Leu
 50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Asp Phe Asp Tyr Trp Gly Gln Gly Thr Thr Leu Thr Val Ser Ser
            100                 105                 110

<210> SEQ ID NO 115
<211> LENGTH: 107
<212> TYPE: PRT
<213> ORGANISM: Artificial Sequence
<220> FEATURE:
<223> OTHER INFORMATION: LC007 Humanized Antibody ML2 VL

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Lys Leu Pro Trp
                85                  90                  95

Thr Phe Gly Gln Gly Thr Lys Val Glu Ile Lys
            100                 105

<210> SEQ ID NO 116
<211> LENGTH: 112
```

```
<212> TYPE: PRT
<213> ORGANISM: Artificial Sequence
<220> FEATURE:
<223> OTHER INFORMATION: LC007 Humanized Antibody M4-3 VH

<400> SEQUENCE: 116
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Tyr Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110

```
<210> SEQ ID NO 117
<211> LENGTH: 862
<212> TYPE: PRT
<213> ORGANISM: Artificial Sequence
<220> FEATURE:
<223> OTHER INFORMATION: MHC-I-VH (MCSP)-IgG1 Fc-region L234A, L235A,
      P329G, T366S, L368A, Y407V mutant amino acid sequence

<400> SEQUENCE: 117
```

Asn Leu Val Pro Met Val Ala Thr Val Gly Gly Gly Ser Gly Gly
1               5                   10                  15

Gly Gly Ser Gly Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
        35                  40                  45

Cys Tyr Val Ser Gly Phe His Pro Ser Asp Ile Glu Val Asp Leu Leu
    50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met Gly Gly Gly Gly Ser
            115                 120                 125

Gly Gly Gly Gly Ser Gly Gly Gly Ser Gly Gly Gly Gly Ser Gly
        130                 135                 140

Ser His Ser Met Arg Tyr Phe Phe Thr Ser Val Ser Arg Pro Gly Arg
145                 150                 155                 160

Gly Glu Pro Arg Phe Ile Ala Val Gly Tyr Val Asp Asp Thr Gln Phe
            165                 170                 175

Val Arg Phe Asp Ser Asp Ala Ala Ser Gln Arg Met Glu Pro Arg Ala
            180                 185                 190

Pro Trp Ile Glu Gln Glu Gly Pro Glu Tyr Trp Asp Gly Glu Thr Arg
            195                 200                 205

Lys Val Lys Ala His Ser Gln Thr His Arg Val Asp Leu Gly Thr Leu

-continued

```
            210                 215                 220
Arg Gly Tyr Tyr Asn Gln Ser Glu Ala Gly Ser His Thr Val Gln Arg
225                 230                 235                 240

Met Tyr Gly Cys Asp Val Gly Ser Asp Trp Arg Phe Leu Arg Gly Tyr
                245                 250                 255

His Gln Tyr Ala Tyr Asp Gly Lys Asp Tyr Ile Ala Leu Lys Glu Asp
                260                 265                 270

Leu Arg Ser Trp Thr Ala Ala Asp Met Ala Ala Gln Thr Thr Lys His
            275                 280                 285

Lys Trp Glu Ala Ala His Val Ala Glu Gln Leu Arg Ala Tyr Leu Glu
        290                 295                 300

Gly Thr Cys Val Glu Trp Leu Arg Arg Tyr Leu Glu Asn Gly Lys Glu
305                 310                 315                 320

Thr Leu Gln Arg Thr Asp Ala Pro Lys Thr His Met Thr His His Ala
                325                 330                 335

Val Ser Asp His Glu Ala Thr Leu Arg Cys Trp Ala Leu Ser Phe Tyr
                340                 345                 350

Pro Ala Glu Ile Thr Leu Thr Trp Gln Arg Asp Gly Glu Asp Gln Thr
            355                 360                 365

Gln Asp Thr Glu Leu Val Glu Thr Arg Pro Ala Gly Asp Gly Thr Phe
        370                 375                 380

Gln Lys Trp Ala Ala Val Val Pro Ser Gly Gln Glu Gln Arg Tyr
385                 390                 395                 400

Thr Cys His Val Gln His Glu Gly Leu Pro Lys Pro Leu Thr Leu Arg
                405                 410                 415

Trp Gly Ser Gly Gln Val Gln Leu Gln Glu Ser Gly Pro Gly Leu Val
                420                 425                 430

Lys Pro Ser Gln Thr Leu Ser Leu Thr Cys Thr Val Ser Gly Gly Ser
            435                 440                 445

Ile Thr Ser Gly Tyr Tyr Trp Asn Trp Ile Arg Gln His Pro Gly Lys
        450                 455                 460

Gly Leu Glu Trp Ile Gly Tyr Ile Thr Tyr Asp Gly Ser Asn Asn Tyr
465                 470                 475                 480

Asn Pro Ser Leu Lys Ser Arg Val Thr Ile Ser Arg Asp Thr Ser Lys
                485                 490                 495

Asn Gln Phe Ser Leu Lys Leu Ser Ser Val Thr Ala Ala Asp Thr Ala
                500                 505                 510

Val Tyr Tyr Cys Ala Asp Phe Asp Tyr Trp Gly Gln Gly Thr Leu Val
            515                 520                 525

Thr Val Ser Ser Ala Ser Thr Lys Gly Pro Ser Val Phe Pro Leu Ala
        530                 535                 540

Pro Ser Ser Lys Ser Thr Ser Gly Gly Thr Ala Ala Leu Gly Cys Leu
545                 550                 555                 560

Val Lys Asp Tyr Phe Pro Glu Pro Val Thr Val Ser Trp Asn Ser Gly
                565                 570                 575

Ala Leu Thr Ser Gly Val His Thr Phe Pro Ala Val Leu Gln Ser Ser
                580                 585                 590

Gly Leu Tyr Ser Leu Ser Ser Val Val Thr Val Pro Ser Ser Ser Leu
            595                 600                 605

Gly Thr Gln Thr Tyr Ile Cys Asn Val Asn His Lys Pro Ser Asn Thr
        610                 615                 620

Lys Val Asp Lys Lys Val Glu Pro Lys Ser Cys Asp Lys Thr His Thr
625                 630                 635                 640
```

```
Cys Pro Pro Cys Pro Ala Pro Glu Ala Ala Gly Gly Pro Ser Val Phe
                645                 650                 655

Leu Phe Pro Pro Lys Pro Lys Asp Thr Leu Met Ile Ser Arg Thr Pro
            660                 665                 670

Glu Val Thr Cys Val Val Val Asp Val Ser His Glu Asp Pro Glu Val
        675                 680                 685

Lys Phe Asn Trp Tyr Val Asp Gly Val Glu Val His Asn Ala Lys Thr
    690                 695                 700

Lys Pro Arg Glu Glu Gln Tyr Asn Ser Thr Tyr Arg Val Val Ser Val
705                 710                 715                 720

Leu Thr Val Leu His Gln Asp Trp Leu Asn Gly Lys Glu Tyr Lys Cys
                725                 730                 735

Lys Val Ser Asn Lys Ala Leu Gly Ala Pro Ile Glu Lys Thr Ile Ser
            740                 745                 750

Lys Ala Lys Gly Gln Pro Arg Glu Pro Gln Val Tyr Thr Leu Pro Pro
        755                 760                 765

Ser Arg Asp Glu Leu Thr Lys Asn Gln Val Ser Leu Ser Cys Ala Val
    770                 775                 780

Lys Gly Phe Tyr Pro Ser Asp Ile Ala Val Glu Trp Glu Ser Asn Gly
785                 790                 795                 800

Gln Pro Glu Asn Asn Tyr Lys Thr Thr Pro Pro Val Leu Asp Ser Asp
                805                 810                 815

Gly Ser Phe Phe Leu Val Ser Lys Leu Thr Val Asp Lys Ser Arg Trp
            820                 825                 830

Gln Gln Gly Asn Val Phe Ser Cys Ser Val Met His Glu Ala Leu His
        835                 840                 845

Asn His Tyr Thr Gln Lys Ser Leu Ser Leu Ser Pro Gly Lys
    850                 855                 860

<210> SEQ ID NO 118
<211> LENGTH: 442
<212> TYPE: PRT
<213> ORGANISM: Artificial Sequence
<220> FEATURE:
<223> OTHER INFORMATION: VH(MCSP)-IgG1 Fc-region L234A, L235A, P329G,
      T366W mutant amino acid sequence

<400> SEQUENCE: 118

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Tyr Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
```

```
                130                 135                 140
Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Gly Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Trp Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 119
<211> LENGTH: 214
<212> TYPE: PRT
<213> ORGANISM: Artificial Sequence
<220> FEATURE:
<223> OTHER INFORMATION: VL(MCSP)-CL amino acid sequence

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Ser Leu His Ser Gly Val Pro Ser Arg Phe Ser Gly
```

```
              50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Lys Leu Pro Trp
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 120
<211> LENGTH: 215
<212> TYPE: PRT
<213> ORGANISM: Artificial Sequence
<220> FEATURE:
<223> OTHER INFORMATION: Ig Light Chain

<400> SEQUENCE: 120

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Lys Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Lys Trp Pro Pro
                 85                  90                  95

Trp Thr Phe Gly Gln Gly Thr Lys Val Glu Ser Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
```

```
               195                 200                 205

Ser Phe Asn Arg Gly Glu Cys
    210                 215

<210> SEQ ID NO 121
<211> LENGTH: 448
<212> TYPE: PRT
<213> ORGANISM: Artificial Sequence
<220> FEATURE:
<223> OTHER INFORMATION: Ig Heavy Chain (IgG1-L234A, L235A mutant)

<400> SEQUENCE: 121

Gln Val Glu Leu Val Glu Ser Gly Gly Val Val Gln Pro Gly Arg
1               5                   10                  15

Ser Gln Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ile Ile Trp Phe Asp Gly Ser Ser Thr Tyr Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
```

```
             340                 345                 350
Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 122
<211> LENGTH: 448
<212> TYPE: PRT
<213> ORGANISM: Artificial Sequence
<220> FEATURE:
<223> OTHER INFORMATION: Ig Heavy Chain (IgG1-L234A, L235A mutant with knob variation)

<400> SEQUENCE: 122

```
Gln Val Glu Leu Val Glu Ser Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 123
<211> LENGTH: 448
<212> TYPE: PRT
<213> ORGANISM: Artificial Sequence
<220> FEATURE:
<223> OTHER INFORMATION: Ig Heavy Chain (IgG1-L234A, L235A mutant with
      hole variation)

<400> SEQUENCE: 123

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
            355                 360                 365

Ala Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 124
<211> LENGTH: 232
<212> TYPE: PRT
<213> ORGANISM: Artificial Sequence
<220> FEATURE:
<223> OTHER INFORMATION: Ig heavy chain Fc region (IgG1-L234A, L235A
      mutant Fc-region)

<400> SEQUENCE: 124

Glu Pro Lys Ser Ala Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
```

```
                    85                  90                  95
Asp Trp Leu Asn Gly Lys Glu Tyr Lys Cys Lys Val Ser Asn Lys Ala
                100                 105                 110
Leu Pro Ala Pro Ile Glu Lys Thr Ile Ser Lys Ala Lys Gly Gln Pro
            115                 120                 125
Arg Glu Pro Gln Val Tyr Thr Leu Pro Pro Cys Arg Asp Glu Leu Thr
        130                 135                 140
Lys Asn Gln Val Ser Leu Trp Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
                180                 185                 190
Ser Lys Leu Thr Val Asp Lys Ser Arg Trp Gln Gln Gly Asn Val Phe
            195                 200                 205
Ser Cys Ser Val Met His Glu Ala Leu His Asn His Tyr Thr Gln Lys
        210                 215                 220
Ser Leu Ser Leu Ser Pro Gly Lys
225                 230

<210> SEQ ID NO 125
<211> LENGTH: 246
<212> TYPE: PRT
<213> ORGANISM: Artificial Sequence
<220> FEATURE:
<223> OTHER INFORMATION: scFv

<400> SEQUENCE: 125

Gln Val Glu Leu Val Glu Ser Gly Gly Gly Val Val Gln Pro Gly Arg
1               5                   10                  15
Ser Gln Arg Leu Ser Cys Ala Ala Ser Gly Phe Thr Phe Ser Ser Tyr
                20                  25                  30
Gly Met His Trp Val Arg Gln Ala Pro Gly Lys Cys Leu Glu Trp Val
            35                  40                  45
Ala Ile Ile Trp Phe Asp Gly Ser Ser Thr Tyr Tyr Ala Asp Ser Val
        50                  55                  60
Arg Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Phe Cys
                85                  90                  95
Ala Arg Glu Leu Gly Arg Arg Tyr Phe Asp Leu Trp Gly Arg Gly Thr
                100                 105                 110
Leu Val Ser Val Ser Ser Gly Gly Gly Gly Ser Gly Gly Gly Gly Ser
            115                 120                 125
Gly Gly Gly Gly Ser Gly Gly Gly Ser Glu Ile Val Leu Thr Gln
        130                 135                 140
Ser Pro Ala Thr Leu Ser Leu Ser Pro Gly Glu Arg Ala Thr Leu Ser
145                 150                 155                 160
Cys Arg Ala Ser Gln Ser Val Ser Ser Tyr Leu Ala Trp Tyr Gln Gln
                165                 170                 175
Lys Pro Gly Gln Ala Pro Arg Leu Leu Ile Tyr Asp Ala Ser Lys Arg
            180                 185                 190
Ala Thr Gly Ile Pro Ala Arg Phe Ser Gly Ser Gly Ser Gly Thr Asp
        195                 200                 205
Phe Thr Leu Thr Ile Ser Ser Leu Glu Pro Glu Asp Phe Ala Val Tyr
```

```
                210                 215                 220
Tyr Cys Gln Gln Arg Ser Lys Trp Pro Pro Trp Thr Phe Gly Cys Gly
225                 230                 235                 240

Thr Lys Val Glu Ser Lys
                245

<210> SEQ ID NO 126
<211> LENGTH: 214
<212> TYPE: PRT
<213> ORGANISM: Artificial Sequence
<220> FEATURE:
<223> OTHER INFORMATION: Murine anti-MCSP monoclonal light chain
      antibody amino acid sequence (kappa)

<400> SEQUENCE: 126

Asp Ile Val Leu Thr Gln Ser Pro Ser Ser Leu Ser Ala Ser Leu Gly
1               5                   10                  15

Asp Arg Val Thr Ile Ser Cys Ser Ala Ser Gln Gly Ile Arg Asn Tyr
                20                  25                  30

Leu Asn Trp Tyr Gln Gln Arg Pro Asp Gly Thr Val Lys Leu Leu Ile
            35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 127
<211> LENGTH: 214
<212> TYPE: PRT
<213> ORGANISM: Artificial Sequence
<220> FEATURE:
<223> OTHER INFORMATION: Humanized anti-MCSP monoclonal light chain
      antibody amino acid sequence (kappa)

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
                20                  25                  30

Leu Asn Trp Tyr Gln Gln Lys Pro Gly Lys Ala Pro Lys Leu Leu Ile
```

```
                35                  40                  45
Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Lys Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 128
<211> LENGTH: 442
<212> TYPE: PRT
<213> ORGANISM: Artificial Sequence
<220> FEATURE:
<223> OTHER INFORMATION: Murine anti-MCSP monoclonal heavy chain
      antibody amino acid sequence (IgG1 L234A, L235A mutant)

<400> SEQUENCE: 128

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Thr Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Asp Phe Asp Tyr Trp Gly Gln Gly Thr Thr Leu Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175
```

```
Leu Ser Ser Val Val Thr Val Pro Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
            325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 129
<211> LENGTH: 442
<212> TYPE: PRT
<213> ORGANISM: Artificial Sequence
<220> FEATURE:
<223> OTHER INFORMATION: Humanized anti-MCSP monoclonal heavy chain
      antibody amino acid sequence (IgG1 L234A, L235A mutant)

<400> SEQUENCE: 129

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Tyr Asp Gly Ser Asn Asn Tyr Asn Pro Ser Leu
    50                  55                  60

Lys Ser Arg Val Thr Ile Ser Arg Asp Thr Lys Asn Gln Phe Ser
65                  70                  75                  80

Leu Lys Leu Ser Ser Val Thr Ala Ala Asp Thr Ala Val Tyr Tyr Cys
            85                  90                  95
```

```
Ala Asp Phe Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
            195                 200                 205

Lys Val Glu Pro Lys Ser Cys Asp Lys Thr His Thr Cys Pro Pro Cys
        210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
            275                 280                 285

Glu Gln Tyr Asn Ser Thr Tyr Arg Val Val Ser Val Leu Thr Val Leu
        290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
        370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 130
<211> LENGTH: 442
<212> TYPE: PRT
<213> ORGANISM: Artificial Sequence
<220> FEATURE:
<223> OTHER INFORMATION: Murine anti-MCSP monoclonal heavy chain
      antibody amino acid sequence (IgG1 L234A, L235A mutant and knob
      variant)

<400> SEQUENCE: 130
```

```
Glu Val Gln Leu Gln Glu Ser Gly Pro Gly Leu Val Lys Pro Ser Gln
 1               5                  10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
                35                  40                  45

Met Gly Tyr Ile Thr Tyr Asp Gly Ser Asn Asn Tyr Asn Pro Ser Leu
        50                  55                  60

Lys Asn Arg Ile Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
                85                  90                  95

Ala Asp Phe Asp Tyr Trp Gly Gln Gly Thr Thr Leu Thr Val Ser Ser
            100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
            130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
            195                 200                 205

Lys Val Glu Pro Lys Ser Cys Asp Lys Thr His Thr Cys Pro Pro Cys
            210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
            275                 280                 285

Glu Gln Tyr Asn Ser Thr Tyr Arg Val Val Ser Val Leu Thr Val Leu
            290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Cys Arg Asp Glu
            340                 345                 350

Leu Thr Lys Asn Gln Val Ser Leu Trp Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
```

```
                    420                 425                 430
Gln Lys Ser Leu Ser Leu Ser Pro Gly Lys
        435                 440

<210> SEQ ID NO 131
<211> LENGTH: 442
<212> TYPE: PRT
<213> ORGANISM: Artificial Sequence
<220> FEATURE:
<223> OTHER INFORMATION: Humanized anti-MCSP monoclonal heavy chain
      antibody amino acid sequence (IgG1 L234A, L235A mutant and knob
      variant)

<400> SEQUENCE: 131

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Tyr Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335
```

```
Gln Pro Arg Glu Pro Gln Val Tyr Thr Leu Pro Pro Cys Arg Asp Glu
            340                 345                 350

Leu Thr Lys Asn Gln Val Ser Leu Trp Cys Leu Val Lys Gly Phe Tyr
            355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
            435                 440

<210> SEQ ID NO 132
<211> LENGTH: 442
<212> TYPE: PRT
<213> ORGANISM: Artificial Sequence
<220> FEATURE:
<223> OTHER INFORMATION: Murine anti-MCSP monoclonal heavy chain
      antibody amino acid sequence (IgG1 L234A, L235A mutant and hole
      variant)

<400> SEQUENCE: 132

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Thr Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Asp Phe Asp Tyr Trp Gly Gln Gly Thr Thr Leu Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Ala Ala Gly Gly Pro Ser Val Phe Leu Phe Pro Pro
225                 230                 235                 240
```

-continued

```
Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Cys Thr Leu Pro Pro Ser Arg Asp Glu
            340                 345                 350

Leu Thr Lys Asn Gln Val Ser Leu Ser Cys Ala Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Val Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 133
<211> LENGTH: 442
<212> TYPE: PRT
<213> ORGANISM: Artificial Sequence
<220> FEATURE:
<223> OTHER INFORMATION: Humanized anti-MCSP monoclonal heavy chain
      antibody amino acid sequence (IgG1 L234A, L235A mutant and hole
      variant)

<400> SEQUENCE: 133

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Tyr Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
```

```
            145                 150                 155                 160

Gly Val His Thr Phe Pro Ala Val Leu Gln Ser Ser Gly Leu Tyr Ser
                    165                 170                 175

Leu Ser Ser Val Val Thr Val Pro Ser Ser Leu Gly Thr Gln Thr
                180                 185                 190

Tyr Ile Cys Asn Val Asn His Lys Pro Ser Asn Thr Lys Val Asp Lys
                195                 200                 205

Lys Val Glu Pro Lys Ser Cys Asp Lys Thr His Thr Cys Pro Pro Cys
210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
                260                 265                 270

Tyr Val Asp Gly Val Glu Val His Asn Ala Lys Thr Lys Pro Arg Glu
                275                 280                 285

Glu Gln Tyr Asn Ser Thr Tyr Arg Val Val Ser Val Leu Thr Val Leu
            290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Cys Thr Leu Pro Pro Ser Arg Asp Glu
            340                 345                 350

Leu Thr Lys Asn Gln Val Ser Leu Ser Cys Ala Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
385                 390                 395                 400

Leu Val Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly Lys
            435                 440

<210> SEQ ID NO 134
<211> LENGTH: 239
<212> TYPE: PRT
<213> ORGANISM: Artificial Sequence
<220> FEATURE:
<223> OTHER INFORMATION: Disulfide-stabilized single chain Fv of murine
      anti-MCSP monoclonal antibody

<400> SEQUENCE: 134

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
                20                  25                  30

Tyr Tyr Trp Asn Trp Ile Arg Gln Phe Pro Gly Asn Lys Leu Glu Trp
            35                  40                  45

Met Gly Tyr Ile Thr Tyr Asp Gly Ser Asn Asn Tyr Asn Pro Ser Leu
    50                  55                  60
```

```
Lys Asn Arg Ile Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
                 85                  90                  95

Ala Asp Phe Asp Tyr Trp Gly Gln Gly Thr Leu Thr Val Ser Ser
            100                 105                 110

Gly Gly Gly Gly Ser Gly Gly Gly Ser Gly Gly Gly Gly Ser Gly
            115                 120                 125

Gly Gly Gly Ser Asp Ile Val Leu Thr Gln Ser Pro Ser Ser Leu Ser
130                 135                 140

Ala Ser Leu Gly Asp Arg Val Thr Ile Ser Cys Ser Ala Ser Gln Gly
145                 150                 155                 160

Ile Arg Asn Tyr Leu Asn Trp Tyr Gln Gln Arg Pro Asp Gly Thr Val
                165                 170                 175

Lys Leu Leu Ile Tyr Tyr Thr Ser Ser Leu His Ser Gly Val Pro Ser
                180                 185                 190

Arg Phe Ser Gly Ser Gly Ser Gly Thr Asp Tyr Ser Leu Thr Ile Ser
            195                 200                 205

Asn Leu Glu Pro Glu Asp Ile Ala Thr Tyr Tyr Cys Gln Gln Tyr Ser
210                 215                 220

Lys Leu Pro Trp Thr Phe Gly Gly Gly Thr Lys Leu Glu Ile Lys
225                 230                 235

<210> SEQ ID NO 135
<211> LENGTH: 239
<212> TYPE: PRT
<213> ORGANISM: Artificial Sequence
<220> FEATURE:
<223> OTHER INFORMATION: Disulfide-stabilized single chain Fv of
      humanized anti-MCSP monoclonal antibody

<400> SEQUENCE: 135

Gln Val Gln Leu Gln Glu Ser Gly Pro Gly Leu Val Lys Pro Ser Gln
 1                5                  10                  15

Thr Leu Ser Leu Thr Cys Thr Val Ser Gly Gly Ser Ile Thr Ser Gly
                 20                  25                  30

Tyr Tyr Trp Asn Trp Ile Arg Gln His Pro Gly Lys Gly Leu Glu Trp
             35                  40                  45

Ile Gly Tyr Ile Thr Tyr Asp Gly Ser Asn Asn Tyr Asn Pro Ser Leu
         50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Asp Phe Asp Tyr Trp Gly Gln Gly Thr Leu Val Thr Val Ser Ser
            100                 105                 110

Gly Gly Gly Gly Ser Gly Gly Gly Gly Ser Gly Gly Gly Gly Ser Gly
            115                 120                 125

Gly Gly Gly Ser Asp Ile Gln Met Thr Gln Ser Pro Ser Ser Leu Ser
130                 135                 140

Ala Ser Val Gly Asp Arg Val Thr Ile Thr Cys Arg Ala Ser Gln Gly
145                 150                 155                 160

Ile Arg Asn Tyr Leu Asn Trp Tyr Gln Gln Lys Pro Gly Lys Ala Pro
                165                 170                 175

Lys Leu Leu Ile Tyr Tyr Thr Ser Ser Leu His Ser Gly Val Pro Ser
                180                 185                 190
```

-continued

```
Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Tyr Ser
    210                 215                 220

Lys Leu Pro Trp Thr Phe Gly Gln Gly Thr Lys Val Glu Ile Lys
225                 230                 235

<210> SEQ ID NO 136
<211> LENGTH: 3
<212> TYPE: PRT
<213> ORGANISM: Artificial Sequence
<220> FEATURE:
<223> OTHER INFORMATION: linker peptide 13

<400> SEQUENCE: 136

Gly Ser Gly
1

<210> SEQ ID NO 137
<211> LENGTH: 862
<212> TYPE: PRT
<213> ORGANISM: Artificial Sequence
<220> FEATURE:
<223> OTHER INFORMATION: disulfide stabilized MHC-I-VH (MCSP)-IgG1
      Fc-region L234A, L235A, P329G, T366S, L368A, Y407V mutant amino
      acid sequence

<400> SEQUENCE: 137

Asn Leu Val Pro Met Val Ala Thr Val Gly Cys Gly Gly Ser Gly Gly
1               5                   10                  15

Gly Gly Ser Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
            35                  40                  45

Cys Tyr Val Ser Gly Phe His Pro Ser Asp Ile Glu Val Asp Leu Leu
        50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met Gly Gly Gly Gly Ser
        115                 120                 125

Gly Gly Gly Gly Ser Gly Gly Gly Ser Gly Gly Gly Gly Ser Gly
    130                 135                 140

Ser His Ser Met Arg Tyr Phe Phe Thr Ser Val Ser Arg Pro Gly Arg
145                 150                 155                 160

Gly Glu Pro Arg Phe Ile Ala Val Gly Tyr Val Asp Asp Thr Gln Phe
                165                 170                 175

Val Arg Phe Asp Ser Asp Ala Ala Ser Gln Arg Met Glu Pro Arg Ala
            180                 185                 190

Pro Trp Ile Glu Gln Glu Gly Pro Glu Tyr Trp Asp Gly Glu Thr Arg
        195                 200                 205

Lys Val Lys Ala His Ser Gln Thr His Arg Val Asp Leu Gly Thr Leu
    210                 215                 220

Arg Gly Cys Tyr Asn Gln Ser Glu Ala Gly Ser His Thr Val Gln Arg
225                 230                 235                 240
```

-continued

```
Met Tyr Gly Cys Asp Val Gly Ser Asp Trp Arg Phe Leu Arg Gly Tyr
            245             250             255

His Gln Tyr Ala Tyr Asp Gly Lys Asp Tyr Ile Ala Leu Lys Glu Asp
        260             265             270

Leu Arg Ser Trp Thr Ala Ala Asp Met Ala Ala Gln Thr Thr Lys His
        275             280             285

Lys Trp Glu Ala Ala His Val Ala Glu Gln Leu Arg Ala Tyr Leu Glu
    290             295             300

Gly Thr Cys Val Glu Trp Leu Arg Arg Tyr Leu Glu Asn Gly Lys Glu
305             310             315             320

Thr Leu Gln Arg Thr Asp Ala Pro Lys Thr His Met Thr His His Ala
            325             330             335

Val Ser Asp His Glu Ala Thr Leu Arg Cys Trp Ala Leu Ser Phe Tyr
            340             345             350

Pro Ala Glu Ile Thr Leu Thr Trp Gln Arg Asp Gly Glu Asp Gln Thr
            355             360             365

Gln Asp Thr Glu Leu Val Glu Thr Arg Pro Ala Gly Asp Gly Thr Phe
        370             375             380

Gln Lys Trp Ala Ala Val Val Pro Ser Gly Gln Glu Gln Arg Tyr
385             390             395             400

Thr Cys His Val Gln His Glu Gly Leu Pro Lys Pro Leu Thr Leu Arg
            405             410             415

Trp Gly Ser Gly Gln Val Gln Leu Gln Glu Ser Gly Pro Gly Leu Val
            420             425             430

Lys Pro Ser Gln Thr Leu Ser Leu Thr Cys Thr Val Ser Gly Gly Ser
            435             440             445

Ile Thr Ser Gly Tyr Tyr Trp Asn Trp Ile Arg Gln His Pro Gly Lys
            450             455             460

Gly Leu Glu Trp Ile Gly Tyr Ile Thr Tyr Asp Gly Ser Asn Asn Tyr
465             470             475             480

Asn Pro Ser Leu Lys Ser Arg Val Thr Ile Ser Arg Asp Thr Ser Lys
            485             490             495

Asn Gln Phe Ser Leu Lys Leu Ser Ser Val Thr Ala Ala Asp Thr Ala
            500             505             510

Val Tyr Tyr Cys Ala Asp Phe Asp Tyr Trp Gly Gln Gly Thr Leu Val
            515             520             525

Thr Val Ser Ser Ala Ser Thr Lys Gly Pro Ser Val Phe Pro Leu Ala
        530             535             540

Pro Ser Ser Lys Ser Thr Ser Gly Gly Thr Ala Ala Leu Gly Cys Leu
545             550             555             560

Val Lys Asp Tyr Phe Pro Glu Pro Val Thr Val Ser Trp Asn Ser Gly
            565             570             575

Ala Leu Thr Ser Gly Val His Thr Phe Pro Ala Val Leu Gln Ser Ser
            580             585             590

Gly Leu Tyr Ser Leu Ser Ser Val Val Thr Val Pro Ser Ser Ser Leu
            595             600             605

Gly Thr Gln Thr Tyr Ile Cys Asn Val Asn His Lys Pro Ser Asn Thr
            610             615             620

Lys Val Asp Lys Lys Val Glu Pro Lys Ser Cys Asp Lys Thr His Thr
625             630             635             640

Cys Pro Pro Cys Pro Ala Pro Glu Ala Ala Gly Gly Pro Ser Val Phe
            645             650             655
```

Leu Phe Pro Pro Lys Pro Lys Asp Thr Leu Met Ile Ser Arg Thr Pro
                660                 665                 670

Glu Val Thr Cys Val Val Val Asp Val Ser His Glu Asp Pro Glu Val
            675                 680                 685

Lys Phe Asn Trp Tyr Val Asp Gly Val Glu Val His Asn Ala Lys Thr
        690                 695                 700

Lys Pro Arg Glu Glu Gln Tyr Asn Ser Thr Tyr Arg Val Val Ser Val
705                 710                 715                 720

Leu Thr Val Leu His Gln Asp Trp Leu Asn Gly Lys Glu Tyr Lys Cys
                725                 730                 735

Lys Val Ser Asn Lys Ala Leu Gly Ala Pro Ile Glu Lys Thr Ile Ser
            740                 745                 750

Lys Ala Lys Gly Gln Pro Arg Glu Pro Gln Val Cys Thr Leu Pro Pro
        755                 760                 765

Ser Arg Asp Glu Leu Thr Lys Asn Gln Val Ser Leu Ser Cys Ala Val
770                 775                 780

Lys Gly Phe Tyr Pro Ser Asp Ile Ala Val Glu Trp Glu Ser Asn Gly
785                 790                 795                 800

Gln Pro Glu Asn Asn Tyr Lys Thr Thr Pro Pro Val Leu Asp Ser Asp
                805                 810                 815

Gly Ser Phe Phe Leu Val Ser Lys Leu Thr Val Asp Lys Ser Arg Trp
            820                 825                 830

Gln Gln Gly Asn Val Phe Ser Cys Ser Val Met His Glu Ala Leu His
        835                 840                 845

Asn His Tyr Thr Gln Lys Ser Leu Ser Leu Ser Pro Gly Lys
850                 855                 860

<210> SEQ ID NO 138
<211> LENGTH: 2322
<212> TYPE: PRT
<213> ORGANISM: Homo sapiens

<400> SEQUENCE: 138

Met Gln Ser Gly Pro Arg Pro Pro Leu Pro Ala Pro Gly Leu Ala Leu
1               5                   10                  15

Ala Leu Thr Leu Thr Met Leu Ala Arg Leu Ala Ser Ala Ala Ser Phe
            20                  25                  30

Phe Gly Glu Asn His Leu Glu Val Pro Val Ala Thr Ala Leu Thr Asp
        35                  40                  45

Ile Asp Leu Gln Leu Gln Phe Ser Thr Ser Gln Pro Glu Ala Leu Leu
    50                  55                  60

Leu Leu Ala Ala Gly Pro Ala Asp His Leu Leu Leu Gln Leu Tyr Ser
65                  70                  75                  80

Gly Arg Leu Gln Val Arg Leu Val Leu Gly Gln Glu Glu Leu Arg Leu
                85                  90                  95

Gln Thr Pro Ala Glu Thr Leu Leu Ser Asp Ser Ile Pro His Thr Val
            100                 105                 110

Val Leu Thr Val Val Glu Gly Trp Ala Thr Leu Ser Val Asp Gly Phe
        115                 120                 125

Leu Asn Ala Ser Ser Ala Val Pro Gly Ala Pro Leu Glu Val Pro Tyr
    130                 135                 140

Gly Leu Phe Val Gly Gly Thr Gly Thr Leu Gly Leu Pro Tyr Leu Arg
145                 150                 155                 160

Gly Thr Ser Arg Pro Leu Arg Gly Cys Leu His Ala Ala Thr Leu Asn
                165                 170                 175

```
Gly Arg Ser Leu Leu Arg Pro Leu Thr Pro Asp Val His Glu Gly Cys
            180                 185                 190

Ala Glu Glu Phe Ser Ala Ser Asp Val Ala Leu Gly Phe Ser Gly
        195                 200                 205

Pro His Ser Leu Ala Ala Phe Pro Ala Trp Gly Thr Gln Asp Glu Gly
            210                 215                 220

Thr Leu Glu Phe Thr Leu Thr Thr Gln Ser Arg Gln Ala Pro Leu Ala
225                 230                 235                 240

Phe Gln Ala Gly Gly Arg Arg Gly Asp Phe Ile Tyr Val Asp Ile Phe
                245                 250                 255

Glu Gly His Leu Arg Ala Val Val Glu Lys Gly Gln Gly Thr Val Leu
            260                 265                 270

Leu His Asn Ser Val Pro Val Ala Asp Gly Gln Pro His Glu Val Ser
            275                 280                 285

Val His Ile Asn Ala His Arg Leu Glu Ile Ser Val Asp Gln Tyr Pro
290                 295                 300

Thr His Thr Ser Asn Arg Gly Val Leu Ser Tyr Leu Glu Pro Arg Gly
305                 310                 315                 320

Ser Leu Leu Leu Gly Gly Leu Asp Ala Glu Ala Ser Arg His Leu Gln
                325                 330                 335

Glu His Arg Leu Gly Leu Thr Pro Glu Ala Thr Asn Ala Ser Leu Leu
            340                 345                 350

Gly Cys Met Glu Asp Leu Ser Val Asn Gly Gln Arg Arg Gly Leu Arg
            355                 360                 365

Glu Ala Leu Leu Thr Arg Asn Met Ala Ala Gly Cys Arg Leu Glu Glu
            370                 375                 380

Glu Glu Tyr Glu Asp Asp Ala Tyr Gly His Tyr Glu Ala Phe Ser Thr
385                 390                 395                 400

Leu Ala Pro Glu Ala Trp Pro Ala Met Glu Leu Pro Glu Pro Cys Val
                405                 410                 415

Pro Glu Pro Gly Leu Pro Pro Val Phe Ala Asn Phe Thr Gln Leu Leu
            420                 425                 430

Thr Ile Ser Pro Leu Val Val Ala Glu Gly Gly Thr Ala Trp Leu Glu
            435                 440                 445

Trp Arg His Val Gln Pro Thr Leu Asp Leu Met Glu Ala Glu Leu Arg
450                 455                 460

Lys Ser Gln Val Leu Phe Ser Val Thr Arg Gly Ala Arg His Gly Glu
465                 470                 475                 480

Leu Glu Leu Asp Ile Pro Gly Ala Gln Ala Arg Lys Met Phe Thr Leu
                485                 490                 495

Leu Asp Val Val Asn Arg Lys Ala Arg Phe Ile His Asp Gly Ser Glu
            500                 505                 510

Asp Thr Ser Asp Gln Leu Val Leu Glu Val Ser Val Thr Ala Arg Val
            515                 520                 525

Pro Met Pro Ser Cys Leu Arg Arg Gly Gln Thr Tyr Leu Leu Pro Ile
            530                 535                 540

Gln Val Asn Pro Val Asn Asp Pro Pro His Ile Ile Phe Pro His Gly
545                 550                 555                 560

Ser Leu Met Val Ile Leu Glu His Thr Gln Lys Pro Leu Gly Pro Glu
                565                 570                 575

Val Phe Gln Ala Tyr Asp Pro Asp Ser Ala Cys Glu Gly Leu Thr Phe
            580                 585                 590
```

```
Gln Val Leu Gly Thr Ser Ser Gly Leu Pro Val Glu Arg Asp Gln
            595                 600                 605

Pro Gly Glu Pro Ala Thr Glu Phe Ser Cys Arg Glu Leu Glu Ala Gly
        610                 615                 620

Ser Leu Val Tyr Val His Arg Gly Pro Ala Gln Asp Leu Thr Phe
625                 630                 635                 640

Arg Val Ser Asp Gly Leu Gln Ala Ser Pro Ala Thr Leu Lys Val
                645                 650                 655

Val Ala Ile Arg Pro Ala Ile Gln Ile His Arg Ser Thr Gly Leu Arg
            660                 665                 670

Leu Ala Gln Gly Ser Ala Met Pro Ile Leu Pro Ala Asn Leu Ser Val
        675                 680                 685

Glu Thr Asn Ala Val Gly Gln Asp Val Ser Val Leu Phe Arg Val Thr
    690                 695                 700

Gly Ala Leu Gln Phe Gly Glu Leu Gln Lys Gln Gly Ala Gly Gly Val
705                 710                 715                 720

Glu Gly Ala Glu Trp Trp Ala Thr Gln Ala Phe His Gln Arg Asp Val
                725                 730                 735

Glu Gln Gly Arg Val Arg Tyr Leu Ser Thr Asp Pro Gln His His Ala
            740                 745                 750

Tyr Asp Thr Val Glu Asn Leu Ala Leu Glu Val Gln Val Gly Gln Glu
        755                 760                 765

Ile Leu Ser Asn Leu Ser Phe Pro Val Thr Ile Gln Arg Ala Thr Val
    770                 775                 780

Trp Met Leu Arg Leu Glu Pro Leu His Thr Gln Asn Thr Gln Gln Glu
785                 790                 795                 800

Thr Leu Thr Thr Ala His Leu Glu Ala Thr Leu Glu Glu Ala Gly Pro
                805                 810                 815

Ser Pro Pro Thr Phe His Tyr Glu Val Val Gln Ala Pro Arg Lys Gly
            820                 825                 830

Asn Leu Gln Leu Gln Gly Thr Arg Leu Ser Asp Gly Gln Gly Phe Thr
        835                 840                 845

Gln Asp Asp Ile Gln Ala Gly Arg Val Thr Tyr Gly Ala Thr Ala Arg
    850                 855                 860

Ala Ser Glu Ala Val Glu Asp Thr Phe Arg Phe Arg Val Thr Ala Pro
865                 870                 875                 880

Pro Tyr Phe Ser Pro Leu Tyr Thr Phe Pro Ile His Ile Gly Gly Asp
                885                 890                 895

Pro Asp Ala Pro Val Leu Thr Asn Val Leu Leu Val Val Pro Glu Gly
            900                 905                 910

Gly Glu Gly Val Leu Ser Ala Asp His Leu Phe Val Lys Ser Leu Asn
        915                 920                 925

Ser Ala Ser Tyr Leu Tyr Glu Val Met Glu Arg Pro Arg His Gly Arg
    930                 935                 940

Leu Ala Trp Arg Gly Thr Gln Asp Lys Thr Thr Met Val Thr Ser Phe
945                 950                 955                 960

Thr Asn Glu Asp Leu Leu Arg Gly Arg Leu Val Tyr Gln His Asp Asp
                965                 970                 975

Ser Glu Thr Thr Glu Asp Asp Ile Pro Phe Val Ala Thr Arg Gln Gly
            980                 985                 990

Glu Ser Ser Gly Asp Met Ala Trp Glu Glu Val Arg Gly Val Phe Arg
        995                 1000                1005

Val Ala Ile Gln Pro Val Asn Asp His Ala Pro Val Gln Thr Ile
```

-continued

```
            1010                1015                1020

Ser Arg Ile Phe His Val Ala Arg Gly Arg Arg Leu Leu Thr
    1025                1030                1035

Thr Asp Asp Val Ala Phe Ser Asp Ala Asp Ser Gly Phe Ala Asp
    1040                1045                1050

Ala Gln Leu Val Leu Thr Arg Lys Asp Leu Leu Phe Gly Ser Ile
    1055                1060                1065

Val Ala Val Asp Glu Pro Thr Arg Pro Ile Tyr Arg Phe Thr Gln
    1070                1075                1080

Glu Asp Leu Arg Lys Arg Arg Val Leu Phe Val His Ser Gly Ala
    1085                1090                1095

Asp Arg Gly Trp Ile Gln Leu Gln Val Ser Asp Gly Gln His Gln
    1100                1105                1110

Ala Thr Ala Leu Leu Glu Val Gln Ala Ser Glu Pro Tyr Leu Arg
    1115                1120                1125

Val Ala Asn Gly Ser Ser Leu Val Val Pro Gln Gly Gly Gln Gly
    1130                1135                1140

Thr Ile Asp Thr Ala Val Leu His Leu Asp Thr Asn Leu Asp Ile
    1145                1150                1155

Arg Ser Gly Asp Glu Val His Tyr His Val Thr Ala Gly Pro Arg
    1160                1165                1170

Trp Gly Gln Leu Val Arg Ala Gly Gln Pro Ala Thr Ala Phe Ser
    1175                1180                1185

Gln Gln Asp Leu Leu Asp Gly Ala Val Leu Tyr Ser His Asn Gly
    1190                1195                1200

Ser Leu Ser Pro Arg Asp Thr Met Ala Phe Ser Val Glu Ala Gly
    1205                1210                1215

Pro Val His Thr Asp Ala Thr Leu Gln Val Thr Ile Ala Leu Glu
    1220                1225                1230

Gly Pro Leu Ala Pro Leu Lys Leu Val Arg His Lys Lys Ile Tyr
    1235                1240                1245

Val Phe Gln Gly Glu Ala Ala Glu Ile Arg Arg Asp Gln Leu Glu
    1250                1255                1260

Ala Ala Gln Glu Ala Val Pro Pro Ala Asp Ile Val Phe Ser Val
    1265                1270                1275

Lys Ser Pro Pro Ser Ala Gly Tyr Leu Val Met Val Ser Arg Gly
    1280                1285                1290

Ala Leu Ala Asp Glu Pro Pro Ser Leu Asp Pro Val Gln Ser Phe
    1295                1300                1305

Ser Gln Glu Ala Val Asp Thr Gly Arg Val Leu Tyr Leu His Ser
    1310                1315                1320

Arg Pro Glu Ala Trp Ser Asp Ala Phe Ser Leu Asp Val Ala Ser
    1325                1330                1335

Gly Leu Gly Ala Pro Leu Glu Gly Val Leu Val Glu Leu Glu Val
    1340                1345                1350

Leu Pro Ala Ala Ile Pro Leu Glu Ala Gln Asn Phe Ser Val Pro
    1355                1360                1365

Glu Gly Gly Ser Leu Thr Leu Ala Pro Pro Leu Leu Arg Val Ser
    1370                1375                1380

Gly Pro Tyr Phe Pro Thr Leu Leu Gly Leu Ser Leu Gln Val Leu
    1385                1390                1395

Glu Pro Pro Gln His Gly Ala Leu Gln Lys Glu Asp Gly Pro Gln
    1400                1405                1410
```

-continued

```
Ala Arg Thr Leu Ser Ala Phe Ser Trp Arg Met Val Glu Glu Gln
    1415                1420                1425

Leu Ile Arg Tyr Val His Asp Gly Ser Glu Thr Leu Thr Asp Ser
    1430                1435                1440

Phe Val Leu Met Ala Asn Ala Ser Glu Met Asp Arg Gln Ser His
    1445                1450                1455

Pro Val Ala Phe Thr Val Thr Val Leu Pro Val Asn Asp Gln Pro
    1460                1465                1470

Pro Ile Leu Thr Thr Asn Thr Gly Leu Gln Met Trp Glu Gly Ala
    1475                1480                1485

Thr Ala Pro Ile Pro Ala Glu Ala Leu Arg Ser Thr Asp Gly Asp
    1490                1495                1500

Ser Gly Ser Glu Asp Leu Val Tyr Thr Ile Glu Gln Pro Ser Asn
    1505                1510                1515

Gly Arg Val Val Leu Arg Gly Ala Pro Gly Thr Glu Val Arg Ser
    1520                1525                1530

Phe Thr Gln Ala Gln Leu Asp Gly Gly Leu Val Leu Phe Ser His
    1535                1540                1545

Arg Gly Thr Leu Asp Gly Gly Phe Arg Phe Arg Leu Ser Asp Gly
    1550                1555                1560

Glu His Thr Ser Pro Gly His Phe Phe Arg Val Thr Ala Gln Lys
    1565                1570                1575

Gln Val Leu Leu Ser Leu Lys Gly Ser Gln Thr Leu Thr Val Cys
    1580                1585                1590

Pro Gly Ser Val Gln Pro Leu Ser Ser Gln Thr Leu Arg Ala Ser
    1595                1600                1605

Ser Ser Ala Gly Thr Asp Pro Gln Leu Leu Leu Tyr Arg Val Val
    1610                1615                1620

Arg Gly Pro Gln Leu Gly Arg Leu Phe His Ala Gln Gln Asp Ser
    1625                1630                1635

Thr Gly Glu Ala Leu Val Asn Phe Thr Gln Ala Glu Val Tyr Ala
    1640                1645                1650

Gly Asn Ile Leu Tyr Glu His Glu Met Pro Pro Glu Pro Phe Trp
    1655                1660                1665

Glu Ala His Asp Thr Leu Glu Leu Gln Leu Ser Ser Pro Pro Ala
    1670                1675                1680

Arg Asp Val Ala Ala Thr Leu Ala Val Ala Val Ser Phe Glu Ala
    1685                1690                1695

Ala Cys Pro Gln Arg Pro Ser His Leu Trp Lys Asn Lys Gly Leu
    1700                1705                1710

Trp Val Pro Glu Gly Gln Arg Ala Arg Ile Thr Val Ala Ala Leu
    1715                1720                1725

Asp Ala Ser Asn Leu Leu Ala Ser Val Pro Ser Pro Gln Arg Ser
    1730                1735                1740

Glu His Asp Val Leu Phe Gln Val Thr Gln Phe Pro Ser Arg Gly
    1745                1750                1755

Gln Leu Leu Val Ser Glu Glu Pro Leu His Ala Gly Gln Pro His
    1760                1765                1770

Phe Leu Gln Ser Gln Leu Ala Ala Gly Gln Leu Val Tyr Ala His
    1775                1780                1785

Gly Gly Gly Gly Thr Gln Gln Asp Gly Phe His Phe Arg Ala His
    1790                1795                1800
```

```
Leu Gln Gly Pro Ala Gly Ala Ser Val Ala Gly Pro Gln Thr Ser
    1805            1810                1815

Glu Ala Phe Ala Ile Thr Val Arg Asp Val Asn Glu Arg Pro Pro
    1820            1825                1830

Gln Pro Gln Ala Ser Val Pro Leu Arg Leu Thr Arg Gly Ser Arg
    1835            1840                1845

Ala Pro Ile Ser Arg Ala Gln Leu Ser Val Val Asp Pro Asp Ser
    1850            1855                1860

Ala Pro Gly Glu Ile Glu Tyr Glu Val Gln Arg Ala Pro His Asn
    1865            1870                1875

Gly Phe Leu Ser Leu Val Gly Gly Gly Leu Gly Pro Val Thr Arg
    1880            1885                1890

Phe Thr Gln Ala Asp Val Asp Ser Gly Arg Leu Ala Phe Val Ala
    1895            1900                1905

Asn Gly Ser Ser Val Ala Gly Ile Phe Gln Leu Ser Met Ser Asp
    1910            1915                1920

Gly Ala Ser Pro Pro Leu Pro Met Ser Leu Ala Val Asp Ile Leu
    1925            1930                1935

Pro Ser Ala Ile Glu Val Gln Leu Arg Ala Pro Leu Glu Val Pro
    1940            1945                1950

Gln Ala Leu Gly Arg Ser Ser Leu Ser Gln Gln Gln Leu Arg Val
    1955            1960                1965

Val Ser Asp Arg Glu Glu Pro Glu Ala Ala Tyr Arg Leu Ile Gln
    1970            1975                1980

Gly Pro Gln Tyr Gly His Leu Leu Val Gly Gly Arg Pro Thr Ser
    1985            1990                1995

Ala Phe Ser Gln Phe Gln Ile Asp Gln Gly Glu Val Val Phe Ala
    2000            2005                2010

Phe Thr Asn Phe Ser Ser Ser His Asp His Phe Arg Val Leu Ala
    2015            2020                2025

Leu Ala Arg Gly Val Asn Ala Ser Ala Val Val Asn Val Thr Val
    2030            2035                2040

Arg Ala Leu Leu His Val Trp Ala Gly Gly Pro Trp Pro Gln Gly
    2045            2050                2055

Ala Thr Leu Arg Leu Asp Pro Thr Val Leu Asp Ala Gly Glu Leu
    2060            2065                2070

Ala Asn Arg Thr Gly Ser Val Pro Arg Phe Arg Leu Leu Glu Gly
    2075            2080                2085

Pro Arg His Gly Arg Val Val Arg Val Pro Arg Ala Arg Thr Glu
    2090            2095                2100

Pro Gly Gly Ser Gln Leu Val Glu Gln Phe Thr Gln Gln Asp Leu
    2105            2110                2115

Glu Asp Gly Arg Leu Gly Leu Glu Val Gly Arg Pro Glu Gly Arg
    2120            2125                2130

Ala Pro Gly Pro Ala Gly Asp Ser Leu Thr Leu Glu Leu Trp Ala
    2135            2140                2145

Gln Gly Val Pro Pro Ala Val Ala Ser Leu Asp Phe Ala Thr Glu
    2150            2155                2160

Pro Tyr Asn Ala Ala Arg Pro Tyr Ser Val Ala Leu Leu Ser Val
    2165            2170                2175

Pro Glu Ala Ala Arg Thr Glu Ala Gly Lys Pro Glu Ser Ser Thr
    2180            2185                2190

Pro Thr Gly Glu Pro Gly Pro Met Ala Ser Ser Pro Glu Pro Ala
```

-continued

```
               2195                2200                2205
Val Ala Lys Gly Gly Phe Leu Ser Phe Leu Glu Ala Asn Met Phe
    2210                2215                2220

Ser Val Ile Ile Pro Met Cys Leu Val Leu Leu Leu Ala Leu
    2225                2230                2235

Ile Leu Pro Leu Leu Phe Tyr Leu Arg Lys Arg Asn Lys Thr Gly
    2240                2245                2250

Lys His Asp Val Gln Val Leu Thr Ala Lys Pro Arg Asn Gly Leu
    2255                2260                2265

Ala Gly Asp Thr Glu Thr Phe Arg Lys Val Glu Pro Gly Gln Ala
    2270                2275                2280

Ile Pro Leu Thr Ala Val Pro Gly Gln Gly Pro Pro Gly Gly
    2285                2290                2295

Gln Pro Asp Pro Glu Leu Leu Gln Phe Cys Arg Thr Pro Asn Pro
    2300                2305                2310

Ala Leu Lys Asn Gly Gln Tyr Trp Val
    2315                2320
```

<210> SEQ ID NO 139
<211> LENGTH: 15
<212> TYPE: PRT
<213> ORGANISM: Artificial Sequence
<220> FEATURE:
<223> OTHER INFORMATION: linker for disulfide-linked multi-function
      protein

<400> SEQUENCE: 139

```
Gly Cys Gly Gly Ser Gly Gly Gly Gly Ser Gly Gly Gly Gly Ser
1               5                   10                  15
```

<210> SEQ ID NO 140
<211> LENGTH: 274
<212> TYPE: PRT
<213> ORGANISM: Artificial Sequence
<220> FEATURE:
<223> OTHER INFORMATION: HLA-A*0201 a1-a3 for disulfide-linked
      multi-function protein

<400> SEQUENCE: 140

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
                20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Gly Glu Thr
        50                  55                  60

Arg Lys Val Lys Ala His Ser Gln Thr His Arg Val Asp Leu Gly Thr
65                  70                  75                  80

Leu Arg Gly Cys Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
```

```
                145                 150                 155                 160
            Glu Gly Thr Cys Val Glu Trp Leu Arg Arg Tyr Leu Glu Asn Gly Lys
                            165                 170                 175
            Glu Thr Leu Gln Arg Thr Asp Ala Pro Lys Thr His Met Thr His His
                            180                 185                 190
            Ala Val Ser Asp His Glu Ala Thr Leu Arg Cys Trp Ala Leu Ser Phe
                            195                 200                 205
            Tyr Pro Ala Glu Ile Thr Leu Thr Trp Gln Arg Asp Gly Glu Asp Gln
                            210                 215                 220
            Thr Gln Asp Thr Glu Leu Val Glu Thr Arg Pro Ala Gly Asp Gly Thr
            225                 230                 235                 240
            Phe Gln Lys Trp Ala Ala Val Val Pro Ser Gly Gln Glu Gln Arg
                                245                 250                 255
            Tyr Thr Cys His Val Gln His Glu Gly Leu Pro Lys Pro Leu Thr Leu
                            260                 265                 270
            Arg Trp

<210> SEQ ID NO 141
<211> LENGTH: 442
<212> TYPE: PRT
<213> ORGANISM: Artificial Sequence
<220> FEATURE:
<223> OTHER INFORMATION: VH (MCSP)-IgG1 Fc-region L234A, L235A, P329G,
      T366S, L368A, Y407V mutant amino acid sequence

<400> SEQUENCE: 141

Gln Val Gln Leu Gln Glu Ser Gly Pro Gly Leu Val Lys Pro Ser Gln
            1               5                   10                  15
            Thr Leu Ser Leu Thr Cys Thr Val Ser Gly Gly Ser Ile Thr Ser Gly
                            20                  25                  30
            Tyr Tyr Trp Asn Trp Ile Arg Gln His Pro Gly Lys Gly Leu Glu Trp
                            35                  40                  45
            Ile Gly Tyr Ile Thr Tyr Asp Gly Ser Asn Asn Tyr Asn Pro Ser Leu
                            50                  55                  60
            Lys Ser Arg Val Thr Ile Ser Arg Asp Thr Ser Lys Asn Gln Phe Ser
            65                  70                  75                  80
            Leu Lys Leu Ser Ser Val Thr Ala Ala Asp Thr Ala Val Tyr Tyr Cys
                            85                  90                  95
            Ala Asp Phe Asp Tyr Trp Gly Gln Gly Thr Leu Val Thr Val Ser Ser
                            100                 105                 110
            Ala Ser Thr Lys Gly Pro Ser Val Phe Pro Leu Ala Pro Ser Ser Lys
                            115                 120                 125
            Ser Thr Ser Gly Gly Thr Ala Ala Leu Gly Cys Leu Val Lys Asp Tyr
                            130                 135                 140
            Phe Pro Glu Pro Val Thr Val Ser Trp Asn Ser Gly Ala Leu Thr Ser
            145                 150                 155                 160
            Gly Val His Thr Phe Pro Ala Val Leu Gln Ser Ser Gly Leu Tyr Ser
                            165                 170                 175
            Leu Ser Ser Val Val Thr Val Pro Ser Ser Ser Leu Gly Thr Gln Thr
                            180                 185                 190
            Tyr Ile Cys Asn Val Asn His Lys Pro Ser Asn Thr Lys Val Asp Lys
                            195                 200                 205
            Lys Val Glu Pro Lys Ser Cys Asp Lys Thr His Thr Cys Pro Pro Cys
                            210                 215                 220
            Pro Ala Pro Glu Ala Ala Gly Gly Pro Ser Val Phe Leu Phe Pro Pro
```

```
            225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
                260                 265                 270

Tyr Val Asp Gly Val Glu Val His Asn Ala Lys Thr Lys Pro Arg Glu
                275                 280                 285

Glu Gln Tyr Asn Ser Thr Tyr Arg Val Val Ser Val Leu Thr Val Leu
                290                 295                 300

His Gln Asp Trp Leu Asn Gly Lys Glu Tyr Lys Cys Lys Val Ser Asn
305                 310                 315                 320

Lys Ala Leu Gly Ala Pro Ile Glu Lys Thr Ile Ser Lys Ala Lys Gly
                325                 330                 335

Gln Pro Arg Glu Pro Gln Val Tyr Thr Leu Pro Pro Cys Arg Asp Glu
                340                 345                 350

Leu Thr Lys Asn Gln Val Ser Leu Trp Cys Leu Val Lys Gly Phe Tyr
                355                 360                 365

Pro Ser Asp Ile Ala Val Glu Trp Glu Ser Asn Gly Gln Pro Glu Asn
                370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly Lys
                435                 440

<210> SEQ ID NO 142
<211> LENGTH: 442
<212> TYPE: PRT
<213> ORGANISM: Artificial Sequence
<220> FEATURE:
<223> OTHER INFORMATION: VH (MCSP)-IgG1 Fc-region L234A, L235A, P329G,
      T366W mutant amino acid sequence

<400> SEQUENCE: 142

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
                20                  25                  30

Tyr Tyr Trp Asn Trp Ile Arg Gln His Pro Gly Lys Gly Leu Glu Trp
                35                  40                  45

Ile Gly Tyr Ile Thr Tyr Asp Gly Ser Asn Asn Tyr Asn Pro Ser Leu
                50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
                100                 105                 110
```

```
Ala Ser Thr Lys Gly Pro Ser Val Phe Pro Leu Ala Pro Ser Ser Lys
        115             120             125
Ser Thr Ser Gly Gly Thr Ala Ala Leu Gly Cys Leu Val Lys Asp Tyr
    130             135             140
Phe Pro Glu Pro Val Thr Val Ser Trp Asn Ser Gly Ala Leu Thr Ser
145             150             155             160
Gly Val His Thr Phe Pro Ala Val Leu Gln Ser Ser Gly Leu Tyr Ser
                165             170             175
Leu Ser Ser Val Val Thr Val Pro Ser Ser Leu Gly Thr Gln Thr
            180             185             190
Tyr Ile Cys Asn Val Asn His Lys Pro Ser Asn Thr Lys Val Asp Lys
        195             200             205
Lys Val Glu Pro Lys Ser Cys Asp Lys Thr His Thr Cys Pro Pro Cys
        210             215             220
Pro Ala Pro Glu Ala Ala Gly Gly Pro Ser Val Phe Leu Phe Pro Pro
225             230             235             240
Lys Pro Lys Asp Thr Leu Met Ile Ser Arg Thr Pro Glu Val Thr Cys
                245             250             255
Val Val Val Asp Val Ser His Glu Asp Pro Glu Val Lys Phe Asn Trp
            260             265             270
Tyr Val Asp Gly Val Glu Val His Asn Ala Lys Thr Lys Pro Arg Glu
        275             280             285
Glu Gln Tyr Asn Ser Thr Tyr Arg Val Val Ser Val Leu Thr Val Leu
    290             295             300
His Gln Asp Trp Leu Asn Gly Lys Glu Tyr Lys Cys Lys Val Ser Asn
305             310             315             320
Lys Ala Leu Gly Ala Pro Ile Glu Lys Thr Ile Ser Lys Ala Lys Gly
                325             330             335
Gln Pro Arg Glu Pro Gln Val Cys Thr Leu Pro Pro Ser Arg Asp Glu
            340             345             350
Leu Thr Lys Asn Gln Val Ser Leu Ser Cys Ala Val Lys Gly Phe Tyr
        355             360             365
Pro Ser Asp Ile Ala Val Glu Trp Glu Ser Asn Gly Gln Pro Glu Asn
    370             375             380
Asn Tyr Lys Thr Thr Pro Pro Val Leu Asp Ser Asp Gly Ser Phe Phe
385             390             395             400
Leu Val Ser Lys Leu Thr Val Asp Lys Ser Arg Trp Gln Gln Gly Asn
                405             410             415
Val Phe Ser Cys Ser Val Met His Glu Ala Leu His Asn His Tyr Thr
            420             425             430
Gln Lys Ser Leu Ser Leu Ser Pro Gly Lys
        435             440
```